United States Patent
Lin et al.

(10) Patent No.: US 10,253,015 B2
(45) Date of Patent: *Apr. 9, 2019

(54) PYRIDINYL QUINOLINONE DERIVATIVES AS MUTANT-ISOCITRATE DEHYDROGENASE INHIBITORS

(71) Applicant: FORMA TM2, Inc., Watertown, MA (US)

(72) Inventors: Jian Lin, Acton, MA (US); Anna Ericsson, Shrewsbury, MA (US); Ann-Marie Campbell, Monroe, CT (US); Gary Gustafson, Ridgefield, CT (US); Zhongguo Wang, Lexington, MA (US); R. Bruce Diebold, Waltham, MA (US); Susan Ashwell, Carlisle, MA (US); David R. Lancia, Jr., Boston, MA (US); Justin Andrew Caravella, Cambridge, MA (US); Wei Lu, Newton, MA (US)

(73) Assignee: FORMA TM2, INC., Watertown, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/964,812

(22) Filed: Apr. 27, 2018

(65) Prior Publication Data

US 2018/0327382 A1    Nov. 15, 2018

Related U.S. Application Data

(63) Continuation of application No. 15/677,748, filed on Aug. 15, 2017, now abandoned, which is a continuation of application No. 14/858,170, filed on Sep. 18, 2015, now Pat. No. 9,771,349.

(60) Provisional application No. 62/150,819, filed on Apr. 21, 2015, provisional application No. 62/128,089, filed on Mar. 4, 2015, provisional application No. 62/053,006, filed on Sep. 19, 2014.

(51) Int. Cl.
| | |
|---|---|
| *C07D 401/12* | (2006.01) |
| *C07D 413/14* | (2006.01) |
| *C07D 401/14* | (2006.01) |
| *C07D 417/14* | (2006.01) |
| *C07D 405/14* | (2006.01) |
| *A61K 31/4704* | (2006.01) |

(52) U.S. Cl.
CPC ......... *C07D 401/12* (2013.01); *C07D 401/14* (2013.01); *C07D 405/14* (2013.01); *C07D 413/14* (2013.01); *C07D 417/14* (2013.01); *A61K 31/4704* (2013.01)

(58) Field of Classification Search
CPC .. C07D 401/12; C07D 401/14; C07D 413/14; A61K 31/4704
See application file for complete search history.

(56) References Cited

U.S. PATENT DOCUMENTS

| | | |
|---|---|---|
| 5,262,564 A | 11/1993 | Kun et al. |
| 9,073,941 B2 | 7/2015 | Wong et al. |
| 9,624,175 B2 | 4/2017 | Lin et al. |
| 9,624,216 B2 | 4/2017 | Lin et al. |
| 9,771,349 B2 | 9/2017 | Lin et al. |
| 9,815,817 B2 | 11/2017 | Lin et al. |
| 9,834,539 B2 | 12/2017 | Lin et al. |
| 10,005,734 B2* | 6/2018 | Lin .................. C07D 215/227 |
| 2014/0235620 A1 | 8/2014 | Caferro et al. |
| 2016/0083349 A1 | 3/2016 | Lin et al. |
| 2016/0083365 A1 | 3/2016 | Lin et al. |
| 2016/0083366 A1 | 3/2016 | Lin et al. |
| 2016/0083367 A1 | 3/2016 | Lin et al. |
| 2016/0311774 A1 | 10/2016 | Lin et al. |
| 2016/0311818 A1 | 10/2016 | Lin et al. |
| 2017/0174658 A1 | 6/2017 | Lin et al. |
| 2018/0086733 A1 | 3/2018 | Lin et al. |

(Continued)

FOREIGN PATENT DOCUMENTS

| | | |
|---|---|---|
| RU | 2284325 C2 | 9/2006 |
| WO | WO-2006/054912 A1 | 5/2006 |

(Continued)

OTHER PUBLICATIONS

U.S. Appl. No. 15/964,844, filed Apr. 2018, Lin.*

(Continued)

*Primary Examiner* — D Margaret M Seaman

(74) *Attorney, Agent, or Firm* — Choate, Hall & Stewart LLP; John P. Rearick; Christopher K. Haley

(57) ABSTRACT

The invention relates to inhibitors of mutant isocitrate dehydrogenase (mt-IDH) proteins with neomorphic activity useful in the treatment of cell-proliferation disorders and cancers, having the Formula:

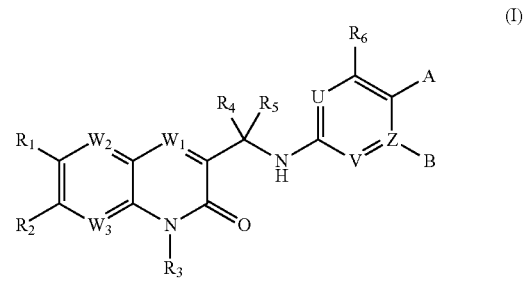

(I)

where A, B, U, V, Z, $W_1$, $W_2$, $W_3$, and $R_1$-$R_6$ are described herein.

12 Claims, 1 Drawing Sheet

(56) References Cited

U.S. PATENT DOCUMENTS

| | | |
|---|---|---|
| 2018/0118732 A1 | 5/2018 | Lin et al. |
| 2018/0134682 A1 | 5/2018 | Lin et al. |
| 2018/0141910 A1 | 5/2018 | Lin et al. |
| 2018/0312487 A1 | 11/2018 | Lin et al. |
| 2018/0327361 A1 | 11/2018 | Lin et al. |

FOREIGN PATENT DOCUMENTS

| | | |
|---|---|---|
| WO | WO-2007/117778 A2 | 10/2007 |
| WO | WO-2008/069242 A1 | 6/2008 |
| WO | WO-2011/072174 A1 | 6/2011 |
| WO | WO-2012/129562 A2 | 9/2012 |
| WO | WO-2012/171506 A1 | 12/2012 |
| WO | WO-2013/102431 A1 | 7/2013 |
| WO | WO-2014/141153 A1 | 9/2014 |
| WO | WO-2015/003146 A1 | 1/2015 |
| WO | WO-2016/044781 A1 | 3/2016 |
| WO | WO-2016/044782 A1 | 3/2016 |
| WO | WO-2016/044787 A1 | 3/2016 |
| WO | WO-2016/044789 A1 | 3/2016 |
| WO | WO-2016/106331 A1 | 6/2016 |
| WO | WO-2016/108045 A2 | 7/2016 |
| WO | WO-2016/171755 A1 | 10/2016 |
| WO | WO-2016/171756 A1 | 10/2016 |
| WO | WO-2017/019429 A1 | 2/2017 |
| WO | WO-2017/146795 A1 | 8/2017 |
| WO | WO-2017/213910 A1 | 12/2017 |
| WO | WO-2017/223202 A1 | 12/2017 |
| WO | WO-2018/111707 A1 | 6/2018 |

OTHER PUBLICATIONS

U.S. Appl. No. 15/977,512, filed May 2018, Lin.*
U.S. Appl. No. 15/977,512, filed May 11, 2018, Lin et al.
U.S. Appl. No. 15/964,844, filed Apr. 27, 2018, Lin et al.
Badr, M.Z.A. et al., Reaction of Quinoxaline Derivatives with Nucleophilic Reagents, , Bull Chem Soc Jpn, 56(1): 326-330 (1983).
Balss, J. et al., Analysis of the IDH1 codon 132 mutation in brain tumors, Acta Neuropathol., 116: 597-602 (2008).
Cui, Z. et al., Structure and properties of N-heterocycle-containing benzotriazoles as UV absorbers, Journal of Molecular Structure, 1054: 94-99 (2013).
Dang, L. et al., Cancer-associated IDH1 mutations produce 2-hydroxyglutarate, Nature, 462: 739-744 (2009).
Dang, L. et al., IDH mutations in glioma and acute myeloid leukemia, Trends Mol. Med., 16(9): 387-397 (2010).
Database Caplus (Online) Chemical Abstracts Service, Columbus, Ohio, US; retrieved from STN Database accession No. 1987: 407040 abstract, Prostakov, N.S. et al., Synthesis of substituted 2-pyridones and 4-aza-3-fluorenones, Khimiya Geterotsiklicheskikh Soedinenii, 7: 939-942 (1986).
Database Registry (Online) Chemical Abstracts Service, Columbus, Ohio, US; Database accession No. 1434379-53-9 (Jun. 5, 2013).
Database Registry (Online) Chemical Abstracts Service, Columbus, Ohio, US; Database accession No. 1497653-96-9 (Dec. 18, 2013).
Database Registry (Online) Chemical Abstracts Service, Columbus, Ohio, US; Database accession No. 1567357-55-4 (Mar. 12, 2014).
Database Registry (Online) Chemical Abstracts Service, Columbus, Ohio, US; Database accession No. 1567456-94-3 (Mar. 12, 2014).
Dinardo, C.D. et al., Serum 2-hydroxyglutarate levels predict isocitrate dehydrogenase mutations and clinical outcome in acute myeloid leukemia, Blood, 121(24): 4917-1924 (2013).
Fatima, S., Molecular docking and 3D-QSAR studies on inhibitors of DNA damage signaling enzyme human PARP-1, J Receptors and Signal Transduction, 32(4) 214-224 (2012).
Gaal, J. et al., Isocitrate Dehydrogenase Mutations Are Rare in Pheochromocytomas and Paragangliomas, J. Clin. Endocrinol. Metab., 95(3): 1274-1278 (2010).
Gross, S. et al., Cancer-associated metabolite 2-hydroxyglutarate accumulates in acute myelogenous leukemia with isocitrate dehydrogenase 1 and 2 mutations, J. Exp. Med., 207(2): 339-344 (2010).
Hayden, J.T. et al., Frequent IDH1 mutations in supratentorial primitive neuroectodermal tumors (sPNET) of adults but not children, Cell Cycle, 8(11): 1806-1807 (2009).
International Search Report for PCT/US2015/051044, 4 pages (dated Nov. 23, 2015).
International Search Report for PCT/US2015/051046, 3 pages (dated Oct. 30, 2015).
International Search Report for PCT/US2015/051053, 4 pages (dated Oct. 28, 2015).
International Search Report for PCT/US2015/051055, 3 pages (dated Nov. 13, 2015).
International Search Report for PCT/US2015/051056, 4 pages (dated Nov. 20, 2015).
International Search Report for PCT/US2015/051059, 3 pages (dated Oct. 30, 2015).
Kombarov, R.V. et al., CA Accession No. 138:368869, abstract only of Chem of Het Compounds, 38(9): 1154-1155 (2002).
Losman, J-A. et al., (R)-2-Hydroxyglutarate is Sufficient to Promote Leukemogenesis and its Effects are Reversible, Science, 339(6127): 1-9 (2013).
Mohamed, E.A. et al., CA Accession No. 122:160601, abstract only of Indian J Chem, Sect B: Org Chem Inc Med Chem, 34B(1):21-26 (1995).
Morshed, M.N. et al., Computational approach to the identification of novel Aurora-A inhibitors, Bioorg & Med Chem, 19: 907-916 (2011).
Schrader, F.C. et al., Novel Type II Fatty Acid Biosynthesis (FAS II) Inhibitors as Multistage Antimalarial Agents, Chem Med Chem, 8: 442-461 (2013).
Sellner, L. et al. Increased levels of 2-hydroxyglutarate in AML patients with IDH1-R132H and IDH2-R140Q mutations, Eur. J. Haematol., 85: 457-459 (2010).
Shibata, T. et al., Mutant IDH1 Confers an in Vivo Growth in a Melanoma Cell Line with BRAF Mutation, Am. J. Pathol., 178(3): 1395-1402 (2011).
Tintori, C. et al., Identification of Hck Inhibitors As Hits for the Development of Antileukemia and Anti-HIV Agents, Chem Med Chem, 8: 1353-1360 (2013).
Wang, F. et. al., Targeted Inhibition of Mutant IDH2 in Leukemia Cells Induces Cellular Differentiation, Science, 340: 622-626 (2013).
Wang, P. et al., Mutations in Isocitrate Dehydrogenase 1 and 2 Occur Frequently in Intrahepatic Cholangiocarcinomas and Share Hypermetylation Targets with Glioblastomas, Oncogene, 32(25): 3091-3100 (2013).
Ward, P.S. et al., The common feature of leukemia-associated IDH1 and IDH2 mutations is a neomorphic enzymatic activity that converts $\alpha$-ketoglutarate to 2-hydroxyglutarate, Cancer Cell, 17(3): 225-234 (2010).
Zhao, S. et. al., Glioma-Derived Mutations in IDH1 Dominantly Inhibit IDH1 Catalytic Activity and Induce HIF-1$\alpha$, Science, 324(5924): 261-265 (2009).
Zheng, B. et al., Crystallographic Investigation and Selective Inhibition of Mutant Isocitrate Dehydrogenase, ACS Medicinal Chemistry Letters, 4(6): 542-546 (2013).
FORMA Therapeutics, Discovery and Optimization of a Novel Series of Inhibitors of mt-IDH1, 7th Annual Advances in Chemical Sciences Symposium, Presentation, 21 slides (May 4, 2018).
Prostakov, N.S. et al., Chemistry of Heterocyclic Compounds, CHCCAL, 22(7): 685-810 (1986).

* cited by examiner

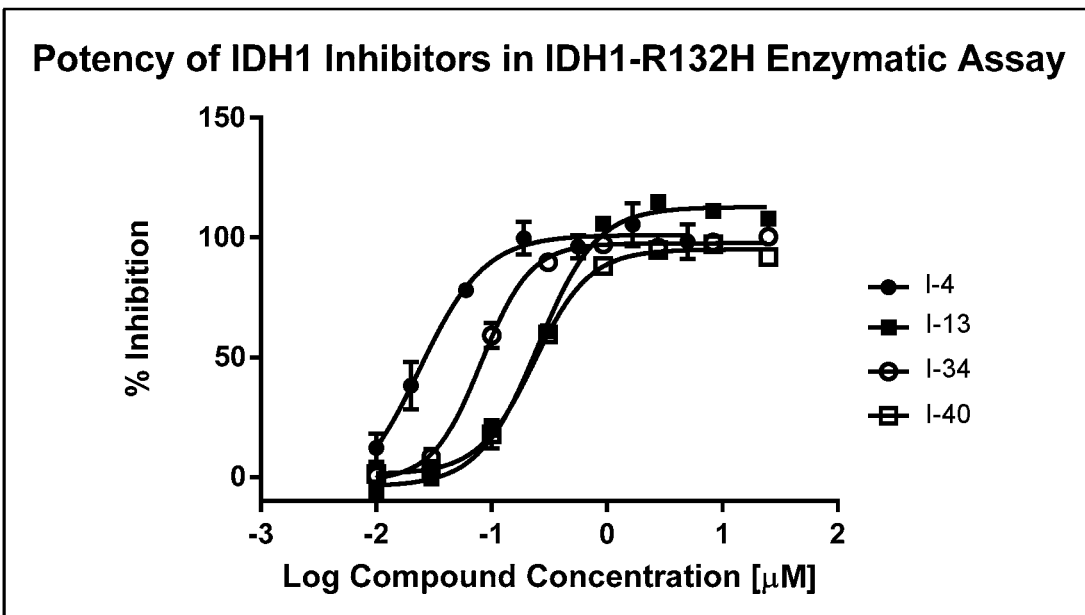

PYRIDINYL QUINOLINONE DERIVATIVES AS MUTANT-ISOCITRATE DEHYDROGENASE INHIBITORS

CROSS-REFERENCE TO RELATED APPLICATIONS

This application is a U.S. Continuation Application of Ser. No. 15/677,748, filed Aug. 15, 2017, which is a U.S. Continuation Application of Ser. No. 14/858,170, filed Sep. 18, 2015, issued as U.S. Pat. No. 9,771,349, on Sep. 26, 2017, which claims the benefit of priority of U.S. Provisional Application No. 62/053,006, filed Sep. 19, 2014 and U.S. Provisional Application No. 62/128,089, filed Mar. 4, 2015, and U.S. Provisional Application No. 62/150,819, filed Apr. 21, 2015, all of which are incorporated herein by reference in their entireties.

FIELD OF INVENTION

The present invention is directed to inhibitors of mutant isocitrate dehydrogenase (mt-IDH) proteins with neomorphic activity useful in the treatment of diseases or disorders associated with such mutant IDH proteins including cell-proliferation disorders and cancers. Specifically, the invention is concerned with compounds and compositions inhibiting mt-IDH, methods of treating diseases or disorders associated with mt-IDH, and methods of synthesis of these compounds.

BACKGROUND OF THE INVENTION

Isocitrate dehydrogenases (IDHs) are enzymes that participate in the citric acid cycle (cellular metabolism). They catalyze the oxidative decarboxylation of isocitrate to 2-oxoglutarate (i.e., α-ketoglutarate, α-KG). There are three isoforms within the IDH family. IDH-1, expressed in the cytoplasm and peroxisome, IDH-2, localized in the mitochondria, both utilize NADP+ as the cofactor and exist as homodimers. IDH-3 is localized in mitochondrial matrix and utilizes NAD+ as a cofactor and exists as tetramer. Mutations in IDH-1 (cytosolic) and IDH-2 (mitochondrial) have been identified in various diseases or disorders including glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, and melanoma (L. Deng et al., Trends Mol. Med., 2010, 16, 387; T. Shibata et al., Am. J. Pathol., 2011, 178(3), 1395; Gaal et al., J. Clin. Endocrinol. Metab. 2010; Hayden et al., Cell Cycle, 2009; Balss et al., Acta Neuropathol., 2008). The mutations have been found at or near key residues in the active site: G97D, R100, R132, H133Q, and A134D for IDH1, and R140 and R172 for IDH2. (See L. Deng et al., Nature, 2009, 462, 739; L. Sellner et al., Eur. J. Haematol., 2011, 85, 457).

Mutant forms of IDH-1 and IDH-2 have been shown to lose wild type activity, and instead exhibit a neomorphic activity (also known as a gain of function activity), of reducing alpha-ketoglutarate to 2-hydroxyglutarate (2-HG). (See P. S. Ward et al., Cancer Cell, 2010, 17, 225; Zhao et. al., Science 324, 261(2009); Dang et. al Nature 462, 739 (2009)). In general, production of 2-HG is enantiospecific, resulting in generation of the D-enantiomer (also known as the R enantiomer or R-2-HG). Normal cells have low basal levels of 2-HG, whereas cells harboring mutations in IDH1 or IDH2 show significantly elevated levels of 2-HG. High levels of 2-HG have also been detected in tumors harboring the mutations. For example, high levels of 2-HG have been detected in the plasma of patients with mutant IDH containing AML. (See S. Gross et al., J. Exp. Med., 2010, 207(2), 339). High levels of 2-HG have been shown to block α-KG dependent DNA and histone demethylases, and ultimately to result in improper dedifferentiation of hematopoietic progenitor cells in AML patients (Wang et. al., Science 340, 622 (2013); Losman et al., Science 339, 1621 (2013)).

Furthermore, patients with Oilier Disease and Mafucci Syndrome (two rare disorders that predispose to cartilaginous tumors) have been shown to be somatically mosaic for IDH1 and 2 mutations and exhibit high levels of D-2-HG. (See Amary et al., Nature Genetics, 2011 and Pansuriya et al., Nature Genetics, 2011).

The inhibition of mt-IDHs and their neomorphic activity with small molecule inhibitors therefore has the potential to be a treatment for cancers and other disorders of cellular proliferation.

SUMMARY OF THE INVENTION

A first aspect of the invention relates to compounds of Formula I:

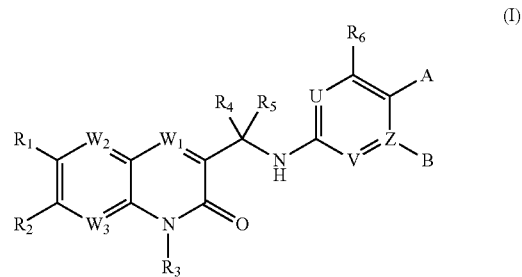

and pharmaceutically acceptable salts, enantiomers, hydrates, solvates, prodrugs, isomers, and tautomers thereof, wherein:

each $W_1$ and $W_2$ is independently CH, CF or N;

$W_3$ is independently $CR_2$ or N;

U and V are independently N, CH or $CR_6$; Z is independently N or C, provided that U and V are not both N; provided that only one of U, V, or Z is N; and provided that when one of U, V, or Z is N, $R_1$ is not H, $C_1$-$C_4$ alkyl, or methoxy;

A is selected from the group consisting of H, D, halogen, CN, —CHO, —COOH, —COOR, —C(O)$NH_2$, —C(O)NHR, R'S(O)$_2$—, —O($CH_2$)$_n$—C(O)R', R'S(O)—, heteroaryl, —SOMe, —$SO_2$Me,

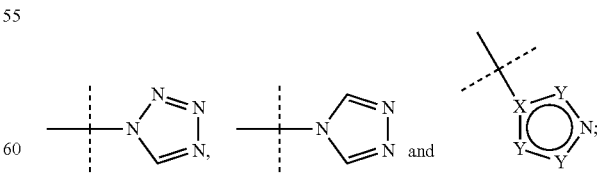

B is selected from the group consisting of null, H, D, $R_6$, OH, $NO_2$, $NH_2$, —$NR_7R_8$, CN, $C_1$-$C_6$ alkyl, $C_3$-$C_8$ cycloalkyl, substituted aryl, $C_1$-$C_6$ alkoxy, substituted heteroaryl, —($CH_2$)$_n$C(O)NHR, —C(O)$NH_2$, —SR, OR, —(CHR')$_n$S(O)R, —(CHR')$_n$S(O)$_2$R, —COOR.

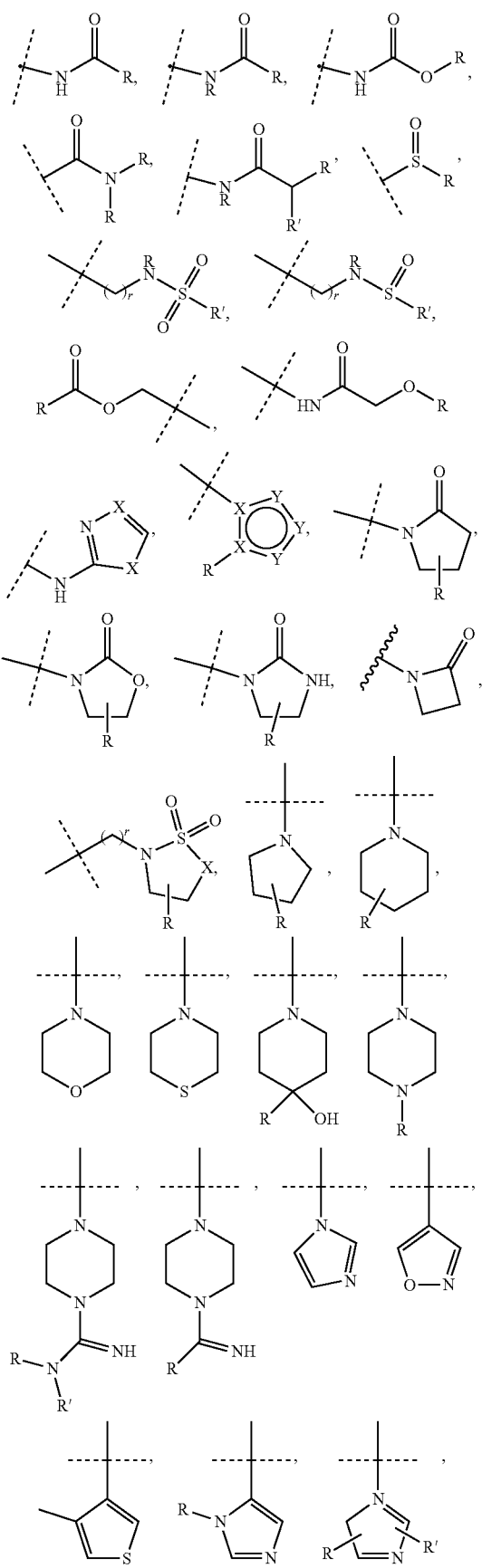

wherein X and Y are independently in each occurrence C, N, NR', S, and O, provided that the ring containing X and Y cannot have more than 4 N or NH atoms or more than one S or O atoms, and wherein the S and O are not contiguous; provided that B is null when Z is N;

R and R' at each occurrence are independently selected from the group consisting of H, OH, CN, —CH$_2$CN, halogen, —NR$_7$R$_8$, CHCF$_2$, CF$_3$, C$_1$-C$_6$ alkyl, R$_7$S(O)$_2$—, C$_1$-C$_6$ alkoxy, C$_2$-C$_6$ alkenyl, C$_2$-C$_6$ alkynyl, C$_3$-C$_8$ cycloalkyl, C$_3$-C$_8$ cycloalkylalkyl, 3- to 8-membered heterocyclyl, aryl, and heteroaryl, wherein each R is optionally substituted with one or more substituents selected from the group consisting of OH, halogen, C$_1$-C$_6$ alkoxy, NH$_2$, R$_7$S(O)$_2$—, CN, C$_3$-C$_8$ cycloalkyl, 3- to 8-membered heterocyclyl, aryl, heteroaryl, and R$_7$S(O)—;

R$_1$ is independently H, OH, CN, halogen, CHCF$_2$, CF$_3$, C$_1$-C$_6$ alkyl, C$_1$-C$_6$ alkoxy, C$_2$-C$_6$ alkenyl, C$_2$-C$_6$ alkenyl, C$_3$-C$_8$ cycloalkyl, 3- to 8-membered heterocyclyl, aryl, or heteroaryl, wherein each C$_1$-C$_6$ alkyl, C$_2$-C$_6$ alkenyl, C$_2$-C$_6$ alkynyl, C$_3$-C$_8$ cycloalkyl, 3- to 8-membered heterocyclyl, aryl, or heteroaryl is optionally substituted one or more times with substituents selected from the group consisting of halogen, OH, NH$_2$, CN, C$_1$-C$_6$ alkyl, and C$_1$-C$_6$ alkoxy;

R$_2$ is independently H, OH, CN, halogen, CF$_3$, CHF$_2$, benzyl, C$_1$-C$_6$ alkyl, C$_1$-C$_6$ alkoxy, NH$_2$, —O(CH$_2$)$_n$R', —O(CH$_2$)$_n$C(O)NHR', —O(CH$_2$)$_n$C(O)R', NHR$_7$, —N(R$_7$)(R$_8$), NHC(O)R$_7$, NHS(O)R$_7$, NHS(O)$_2$R$_7$, NHC(O)OR$_7$, NHC(O)NHR$_7$, —S(O)$_2$NHR$_7$, NHC(O)N(R$_8$)R$_7$, OCH$_2$R$_7$, CHRR' or OCHR'R$_7$, wherein C$_1$-C$_6$ alkyl, C$_1$-C$_6$ alkoxy is optionally substituted with one or more substituents selected from the group consisting of C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, C$_3$-C$_8$ cycloalkyl substituted with one or more halogen, 3- to 8-membered heterocyclyl, aryl, -heteroaryl-C(O)NH$_2$, and heteroaryl;

or R$_1$ and R$_2$ can combine to form a C$_4$-C$_6$ cycloalkyl or a 3- to 8-membered heterocyclyl containing at least one atom selected from the group consisting of N, O, and S;

R$_3$ is H, D, C$_1$-C$_6$ alkyl, or; —OH,

R$_4$ and R$_5$ are independently H, D, halogen, CH$_2$OH, C$_1$-C$_3$ alkyl, or C$_1$-C$_3$ alkyl substituted with halogen, or R$_4$ and R$_5$ when combined can form a C$_3$-C$_5$ cycloalkyl or C$_3$-C$_5$ heterocyclyl;

R$_6$ is H, halogen, C$_1$-C$_6$ alkyl, C$_1$-C$_6$ alkyl substituted with halogen, C$_1$-C$_6$ alkoxy, C$_1$-C$_6$ alkoxy substituted with one or more halogen, C$_2$-C$_6$ alkenyl, C$_2$-C$_6$ alkynyl, C$_3$-C$_8$ cycloalkyl, 3- to 8-membered heterocyclyl, aryl, or heteroaryl;

R$_7$ and R$_8$ are independently H, C$_1$-C$_6$ alkyl, C$_1$-C$_6$ alkoxy, C$_2$-C$_6$ alkenyl, C$_2$-C$_6$ alkynyl, C$_3$-C$_8$ cycloalkyl, 3- to 8-membered heterocyclyl, aryl, and heteroaryl; or when combined $R_7$ and $R_8$ can form a 3- to 8-membered heterocyclyl or heteroaryl ring;

n is 0, 1, or 2; and r is 0, 1, or 2.

Another aspect of the invention relates to a method of treating a disease or disorder associated with mutant isocitrate dehydrogenase. The method involves administering to a patient in need of a treatment for diseases or disorders associated with mutant isocitrate dehydrogenase an effective amount of a compound of Formula I.

Another aspect of the invention is directed to a method inhibiting mutant isocitrate dehydrogenase. The method involves administering to a patient in need thereof an effective amount of the compound of Formula I.

Another aspect of the invention relates to method of reducing alpha-ketoglutarate. The method comprises administering to a patient in need thereof an effective amount of the compound of Formula I.

Another aspect of the invention is directed to pharmaceutical compositions comprising a compound of Formula I and a pharmaceutically acceptable carrier. The pharmaceutically acceptable carrier may further include an excipient, diluent, or surfactant.

The present invention further provides methods of treating cell proliferative diseases and cancers including, without limitation, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), myeloproliferative disease (MPD), and other solid tumors.

The present invention also provides potent mt-IDH inhibitors with excellent drug-like properties to cancers and other cell proliferative disorders. The inhibitors of the present invention may target mutated IDH1 or IDH2.

The present invention further provides development of potent, orally active, and selective IDH inhibitors as therapeutic agents for various diseases or disorders including cancers. The invention also provides treatment for solid and hematologic cancers for which there are no currently targeted therapies available for patients suffering from these conditions or disorders.

BRIEF DESCRIPTION OF THE DRAWINGS OF THE INVENTION

FIG. 1 illustrates a graph showing the potency of IDH1 inhibitors in IDH1-R132H Enzymatic Assay using compounds I-4, I-13, I-34 and I-40

DETAILED DESCRIPTION OF THE INVENTION

IDH1 or IDH2 mutations are a genetically validated target in many solid and hematologic cancers, but there are currently no targeted therapies available for patients in need of treatment for specific conditions associated with mt-IDH activity. Non-mutant IDH (e.g., wild-type) catalyze the oxidative decarboxylation of isocitrate to α-ketoglutarate thereby reducing $NAD^+$ ($NADP^+$) to NADH (NADPH) (WO 2013/102431 to Cianchetta et al., hereby incorporated by reference in its entirety). Mutations of IDH present in certain cancer cells result in a new ability of the enzyme to catalyze the NADPH-dependent reduction of α-ketoglutarate R(−)-2-hydroxyglutarate (2HG). 2HG is not formed by wild-type IDH. The production of 2HG contributes to the formation and progression of cancer (Dang, L et al., Nature, 2009, 462:739-44, hereby incorporated by reference in its entirety). The present invention provides inhibitors of mt-IDH, and prophylactic measures to reduce the formation and progression of 2HG in cells.

In a first aspect of the invention, are described the compounds of Formula I:

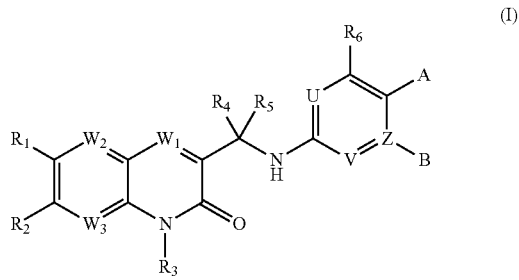

(I)

and pharmaceutically acceptable salts, enantiomers, hydrates, solvates, prodrugs, isomers, and tautomers thereof, where A, B, U, V, Z, $W_1$, $W_2$, $W_3$, and $R_1$-$R_6$ are as described above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, CN, —COOH, —CH$_2$CN, —O—C$_1$-C$_6$alkyl, C$_1$-C$_6$alkyl, —OC$_1$-

C$_6$alkenyl, —OC$_1$-C$_6$alkynyl, —C$_1$-C$_6$alkenyl, —C$_1$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, NH$_2$, NH(C$_1$-C$_6$alkyl), N(C$_1$-C$_6$alkyl)$_2$, —NHC(O)C$_1$-C$_6$alkyl, —C(O)NHC$_1$-C$_6$alkyl, —S(O)$_2$—C$_1$-C$_6$alkyl, —S(O)NHC$_1$-C$_6$alkyl, and S(O)N(C$_1$-C$_6$alkyl)$_2$ Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—C$_1$-C$_6$alkyl, C$_1$-C$_6$alkyl, —OC$_1$-C$_6$alkenyl, —OC$_1$-C$_6$alkynyl, —C$_1$-C$_6$alkenyl, —C$_1$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, NH$_2$, NH(C$_1$-C$_6$alkyl), N(C$_1$-C$_6$alkyl)$_2$, —S(O)$_2$—C$_1$-C$_6$alkyl, —S(O)NHC$_1$-C$_6$alkyl, and S(O)N(C$_1$-C$_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 10 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, and dihydrobenzoxanyl.

Halogen or "halo" refers to fluorine, chlorine, bromine and iodine.

Alkyl refers to a straight or branched chain saturated hydrocarbon containing 1-12 carbon atoms. Examples of a C$_1$-C$_6$ alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain. Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. Examples of alkenyl groups include ethenyl, propenyl, n-butenyl, iso-butenyl, pentenyl, or hexenyl.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

"Cycloalkylalkyl" means monocyclic saturated carbon rings containing 3-18 carbon atoms further substituted with C$_1$-C$_6$ alkyl groups. In general cycloalkylalkyl groups

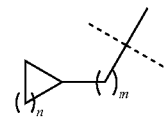

herein described display the following formula where m is an integer from 1 to 6 and n is an integer from 1 to 16.

"Heterocyclyl" or "heterocycloalkyl" monocyclic rings containing carbon and heteroatoms taken from oxygen, nitrogen, or sulfur and wherein there is not delocalized π electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. In accordance with the present invention, 3- to 8-membered heterocyclyl refers to saturated or partially saturated non aromatic rings structures containing between 3 and 8 atoms in which there is at least one heteroatoms selected from the group N, O, or S.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

In one embodiment of the invention, A is CN. In this embodiment, B may further be $C_1$-$C_6$ alkoxy or $C_1$-$C_6$ alkyl. In another embodiment, B may also be methoxy. In another embodiment, B is methyl.

In another embodiment of the compounds of Formula I, U is N or V is N. In this embodiment, A may further be CN.

In another embodiment of the invention, A is CN and B is methyl.

In another embodiment, of the compounds of Formula I, B may be

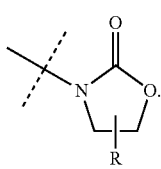

In this embodiment A may also be H or F.

In another embodiment of the compounds of Formula I, B is

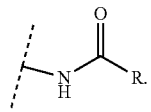

In this embodiment, A may also be H or F. In this embodiment, R may also be methyl, ethyl, or cyclopropyl.

In another embodiment of the compounds of Formula I, B is

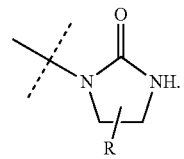

In this embodiment, A may also be H or F. In this embodiment, R may also be methyl, ethyl, cyclopropyl.

In another embodiment of the invention, B may be

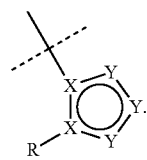

In this embodiment, A may also be H or F.

Yet another embodiment of the invention relates to compounds of Formula I where B is

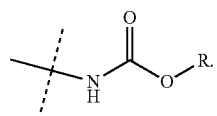

This embodiment also optionally provides for compounds of Formula I where A is H or F.

In another embodiment of the compounds of Formula I, B is

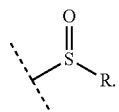

This embodiment may further provide for compounds of Formula I where A is H or F.

In another embodiment of the invention, B is

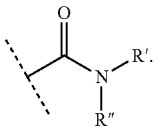

In this embodiment, A may also further be H or F.

In other embodiments of the invention, are described the compounds of Formula I where A is H or F.

Another embodiment of the invention pertains to compounds of Formula I where $R_4$ and $R_5$ are H.

In another embodiment of the compounds of Formula I, $R_4$ is H and $R_5$ is methyl.

In yet another embodiment of the invention, $R_4$ is H and $R_5$ is (S)-methyl.

In another embodiment, $R_4$ and $R_5$ are halogen.

In another embodiment of the compounds of Formula I, $R_4$ is F and $R_5$ is methyl.

In another embodiment, $R_4$ and $R_5$ can combine to form a $C_3$-$C_5$ cycloalkyl.

In one embodiment of the compounds of Formula I, $W_1$, $W_2$, and $W_3$ are all CH.

In one embodiment of the compounds of Formula I, $W_1$, $W_2$, or $W_3$ are CF.

In one embodiment, $W_1$ or $W_3$ is CH or N.

In one embodiment, $W_3$ is $CR_2$.

In another embodiment of the invention, $R_1$ can be halogen. In another embodiment, $R_1$ is chloro.

In one embodiment of the invention $R_2$ can be H, halogen, or $C_1$-$C_6$ alkoxy. In another embodiment, $R_2$ can also be $C_1$-$C_6$ alkoxy substituted with heteroaryl or 3- to 8-membered heterocyclyl.

In another embodiment, illustrative compounds of Formula I are:
6-{[(1S)-1-(6-chloro-2-oxo-1,2-dihydroquinolin-3-yl)ethyl]amino}-4-methoxypyridine-3-carbonitrile;
6-{[(1S)-1-(6-chloro-1-methyl-2-oxo-1,2-dihydroquinolin-3-yl)ethyl]amino}-4-methoxypyridine-3-carbonitrile;
6-{[(1R)-1-(6-chloro-2-oxo-1,2-dihydroquinolin-3-yl)ethyl]amino}-4-methoxypyridine-3-carbonitrile;
6-{[(1S)-1-(6-chloro-2-oxo-1,2-dihydroquinolin-3-yl)ethyl]amino}-2-methylpyridine-3-carbonitrile;
6-{[(1S)-1-(6-chloro-2-oxo-1,2-dihydroquinolin-3-yl)ethyl]amino}-4-methylpyridine-3-carbonitrile;
6-{[(1S)-1-(6-chloro-2-oxo-1,2-dihydroquinolin-3-yl)ethyl]amino}-2-methoxypyridine-3-carbonitrile;
5-{[(1S)-1-(6-chloro-2-oxo-1,2-dihydroquinolin-3-yl)ethyl]amino}-6-methoxypyridine-2-carbonitrile;
6-{[(1R)-1-(6-chloro-2-oxo-1,2-dihydroquinolin-3-yl)ethyl]amino}-2-methylpyridine-3-carbonitrile;
6-{[1-(6-chloro-2-oxo-1,2-dihydroquinolin-3-yl)ethyl]amino}-2-methylpyridine-3-carbonitrile;
6-chloro-3-[(1S)-1-{[4-(2-oxo-1,3-oxazolidin-3-yl)pyridin-2-yl]amino}ethyl]-1,2-dihydroquinolin-2-one;
6-chloro-3-[(1S)-1-{[6-(2-oxo-1,3-oxazolidin-3-yl)pyridin-2-yl]amino}ethyl]-1,2-dihydroquinolin-2-one;
6-chloro-3-[(1S)-1-{[6-methyl-4-(2-oxo-1,3-oxazolidin-3-yl)pyridin-2-yl]amino}ethyl]-1,2-dihydroquinolin-2-one;
6-chloro-3-[(1S)-1-{[4-(4,4-dimethyl-2-oxo-1,3-oxazolidin-3-yl)pyridin-2-yl]amino}ethyl]-1,2-dihydroquinolin-2-one;
6-chloro-3-[(1S)-1-{[3-fluoro-4-(2-oxo-1,3-oxazolidin-3-yl)pyridin-2-yl]amino}ethyl]-1,2-dihydroquinolin-2-one;
6-chloro-3-[(1S)-1-{[3-methyl-4-(2-oxo-1,3-oxazolidin-3-yl)pyridin-2-yl]amino}ethyl]-1,2-dihydroquinolin-2-one;
6-chloro-3-[(1S)-1-{[4-fluoro-6-(2-oxo-1,3-oxazolidin-3-yl)pyridin-2-yl]amino}ethyl]-1,2-dihydroquinolin-2-one;
6-chloro-3-[(1S)-1-{[6-fluoro-4-(2-oxo-1,3-oxazolidin-3-yl)pyridin-2-yl]amino}ethyl]-1,2-dihydroquinolin-2-one;
6-chloro-3-[1-({4-[(4 S)-2-oxo-4-(propan-2-yl)-1,3-oxazolidin-3-yl]pyridin-2-yl}amino)ethyl]-1,2-dihydroquinolin-2-one;
6-chloro-3-[(1S)-1-({6-[(4S)-2-oxo-4-(propan-2-yl)-1,3-oxazolidin-3-yl]pyridin-2-yl}amino)ethyl]-1,2-dihydroquinolin-2-one;
6-chloro-3-[(1R)-1-({6-[(4S)-2-oxo-4-(propan-2-yl)-1,3-oxazolidin-3-yl]pyridin-2-yl}amino)ethyl]-1,2-dihydroquinolin-2-one;
6-{[1-(6-chloro-7-fluoro-2-oxo-1,2-dihydroquinolin-3-yl)ethyl]amino}-2-methylpyridine-3-carbonitrile;
6-{[(1S)-1-(6-chloro-7-fluoro-2-oxo-1,2-dihydroquinolin-3-yl)ethyl]amino}-2-methylpyridine-3-carbonitrile;
6-{[(1S)-1-(6-chloro-7-methoxy-2-oxo-1,2-dihydroquinolin-3-yl)ethyl]amino}-2-methylpyridine-3-carbonitrile;
6-{[1-(6-chloro-7-methoxy-2-oxo-1,2-dihydroquinolin-3-yl)ethyl]amino}-2-methylpyridine-3-carbonitrile;
6-{[(1S)-1-(6-chloro-7-methoxy-2-oxo-1,2-dihydroquinolin-3-yl)ethyl]amino}-4-methoxypyridine-3-carbonitrile;
6-{[(1S)-1-(6-chloro-7-methoxy-2-oxo-1,2-dihydroquinolin-3-yl)ethyl]amino}-2-methoxypyridine-3-carbonitrile;
6-{[(1S)-1-(6-chloro-7-methoxy-2-oxo-1,2-dihydroquinolin-3-yl)ethyl]amino}-4-methylpyridine-3-carbonitrile;
6-{[(1S)-1-[6-chloro-2-oxo-7-(pyridin-2-ylmethoxy)-1,2-dihydroquinolin-3-yl]ethyl]amino}-2-methylpyridine-3-carbonitrile;
6-({1-[6-chloro-2-oxo-7-(pyridin-2-ylmethoxy)-1,2-dihydroquinolin-3-yl]ethyl}amino)-2-methylpyridine-3-carbonitrile;
6-[(1-{6-chloro-7-[(3,3-difluorocyclobutyl)methoxy]-2-oxo-1,2-dihydroquinolin-3-yl}ethyl)amino]-2-methylpyridine-3-carbonitrile;
6-{[1-(6-chloro-2-oxo-1,2-dihydroquinolin-3-yl)cyclopropyl]amino}-2-methylpyridine-3-carbonitrile;
6-{[2-(6-chloro-2-oxo-1,2-dihydroquinolin-3-yl)propan-2-yl]amino}-2-methylpyridine-3-carbonitrile;
6-chloro-3-[(1S)-1-({4-[(2-hydroxyethyl)amino]-6-methylpyridin-2-yl}amino)ethyl]-1,2-dihydroquinolin-2-one;
N-(2-{[(1S)-1-(6-chloro-2-oxo-1,2-dihydroquinolin-3-yl)ethyl]amino}-3-fluoropyridin-4-yl)acetamide;
2-(6-{[(1S)-1-(6-chloro-2-oxo-1,2-dihydroquinolin-3-yl)ethyl]amino}pyridin-2-yl)-1$\lambda^6$,2-thiazolidine-1,1-dione;
6-chloro-3-[(1S)-1-({3-fluoro-4-[(2-hydroxyethyl)amino]pyridin-2-yl}amino)ethyl]-1,2-dihydroquinolin-2-one;
6-chloro-3-[(1S)-1-{[3-fluoro-4-(1H-imidazol-1-yl)pyridin-2-yl]amino}ethyl]-1,2-dihydroquinolin-2-one;
6-chloro-3-[(1S)-1-{[3-fluoro-4-(4-methyl-1H-imidazol-1-yl)pyridin-2-yl]amino}ethyl]-1,2-dihydroquinolin-2-one;
6-chloro-3-[(1S)-1-{[4-(1,3-dimethyl-1H-pyrazol-5-yl)pyridin-2-yl]amino}ethyl]-1,2-dihydroquinolin-2-one;
6-chloro-3-[(1S)-1-{[4-(1,5-dimethyl-1H-pyrazol-4-yl)pyridin-2-yl]amino}ethyl]-1,2-dihydroquinolin-2-one;
6-chloro-3-[(1S)-1-{[4-(1H-pyrazol-5-yl)pyridin-2-yl]amino}ethyl]-1,2-dihydroquinolin-2-one;
6-chloro-3-[(1S)-1-{[3-fluoro-4-(1-methyl-1H-pyrrol-2-yl)pyridin-2-yl]amino}ethyl]-1,2-dihydroquinolin-2-one;
6-chloro-3-[(1S)-1-({4-[1-(2-methylpropyl)-1H-pyrazol-5-yl]pyridin-2-yl}amino)ethyl]-1,2-dihydroquinolin-2-one;
6-chloro-3-[(1S)-1-({4-[1-(propan-2-yl)-1H-pyrazol-5-yl]pyridin-2-yl}amino)ethyl]-1,2-dihydroquinolin-2-one;
6-chloro-3-[(1S)-1-{[4-(1,5-dimethyl-1H-pyrazol-4-yl)-3-fluoropyridin-2-yl]amino}ethyl]-1,2-dihydroquinolin-2-one;
6-chloro-3-[(1S)-1-{[3-fluoro-4-(4-methylthiophen-3-yl)pyridin-2-yl]amino}ethyl]-1,2-dihydroquinolin-2-one;
6-chloro-3-[(1S)-1-({4-[1-(oxan-2-yl)-1H-pyrazol-5-yl]pyridin-2-yl}amino)ethyl]-1,2-dihydroquinolin-2-one;
6-chloro-3-[(1S)-1-{[4-(4-methylthiophen-3-yl)pyridin-2-yl]amino}ethyl]-1,2-dihydroquinolin-2-one;
6-chloro-3-[(1S)-1-{[4-(1-methyl-1H-pyrazol-5-yl)pyridin-2-yl]amino}ethyl]-1,2-dihydroquinolin-2-one;
6-chloro-3-[(1S)-1-({4-[3-(trifluoromethyl)-1H-pyrazol-4-yl]pyridin-2-yl}amino)ethyl]-1,2-dihydroquinolin-2-one;

6-chloro-3-[(1S)-1-{[4-(3,5-dimethyl-1H-pyrazol-4-yl)-3-fluoropyridin-2-yl]amino}ethyl]-1,2-dihydroquinolin-2-one;

6-chloro-3-[(1S)-1-{[4-(1,3-dimethyl-1H-pyrazol-5-yl)-3-fluoropyridin-2-yl]amino}ethyl]-1,2-dihydroquinolin-2-one;

6-chloro-3-[(1S)-1-{[3-fluoro-4-(1-methyl-1H-pyrazol-5-yl)pyridin-2-yl]amino}ethyl]-1,2-dihydroquinolin-2-one;

6-chloro-3-[(1S)-1-{[4-(dimethyl-1,2-oxazol-4-yl)-3-fluoropyridin-2-yl]amino}ethyl]-1,2-dihydroquinolin-2-one;

6-chloro-3-[(1S)-1-({3-fluoro-4-[1-(oxan-2-yl)-1H-pyrazol-5-yl]pyridin-2-yl}amino)ethyl]-1,2-dihydroquinolin-2-one;

6-chloro-3-[(1S)-1-({3-fluoro-4-[1-(2-methylpropyl)-1H-pyrazol-5-yl]pyridin-2-yl}amino)ethyl]-1,2-dihydroquinolin-2-one;

6-chloro-3-[(1S)-1-({3-fluoro-4-[1-(propan-2-yl)-1H-pyrazol-5-yl]pyridin-2-yl}amino)ethyl]-1,2-dihydroquinolin-2-one;

6-{[(6-chloro-2-oxo-1,2-dihydroquinolin-3-yl)methyl]amino}-2-methylpyridine-3-carbonitrile;

6-{[(6-chloro-2-oxo-1,2-dihydroquinolin-3-yl)methyl]amino}-4-methylpyridine-3-carbonitrile;

6-{[(6-chloro-2-oxo-1,2-dihydroquinolin-3-yl)methyl]amino}2-(trifluoromethyl)pyridine-3-carbonitrile;

5-{[(6-chloro-2-oxo-1,2-dihydroquinolin-3-yl)methyl]amino}-6-methoxypyridine-2-carbonitrile;

2-chloro-6-{[(6-chloro-2-oxo-1,2-dihydroquinolin-3-yl)methyl]amino}pyridine-3-carbonitrile;

6-{[(6-chloro-2-oxo-1,2-dihydroquinolin-3-yl)methyl]amino}-2-(2-oxo-1,3-oxazolidin-3-yl)pyridine-3-carbonitrile;

6-{[(6-chloro-2-oxo-1,2-dihydroquinolin-3-yl)methyl]amino}-2-[2-(propan-2-yl)pyrrolidin-1-yl]pyridine-3-carbonitrile;

6-{[(6-chloro-2-oxo-1,2-dihydroquinolin-3-yl)methyl]amino}-2-[methyl(2-methylpropyl)amino]pyridine-3-carbonitrile;

6-{[(6-chloro-2-oxo-1,2-dihydroquinolin-3-yl)methyl]amino}-2-methoxypyridine-3-carbonitrile;

6-{[(6-chloro-2-oxo-1,2-dihydroquinolin-3-yl)methyl]amino}pyridine-3-carbonitrile;

6-chloro-3-({[3-(propan-2-yl)pyridin-2-yl]amino}methyl)-1,2-dihydroquinolin-2-one;

6-chloro-3-{[(4,6-dimethylpyridin-2-yl)amino]methyl}-1,2-dihydroquinolin-2-one;

6-chloro-3-{[(4-methoxypyridin-2-yl)amino]methyl}-1,2-dihydroquinolin-2-one;

6-chloro-3-{[(5-fluoropyridin-2-yl)amino]methyl}-1,2-dihydroquinolin-2-one;

2-{[(6-chloro-2-oxo-1,2-dihydroquinolin-3-yl)methyl]amino}pyridine-4-carbonitrile;

methyl 6-{[(6-chloro-2-oxo-1,2-dihydroquinolin-3-yl)methyl]amino}pyridine-2-carboxylate;

6-chloro-3-{[(4-methylpyridin-2-yl)amino]methyl}-1,2-dihydroquinolin-2-one;

6-chloro-3-{[(5-chloropyridin-2-yl)amino]methyl}-1,2-dihydroquinolin-2-one;

6-chloro-3-{[(2-hydroxypyridin-3-yl)amino]methyl}-1,2-dihydroquinolin-2-one;

6-chloro-3-({[5-(trifluoromethyl)pyridin-2-yl]amino}methyl)-1,2-dihydroquinolin-2-one;

5-{[(6-chloro-2-oxo-1,2-dihydroquinolin-3-yl)methyl]amino}pyridine-2-carbonitrile;

6-chloro-3-({[4-(trifluoromethyl)pyridin-2-yl]amino}methyl)-1,2-dihydroquinolin-2-one;

6-{[(6,7-dimethyl-2-oxo-1,2-dihydroquinolin-3-yl)methyl]amino}pyridine-3-carbonitrile;

6-{[(6-methoxy-2-oxo-1,2-dihydroquinolin-3-yl)methyl]amino}pyridine-3-carbonitrile;

6-methoxy-3-{[(4-methylpyridin-2-yl)amino]methyl}-1,2-dihydroquinolin-2-one;

6-{[(6-chloro-7-methoxy-2-oxo-1,2-dihydroquinolin-3-yl)methyl]amino}-2-methylpyridine-3-carbonitrile;

6-({[6-chloro-2-oxo-7-(pyridin-2-ylmethoxy)-1,2-dihydroquinolin-3-yl]methyl}amino)-2-methylpyridine-3-carbonitrile; and 6-[({6-chloro-7-[2-(4-methanesulfonylpiperazin-1-yl)ethoxy]-2-oxo-1,2-dihydroquinolin-3-yl}methyl)amino]-2-methylpyridine-3-carbonitrile.

In another embodiment, illustrative compounds of Formula I include:

Methyl N-(2-{[(1S)-1-(6-chloro-2-oxo-1,2-dihydroquinolin-3-yl)ethyl]amino}pyridin-4-yl)carbamate;

2-{[(1S)-1-(6-chloro-2-oxo-1,2-dihydroquinolin-3-yl)ethyl]amino}pyridine-4-carboxamide;

6-chloro-3-[(1S)-1-{[4-(5-methyl-1H-1,2,3,4-tetrazol-1-yl)pyridin-2-yl]amino}ethyl]-1,2-dihydroquinolin-2-one;

N-(2-{[(1S)-1-(6-chloro-2-oxo-1,2-dihydroquinolin-3-yl)ethyl]amino}pyridin-4-yl)acetamide;

6-chloro-3-[(1S)-1-{[4-(1H-imidazol-1-yl)pyridin-2-yl]amino}ethyl]-1,2-dihydroquinolin-2-one;

6-chloro-3-[(1S)-1-{[4-(1,2-oxazol-4-yl)pyridin-2-yl]amino}ethyl]-1,2-dihydroquinolin-2-one;

3-[(1S)-1-{[4-(1-benzyl-1H-imidazol-5-yl)pyridin-2-yl]amino}ethyl]-6-chloro-1,2-dihydroquinolin-2-one;

6-chloro-3-[(1S)-1-{[4-(1-methyl-1H-imidazol-5-yl)pyridin-2-yl]amino}ethyl]-1,2-dihydroquinolin-2-one;

6-chloro-3-[(1S)-1-{[4-(3-methylpyridin-4-yl)pyridin-2-yl]amino}ethyl]-1,2-dihydroquinolin-2-one;

N-(2-{[(1S)-1-(6-chloro-2-oxo-1,2-dihydroquinolin-3-yl)ethyl]amino}pyridin-4-yl)-N-(2-methylpropyl)methanesulfonamide;

methyl N-(2-{[(1S)-1-[6-chloro-2-oxo-7-(pyridin-2-ylmethoxy)-1,2-dihydroquinolin-3-yl]ethyl]amino}pyridin-4-yl)carbamate;

2-{[(1S)-1-[6-chloro-2-oxo-7-(pyridin-2-ylmethoxy)-1,2-dihydroquinolin-3-yl]ethyl]amino}pyridine-4-carboxamide;

6-chloro-3-[(1S)-1-{[3-fluoro-4-(2-oxo-1,3-oxazolidin-3-yl)pyridin-2-yl]amino}ethyl]-7-(pyridin-2-ylmethoxy)-1,2-dihydroquinolin-2-one;

6-chloro-3-[(1S)-1-{[4-(5-methyl-1H-1,2,3,4-tetrazol-1-yl)pyridin-2-yl]amino}ethyl]-7-(pyridin-2-ylmethoxy)-1,2-dihydroquinolin-2-one;

N-(2-{[(1S)-1-[6-chloro-2-oxo-7-(pyridin-2-ylmethoxy)-1,2-dihydroquinolin-3-yl]ethyl]amino}pyridin-4-yl)acetamide;

6-chloro-3-[(1S)-1-{[4-(1H-imidazol-1-yl)pyridin-2-yl]amino}ethyl]-7-(pyridin-2-ylmethoxy)-1,2-dihydroquinolin-2-one;

6-chloro-3-[(1S)-1-{[4-(1,2-oxazol-4-yl)pyridin-2-yl]amino}ethyl]-7-(pyridin-2-ylmethoxy)-1,2-dihydroquinolin-2-one;

6-chloro-3-[(1S)-1-{[4-(4-methylthiophen-3-yl)pyridin-2-yl]amino}ethyl]-7-(pyridin-2-ylmethoxy)-1,2-dihydroquinolin-2-one;

3-[(1S)-1-{[4-(1-benzyl-1H-imidazol-5-yl)pyridin-2-yl]amino}ethyl]-6-chloro-7-(pyridin-2-ylmethoxy)-1,2-dihydroquinolin-2-one;

6-chloro-3-[(1S)-1-{[4-(1-methyl-1H-imidazol-5-yl)pyridin-2-yl]amino}ethyl]-7-(pyridin-2-ylmethoxy)-1,2-dihydroquinolin-2-one;

6-chloro-3-[(1S)-1-{[4-(3-methylpyridin-4-yl)pyridin-2-yl]amino}ethyl]-7-(pyridin-2-ylmethoxy)-1,2-dihydroquinolin-2-one;
N-(2-{[(1S)-1-[6-chloro-2-oxo-7-(pyridin-2-ylmethoxy)-1,2-dihydroquinolin-3-yl]ethyl]amino}pyridin-4-yl)-N-(2-methylpropyl)methanesulfonamide;
6-{[(1S)-1-(6-chloro-7-methoxy-2-oxo-1,2-dihydroquinolin-3-yl)ethyl]amino}-2-methylpyridine-3-carbonitrile;
methyl N-(2-{[(1S)-1-(6-chloro-7-methoxy-2-oxo-1,2-dihydroquinolin-3-yl)ethyl]amino}pyridin-4-yl)carbamate;
2-{[(1S)-1-(6-chloro-7-methoxy-2-oxo-1,2-dihydroquinolin-3-yl)ethyl]amino}pyridine-4-carboxamide;
6-chloro-3-[(1S)-1-{[3-fluoro-4-(2-oxo-1,3-oxazolidin-3-yl)pyridin-2-yl]amino}ethyl]-7-methoxy-1,2-dihydroquinolin-2-one;
6-chloro-7-methoxy-3-[(1S)-1-{[4-(5-methyl-1H-1,2,3,4-tetrazol-1-yl)pyridin-2-yl]amino}ethyl]-1,2-dihydroquinolin-2-one;
N-(2-{[(1S)-1-(6-chloro-7-methoxy-2-oxo-1,2-dihydroquinolin-3-yl)ethyl]amino}pyridin-4-yl)acetamide;
6-chloro-3-[(1S)-1-{[4-(1H-imidazol-1-yl)pyridin-2-yl]amino}ethyl]-7-methoxy-1,2-dihydroquinolin-2-one;
6-chloro-7-methoxy-3-[(1S)-1-{[4-(1,2-oxazol-4-yl)pyridin-2-yl]amino}ethyl]-1,2-dihydroquinolin-2-one;
6-chloro-7-methoxy-3-[(1S)-1-{[4-(4-methylthiophen-3-yl)pyridin-2-yl]amino}ethyl]-1,2-dihydroquinolin-2-one;
3-[(1S)-1-{[4-(1-benzyl-1H-imidazol-5-yl)pyridin-2-yl]amino}ethyl]-6-chloro-7-methoxy-1,2-dihydroquinolin-2-one;
6-chloro-7-methoxy-3-[(1S)-1-{[4-(1-methyl-1H-imidazol-5-yl)pyridin-2-yl]amino}ethyl]-1,2-dihydroquinolin-2-one;
6-chloro-7-methoxy-3-[(1S)-1-{[4-(3-methylpyridin-4-yl)pyridin-2-yl]amino}ethyl]-1,2-dihydroquinolin-2-one;
N-(2-{[(1S)-1-(6-chloro-7-methoxy-2-oxo-1,2-dihydroquinolin-3-yl)ethyl]amino}pyridin-4-yl)-N-(2-methylpropyl)methanesulfonamide;
6-{[(1S)-1-[6-chloro-2-oxo-7-(propan-2-yloxy)-1,2-dihydroquinolin-3-yl]ethyl]amino}-2-methylpyridine-3-carbonitrile;
methyl N-(2-{[(1S)-1-[6-chloro-2-oxo-7-(propan-2-yloxy)-1,2-dihydroquinolin-3-yl]ethyl]amino}pyridin-4-yl)carbamate;
2-{[(1S)-1-[6-chloro-2-oxo-7-(propan-2-yloxy)-1,2-dihydroquinolin-3-yl]ethyl]amino}pyridine-4-carboxamide;
6-chloro-3-[(1S)-1-{[3-fluoro-4-(2-oxo-1,3-oxazolidin-3-yl)pyridin-2-yl]amino}ethyl]-7-(propan-2-yloxy)-1,2-dihydroquinolin-2-one;
6-chloro-3-[(1S)-1-{[4-(5-methyl-1H-1,2,3,4-tetrazol-1-yl)pyridin-2-yl]amino}ethyl]-7-(propan-2-yloxy)-1,2-dihydroquinolin-2-one;
N-(2-{[(1S)-1-[6-chloro-2-oxo-7-(propan-2-yloxy)-1,2-dihydroquinolin-3-yl]ethyl]amino}pyridin-4-yl)acetamide;
6-chloro-3-[(1S)-1-{[4-(1H-imidazol-1-yl)pyridin-2-yl]amino}ethyl]-7-(propan-2-yloxy)-1,2-dihydroquinolin-2-one;
6-chloro-3-[(1S)-1-{[4-(1,2-oxazol-4-yl)pyridin-2-yl]amino}ethyl]-7-(propan-2-yloxy)-1,2-dihydroquinolin-2-one;
6-chloro-3-[(1S)-1-{[4-(4-methylthiophen-3-yl)pyridin-2-yl]amino}ethyl]-7-(propan-2-yloxy)-1,2-dihydroquinolin-2-one;
3-[(1S)-1-{[4-(1-benzyl-1H-imidazol-5-yl)pyridin-2-yl]amino}ethyl]-6-chloro-7-(propan-2-yloxy)-1,2-dihydroquinolin-2-one;
6-chloro-3-[(1S)-1-{[4-(1-methyl-1H-imidazol-5-yl)pyridin-2-yl]amino}ethyl]-7-(propan-2-yloxy)-1,2-dihydroquinolin-2-one;
6-chloro-3-[(1S)-1-{[4-(3-methylpyridin-4-yl)pyridin-2-yl]amino}ethyl]-7-(propan-2-yloxy)-1,2-dihydroquinolin-2-one;
N-(2-{[(1S)-1-[6-chloro-2-oxo-7-(propan-2-yloxy)-1,2-dihydroquinolin-3-yl]ethyl]amino}pyridin-4-yl)-N-(2-methylpropyl)methanesulfonamide;
6-{[(1S)-1-[6-chloro-7-(cyclopropylmethoxy)-2-oxo-1,2-dihydroquinolin-3-yl]ethyl]amino}-2-methylpyridine-3-carbonitrile;
methyl N-(2-{[(1S)-1-[6-chloro-7-(cyclopropylmethoxy)-2-oxo-1,2-dihydroquinolin-3-yl]ethyl]amino}pyridin-4-yl)carbamate;
2-{[(1S)-1-[6-chloro-7-(cyclopropylmethoxy)-2-oxo-1,2-dihydroquinolin-3-yl]ethyl]amino}pyridine-4-carboxamide;
6-chloro-7-(cyclopropylmethoxy)-3-[(1S)-1-{[3-fluoro-4-(2-oxo-1,3-oxazolidin-3-yl)pyridin-2-yl]amino}ethyl]-1,2-dihydroquinolin-2-one;
6-chloro-7-(cyclopropylmethoxy)-3-[(1S)-1-{[4-(5-methyl-1H-1,2,3,4-tetrazol-1-yl)pyridin-2-yl]amino}ethyl]-1,2-dihydroquinolin-2-one;
N-(2-{[(1S)-1-[6-chloro-7-(cyclopropylmethoxy)-2-oxo-1,2-dihydroquinolin-3-yl]ethyl]amino}pyridin-4-yl)acetamide;
6-chloro-7-(cyclopropylmethoxy)-3-[(1S)-1-{[4-(1H-imidazol-1-yl)pyridin-2-yl]amino}ethyl]-1,2-dihydroquinolin-2-one;
6-chloro-7-(cyclopropylmethoxy)-3-[(1S)-1-{[4-(1,2-oxazol-4-yl)pyridin-2-yl]amino}ethyl]-1,2-dihydroquinolin-2-one;
6-chloro-7-(cyclopropylmethoxy)-3-[(1S)-1-{[4-(4-methylthiophen-3-yl)pyridin-2-yl]amino}ethyl]-1,2-dihydroquinolin-2-one;
3-[(1S)-1-{[4-(1-benzyl-1H-imidazol-5-yl)pyridin-2-yl]amino}ethyl]-6-chloro-7-(cyclopropylmethoxy)-1,2-dihydroquinolin-2-one;
6-chloro-7-(cyclopropylmethoxy)-3-[(1S)-1-{[4-(1-methyl-1H-imidazol-5-yl)pyridin-2-yl]amino}ethyl]-1,2-dihydroquinolin-2-one;
6-chloro-7-(cyclopropylmethoxy)-3-[(1S)-1-{[4-(3-methylpyridin-4-yl)pyridin-2-yl]amino}ethyl]-1,2-dihydroquinolin-2-one;
N-(2-{[(1S)-1-[6-chloro-7-(cyclopropylmethoxy)-2-oxo-1,2-dihydroquinolin-3-yl]ethyl]amino}pyridin-4-yl)-N-(2-methylpropyl)methanesulfonamide;
6-{[(1S)-1-(6-chloro-7-fluoro-2-oxo-1,2-dihydroquinolin-3-yl)ethyl]amino}-2-methylpyridine-3-carbonitrile;
methyl N-(2-{[(1S)-1-(6-chloro-7-fluoro-2-oxo-1,2-dihydroquinolin-3-yl)ethyl]amino}pyridin-4-yl)carbamate;
2-{[(1S)-1-(6-chloro-7-fluoro-2-oxo-1,2-dihydroquinolin-3-yl)ethyl]amino}pyridine-4-carboxamide;
6-chloro-7-fluoro-3-[(1S)-1-{[3-fluoro-4-(2-oxo-1,3-oxazolidin-3-yl)pyridin-2-yl]amino}ethyl]-1,2-dihydroquinolin-2-one;
6-chloro-7-fluoro-3-[(1S)-1-{[4-(5-methyl-1H-1,2,3,4-tetrazol-1-yl)pyridin-2-yl]amino}ethyl]-1,2-dihydroquinolin-2-one;
N-(2-{[(1S)-1-(6-chloro-7-fluoro-2-oxo-1,2-dihydroquinolin-3-yl)ethyl]amino}pyridin-4-yl)acetamide;
6-chloro-7-fluoro-3-[(1S)-1-{[4-(1H-imidazol-1-yl)pyridin-2-yl]amino}ethyl]-1,2-dihydroquinolin-2-one;
6-chloro-7-fluoro-3-[(1S)-1-{[4-(1,2-oxazol-4-yl)pyridin-2-yl]amino}ethyl]-1,2-dihydroquinolin-2-one;

6-chloro-7-fluoro-3-[(1S)-1-{[4-(4-methylthiophen-3-yl)pyridin-2-yl]amino}ethyl]-1,2-dihydroquinolin-2-one;
3-[(1S)-1-{[4-(1-benzyl-1H-imidazol-5-yl)pyridin-2-yl]amino}ethyl]-6-chloro-7-fluoro-1,2-dihydroquinolin-2-one;
6-chloro-7-fluoro-3-[(1S)-1-{[4-(1-methyl-1H-imidazol-5-yl)pyridin-2-yl]amino}ethyl]-1,2-dihydroquinolin-2-one;
6-chloro-7-fluoro-3-[(1S)-1-{[4-(3-methylpyridin-4-yl)pyridin-2-yl]amino}ethyl]-1,2-dihydroquinolin-2-one;
N-(2-{[(1S)-1-(6-chloro-7-fluoro-2-oxo-1,2-dihydroquinolin-3-yl)ethyl]amino}pyridin-4-yl)-N-(2-methylpropyl)methanesulfonamide;
6-{[(1S)-1-(6-chloro-8-fluoro-2-oxo-1,2-dihydroquinolin-3-yl)ethyl]amino}-2-methylpyridine-3-carbonitrile;
methyl N-(2-{[(1S)-1-(6-chloro-8-fluoro-2-oxo-1,2-dihydroquinolin-3-yl)ethyl]amino}pyridin-4-yl)carbamate;
2-{[(1S)-1-(6-chloro-8-fluoro-2-oxo-1,2-dihydroquinolin-3-yl)ethyl]amino}pyridine-4-carboxamide;
6-chloro-8-fluoro-3-[(1S)-1-{[3-fluoro-4-(2-oxo-1,3-oxazolidin-3-yl)pyridin-2-yl]amino}ethyl]-1,2-dihydroquinolin-2-one;
6-chloro-8-fluoro-3-[(1S)-1-{[4-(5-methyl-1H-1,2,3,4-tetrazol-1-yl)pyridin-2-yl]amino}ethyl]-1,2-dihydroquinolin-2-one;
N-(2-{[(1S)-1-(6-chloro-8-fluoro-2-oxo-1,2-dihydroquinolin-3-yl)ethyl]amino}pyridin-4-yl)acetamide;
6-chloro-8-fluoro-3-[(1S)-1-{[4-(1H-imidazol-1-yl)pyridin-2-yl]amino}ethyl]-1,2-dihydroquinolin-2-one;
6-chloro-8-fluoro-3-[(1S)-1-{[4-(1,2-oxazol-4-yl)pyridin-2-yl]amino}ethyl]-1,2-dihydroquinolin-2-one;
6-chloro-8-fluoro-3-[(1S)-1-{[4-(4-methylthiophen-3-yl)pyridin-2-yl]amino}ethyl]-1,2-dihydroquinolin-2-one;
3-[(1S)-1-{[4-(1-benzyl-1H-imidazol-5-yl)pyridin-2-yl]amino}ethyl]-6-chloro-8-fluoro-1,2-dihydroquinolin-2-one;
6-chloro-8-fluoro-3-[(1S)-1-{[4-(1-methyl-1H-imidazol-5-yl)pyridin-2-yl]amino}ethyl]-1,2-dihydroquinolin-2-one;
6-chloro-8-fluoro-3-[(1S)-1-{[4-(3-methylpyridin-4-yl)pyridin-2-yl]amino}ethyl]-1,2-dihydroquinolin-2-one;
N-(2-{[(1S)-1-(6-chloro-8-fluoro-2-oxo-1,2-dihydroquinolin-3-yl)ethyl]amino}pyridin-4-yl)-N-(2-methylpropyl)methanesulfonamide;
6-{[(1S)-1-(6-chloro-2-oxo-1,2-dihydro-1,8-naphthyridin-3-yl)ethyl]amino}-2-methylpyridine-3-carbonitrile;
methyl N-(2-{[(1S)-1-(6-chloro-2-oxo-1,2-dihydro-1,8-naphthyridin-3-yl)ethyl]amino}pyridin-4-yl)carbamate;
2-{[(1S)-1-(6-chloro-2-oxo-1,2-dihydro-1,8-naphthyridin-3-yl)ethyl]amino}pyridine-4-carboxamide;
6-chloro-3-[(1S)-1-{[3-fluoro-4-(2-oxo-1,3-oxazolidin-3-yl)pyridin-2-yl]amino}ethyl]-1,2-dihydro-1,8-naphthyridin-2-one;
6-chloro-3-[(1S)-1-{[4-(5-methyl-1H-1,2,3,4-tetrazol-1-yl)pyridin-2-yl]amino}ethyl]-1,2-dihydro-1,8-naphthyridin-2-one;
N-(2-{[(1S)-1-(6-chloro-2-oxo-1,2-dihydro-1,8-naphthyridin-3-yl)ethyl]amino}pyridin-4-yl)acetamide;
6-chloro-3-[(1S)-1-{[4-(1H-imidazol-1-yl)pyridin-2-yl]amino}ethyl]-1,2-dihydro-1,8-naphthyridin-2-one;
6-chloro-3-[(1S)-1-{[4-(1,2-oxazol-4-yl)pyridin-2-yl]amino}ethyl]-1,2-dihydro-1,8-naphthyridin-2-one;
6-chloro-3-[(1S)-1-{[4-(4-methylthiophen-3-yl)pyridin-2-yl]amino}ethyl]-1,2-dihydro-1,8-naphthyridin-2-one;
3-[(1S)-1-{[4-(1-benzyl-1H-imidazol-5-yl)pyridin-2-yl]amino}ethyl]-6-chloro-1,2-dihydro-1,8-naphthyridin-2-one;
6-chloro-3-[(1S)-1-{[4-(1-methyl-1H-imidazol-5-yl)pyridin-2-yl]amino}ethyl]-1,2-dihydro-1,8-naphthyridin-2-one;
6-chloro-3-[(1S)-1-{[4-(3-methylpyridin-4-yl)pyridin-2-yl]amino}ethyl]-1,2-dihydro-1,8-naphthyridin-2-one;
N-(2-{[(1S)-1-(6-chloro-2-oxo-1,2-dihydro-1,8-naphthyridin-3-yl)ethyl]amino}pyridin-4-yl)-N-(2-methylpropyl)methanesulfonamide;
6-{[(1S)-1-(7-chloro-3-oxo-3,4-dihydroquinoxalin-2-yl)ethyl]amino}-2-methylpyridine-3-carbonitrile;
methyl N-(2-{[(1S)-1-(7-chloro-3-oxo-3,4-dihydroquinoxalin-2-yl)ethyl]amino}pyridin-4-yl)carbamate;
6-chloro-3-[(1S)-1-{[3-fluoro-4-(2-oxo-1,3-oxazolidin-3-yl)pyridin-2-yl]amino}ethyl]-1,2-dihydroquinoxalin-2-one;
6-chloro-3-[(1S)-1-{[4-(5-methyl-1H-1,2,3,4-tetrazol-1-yl)pyridin-2-yl]amino}ethyl]-1,2-dihydroquinoxalin-2-one;
N-(2-{[(1S)-1-(7-chloro-3-oxo-3,4-dihydroquinoxalin-2-yl)ethyl]amino}pyridin-4-yl)acetamide;
6-chloro-3-[(1S)-1-{[4-(1H-imidazol-1-yl)pyridin-2-yl]amino}ethyl]-1,2-dihydroquinoxalin-2-one;
6-chloro-3-[(1S)-1-{[4-(1,2-oxazol-4-yl)pyridin-2-yl]amino}ethyl]-1,2-dihydroquinoxalin-2-one
6-chloro-3-[(1S)-1-{[4-(4-methylthiophen-3-yl)pyridin-2-yl]amino}ethyl]-1,2-dihydroquinoxalin-2-one;
3-[(1S)-1-{[4-(1-benzyl-1H-imidazol-5-yl)pyridin-2-yl]amino}ethyl]-6-chloro-1,2-dihydroquinoxalin-2-one;
6-chloro-3-[(1S)-1-{[4-(1-methyl-1H-imidazol-5-yl)pyridin-2-yl]amino}ethyl]-1,2-dihydroquinoxalin-2-one;
6-chloro-3-[(1S)-1-{[4-(3-methylpyridin-4-yl)pyridin-2-yl]amino}ethyl]-1,2-dihydroquinoxalin-2-one;
N-(2-{[(1S)-1-(7-chloro-3-oxo-3,4-dihydroquinoxalin-2-yl)ethyl]amino}pyridin-4-yl)-N-(2-methylpropyl)methanesulfonamide; and
(S)-6-chloro-3-(1-((4-(5-methyl-1H-tetrazol-1-yl)pyridin-2-yl)amino)ethyl)-1,8-naphthyridin-2(1H)-one.

In one embodiment, the compounds of the invention have the Formula Ia:

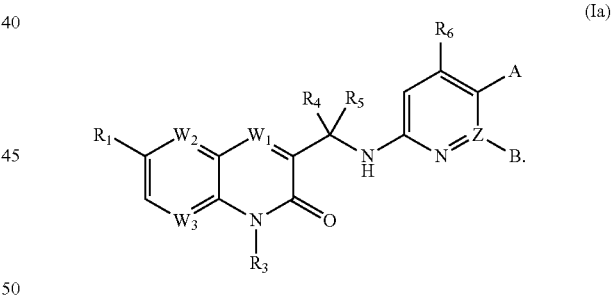

(Ia)

In another embodiment, the compounds of the invention have the Formula Ia-1:

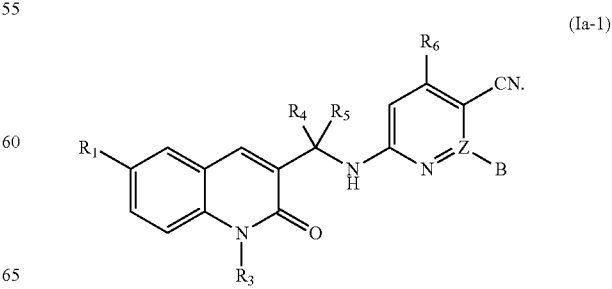

(Ia-1)

In another embodiment, the compounds of the invention have the Formula Ia-2:

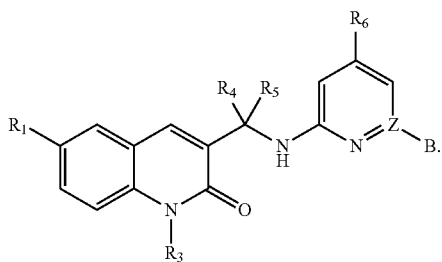

(Ia-2)

In another embodiment, the compounds of the invention have the Formula Ib:

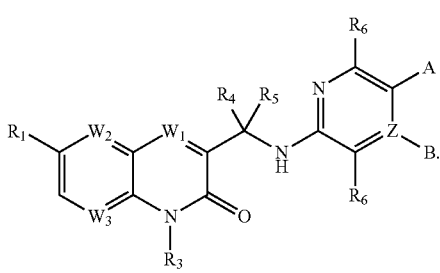

(Ib)

In another embodiment, the compounds of the invention have the Formula Ib-1:

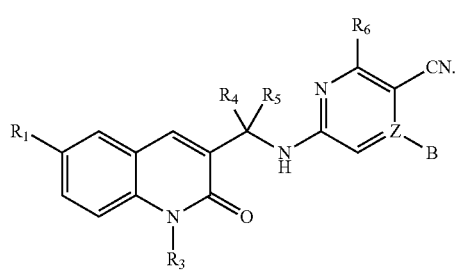

(Ib-1)

In another embodiment, the compounds of the invention have the Formula Ic:

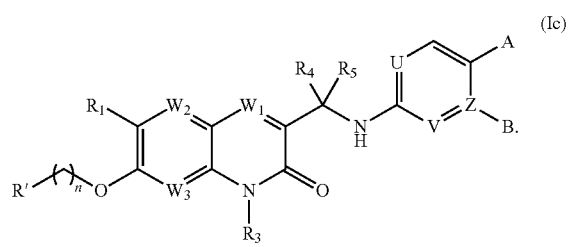

(Ic)

In another embodiment of the invention, the compounds of Formula I are enantiomers. In some embodiments the compounds are (S)-enantiomer. In other embodiments the compounds may also be (R)-enantiomer. In yet other embodiments, the compounds of Formula I may be (+) or (−) enantiomers.

In another embodiment of the invention, the compounds of Formula I contain isotopes of atoms forming the structure of Formula I. Isotopes herein means, each of two or more forms of the same element (e.g., H and D; $^{12}C$ and $^{13}C$) that contain equal numbers of protons but different numbers of neutrons in their nuclei, and hence differ in relative atomic mass.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis or trans configuration. All tautomeric forms are also intended to be included.

Methods of Using the Disclosed Compounds

Another aspect of the invention relates to a method of treating a disease or disorder associated with mutant isocitrate dehydrogenase. The method involves administering to a patient in need of a treatment for diseases or disorders associated with mutant isocitrate dehydrogenase an effective amount of the compositions and compounds of Formula I.

Another aspect of the invention is directed to a method inhibiting mutant isocitrate dehydrogenase. The method involves administering to a patient in need thereof an effective amount of the compositions or compounds of Formula I.

Examples of a mutant IDH protein having a neomorphic activity are mutant IDH1 and mutant IDH2. A neomorphic activity associated with mutant IDH1 and mutant IDH2 is the ability to produce 2-hydroxyglutarate (2-HG neomorphic activity), specifically R-2-HG (R-2-HG neomorphic activity). Mutations in IDH 1 associated with 2-HG neomorphic activity, specifically R-2-HG neomorphic activity, include mutations at residues 97, 100, and 132, e.g. G97D, R100Q, R132H, R132C, R132S, R132G, R132L, and R132V. Mutations in IDH2 associated with 2-HG neoactivity, specifically R-2-HG neomorphic activity, include mutations at residues 140 and 172, e.g. R140Q, R140G, R172K, R172M, R172S, R172G, and R172W.

Another aspect of the invention relates to method of reducing alpha-ketoglutarate. The method comprises administering to a patient in need thereof an effective amount of the compositions or compounds of Formula I.

One therapeutic use of the compounds or compositions of the present invention which inhibit mt-IDH is to provide treatment to patients or subjects suffering from cell proliferative diseases and cancers including, without limitation, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, melanoma, intrahepatic cholangiocarcinoma (IHCC), myelodysplastic syndrome (MDS), myeloproliferative disease (MPD), and other solid tumors. Targeted treatments for these cancers and cell proliferative diseases are not currently available to patients suffering from these conditions. Therefore, there is a need for new therapeutic agents selective to these conditions.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula I and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Method of Synthesizing the Compounds

The compounds of the present invention may be made by a variety of methods, including standard chemistry. Suitable synthetic routes are depicted in the Schemes given below.

The compounds of formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of formula (I).

Those skilled in the art will recognize if a stereocenter exists in the compounds of formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention formula (I) can be synthesized by following the steps outlined in Schemes 1-5, which comprise different sequences of assembling intermediates II, III, IV, V, VI and VII. Starting materials are either commercially available or made by known procedures in the reported literature or as illustrated.

Scheme 1

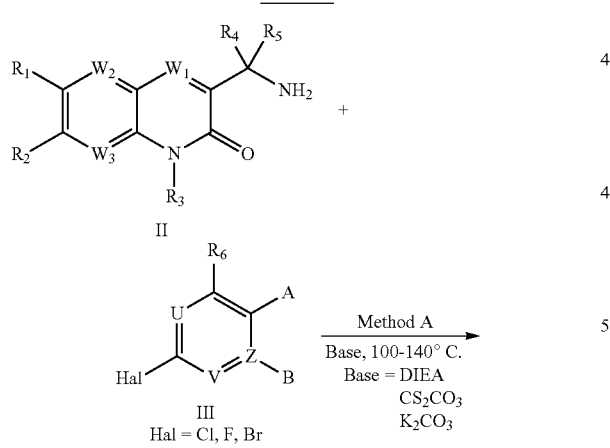

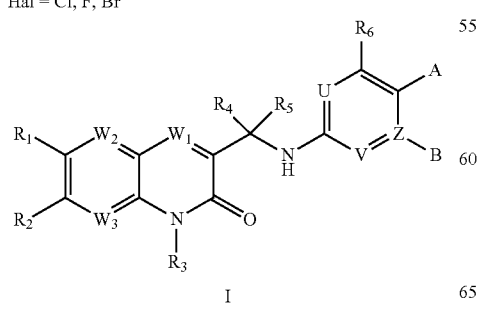

Scheme 2

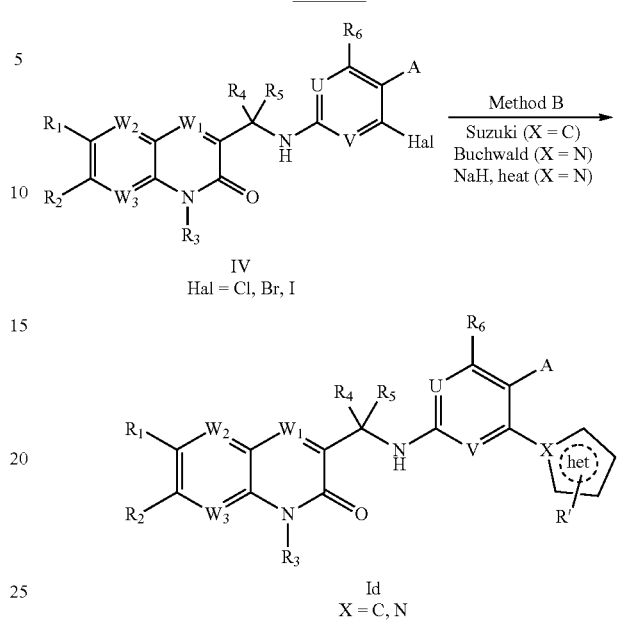

Scheme 3

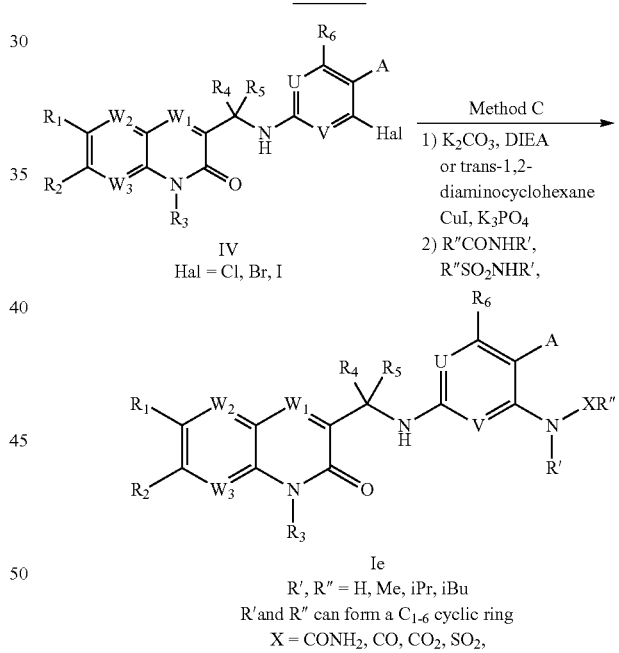

Scheme 4

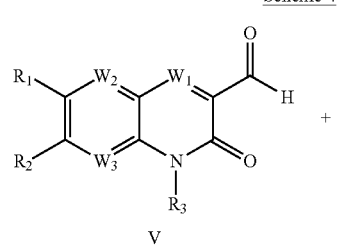

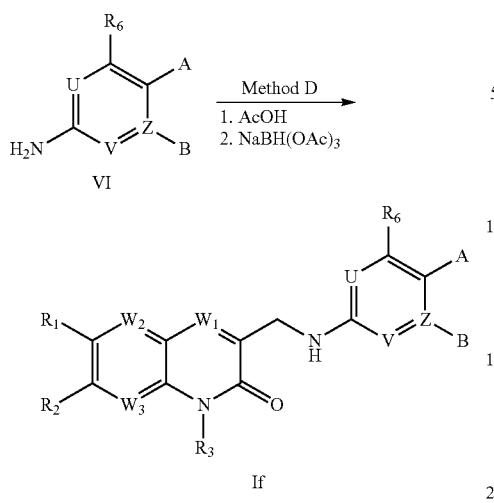

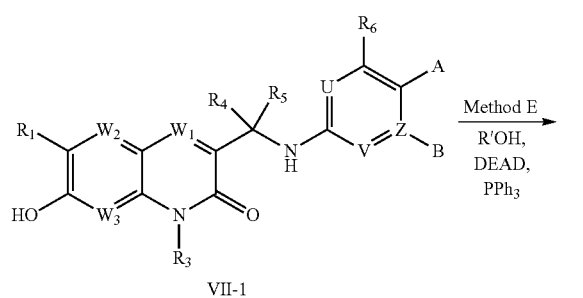

Scheme 5

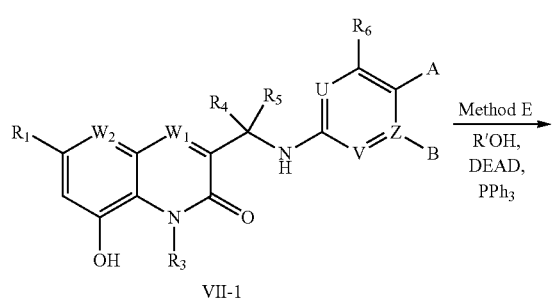

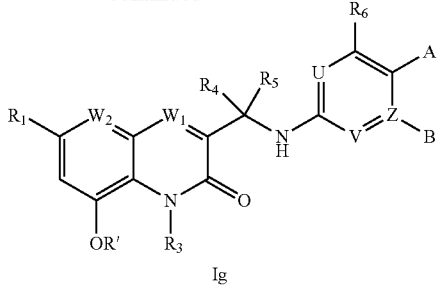

Wherein A, B, $R_1$-$R_6$, U, V, Z, $W_1$, $W_2$, and $W_3$ are defined in Formula (I).

The general ways of preparing target molecules I-a-I-e by using intermediates II, III, IV, V, VI and VII are outlined in Scheme 1-5. Displacement of aryl halides (III) with intermediates amine (II) under standard nucleophilic substitution conditions using base such as N,N-diisopropylethylamine, and/or potassium carbonate, cesium carbonate in solvent DMSO or DMF gives the compounds of Formula I (I-a). Coupling of aryl halides (IV) with aryl-, heterocyclic boronic acid/ester or with 2° amine and amide in presence of palladium catalyst under elevated temperature yields the compound of formula I (Id). Displacement of aryl halides (IV) with 2° amine, amide or sulfonamide in presence of base such as $K_2CO_3$, or $Cs_2CO_3$ combined with organic base such as DIEA or TEA under elevated temperature also yields the compound of formula I (Ie). Copper-diamine-catalyzed N-arylation of amide, sulfonamide, lactam and sultam with aryl halides (IV) by using trans-1,2-diaminocyclohexane, CuI and $K_3PO_4$ can produce the compound of formula I (Ie). Reductive amination of aldehyde (V) with amine (VI) is performed under standard procedure (AcOH and NaBH$(OAc)_3$) to prepare the compound of formula I (If). Mitsunobu reaction of intermediate (VII) with various alcohols give phenyl ether compounds of formula I (Ig). A mixture of enantiomers, diastereomers, cis/trans isomers resulted from the process can be separated into their single components by chiral salt technique, chromatography using normal phase, reverse phase or chiral column, depending on the nature of the separation.

It should be understood that in the description and formulae shown above, the various groups A, B, $W_1$, $W_2$, $W_3$, U, V, Z, $R_1$-$R_6$ and other variables are as defined above, except where otherwise indicated. Furthermore, for synthetic purposes, the compounds of schemes 1, 2, 3, 4 and 5 are mere representative with elected radicals to illustrate the general synthetic methodology of the compound of formula I as defined herein.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Table 16 provides activity of illustrative compounds of Formula I in IDH1-R132H, IDH1-R132C, IDH1-MS-HTC116-R132H, and IDH1-MS-HTC116-R132C assays.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 300 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). High performance liquid chromatograph (HPLC) analyses were obtained using a XBridge Phenyl or C18 column (5 μm, 50×4.6 mm, 150×4.6 mm or 250×4.6 mm) with UV detection (Waters 996 PDA) at 254 nm or 223 nm using a standard solvent gradient program (Method 1-4).

LCMS Method 1 (ESI, 4 Min Method):
Instruments:
HPLC: Waters HT2790 Alliance MS: Waters ZQ Single Quad Mass Spectrometer
UV: Waters 996 PDA
Conditions:

| | |
|---|---|
| Mobile phase A | 95% water/5% methanol with 0.1% Formic Acid |
| Mobile phase B (B) | 95% methanol/5% water with 0.1% Formic Acid |
| Column | XBridge Phenyl or C18, 5 μm 4.6 × 50 mm |
| Column temperature | Ambient |
| LC gradient | Linear 5-95% B in 2.5 min, hold 95% B to 3.5 min |
| LC Flow rate | 3 mL/min |
| UV wavelength | 220 nm and 254 nm |
| Ionization Mode | Electrospray Ionization; positive/negative |

LCMS Method 2 (ESI, 10 Min Method):
Instruments:

| | |
|---|---|
| HPLC: Waters HT2790 Alliance | MS: Waters ZQ Single Quad Mass Spectrometer |
| UV: Waters 996 PDA | |

Conditions:

| | |
|---|---|
| Mobile phase A (A) | 95% water/5% methanol with 0.1% Formic Acid |
| Mobile phase B (B) | 95% methanol/5% water with 0.1% Formic Acid |
| Column | XBridge C18, 5 μm 4.6 × 150 mm |
| Column temperature | Ambient |
| LC gradient | Linear 5-95% B in 5.5 min, hold 95% B to 7.5 min |
| LC Flow rate | 1.2 mL/min |
| UV wavelength | 220 nm and 254 nm |
| Ionization Mode | Electrospray Ionization; positive/negative |

LCMS Method 3: (APCI, 20 Min)
Instruments and Conditions:
HPLC-Agilent 1100 series.
Column: Agela Technologies Durashell C18, 3 μm, 4.6×50 mm,).
Mobile Phase A: ACN+0.1% TFA.
Mobile Phase B: Water+0.1% TFA.
Gradient:

| Time (min) | % B |
|---|---|
| 00 | 95 |
| 15 | 05 |
| 18 | 05 |
| 20 | 95 |

Flow Rate: 1 mL/min.
Column Temperature: Ambient.
Detector: 254 nm.
LCMS Method 4 (ESI, 2.5 Min Method):
Instruments and Conditions:

| | |
|---|---|
| HPLC: Waters Acquity Binary Solvent Manager | MS: Waters ZQ Mass Detector |
| UV: Waters Acquity PDA | |
| Mobile phase A (A) | 95% water/5% acetonitrile with 0.1% formic acid in 10 mM ammonium formate |
| Mobile phase B (B) | 95% acetonitrile/5% water with 0.09% formic acid |
| Column | Waters Acquity UPLC BEH C18, 1.7 μm, 2.1 × 50 mm |
| Column temperature | 35° C. |
| LC gradient | 5-100% B in 2.0 min, hold 100% B to 2.2 min |
| LC Flow rate | 0.6 mL/min |
| UV wavelength | 220 nm and 254 nm |
| Ionization Mode | Electrospray Ionization; positive/negative |

Abbreviations Used in the Following Examples and Elsewhere Herein are $Ac_2O$ acetic anhydride
ACN Acetonitrile
BOP ammonium 4-(3-(pyridin-3-ylmethyl)ureido)benzene-sulfinate
$CDCl_3$ deuterated chloroform
$Cs_2CO_3$ cesium carbonate$CuSO_4$ copper sulfate
δ chemical shift
DCM dichloromethane or methylene chloride DCE 1,2-dichloroethane
DEAD diethyl azodicarboxylate
DIAD diisopropyl azodicarboxylate
DIEA N,N-diisopropylethylamine
DMA N,N-dimethylacetamide
DME dimethoxyethane
DMF N,N-dimethylformamide
DMP Dess-Martin Periodinane
DMSO dimethylsulfoxide
DMSO-$d_6$ deuterated dimethylsulfoxide
dppf 1,1'-Bis(diphenylphosphino)ferrocene
EDCI N-(3-dimethylaminopropyl)-N'-ethylcarbodiimide hydrochloride
EDTA ethylenediaminetetraacetic acid
ee enantiomeric excess
EtOAc ethyl acetate
EtOH ethanol
$^1$H NMR proton nuclear magnetic resonance
HOAc acetic acid
HATU 2-(3H-[1,2,3]triazolo[4,5-b]pyridin-3-yl)-1,1,3,3-tetramethylisouronium hexafluorophosphate
HCl hydrochloric acid
HOBT 1H-benzo[d][1,2,3]triazol-1-ol hydrate
HPLC high pressure liquid chromatography
Hz hertz
IPA isopropyl alcohol
KOAc potassium acetate
$K_2CO_3$ potassium carbonate LAH lithium aluminum hydride
LCMS liquid chromatography/mass spectrometry
(M+1) mass+1
m-CPBA m-chloroperbenzoic acid
MeOH methanol
MeMgBr methyl magnesium bromide
MS mass spectrometry
NaBH$_4$ sodium borohydride
Na$_2$SO$_4$ sodium sulfate
Pd(dppf)Cl$_2$ [1,1'-Bis(diphenylphosphino)ferrocene]dichloropalladium(II)
Palladium tetrakis Tetrakis(triphenylphosphine)palladium (0)
Rt retention time
TBDMS-Cl Tert-butyl dimethylsilyl chloride
TEA triethylamine
THF tetrahydrofuran
TLC thin layer chromatography
Xantphos 4,5-Bis(diphenylphosphino)-9,9-dimethylxanthene Example 1—Intermediate II-1: (S)-3-(1-aminoethyl)-6-chloroquinolin-2(1H)-one hydrochloride

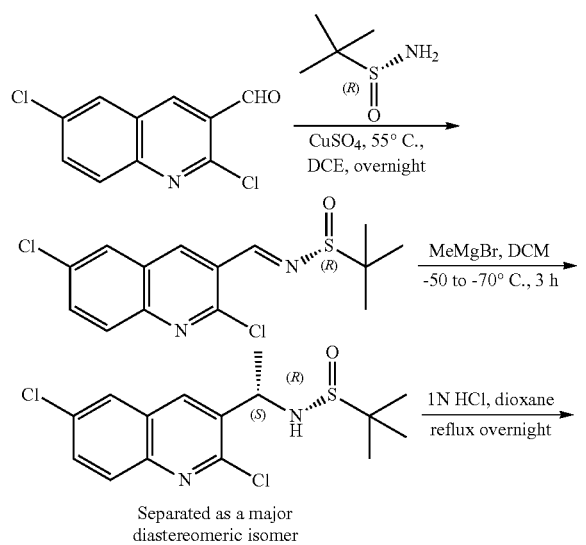

Step-1: (R,E)-N-((2,6-dichloroquinolin-3-yl)methylene)-2-methylpropane-2-sulfinamide

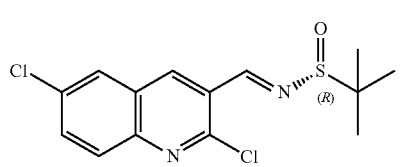

To a mixture of 2,6-dichloroquinoline-3-carbaldehyde (15.0 g, 66.37 mmol) and (R)-2-methylpropane-2-sulfinamide (8.85 g, 73.14 mmol) in 1,2-dichloroethane (150 mL) was added CuSO$_4$ (16.0 g, 100.25 mmol). The resulting mixture was heated to 55° C. and stirred at 55° C. overnight. After TLC and MS showed complete disappearance of starting materials, the mixture was cooled to room temperature and filtered through a pad of Celite®. The pad of celite was then rinsed with CH$_2$Cl$_2$. The filtrate was evaporated to dryness in vacuo and purified by SiO$_2$ column chromatography (0 to 25% hexanes/EtOAc) to afford the title compound, (R,E)-N-((2,6-dichloroquinolin-3-yl)methylene)-2-methylpropane-2-sulfinamide, as a yellow solid (17.7 g, 81% yield).

Step-2: (R)—N—((S)-1-(2,6-dichloroquinolin-3-yl)ethyl)-2-methylpropane-2-sulfinamide To a solution of (R,E)-N-((2,6-dichloroquinolin-3-yl)methylene)-2-methylpropane-2-sulfinamide (8.85 g, 26.88 mmol) in anhydrous CH$_2$Cl$_2$ (200 mL) at −60° C. was added dropwise MeMgBr (3M solution in diethyl ether, 13.5 mL, 40.54 mmol). The resulting reaction mixture was stirred at about −60 to −50° C. for 3 hours and then stirred at −20° C. overnight under an atmosphere of N$_2$. After TLC and MS showed complete disappearance of starting materials, saturated NH$_4$Cl (163 mL) was added at −20° C. and the resulting mixture was stirred for 10 minutes. The aqueous phase was extracted with CH$_2$Cl$_2$ (100 mL×3), dried over anhydrous Na$_2$SO$_4$ filtered, and evaporated. The residue was purified by column chromatography on an ISCO® chromatography system (SiO$_2$: Gold column; gradient; hexanes to 100% EtOAc) to provide the title compound, (R)—N—((S)-1-(2,6-dichloroquinolin-3-yl)ethyl)-2-methylpropane-2-sulfinamide, as a yellow solid (5.8 g, 63% yield).

Step-3: (S)-3-(1-aminoethyl)-6-chloroquinolin-2(1H)-one hydrochloride (II-1)

A mixture of (R)—N—((S)-1-(2,6-dichloroquinolin-3-yl)ethyl)-2-methylpropane-2-sulfinamide (6.6 g, 19.13 mmol) in 1,4-dioxane (41 mL) and 1N HCl (41 mL) was heated at reflux overnight. The solvents were evaporated in vacuo and the resulting residue was dissolved in hot water and lyophilized. The crude product was triturated with diethyl ether to afford the title compound II-1 as a yellow solid (9.0 g, ee: 98.4%). $^1$H NMR (300 MHz, DMSO-d$_6$): δ ppm 12.4 (br s, 1H), 8.32 (br s, 2H), 8.07 (s, 1H), 7.85 (d, J=2.2 Hz, 1H), 7.63 (dd, J$_1$=8.8 Hz, J$_2$=2.5 Hz, 1H), 7.40 (d, J=8.8 Hz, 1H), 4.40-4.45 (m, 1H), 1.53 (d, J=8.5 Hz, 3H). LCMS (Method 3): Rt 3.42 min, m/z 223.1 [M+H]$^+$.

Example 2—Intermediate II-2: (R)-3-(1-amino-ethyl)-6-chloroquinolin-2(1H)-one hydrochloride

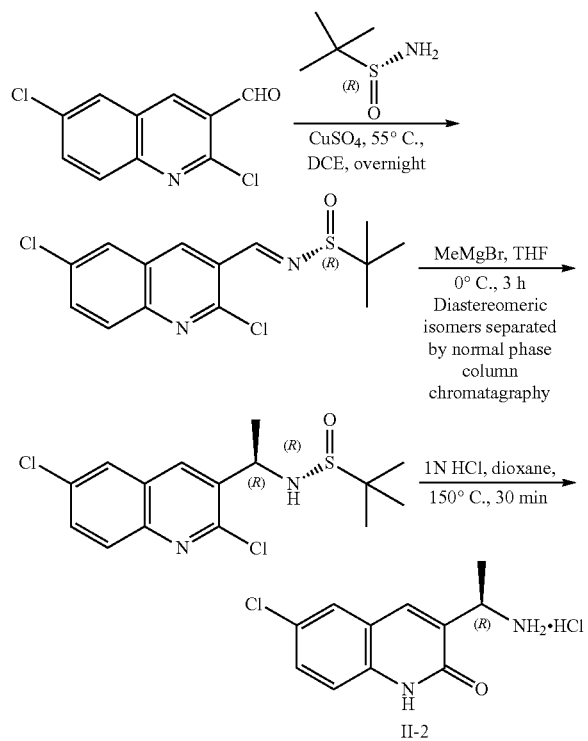

Step-1: (R)—N-((2,6-dichloroquinolin-3-yl)methyl-ene)-2-methylpropane-2-sulfinamide To a mixture of 2,6-dichloroquinoline-3-carbaldehyde (500 mg, 2.21 mmol) and (R)-2-methylpropane-2-sulfina-mide (295 g, 2.43 mmol) in 1,2-dichloroethane (15 mL) was added CuSO$_4$ (530 mg, 3.31 mmol). The resulting mixture was heated to 55° C. and stirred at 55° C. for 18 hours. Once TLC and MS showed complete disappearance of starting materials, the reaction mixture was cooled to room temperature and filtered through a pad of Celite®. The pad of celite was then rinsed with CH$_2$Cl$_2$. The filtrate was evaporated to dryness in vacuo and purified by column chromatography on an ISCO® chromatography system (SiO$_2$; hexanes to 60% EtOAc/hexanes) to afford the title compound, (R)—N-((2,6-dichloroquinolin-3-yl)methylene)-2-methylpropane-2-sulfinamide, as a yellow solid (510 mg, 70% yield).

Step-2: (R)—N—((R)-1-(2,6-dichloroquinolin-3-yl)ethyl)-2-methylpropane-2-sulfinamide To a solution of (R)—N-((2,6-dichloroquinolin-3-yl)methylene)-2-methylpropane-2-sulfinamide (505 mg, 1.534 mmol) in anhydrous THF (8 mL) at 0° C. was added dropwise MeMgBr (3M solution in diethyl ether, 0.56 mL, 1.687 mmol). The mixture was stirred at 0° C. for 3 hours under an atmosphere of N$_2$. After TLC and MS showed complete disappearance of starting materials, saturated NH$_4$Cl (5 mL) was added at 0° C. and the resulting mixture was stirred for 10 minutes. The aqueous phase was extracted with EtOAc (10 mL×3), dried over anhydrous Na$_2$SO$_4$, filtered, and evaporated. The residue was purified by column chromatography on an ISCO® chromatography system (SiO$_2$; hexanes to 80% EtOAc/hexanes) to afford the title compound as the R,R isomer as a pale yellow solid (200 mg, 38%) and the R,S isomer as a pale yellow solid (93 mg, 18% yield).

Step-3: (R)-3-(1-aminoethyl)-6-chloroquinolin-2(1H)-one hydrochloride (II-2)

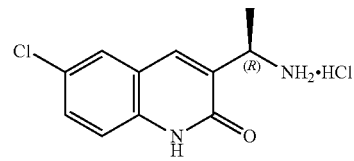

A mixture of (R)—N—((R)-1-(2,6-dichloroquinolin-3-yl)ethyl)-2-methylpropane-2-sulfinamide (190 mg, 0.55 mmol) in 1,4-dioxane (2 mL) and 1N HCl (1.1 mL, 1.1 mmol) was heated to 150° C. for 30 minutes in a microwave reactor. The solvents were evaporated and the residue was dissolved in hot water and lyophilized to afford the title compound II-2 as a yellow solid (148 mg, quantitative yield). $^1$H NMR (300 MHz, DMSO-d$_6$): δ ppm 12.35 (br s, 1H), 8.28 (br s, 2H), 8.05 (s, 1H), 7.86 (d, J=2.2 Hz, 1H), 7.63 (dd, J$_1$=8.8 Hz, J$_2$=2.5 Hz, 1H), 7.40 (d, J=8.8 Hz, 1H), 4.40-4.45 (m, 1H), 1.53 (d, J=8.5 Hz, 3H). LCMS (Method 3): Rt 3.40 min, m/z 223.1 [M+H]$^+$.

Example 3—an Alternative Approach to Intermediate II-1

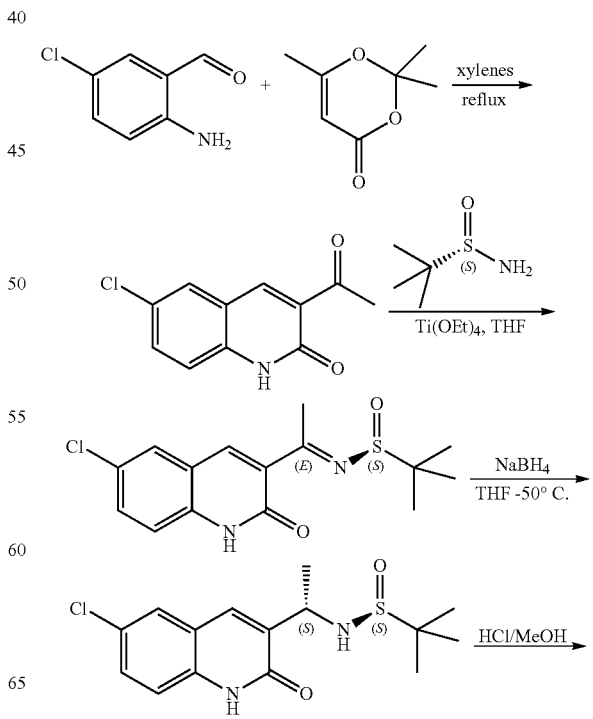

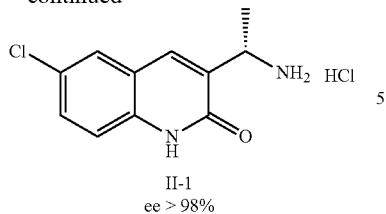

II-1
ee > 98%

Step-1: 3-acetyl-6-chloroquinolin-2(1H)-one

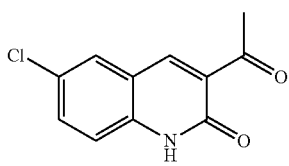

A mixture of 2-amino-5-chlorobenzaldehyde (0.5 g, 3.21 mmol) and 2,2,6-trimethyl-4H-1,3-dioxin-4-one (0.594 g, 4.18 mmol) in xylenes (10 mL) under an atmosphere of nitrogen was heated to reflux for 3 hours and then cooled to room temperature. The reaction mixture was filtered and washed with xylenes twice to afford the title compound, 3-acetyl-6-chloroquinolin-2(1H)-one (330 mg, 46.3%). $^1$H NMR (300 MHz, DMSO-d$_6$): δ ppm 12.22 (br, 1H), 8.41 (s, 2H), 8.00 (s, 1H), 7.63 (d, J=8.8 Hz, 1H), 7.32 (dd, J=8.8 Hz, J$_2$=2.5 Hz, 1H), 2.58 (s, 3H). LCMS (Method 1): m/z 222.94 [M+H]$^+$.

Step-2: ((S)—N—((S)-1-(6-chloro-2-oxo-1,2-dihydroquinolin-3-yl)ethyl)-2-methyl propane-2-sulfinamide

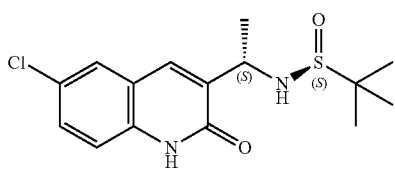

A mixture of tetraethoxytitanium (144 mg, 0.632 mmol), (S)-2-methylpropane-2-sulfinamide (38.3 mg, 0.316 mmol), and 3-acetyl-6-chloroquinolin-2(1H)-one (70 mg, 0.316 mmol) in THF (20 mL) was heated to 80° C. overnight and then cooled to room temperature. To this mixture was added NaBH$_4$ (59.7 mg, 1.579 mmol) at −50° C. The mixture was then slowly warmed up to room temperature overnight. MeOH (2 mL) was added to quench excess NaBH$_4$ and was followed by the addition of water. The resulting mixture was filtered to remove solids and the aqueous phase was extracted with EtOAc twice, dried over Na$_2$SO$_4$ and concentrated. The residue was purified on a Biotage® chromatography system using a 25 g SiO$_2$ column with gradient elution (20% to 100% EtOAc/Hexanes, then 0-5% MeOH/DCM) to afford (S)—N—((S)-1-(2,6-dichloroquinolin-3-yl)ethyl)-2-methylpropane-2-sulfinamide (39 mg, 38% yield). $^1$H NMR (300 MHz, DMSO-d$_6$): δ ppm 12.05 (br, 1H), 7.95 (s, 1H), 7.84 (s, 1H), 7.38 (d, J=8.8 Hz, 1H), 5.76 (d, J=8.06 Hz, 1H), 5.37 (m, 1H), 4.55 (m, 1H), 1.44 (d, J=6.82 Hz, 3H), 1.18 (s, 9H). LCMS (Method 1): Rt 2.22 min; m/z 327.96 [M+H]$^+$.

Step-3: (S)-3-(1-aminoethyl)-6-chloroquinolin-2(1H)-one hydrochloride (II-1)

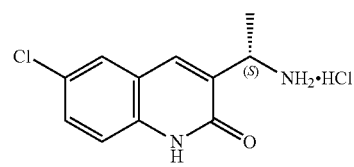

To a solution of ((S)—N—((S)-1-(6-chloro-2-oxo-1,2-dihydroquinolin-3-yl)ethyl)-2-methyl propane-2-sulfinamide (150 mg, 0.459 mmol) in MeOH (5 mL) was added HCl (2 mL, 8.0 mmol, 4M in 1,4-dioxane). The mixture was stirred at room temperature overnight. To this mixture was added 6 mL of ethyl ether and the resulting precipitate was collected by filtration, washed with ethyl ether (2×), and then dried to afford (S)-3-(1-aminoethyl)-6-chloroquinolin-2(1H)-one hydrochloride (50 mg, 42% yield). $^1$H NMR (300 MHz, DMSO-d$_6$): δ ppm 12.4 (br s, 1H), 8.32 (br s, 2H), 8.07 (s, 1H), 7.85 (d, J=2.2 Hz, 1H), 7.63 (dd, J=8.8 Hz, J$_2$=2.5 Hz, 1H), 7.40 (d, J=8.8 Hz, 1H), 4.40-4.45 (m, 1H), 1.53 (d, J=8.5 Hz, 3H). LCMS (Method 1): Rt 1.22 min, m/z 223.1 [M+H]$^+$. The enantiomer purity (ee %) of II-1 (>98%) was determined by chiral HPLC analysis.

Example 4—Alternate approach (R)-3-(1-aminoethyl)-6-chloroquinolin-2(1H)-one hydrochloride (1-2)

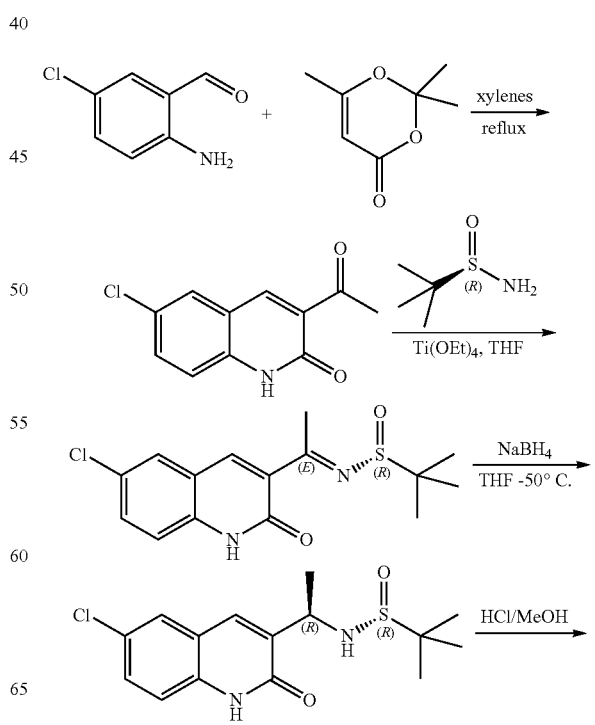

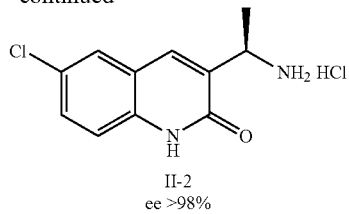

II-2
ee >98%

Step-1: ((R)—N—((R)-1-(6-chloro-2-oxo-1,2-dihydroquinolin-3-yl)ethyl)-2-methyl propane-2-sulfinamide

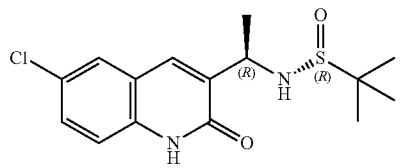

A mixture of tetraethoxytitanium (412 mg, 1.805 mmol) (R)-2-methylpropane-2-sulfinamide (131 mg, 1.083 mmol) and 3-acetyl-6-chloroquinolin-2(1H)-one (160 mg, 0.722 mmol) in THF (20 mL) was heated to 80° C. overnight, then cooled to room temperature. To this mixture was added NaBH$_4$ (137 mg, 3.61 mmol) −50° C. The mixture was then slowly warmed up to room temperature overnight. MeOH (2 mL) was added to quench excess NaBH$_4$ and was followed by the addition of water. The resulting mixture was filtered to remove solids and the aqueous phase was extracted with EtOAc twice, dried over Na$_2$SO$_4$ and concentrated. The residue was purified on a Biotage® chromatography system using a 25 g SiO$_2$ column with gradient elution (20 to 100%/EtOAc/Hexanes, then 0-5% MeOH/DCM) to afford ((R)—N—((R)-1-(6-chloro-2-oxo-1,2-dihydroquinolin-3-yl)ethyl)-2-methyl propane-2-sulfinamide (157 mg, 66% yield). $^1$H NMR (300 MHz, CDCl$_3$): δ ppm 11.31 (br, 1H), 7.35 (s, 1H), 7.07-7.22 (m, 2H), 5.86 (d, J=9.3 Hz, 1H), 5.37 (m, 1H), 4.55 (m, 1H), 1.56 (d, J=6.94 Hz, 3H), 1.32 (s, 9H). LCMS (Method 1): Rt 2.20 min, m/z 327.96 [M+H]$^+$.

Step-2: (R)-3-(1-aminoethyl)-6-chloroquinolin-2(1H)-one hydrochloride (II-2)

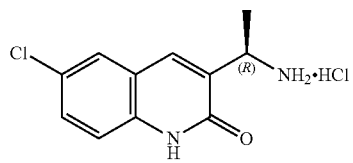

To a solution of (R)—N—((R)-1-(6-chloro-2-oxo-1,2-dihydroquinolin-3-yl)ethyl)-2-methylpropane-2-sulfinamide (150 mg, 0.459 mmol) in MeOH (5 mL) was added HCl (2 mL, 8.00 mmol, 4M in 1,4-dioxane). The mixture was stirred at room temperature overnight. To this mixture was added 6 mL of ethyl ether and the resulting precipitate was collected by filtration, washed with ethyl ether (2×), and then dried to afford (R)-3-(1-aminoethyl)-6-chloroquinolin- 2(1H)-one hydrochloride (80 mg, 67% yield). $^1$H NMR (300 MHz, DMSO-d$_6$): δ ppm 12.32 (br s, 1H), 8.34 (br, 2H), 8.06 (s, 1H), 7.81 (s, 1H), 7.58 (d, J=8.82 Hz, 1H), 7.31 (d, J=8.83 Hz, 1H), 4.40-4.45 (m, 1H), 1.53 (d, J=6.81 Hz, 3H). LCMS (Method 1): Rt 1.20 min, m/z 223.1 [M+H]$^+$. The enantiomer purity (ee %) of II-2 (>98%) was determined by chiral HPLC analysis.

Example 5—Intermediate II-3: (S)-3-(1-aminoethyl)-6-chloro-7-fluoroquinolin-2(1H)-one

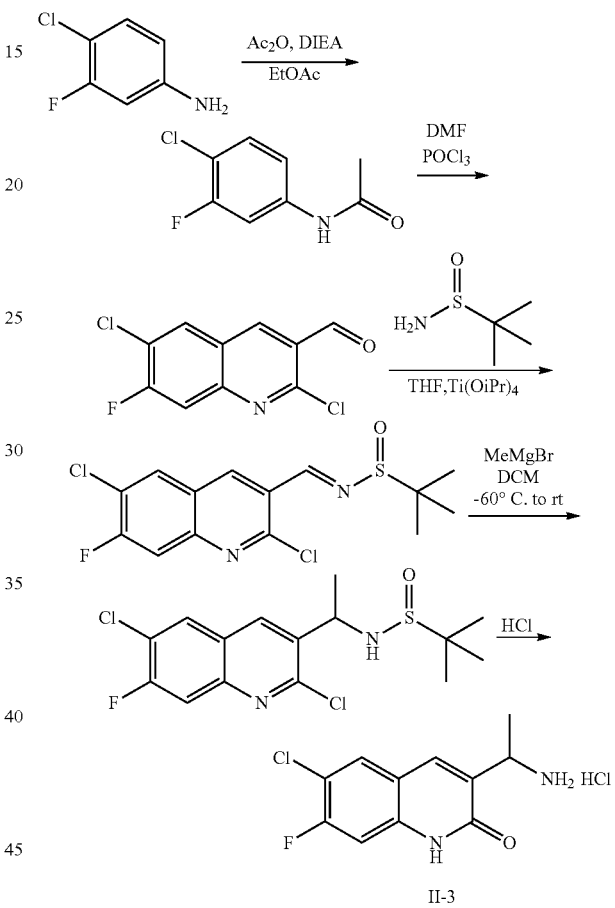

II-3

Step-1: N-(4-chloro-3-fluorophenyl)acetamide

To a solution of 4-chloro-3-fluoroaniline (10.00 g, 68.7 mmol) and DIEA (13.2 mL, 76 mmol) in EtOAc (200 mL) was added Ac$_2$O (7.1 mL, 75 mmol) dropwise The solution was stirred at room temperature overnight. Once LCMS indicated the reaction had gone to completion, the solution was washed with water (2×100 mL) and brine (100 mL), dried (Na$_2$SO$_4$), filtered, and evaporated under reduced pressure to provide the product as a white solid. LCMS and ¹H NMR are consistent with N-(4-chloro-3-fluorophenyl) acetamide (12.39 g, 66.0 mmol, 96% yield) ¹H NMR (300 MHz, DMSO-d₆): δ ppm 10.26 (s, 1H), 7.77 (dd, J=12.17, 2.20 Hz, 1H), 7.49 (dd, J=8.60, 8.60 Hz, 1H), 7.30 (dd, J=8.79, 2.35 Hz, 1H), 2.06 (s, 3H). LCMS (Method 1): m/z 188 [M+H]⁺.

Step-2: 2,6-dichloro-7-fluoroquinoline-3-carbaldehyde

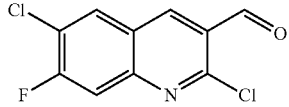 [SMILES: O=Cc1cc2cc(Cl)c(F)cc2nc1Cl]

A tube was capped with a septum and placed under an atmosphere of nitrogen. DMF (9.5 mL, 123 mmol) was added by syringe and then cooled on an ice bath. POCl₃ (37 mL, 397 mmol) was added dropwise by syringe (over 25 minutes). The red solution was allowed to warm to room temperature (over 20 minutes), then the septum was removed and the mixture was treated with N-(4-chloro-3-fluorophenyl)acetamide (7.00 g, 37.3 mmol). The tube was then sealed and the solution was stirred at 80° C. overnight. The solution was pipetted onto ice, resulting in formation of a yellow precipitate. The precipitate was collected on a Buchner funnel and washed with water (500 mL), during which most of the precipitate dissolved. The filter cake was dried to provide 427.6 mg of the title compound as a pale yellow solid. LCMS and ¹H NMR are consistent with impure 2,6-dichloro-7-fluoroquinoline-3-carbaldehyde (427.6 mg, 1.752 mmol, 4.70% yield). The material was used as is. ¹H NMR (300 MHz, DMSO-d₆): δ ppm 10.36 (s, 1H), 8.99 (s, 1H), 8.67 (d, J=8.21 Hz, 1H), 8.13 (d, J=10.26 Hz, 1H), 5.76 (s, 1H). LCMS (Method 1): m/z 244 [M+H].

Step-3: N-((2,6-dichloro-7-fluoroquinolin-3-yl) methylene)-2-methylpropane-2-sulfinamide

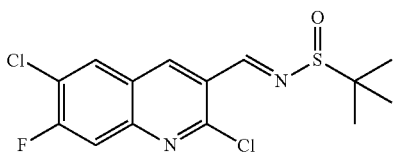 [SMILES: CC(C)(C)S(=O)/N=C/c1cc2cc(Cl)c(F)cc2nc1Cl]

A mixture of 2,6-dichloro-7-fluoroquinoline-3-carbaldehyde (424.4 mg, 1.739 mmol) and 2-methylpropane-2-sulfinamide (253.8 mg, 2.094 mmol) was placed under an atmosphere of nitrogen. THF (4 mL) and titanium (IV) isopropoxide (Ti(OⁱPr)₄) (1.00 mL, 3.41 mmol) were then added by syringe and the resulting suspension was stirred at room temperature for 48 hours. Once LCMS indicated the reaction had gone cleanly to completion. The reaction was quenched by dropwise addition of aqueous saturated NH₄Cl (2 mL). The mixture was triturated with EtOAc (100 mL), and the solid was collected on a Buchner funnel, and was washed with EtOAc (50 mL). The filtrate was washed with brine (50 mL), dried (Na₂SO₄), filtered, and evaporated under reduced pressure to provide 574.3 mg of the title compound as a yellow solid. LCMS and ¹H NMR are consistent with (E)-N-((2,6-dichloro-7-fluoroquinolin-3-yl) methylene)-2-methylpropane-2-sulfinamide (574.3 mg, 1.654 mmol, 95% yield). ¹H NMR (300 MHz, DMSO-d₆): δ ppm 9.13 (s, 1H), 8.87 (s, 1H), 8.67 (d, J=8.21 Hz, 1H), 8.11 (d, J=10.26 Hz, 1H), 1.25 (s, 9H). LCMS (Method 1): m/z 347 [M+H]⁺.

Step-4: N-(1-(2,6-dichloro-7-fluoroquinolin-3-yl) ethyl)-2-methylpropane-2-sulfinamide

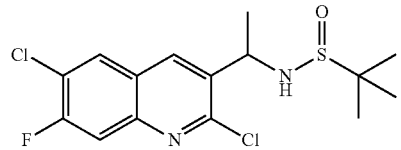 [SMILES: CC(NS(=O)C(C)(C)C)c1cc2cc(Cl)c(F)cc2nc1Cl]

N-((2,6-dichloro-7-fluoroquinolin-3-yl)methylene)-2-methylpropane-2-sulfinamide (573.6 mg, 1.652 mmol) was placed in a 100 mL round-bottom flask under an atmosphere of nitrogen. DCM (14 mL) was added and the resulting suspension was cooled in a dry ice/chloroform bath (to approx. −60° C.). Methyl magnesium bromide (MeMgBr) (3M in ethyl ether, 0.83 mL, 2.490 mmol) was then added dropwise. The reaction was stirred at −60° C. for several hours, and then at −20° C. overnight. The mixture was placed in an ice bath and treated dropwise with water (7 mL). The mixture was diluted with water (150 mL) and extracted with EtOAc (3×50 mL). Silica gel was added to the combined extracts and the sample was evaporated under reduced pressure. The sample was purified by column chromatography on a Biotage® MPLC chromatography system (eluted with 0 to 100%/EtOAc in hexanes and with isocratic elution when peaks eluted) to provide 226.3 mg of the title compound as a yellowish solid. LCMS and ¹H NMR are consistent with N-(1-(2,6-dichloro-7-fluoroquinolin-3-yl) ethyl)-2-methylpropane-2-sulfinamide (226.3 mg, 0.623 mmol, 25.02% yield) ¹H NMR indicates a single diastereomer. ¹H NMR (300 MHz, DMSO-d₆): δ ppm 8.52 (s, 1H), 8.47 (d, J=7.92 Hz, 1H), 8.01 (d, J=10.26 Hz, 1H), 5.66 (d, J=6.16 Hz, 1H), 4.83 (q, J=6.60 Hz, 1H), 1.60 (d, J=6.74 Hz, 3H), 1.13 (s, 9H). LCMS (Method 1): m/z 363 [M+H]⁺.

Step-5: 3-(1-aminoethyl)-6-chloro-7-fluoroquinolin-2(1H)-one hydrochloride (II-3)

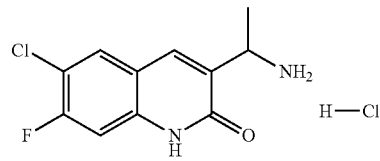

A sample of N-(1-(2,6-dichloro-7-fluoroquinolin-3-yl) ethyl)-2-methylpropane-2-sulfinamide (226.3 mg, 0.623 mmol) was mixed with 1,4-dioxane (3.5 mL) and 3.6% HCl (aqueous, 3.5 mL) and stirred at 95° C. overnight; the material quickly went into solution upon heating. Once LCMS showed the reaction had gone to completion, the solution was evaporated under reduced pressure. The residue was dissolved in MeOH (~10 mL), treated with heptane (~15 mL), and evaporated again under reduced pressure. The resulting residue was then triturated with Et₂O, collected on a Hirsch funnel, and washed with Et₂O (20 mL) to provide 179.8 mg of the title compound as a yellow solid. LCMS and ¹H NMR are consistent with 3-(1-aminoethyl)-6-chloro-7-fluoroquinolin-2(1H)-one hydrochloride (179.8 mg, 0.649 mmol, 104% yield) ¹H NMR (300 MHz, Methanol-d₄): δ ppm 8.02 (s, 1H), 7.92 (d, J=7.62 Hz, 1H), 7.23 (d, J=9.97 Hz, 1H), 4.53 (q, J=6.84 Hz, 1H), 1.68 (d, J=6.74 Hz, 3H). LCMS (Method 1): m/z 241 [M+H]⁺.

Example 6—Intermediate II-4: (S)-3-(1-aminoethyl)-6-chloro-7-fluoroquinolin-2(1H)-one (II-3)

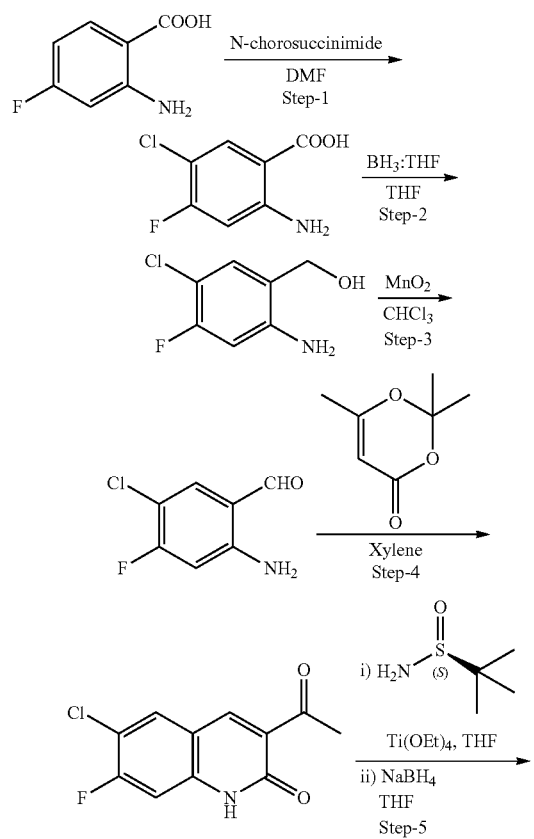

Step-1: 2-Amino-5-chloro-4-fluorobenzoic Acid

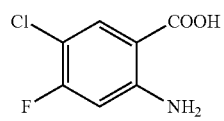 [SMILES: Nc1cc(F)c(Cl)cc1C(=O)O]

2-Amino-4-fluorobenzoic acid (50 g, 322.6 mmol) was dissolved in 700 mL of DMF and N-chlorosuccinimide (41 g, 305.5 mmol) was added portion wise. The reaction mixture was heated at 50° C. for 5 h. The mixture was cooled to room temperature, poured on to ice cold water to get the solid. The solid was filtered and dissolved in EtOAc, then sat. NaCl (300 mL) was added. The aqueous layer was extracted with EtOAc (3×200 mL). The combined organic phase was dried (Na₂SO₄) and evaporated to a brown solid (42 g, 69%) as desired product 2-amino-5-chloro-4-fluorobenzoic acid.

Step-2: (2-Amino-5-chloro-4-fluorophenyl)methanol

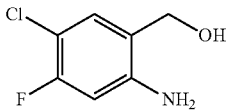

2-Amino-5-chloro-4-fluorobenzoic acid (42 g, 221 mmol) was dissolved in 100 mL of THF and BH₃.THF (712 mL of 1 M solution in THF, 712 mmol) was added drop wise over the period of 1 h at room temperature. The reaction mixture was heated at 50° C. overnight (18 h). The mixture was cooled to room temperature, poured onto ice cold water, and sat. NaCl solution was added. The aqueous was extracted with EtOAc (3×200 mL). The combined organic phase was dried (Na₂SO₄), evaporated and purified by flash chromatography using 0-100% hexanes/ethyl acetate as eluent to afford the desired product as a brown solid (17 g, 45%).

Step-3: 2-Amino-5-chloro-4-fluorobenzaldehyde

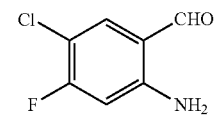

To a solution of (2-amino-5-chloro-4-fluorophenyl)methanol (22 g, 125.7 mmol) in 1000 mL of chloroform was added MnO₂ (109 g, 1250 mmol) and the reaction mixture was stirred overnight at ambient temperature. The reaction mixture was filtered, washed with EtOAc and evaporated. The resulting crude product was passed through a pad of silica gel eluting with 0 to 20% hexanes/EtOAc to give the pure product as a brown solid (19 g, 87%).

Step-4:
3-acetyl-6-chloro-7-fluoroquinolin-2(1H)-one

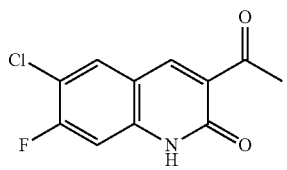 [SMILES: CC(=O)c1cc2cc(Cl)c(F)cc2[nH]c1=O]

A mixture of 2-Amino-5-chloro-4-fluorobenzaldehyde (14 g, 173.6 mmol) and 2,2,6-trimethyl-4H-1,3-dioxin-4-one (16 mL, 121 mmol) in m-xylene (500 mL) was refluxed for 1.5 h. The reaction mixture was cooled to room temperature and filtered. The collected solid was washed with m-xylene and dried to yield the desired product (9.6 g, 50%) as off-white solid.

Step-5: (S)—N—((S)-1-(6-chloro-7-fluoro-2-oxo-1,2-dihydroquinolin-3-yl)ethyl)-2-methyl propane-2-sulfinamide

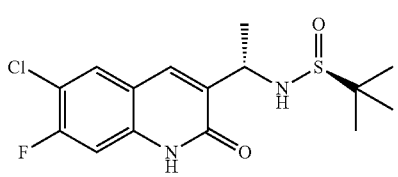 [SMILES: C[C@H](N[S@@](=O)C(C)(C)C)c1cc2cc(Cl)c(F)cc2[nH]c1=O]

To a mixture of 3-acetyl-6-chloro-7-fluoroquinolin-2(1H)-one (6.4 g, 26.7 mmol) and (S)-2-methylpropane-2-sulfinamide (4.85 g, 40.06 mmol) in THF (450 mL) was added Ti(OEt)$_4$ (14 mL, 66.7 mmol). The resultant mixture was stirred at 80° C. overnight. Upon the completion of the reaction, the reaction mixture was cooled to −60° C. and NaBH$_4$ (5.1 g, 134 mmol) was added portion wise and then allowed to warm to room temperature overnight. The excess NaBH$_4$ was quenched with MeOH (20 mL), then with water (20 mL) and EtOAc (300 mL). The solution was filtered through a pad of celite. The filtrate was taken into a separatory funnel and the organic layer was separated, dried (Na$_2$SO$_4$), concentrated and purified by flash chromatography (SiO$_2$: hexanes/$^i$PrOH 0 to 20%) to give the title compound (4.5 g, 49%) as a yellow solid.

Step-6: (S)-3-(1-aminoethyl)-6-chloro-7-fluoroquinolin-2(1H)-one. HCl, II-4

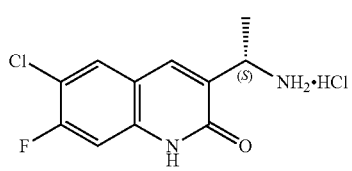

To a mixture of (S)—N—((S)-1-(6-chloro-7-fluoro-2-oxo-1,2-dihydroquinolin-3-yl)ethyl)-2-methyl propane-2-sulfinamide (3.5 g, 10.1 mmol) in MeOH (80 mL) was added 3N methanolic HCl (80 mL, 121 mmol). The resultant mixture was stirred at room temperature overnight. To this mixture was added diethyl ether (60 mL) and the resulting solid was filtered and dried to give the desired product II-4 (2.1 g, 75%) as a yellow solid. $^1$H NMR (300 MHz, DMSO-d$_6$): δ 12.40 (br s, 1H), 8.24 (br s, 2H), 8.07-8.05 (m, 2H), 7.32 (d, J=10.4 Hz, 1H), 4.5-4.15 (m, 1H), 1.53 (d, J=6.8 Hz, 3H). LCMS (method LCMS3, APCI): Rt 3.47 min, m/z 241.1 [M+H]$^+$.

Example 7—Intermediate II-5: (R)-3-(1-aminoethyl)-6-chloro-7-fluoroquinolin-2(1H)-one

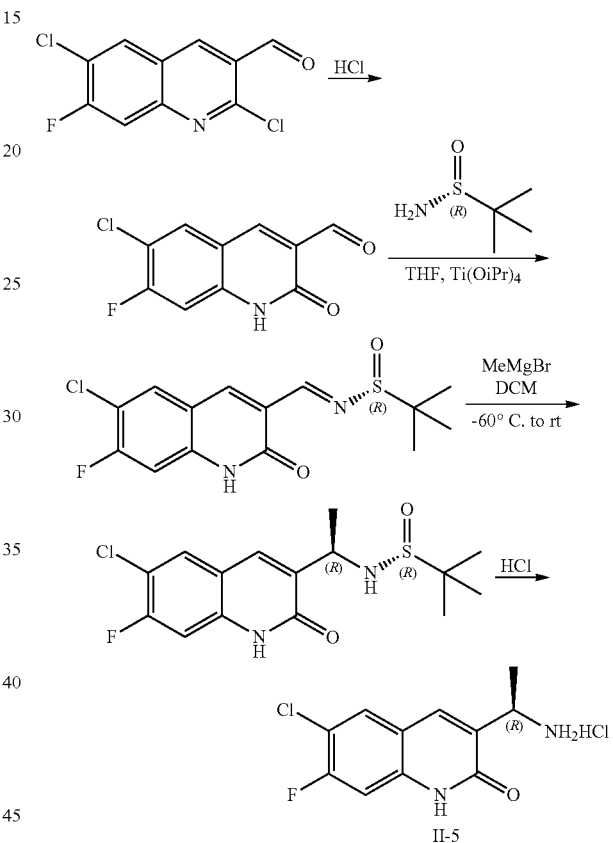

Step-1: 6-chloro-7-fluoro-2-oxo-1,2-dihydroquinoline-3-carbaldehyde 2,6-dichloro-7-fluoroquinoline-3-carbaldehyde (2.56 g, 10.49 mmol) was heated at reflux in concentrated HCl (12M, 100 mL) overnight, during which the material did not appear to go into solution. The mixture was allowed to cool, then was poured into water (750 mL). The slurry was filtered on a Buchner funnel, washed with water (750 mL), and dried to provide impure 6-chloro-7-fluoro-2-oxo-1,2-dihydroquinoline-3-carbaldehyde (2.1991 g, 9.75 mmol, 93% yield) as a reddish brown solid. The material was suitable for use as is. $^1$H NMR (300 MHz, DMSO-d$_6$): δ ppm 12.41 (s, 1H), 10.20 (s, 1H), 8.49 (s, 1H), 8.28 (d, J=7.92 Hz, 1H), 7.25 (d, J=10.26 Hz, 1H). LCMS: m/z+226 [M+H]$^+$.

Step-2: (R,E)-N-((6-chloro-7-fluoro-2-oxo-1,2-dihydroquinolin-3-yl)methylene)-2-methylpropane-2-sulfinamide

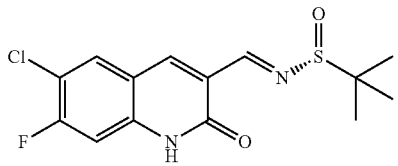 [SMILES: CC(C)(C)[S@@](=O)/N=C/c1cc2cc(Cl)c(F)cc2[nH]c1=O]

A mixture of 6-chloro-7-fluoro-2-oxo-1,2-dihydroquinoline-3-carbaldehyde (2.20 g, 9.75 mmol) and (R)-2-methylpropane-2-sulfinamide (1.42 g, 11.72 mmol) was placed in a 50 mL round bottom flask under an atmosphere of nitrogen. THF (20 mL) and titanium (IV) isopropoxide (Ti(O$^i$Pr)$_4$) (5.8 mL, 19.79 mmol) were added by syringe and the resulting suspension was stirred at room temperature for one day, during which the mixture turned dark. The reaction mixture was quenched by dropwise addition of saturated aqueous NH$_4$Cl, resulting in precipitation. The mixture was triturated with EtOAc (400 mL) and filtered on a Buchner funnel. The filter cake was then sonicated in 300 mL EtOAc for 15 minutes. The mixture was filtered on a Buchner funnel, and the filtrates from the two filtrations were combined. The combined filtrate solution was washed with brine (200 mL), dried (Na$_2$SO$_4$), filtered, and evaporated under reduced pressure to provide (R,E)-N-((6-chloro-7-fluoro-2-oxo-1,2-dihydroquinolin-3-yl)methylene)-2-methylpropane-2-sulfinamide (3.22 g, 9.79 mmol, 100% yield) as an orange solid. $^1$H NMR (300 MHz, DMSO-d$_6$): δ ppm 12.40 (br s, 1H), 8.75 (br s, 1H), 8.65 (s, 1H), 8.27 (d, J=8.21 Hz, 1H), 7.25 (d, J=10.26 Hz, 1H), 1.20 (s, 9H). LCMS: m/z 329 [M+H]$^+$.

Step-3: (R)—N—((R)-1-(6-chloro-7-fluoro-2-oxo-1,2-dihydroquinolin-3-yl)ethyl)-2-methylpropane-2-sulfinamide

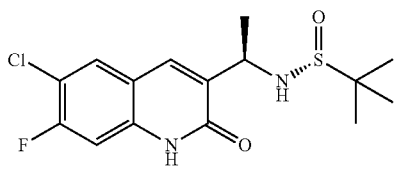 [SMILES: C[C@@H](N[S@](=O)C(C)(C)C)c1cc2cc(Cl)c(F)cc2[nH]c1=O]

(R,E)-N-((6-chloro-7-fluoro-2-oxo-1,2-dihydroquinolin-3-yl)methylene)-2-methylpropane-2-sulfinamide (3.22 g, 9.79 mmol) was placed in a 500 mL round-bottom flask under an atmosphere of nitrogen. DCM (100 mL) was added and the resulting suspension was cooled on a dry ice/chloroform bath (to approximately −60° C.). Methyl magnesium bromide (MeMgBr) (3M in ether, 10 mL, 30.0 mmol) was added dropwise. The reaction mixture was stirred at −60° C. for several hours, and then allowed to warm to room temperature overnight, resulting in a red solution. The solution was then cooled on an ice bath, treated dropwise with water (40 mL) and concentrated under reduced pressure. The resulting slurry was diluted with water (300 mL) and washed with EtOAc. The resulting emulsion was allowed to separate overnight. The layers were separated, and silica gel was added to the organic layer. Most of the solvent was evaporated under reduced pressure. MeOH and heptane were added and the mixture was evaporated under reduced pressure to dryness. The material was purified by column chromatography on a Biotage® MPLC chromatography system (using 50 g silica gel column; eluted with 0 to 50% EtOAc in hexanes, with isocratic elution when peaks eluted) to provide (R)—N—((R)-1-(6-chloro-7-fluoro-2-oxo-1,2-dihydroquinolin-3-yl)ethyl)-2-methylpropane-2-sulfinamide (774.3 mg, 2.245 mmol, 23% yield) as a greenish solid. $^1$H NMR shows a single diastereomer. $^1$H NMR (300 MHz, DMSO-d$_6$): δ ppm 12.03 (s, 1H), 7.98 (d, J=7.92 Hz, 1H), 7.89 (s, 1H), 7.22 (d, J=10.26 Hz, 1H), 5.67 (d, J=7.92 Hz, 1H), 4.41-4.55 (m, 1H), 1.37 (d, J=6.74 Hz, 3H), 1.12 (s, 9H). LCMS: m/z+345 [M+H]$^+$.

Step 4: (R)-3-(1-aminoethyl)-6-chloro-7-fluoroquinolin-2(1H)-one hydrochloride (II-5)

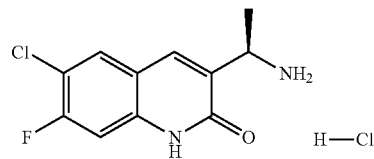 [SMILES: C[C@@H](N)c1cc2cc(Cl)c(F)cc2[nH]c1=O ; Cl]

A solution of (R)—N—((R)-1-(6-chloro-7-fluoro-2-oxo-1,2-dihydroquinolin-3-yl)ethyl)-2-methylpropane-2-sulfinamide (773 mg, 2.242 mmol) in MeOH (20 mL) was cooled on an ice bath and treated dropwise with 4M HCl in dioxane (12 mL), during which the material went into solution. The reaction was stirred 25 minutes, during which time precipitate formed. The solvents were evaporated under reduced pressure at room temperature. The residue was triturated with ethyl ether (50 mL), then the solid was collected on a Hirsch funnel and washed with more ethyl ether (50 mL) to provide (R)-3-(1-aminoethyl)-6-chloro-7-fluoroquinolin-2(1H)-one hydrochloride (613.5 mg, 2.214 mmol, 99% yield) as a yellow solid. $^1$H NMR (300 MHz, Methanol-d$_4$): δ ppm 7.99 (s, 1H), 7.90 (d, J=7.62 Hz, 1H), 7.22 (d, J=9.67 Hz, 1H), 4.51 (q, J=6.64 Hz, 1H), 1.66 (d, J=7.04 Hz, 3H). LCMS: m/z+241 [M+H]$^+$.

Example 8—Intermediate II-6: 3-(1-aminoethyl)-6-chloro-7-methoxyquinolin-2(1H)-one

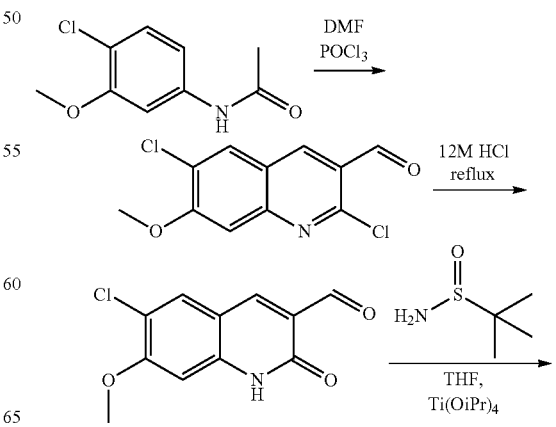

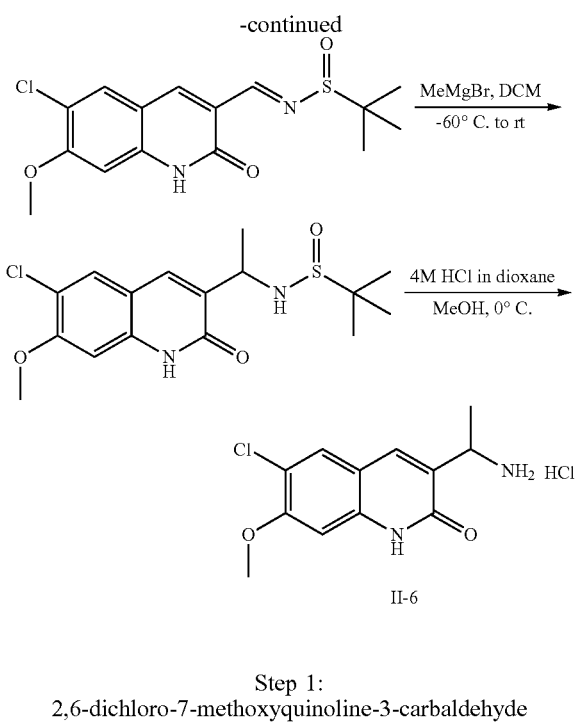

Step 1:
2,6-dichloro-7-methoxyquinoline-3-carbaldehyde

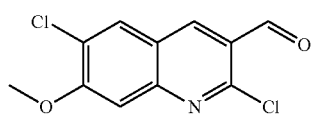 [SMILES: COc1cc2nc(Cl)c(C=O)cc2cc1Cl]

A tube was capped with a septum and placed under an atmosphere of nitrogen. DMF (6.4 mL, 83 mmol) was added by syringe and then cooled on an ice bath. POCl$_3$ (25 mL, 268 mmol) was added dropwise by syringe (over 20 minutes). The red solution was allowed to warm to room temperature (over 20 minutes), then the septum was removed, and the mixture was treated with N-(4-chloro-3-methoxyphenyl)acetamide (5 g, 25.05 mmol) The tube was sealed and the solution was stirred at 80° C. overnight. The solution was then pipetted onto ice, resulting in formation of a yellow precipitate. The precipitate was collected on a Buchner funnel, washed with water (1200 mL), and dried to provide 5.06 g of the title compound as a pale yellow solid. LCMS and $^1$H NMR are consistent with 2,6-dichloro-7-methoxyquinoline-3-carbaldehyde (5.06 g, 19.76 mmol, 79% yield) $^1$H NMR (300 MHz, DMSO-d$_6$): δ ppm 10.33 (s, 1H), 8.87 (s, 1H), 8.47 (s, 1H), 7.64 (s, 1H), 4.08 (s, 3H). LCMS (Method 1): m/z 256 [M+H]$^+$.

Step-2: 6-chloro-7-methoxy-2-oxo-1,2-dihydroquinoline-3-carbaldehyde V-2

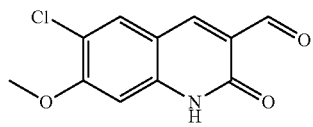 [SMILES: COc1cc2[nH]c(=O)c(C=O)cc2cc1Cl]

2,6-Dichloro-7-methoxyquinoline-3-carbaldehyde (5.06 g, 19.76 mmol) was heated at reflux in concentrated HCl (12M, 185 mL) overnight. The material went into solution during heating and then a solid precipitated during the course of the reaction. The mixture was allowed to cool and then was poured into water (1500 mL) resulting in further precipitation. The slurry was filtered on a Buchner funnel, washed with water (1500 mL), and dried to provide 4.04 g of the title compound as a yellowish-brown solid. LCMS and $^1$H NMR are consistent with 6-chloro-7-methoxy-2-oxo-1,2-dihydroquinoline-3-carbaldehyde (4.04 g, 17.00 mmol, 86% yield) $^1$H NMR (300 MHz, DMSO-d$_6$): δ ppm 12.22 (s, 1H), 10.16-10.18 (m, 1H), 8.43 (s, 1H), 8.08 (s, 1H), 6.95 (s, 1H), 3.94 (s, 3H). LCMS (Method 1): m/z 238 [M+H]$^+$.

Step-3: N-((6-chloro-7-methoxy-2-oxo-1,2-dihydroquinolin-3-yl)methylene)-2-methylpropane-2-sulfinamide

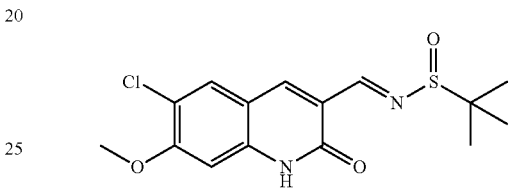

A mixture of 6-chloro-7-methoxy-2-oxo-1,2-dihydroquinoline-3-carbaldehyde (2.00 g, 8.42 mmol) and 2-methylpropane-2-sulfinamide (1.22 g, 10.07 mmol) was placed under an atmosphere of nitrogen. THF (20 mL) and titanium (IV) isopropoxide (Ti(O$^i$Pr)$_4$) (5.0 mL, 17.06 mmol) were added by syringe and the resulting suspension was stirred at room temperature overnight. Once LCMS indicated the reaction had gone to completion, the reaction was quenched by dropwise addition of aqueous saturated NH$_4$Cl (10 mL). The mixture was triturated with EtOAc (450 mL), then filtered through Celite® 545, and the Celite® was washed further with EtOAc (200 mL). The filter cake was then sonicated in EtOAc (450 mL) for 15 minutes, then filtered on a Buchner funnel. The two filtrates were combined, washed with brine (200 mL), dried (Na$_2$SO$_4$), filtered, and evaporated under reduced pressure to provide 1.01 g of the title compound as a yellow solid. LCMS and $^1$H NMR are consistent with (E)-N-((6-chloro-7-methoxy-2-oxo-1,2-dihydroquinolin-3-yl)methylene)-2-methylpropane-2-sulfinamide (1.01 g, 2.96 mmol, 35.2% yield) $^1$H NMR (300 MHz, DMSO-d$_6$): δ ppm 12.21 (s, 1H), 8.74 (s, 1H), 8.59 (s, 1H), 8.08 (s, 1H), 6.97 (s, 1H), 3.94 (s, 3H), 1.19 (s, 9H). LCMS (Method 1): m/z 341 [M+H]$^+$.

Step-4: N-(1-(6-chloro-7-methoxy-2-oxo-1,2-dihydroquinolin-3-yl)ethyl)-2-methylpropane-2-sulfinamide

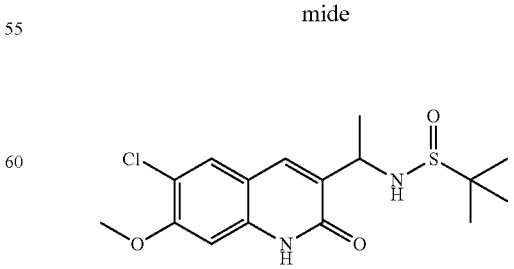

N-((6-chloro-7-methoxy-2-oxo-1,2-dihydroquinolin-3-yl)methylene)-2-methylpropane-2-sulfinamide (265 mg, 0.778 mmol) was placed in a 50 mL round-bottom flask under an atmosphere of nitrogen. DCM (7 mL) was added, and the suspension was cooled on a dry ice/chloroform bath (to approx. −60° C.). Methylmagnesium bromide (MeMgBr) (3M in ether, 0.80 mL, 2.40 mmol) was added dropwise. The reaction mixture was stirred at −60° C. for several hours, then allowed to warm to room temperature overnight, resulting in an orange solution. Once LCMS indicated the reaction had gone to completion, the suspension was cooled on an ice bath and treated dropwise with water (3 mL). The resulting mixture was diluted with water (75 mL) and extracted with EtOAc (75 mL+20 mL). Silica gel was added and the EtOAc was evaporated under reduced pressure to provide a wet globular mass. Heptane and MeOH were added and the mixture was evaporated under reduced pressure to provide a powder. The material was purified by column chromatography on a Biotage® MPLC chromatography system (eluted with 0 to 4.2% MeOH in DCM, with isocratic elution when peaks eluted). The product fractions provided 152.7 mg of the title compound as a blue-green brittle foam. LCMS and $^1$H NMR are consistent with N-(1-(6-chloro-7-methoxy-2-oxo-1,2-dihydroquinolin-3-yl)ethyl)-2-methylpropane-2-sulfinamide (152.7 mg, 0.428 mmol, 55% yield). LCMS (Method 1): m/z 357 [M+H]$^+$.

Step-5: 3-(1-aminoethyl)-6-chloro-7-methoxyquinolin-2(1H)-one hydrochloride (II-6)

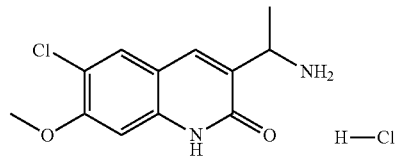 [SMILES: COc1cc2[nH]c(=O)c(C(C)N)cc2cc1Cl ; Cl]

A solution of N-(1-(6-chloro-7-methoxy-2-oxo-1,2-dihydroquinolin-3-yl)ethyl)-2-methyl propane-2-sulfinamide (149.6 mg, 0.419 mmol) in MeOH (3.8 mL) was cooled on an ice bath and treated dropwise with 4M HCl in 1,4-dioxane (2.2 mL). The reaction was stirred for 25 minutes, during which time a small amount of precipitate formed. The solvents were evaporated under reduced pressure at room temperature. The residue was triturated with 10 mL of ethyl ether, then collected on a Hirsch funnel, and washed with more ethyl ether to provide 115.6 mg of the title compound as a pale green solid. LCMS and $^1$H NMR are consistent with 3-(1-aminoethyl)-6-chloro-7-methoxyquinolin-2(1H)-one hydrochloride (115.6 mg, 0.400 mmol, 95% yield) $^1$H NMR (300 MHz, Methanol-d$_4$): δ ppm 7.95 (s, 1H), 7.77 (s, 1H), 6.97 (s, 1H), 4.51 (q, J=6.84 Hz, 1H), 3.98 (s, 3H), 1.68 (d, J=7.04 Hz, 3H). LCMS (Method 1): m/z 253 [M+H]$^+$.

Example 9—Intermediate II-7: (S)-3-(1-aminoethyl)-6-chloro-7-methoxyquinolin-2(1H)-one

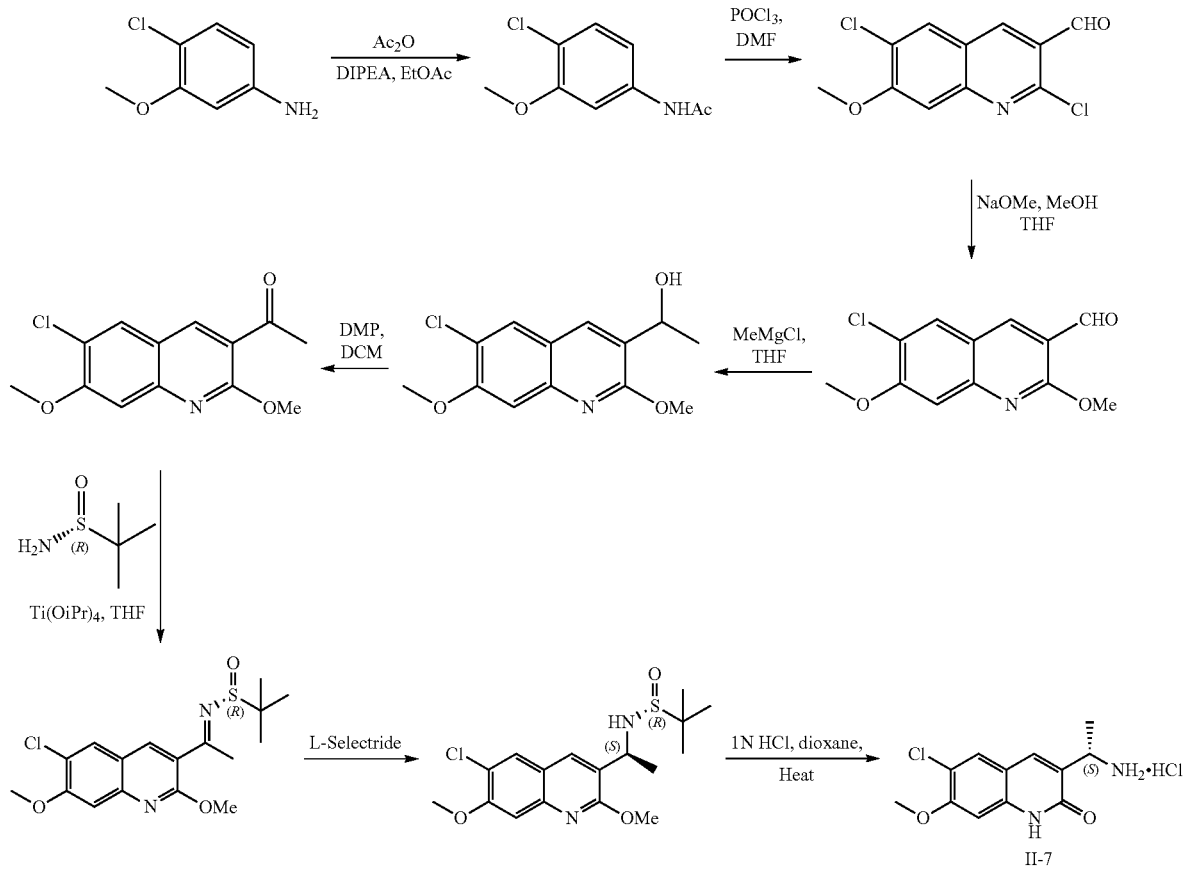

Step-1: N-(4-chloro-3-methoxyphenyl)acetamide

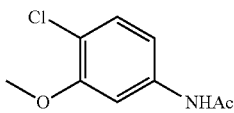

To a solution of 4-chloro-3-methoxyaniline (50 g, 317 mmol) and DIPEA (110 mL, 635 mmol) in CH$_2$Cl$_2$ (700 mL) was added acetic anhydride (36 mL, 381 mmol) drop wise at 0° C. and the reaction mixture was stirred at room temperature for 3 h. The reaction then was quenched with water (250 mL) and the organic layer was separated. The aqueous layer was extracted with CH$_2$Cl$_2$ (100 mL×3). The combined organic layers were dried (Na$_2$SO$_4$), concentrated and purified by flash chromatography with CH$_2$Cl$_2$/MeOH to give N-(4-chloro-3-methoxy phenyl)acetamide (71 g, quantitative yield) as a white solid.

Step-2: 2,6-Dichloro-7-methoxyquinoline-3-carbaldehyde

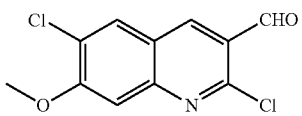 [SMILES: COc1cc2nc(Cl)c(C=O)cc2cc1Cl]

To POCl$_3$ (450 g, 274 mL, 2.95 mol) in a 2 L flask was added anhydrous DMF (83.5 g, 89 mL, 14 mol) drop wise. The reaction mixture was warmed up to room temperature and stirred for 20 min. After that N-(4-chloro-3-methoxyphenyl)acetamide (65 g, 327 mmol) was added portion wise at room temperature and the mixture was heated to 90° C. overnight. The reaction mixture was then cooled to room temperature and carefully quenched into aqueous NaHCO$_3$ solution. The precipitation obtained was filtered, washed with water (100 mL×3) and then dried in vacuum oven to give 60 g of title compound (73%).

Step-3: 6-Chloro-2,7-dimethoxyquinoline-3-carbaldehyde

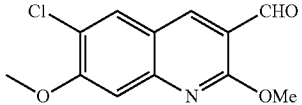 [SMILES: COc1cc2nc(OC)c(C=O)cc2cc1Cl]

To 2,6-dichloro-7-methoxyquinoline-3-carbaldehyde (40 g, 157 mmol) in MeOH (1 L) and THF (200 mL) was added NaOMe (16.9 g, 314 mmol) portion wise at room temperature. The reaction mixture was refluxed for 3 h. After cooling to room temperature, the reaction was quenched by addition of aqueous NH$_4$Cl solution (200 mL). The mixture was extracted with EtOAc (200 mL×3). The combined organic layers were dried (Na$_2$SO$_4$), concentrated and purified by flash chromatography with hexanes/EtOAc (3:1) to give the desired product (37.89 g, 96%) as a yellow solid.

Step-4: 1-(6-chloro-2,7-dimethoxyquinolin-3-yl)ethanol

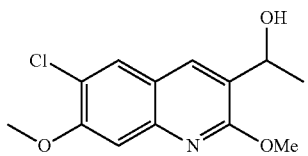 [SMILES: COc1cc2nc(OC)c(C(C)O)cc2cc1Cl]

To a solution of 6-chloro-2,7-dimethoxyquinoline-3-carbaldehyde (36.74 g, 151 mmol) in THF (1 L) at −78° C. was added a solution of MeMgCl in THF (3 M, 75.5 mL, 226 mmol) drop wise. The reaction was stirred at room temperature for 3 h and then quenched with aqueous NH$_4$Cl solution (250 mL). The organic layer was separated and the aqueous layer was extracted with EtOAc (100 mL×3). The combined organic layers were dried (Na$_2$SO$_4$), concentrated, and purified by silica gel chromatography with hexanes/EtOAc (3:1) to afford the title compound (38.06 g, 91%).

Step-5: 1-(6-chloro-2,7-dimethoxyquinolin-3-yl)ethanone

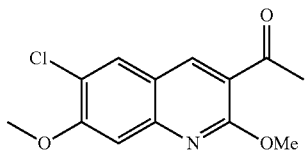 [SMILES: COc1cc2nc(OC)c(C(C)=O)cc2cc1Cl]

To 1-(6-chloro-2,7-dimethoxyquinolin-3-yl)ethanol (36.74 g, 137.6 mmol) in CH$_2$Cl$_2$ (1 L) at 0° C. was added DMP (70.0 g, 165.1 mmol) portion wise. The reaction was stirred at room temperature for 2 h, and then was quenched with an aqueous solution of NaHCO$_3$ and Na$_2$S$_2$O$_3$. After stirring for 15 min, both layers became clear. The organic layer was separated and the aqueous layer was extracted with CH$_2$Cl$_2$ (100 mL×2). The combined organic layers were dried (Na$_2$SO$_4$), concentrated and purified by silica gel chromatography with hexanes/EtOAc (4:1) to afford the title compound (30.02 g, 80%) as a white solid.

Step-6: (R,E)-N-(1-(6-chloro-2,7-dimethoxyquinolin-3-yl)ethylidene)-2-methylpropane-2-sulfinamide

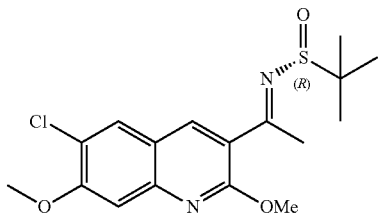

To 1-(6-chloro-2,7-dimethoxyquinolin-3-yl)ethanone (30.07 g, 113.5 mmol) in THF/toluene (100 mL/1 L) at room temperature was added (R)-2-methylpropane-2-sulfinamide (27.5 g, 227 mmol) and Ti(OiPr)$_4$ (97 mL, 340.5 mmol,). The reaction was refluxed with a Dean-Stark apparatus.

After the reaction was refluxed for 4 h and 300 mL of solvent was removed, the reaction was cooled to room temperature. The solvent was removed under vacuum, and 200 mL of EtOAc was added to the residue, followed by 100 mL of saturated aqueous NaHCO₃ solution. After stirring for 10 min, the reaction mixture was passed through a pad of celite. The filtrate was extracted with EtOAc (200 mL×2), dried (Na₂SO₄), concentrated and purified by silica gel chromatography with hexanes/EtOAc (1:1) to give the title compound (34.28 g, 82%).

Step-7: (R)—N—((S)-1-(6-chloro-2,7-dimethoxy-quinolin-3-yl)ethyl)-2-methylpropane-2-sulfinamide

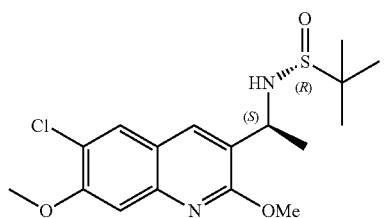

To (R,E)-N-(1-(6-chloro-2,7-dimethoxyquinolin-3-yl)ethylidene)-2-methylpropane-2-sulfinamide (34.28 g, 93.15 mmol) in THF (600 mL) at −78° C., was added 1 M L-selectride (121 mL, 121 mmol) in THF drop wise. The reaction mixture was warmed to room temperature and stirred for 3 h. The reaction was quenched with aqueous saturated NH₄Cl (300 mL) solution and then extracted with EtOAc (200 mL×2). The combined organic layers were dried (Na₂SO₄), concentrated and purified by silica gel chromatography with hexanes/EtOAc (1:1) to afford the title compound (29.27 g, 85%).

Step-8: (S)-3-(1-aminoethyl)-6-chloro-7-methoxy-quinolin-2(1H)-one hydrochloride salt (III-7)

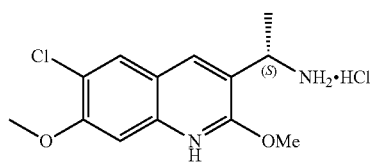

To (R)—N—((S)-1-(6-chloro-2,7-dimethoxyquinolin-3-yl)ethyl)-2-methylpropane-2-sulfinamide (30.35 g, 82 mmol) in dioxane (250 mL) was added 2 N HCl (250 mL) at rt. The reaction mixture was refluxed for 3 h, cooled to room temperature and the solvent was removed under vacuum. The crude residue obtained was dried under vacuum to give a crude product, which was further purified by trituration (CH₂Cl₂/MeOH/hexane) to obtain pure title compound III-7 (17.65 g, 75%) as a white solid. ¹H NMR (300 MHz, DMSO-d₆): δ 12.18 (s, 1H), 8.24 (br, s, 3H), 7.99 (s, 1H), 7.86 (s, 1H), 7.02 (s, 1H), 4.41 (m, 1H), 3.91 (s, 3H), 1.52 (d, J=6.87 Hz, 3H). LCMS (Method 3): Rt 3.48 min, m/z 253.1 [M+H]⁺.

Example 10—Intermediate II-8: (R)-3-(1-amino-ethyl)-6-chloro-7-methoxyquinolin-2(1H)-one

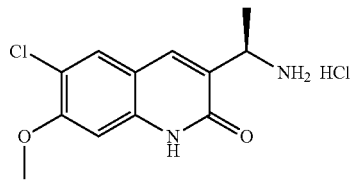 [SMILES: COc1cc2[nH]c(=O)c([C@@H](C)N)cc2cc1Cl ; Cl]

The title compound I-8 was prepared in the same procedure described for II-7, except using (S)-2-methylpropane-2-sulfinamide in Step-6 (Scheme-3). ¹H NMR (300 MHz, Methanol-d₄): δ ppm 7.92 (s, 1H), 7.75 (s, 1H), 6.95 (s, 1H), 4.48 (q, J=6.84 Hz, 1H), 3.96 (s, 3H), 1.65 (d, J=6.74 Hz, 3H). LCMS: m/z 253 [M+H]⁺.

Example 11—Intermediate II-9: 3-(1-aminoethyl)-6-chloro-7-(pyridin-2-ylmethoxy) quinolin-2(1H)-one

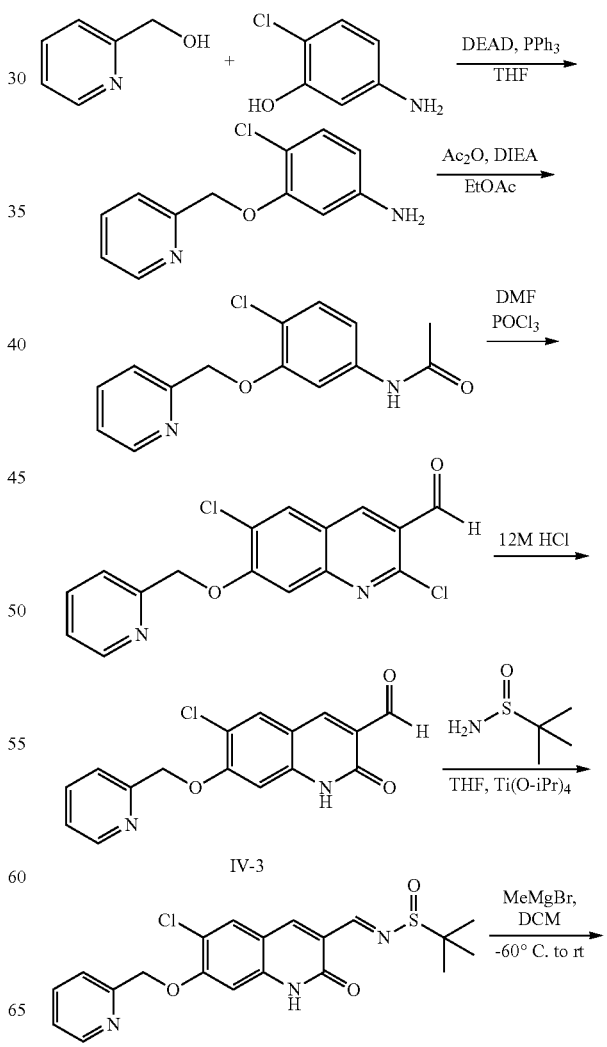

-continued

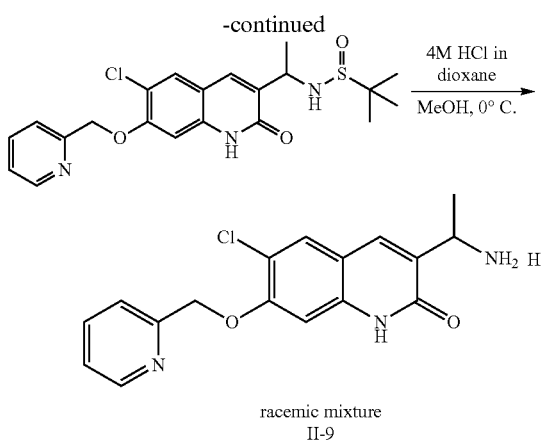

racemic mixture
II-9

Step-1: 4-chloro-3-(pyridin-2-ylmethoxy)aniline

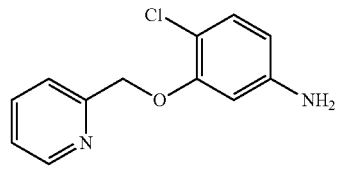 [SMILES: Nc1ccc(Cl)c(OCc2ccccn2)c1]

A solution of 5-amino-2-chlorophenol (2.00 g, 13.93 mmol) pyridin-2-ylmethanol (1.4 mL, 14.51 mmol), and triphenylphosphine (4.30 g, 16.39 mmol) in THF (250 mL) was placed under an atmosphere of nitrogen and treated with DEAD (2.6 mL, 16.42 mmol) The solution was stirred at room temperature overnight. Once LCMS indicated the reaction had gone to completion, the solution was treated with silica gel and evaporated under reduced pressure. The material was purified by column chromatography on a Biotage® MPLC chromatography system (using a 340 g silica gel column, eluted with 0 to 100% EtOAc in hexanes, then 2.3% MeOH in EtOAc) to provide the title compound as a light brown solid. LCMS and $^1$H NMR are consistent with 4-chloro-3-(pyridin-2-ylmethoxy)aniline (2.29 g, 9.76 mmol, 70.0% yield) with residual triphenylphosphine oxide. The crude was used in the next step without further purification. $^1$H NMR (300 MHz, DMSO-d$_6$): δ ppm 8.55-8.62 (m, 1H), 7.86 (ddd, J=7.77, 7.77, 1.76 Hz, 1H), 7.52 (d, J=7.92 Hz, 1H), 7.35 (dd, J=6.89, 5.42 Hz, 1H), 7.02 (d, J=8.50 Hz, 1H), 6.37 (d, J=2.35 Hz, 1H), 6.15 (dd, J=8.50, 2.35 Hz, 1H), 5.28 (s, 2H), 5.14 (s, 2H). LCMS (Method 1, ESI): m/z 235 [M+H]$^+$.

Step-2: N-(4-chloro-3-(pyridin-2-ylmethoxy)phenyl)acetamide

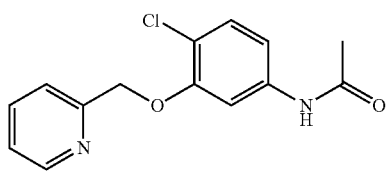 [SMILES: CC(=O)Nc1ccc(Cl)c(OCc2ccccn2)c1]

A solution of 4-chloro-3-(pyridin-2-ylmethoxy)aniline (5.22 g, 22.24 mmol) and DIEA (4.30 mL, 24.62 mmol) in EtOAc (125 mL) was treated with Ac$_2$O (2.30 mL, 24.38 mmol) The solution was stirred at room temperature overnight, after which a thick white precipitate formed. EtOAc (300 mL) was added and the mixture was shaken until most of the precipitate dissolved. The organic layer was then washed with water and brine (125 mL each), dried (Na$_2$SO$_4$) and filtered. Silica gel was added, and the mixture was evaporated under reduced pressure. The residue was purified by column chromatography on a Biotage® MPLC chromatography system (using a 100 g silica gel column, eluted with 0 to 5% MeOH in DCM) to provide 3.23 g of the title compound as a white solid. LCMS and $^1$H NMR are consistent with N-(4-chloro-3-(pyridin-2-ylmethoxy)phenyl)acetamide (3.23 g, 11.67 mmol, 52.5% yield) $^1$H NMR (300 MHz, DMSO-d$_6$): δ ppm 10.06 (s, 1H), 8.56-8.62 (m, 1H), 7.87 (ddd, J=7.80, 7.80, 1.80 Hz, 1H), 7.53 (d, J=7.62 Hz, 1H), 7.49 (d, J=2.05 Hz, 1H), 7.33-7.40 (m, 2H), 7.22 (dd, J=8.65, 2.20 Hz, 1H), 5.21 (s, 2H), 2.02 (s, 3H). LCMS (Method 1): m/z 277 [M+H]$^+$.

Step-3: 2,6-dichloro-7-(pyridin-2-ylmethoxy)quinoline-3-carbaldehyde

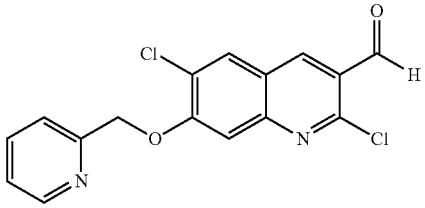 [SMILES: O=Cc1cc2cc(Cl)c(OCc3ccccn3)cc2nc1Cl]

A tube was capped with a septum and placed under an atmosphere of nitrogen. DMF (2.9 mL, 37.5 mmol) was added by syringe and then cooled on an ice bath. POCl$_3$ (11.4 mL, 122 mmol) was added dropwise by syringe (over 20 minutes). The solution was allowed to warm to room temperature (over 15 minutes) and the septum was removed. The mixture was treated with N-(4-chloro-3-(pyridin-2-ylmethoxy)phenyl)acetamide (3.16 g, 11.42 mmol) The tube was again sealed and the solution was stirred at 80° C. overnight. The solution was then pipetted onto ice, resulting in the formation of a yellow precipitate. The precipitate was collected on a Buchner funnel, washed with water (500 mL), and dried to provide 2.88 g of the title compound as a pale yellow solid. LCMS and $^1$H NMR are consistent with 2,6-dichloro-7-(pyridin-2-ylmethoxy)quinoline-3-carbaldehyde (2.88 g, 8.64 mmol, 76% yield) $^1$H NMR (300 MHz, DMSO-d$_6$): δ ppm 10.34 (s, 1H), 8.89 (s, 1H), 8.66 (br d, J=4.10 Hz, 1H), 8.52 (s, 1H), 7.92-8.01 (m, 1H), 7.75 (s, 1H), 7.69 (br d, J=7.62 Hz, 1H), 7.41-7.50 (m, 1H), 5.55 (s, 2H). LCMS (Method 1): m/z 333 [M+H]$^+$.

Step-4: 6-chloro-2-oxo-7-(pyridin-2-ylmethoxy)-1,2-dihydroquinoline-3-carbaldehyde IV-3

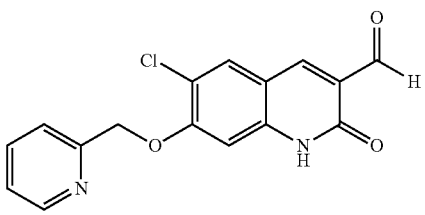 [SMILES: O=Cc1cc2cc(Cl)c(OCc3ccccn3)cc2[nH]c1=O]

A solution of 2,6-dichloro-7-(pyridin-2-ylmethoxy)quinoline-3-carbaldehyde (2.88 g, 8.64 mmol) in concentrated HCl (81 mL) was stirred at reflux (bath temperature 100° C.) for one day, during which time the solution turned orange. The solution was diluted with water (900 mL), resulting in the formation of a yellow precipitate. The precipitate was collected on a Buchner funnel, washed with water (750 mL), and dried under vacuum at 60° C. to provide 2.27 g of the title compound as a yellow solid. LCMS and $^1$H NMR are consistent with 6-chloro-2-oxo-7-(pyridin-2-ylmethoxy)-1,2-dihydroquinoline-3-carbaldehyde IV-3 (2.27 g, 7.21 mmol, 83% yield) $^1$H NMR (300 MHz, DMSO-$d_6$): δ ppm 12.20 (s, 1H), 10.16-10.19 (m, 1H), 8.60-8.64 (m, 1H), 8.44 (s, 1H), 8.14 (s, 1H), 7.90 (ddd, J=7.60, 7.60, 1.80 Hz, 1H), 7.57 (d, J=7.62 Hz, 1H), 7.36-7.43 (m, 1H), 7.05 (s, 1H), 5.37 (s, 2H). LCMS (Method 1): m/z 315 [M+H]$^+$.

Step-5: (E)-N-((6-chloro-2-oxo-7-(pyridin-2-ylmethoxy)-1,2-dihydroquinolin-3-yl)methylene)-2-methylpropane-2-sulfinamide

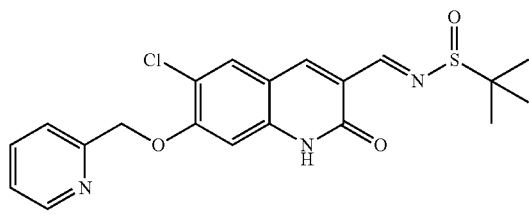 [SMILES: CC(C)(C)S(=O)/N=C/c1cc2cc(Cl)c(OCc3ccccn3)cc2[nH]c1=O]

A mixture of 6-chloro-2-oxo-7-(pyridin-2-ylmethoxy)-1,2-dihydroquinoline-3-carbaldehyde (2.27 g, 7.21 mmol) and 2-methylpropane-2-sulfinamide (1.05 g, 8.66 mmol) was placed in a 25 mL round bottom flask under an atmosphere of nitrogen. THF (9 mL) and titanium (IV) isopropoxide (Ti(O$^i$Pr)$_4$) (4.3 mL, 14.68 mmol) were added by syringe and the suspension was stirred at room temperature for one day. Once LCMS indicated the reaction had gone to completion, the material was triturated with EtOAc (400 mL), then filtered through Celite® 545, and the filter cake was washed with EtOAc (100 mL). The filter cake was sonicated in EtOAc (400 mL) for fifteen minutes and then filtered on a Buchner funnel. The two filtrates were combined and washed with brine (250 mL). The aqueous layer was back-extracted with EtOAc (200 mL+100 mL). The three combined organic layers were dried (Na$_2$SO$_4$), filtered, and evaporated under reduced pressure to provide 1.44 g of the title compound as a yellow solid. LCMS and $^1$H NMR are consistent with (E)-N-((6-chloro-2-oxo-7-(pyridin-2-ylmethoxy)-1,2-dihydroquinolin-3-yl)methylene)-2-methylpropane-2-sulfinamide (1.44 g, 3.45 mmol, 47.8% yield) $^1$H NMR (300 MHz, DMSO-$d_6$): δ ppm 12.20 (s, 1H), 8.74 (s, 1H), 8.62 (d, J=4.10 Hz, 1H), 8.60 (s, 1H), 8.13 (s, 1H), 7.90 (ddd, J=7.80, 7.80, 1.80 Hz, 1H), 7.58 (d, J=7.92 Hz, 1H), 7.40 (dd, J=7.18, 4.54 Hz, 1H), 7.06 (s, 1H), 5.36 (s, 2H), 1.19 (s, 9H). LCMS (Method 1): m/z 418 [M+H]$^+$.

Step-6: N-(1-(6-chloro-2-oxo-7-(pyridin-2-ylmethoxy)-1,2-dihydroquinolin-3-yl)ethyl)-2-methylpropane-2-sulfinamide

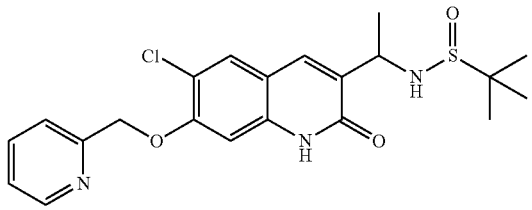 [SMILES: CC(NS(=O)C(C)(C)C)c1cc2cc(Cl)c(OCc3ccccn3)cc2[nH]c1=O]

(E)-N-((6-chloro-2-oxo-7-(pyridin-2-ylmethoxy)-1,2-dihydroquinolin-3-yl)methylene)-2-methyl propane-2-sulfinamide (1.44 g, 3.45 mmol) was placed in a 250 mL round-bottom flask under an atmosphere of nitrogen. DCM (27 mL) was added and the suspension was cooled on a dry ice/chloroform bath (to approx. −60° C.). Methylmagnesium bromide (MeMgBr) (3M in ether, 3.50 mL, 10.50 mmol) was added dropwise. The cold bath was allowed to warm to room temperature overnight resulting in an orange suspension. Once LCMS indicated the reaction had gone to completion, the suspension was cooled on an ice bath and treated dropwise with water (10 mL) resulting in emulsification. The emulsion was diluted with EtOAc (400 mL) and washed with water (400 mL). Silica gel was added to the organic layer and the solvent was evaporated under reduced pressure. The material was purified by column chromatography on a Biotage® MPLC chromatography system (eluted with 0 to 6% MeOH in DCM with isocratic elution when peaks eluted) to provide 1.17 g of the title compound as a yellow brittle foam. LCMS and $^1$H NMR are consistent with N-(1-(6-chloro-2-oxo-7-(pyridin-2-ylmethoxy)-1,2-dihydroquinolin-3-yl)ethyl)-2-methylpropane-2-sulfinamide (1.17 g, 2.70 mmol, 78% yield). NMR indicated a mixture of diastereomers. LCMS (Method 1): m/z 434 [M+H]$^+$.

Step-7: 3-(1-aminoethyl)-6-chloro-7-(pyridin-2-ylmethoxy)quinolin-2(1H)-one hydrochloride (II-9)

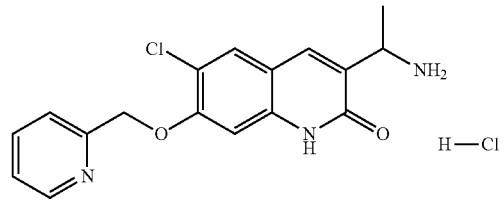 [SMILES: CC(N)c1cc2cc(Cl)c(OCc3ccccn3)cc2[nH]c1=O ; Cl]

A solution of N-(1-(6-chloro-2-oxo-7-(pyridin-2-ylmethoxy)-1,2-dihydroquinolin-3-yl)ethyl)-2-methylpropane-2-sulfinamide (167.3 mg, 0.386 mmol) in MeOH (3.5 mL) was cooled on an ice bath and treated dropwise with 4M HCl in 1,4-dioxane (2 mL). The reaction was stirred for 20 minutes and within five minutes a precipitate began to form. The solvents were evaporated under reduced pressure at room temperature. The residue was triturated with 10 mL of ethyl ether, collected on a Hirsch funnel and washed with more ethyl ether to provide 145.8 mg of the title compound as a pale yellow solid. LCMS and $^1$H NMR are consistent with 3-(1-aminoethyl)-6-chloro-7-(pyridin-2-ylmethoxy)quinolin-2(1H)-one hydrochloride (145.8 mg, 0.398 mmol, 103% yield) $^1$H NMR (300 MHz, Methanol-$d_4$): δ ppm 8.91-8.95 (m, 1H), 8.68 (ddd, J=7.90, 7.90, 1.50 Hz, 1H), 8.29 (d, J=7.62 Hz, 1H), 8.04-8.11 (m, 1H), 8.00 (s, 1H), 7.90 (s, 1H), 7.17 (s, 1H), 5.66 (s, 2H), 4.53 (q, J=6.84 Hz, 1H), 1.69 (d, J=6.74 Hz, 3H). LCMS (Method 1): m/z 352 [M+Na]$^+$.

Example 12—Intermediate II-10: (S)-3-(1-amino-ethyl)-6-chloro-7-(pyridin-2-ylmethoxy) quinolin-2 (1H)-one

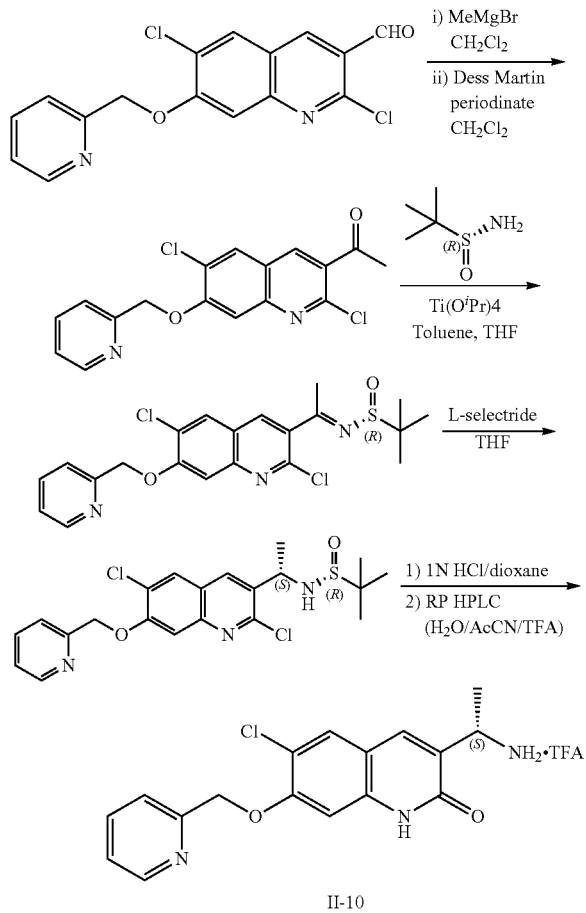

Step-1: 1-(2,6-Dichloro-7-(pyridin-2-ylmethoxy) quinolin-3-yl)ethanone

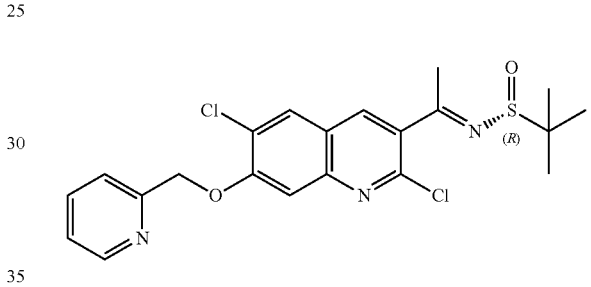

To a solution of 2,6-dichloro-7-(pyridin-2-ylmethoxy) quinoline-3-carbaldehyde (1.0 g, 3.0 mmol) (prepared in the same procedure described for step-1-3 shown in Scheme-4) in CH$_2$Cl$_2$ (40 mL) was added dropwise methyl magnesium bromide (MeMgBr) (3 M solution in diethyl ether, 1.5 mL, 4.50 mmol) at 0° C. The resulting mixture was then stirred at ambient temperature for 1.5 hours. Upon completion of reaction, the mixture was slowly quenched with water (3 mL) and extracted with CH$_2$Cl$_2$ (50 mL). The organic layer was separated and dried over anhydrous Na$_2$SO$_4$. The solvents were evaporated to dryness. The resulting residue was dissolved in CH$_2$Cl$_2$ (25 mL) and treated with Dess-Martin Periodinate (2.54 g, 6.00 mmol). The mixture was stirred at ambient temperature overnight. The mixture was then quenched with an aqueous co-solution of 20% NaHCO$_3$ and 20% Na$_2$S$_2$O$_3$ (10 mL) and stirred for 5 minutes at room temperature. The solution was extracted with CH$_2$Cl$_2$ (40 mL), dried over anhydrous Na$_2$SO$_4$, filtered and evaporated. The resulting residue was purified by column chromatography on an ISCO® chromatography system (SiO$_2$ column: eluted with CH$_2$Cl$_2$/MeOH 0 to 10%) to afford the title compound (800 mg, 79%).

Step-2: (R,E)-N-(1-(2,6-dichloro-7-(pyridin-2-yl-methoxy)quinolin-3-yl)ethylidene)-2-methylpropane-2-sulfinamide

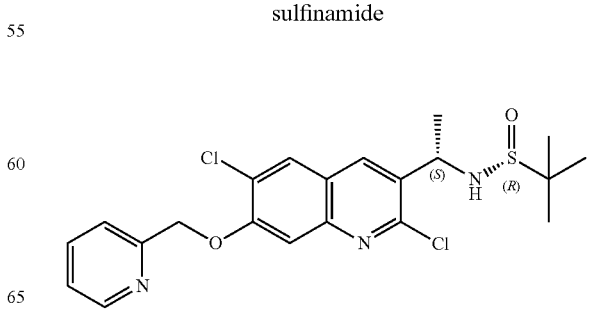

To a mixture of 1-(2,6-dichloro-7-(pyridin-2-ylmethoxy) quinolin-3-yl)ethanone (2.18 g, 6.56 mmol) and (R)-2-methylpropane-2-sulfinamide (1.19 g, 9.84 mmol) in THF: Toluene (40 mL:180 mL), was added titanium (IV) isopropoxide (Ti(O$^i$Pr)$_4$) (3.96 mL, 13.30 mmol). The resulting mixture was refluxed with a Dean-Stark apparatus for 7 hours. The mixture was then cooled to room temperature, quenched with water, and diluted with EtOAc (300 mL). The organic layer was washed with water (100 mL), dried over anhydrous Na$_2$SO$_4$, filtered and evaporated to dryness. The resulting residue was purified by column chromatography on an ISCO® chromatography system (SiO$_2$ column: eluted with Hex/EtOAc 0 to 100%) to afford the title compound as yellow solid (1.4 g, 50% yield). The starting material ketone was also recovered (250 mg, 11% yield).

Step-3: (R)—N—((S)-1-(2,6-dichloro-7-(pyridin-2-ylmethoxy)quinolin-3-yl)ethyl)-2-methyl propane-2-sulfinamide To a solution of (R,E)-N-(1-(2,6-dichloro-7-(pyridin-2-ylmethoxy)quinolin-3-yl)ethylidene)-2-methyl propane-2-sulfinamide (900 mg, 1.99 mmol) in THF (25 mL) at −40 to −50° C. was added L-selectride (1M in THF, 1.98 mL, 2.59 mmol) dropwise. The resulting mixture was stirred at −40 to −50° C. for 2 hours. Upon completion of reaction, the mixture was quenched with ice at −50° C., extracted with EtOAc (100 mL), dried, and evaporated. The resulting residue was purified by column chromatography on an ISCO® chromatography system (SiO₂ column: Hex/EtOAc 0 to 100%) followed by trituration with hexanes-methylene chloride to afford the title compound (266 mg, 30% yield).

Step-4: (S)-3-(1-Aminoethyl)-6-chloro-7-(pyridin-2-ylmethoxy)quinolin-2(1H)-one TFA salt

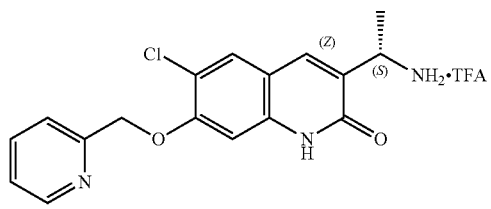

To a mixture of (R)—N—((S)-1-(2,6-dichloro-7-(pyridin-2-ylmethoxy)quinolin-3-yl)ethyl)-2-methylpropane-2-sulfinamide (1.1 g, 2.43 mmol) in 1,4-dioxane (6.6 mL), was added aqueous 1N HCl (6.6 mL) at room temperature. The resulting mixture was heated to 120° C. overnight. After TLC and MS showed completion of reaction, the solvents were removed on a rotary evaporator and lyophilized to provide yellow solid. The crude solid was purified by reverse phase chromatography on an ISCO® chromatography system (C18 column: eluted with H₂O/MeCN/0.1% CF₃CO₂H 0 to 100%) and the fractions were monitored by LCMS. The pure fractions were combined and lyophilized to afford the title compound II-10 (920 mg, 86% yield) as the TFA salt. ¹H NMR (300 MHz, DMSO-d₆): δ 12.17 (br s, 1H), 8.62 (d, J=4.95 Hz, 1H), 8.09 (br s, 2H), 7.96-7.85 (m, 3H), 7.59 (d, J=7.9 Hz, 1H), 7.42-7.37 (m, 1H), 7.08 (d, J=2.5 Hz, 1H), 5.33 (s, 2H), 4.39-4.38 (m, 1H), 1.51 (d, J=6.8 Hz, 3H). LCMS (method 3): Rt 3.3 min, m/z 329.1 [M+H]⁺.

Example 13—Intermediate II-11: (S)-3-(1-aminoethyl)-6-chloro-1,8-naphthyridin-2(1H)-one

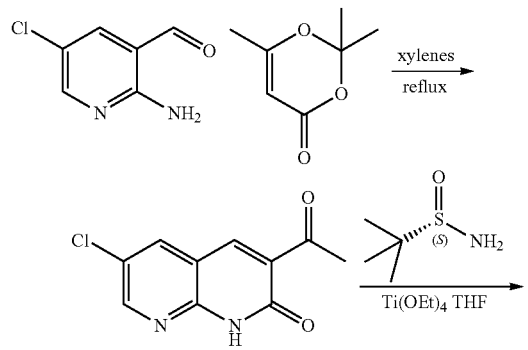

Step-1: 3-acetyl-6-chloro-1,8-naphthyridin-2(1H)-one

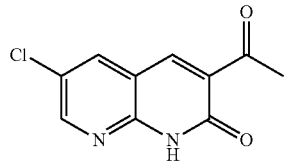

A mixture of 2-amino-5-chloronicotinaldehyde (1 g, 6.39 mmol) and 2,2,6-trimethyl-4H-1,3-dioxin-4-one (1.362 g, 9.58 mmol) in xylenes (10 mL) was heated to reflux for 3 hours, then cooled to room temperature, filtered, and washed with xylenes twice to afford 914 mg of 3-acetyl-6-chloro-1,8-naphthyridin-2(1H)-one (64.3% yield). ¹H NMR (300 MHz, DMSO-d₆): δ 12.68 (br, 1H), 8.63 (s, 1H), 8.49 (s, 1H), 8.39 (s, 1H), 2.48 (s, 3H). LCMS (Method 1): Rt 1.60 min, m/z 223.03[M+H]⁺.

Step-2: (S)—N—((S)-1-(2,6-dichloroquinolin-3-yl)ethyl)-2-methylpropane-2-sulfinamide

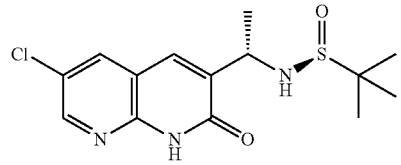 [SMILES: C[C@H](N[S@@](=O)C(C)(C)C)c1cc2cc(Cl)cnc2[nH]c1=O]

A mixture of tetraethoxytitanium (512 mg, 2.25 mmol), (R)-2-methylpropane-2-sulfinamide (163 mg, 1.35 mmol) and 3-acetyl-6-chloro-1,8-naphthyridin-2(1H)-one (200 mg, 0.898 mmol) in THF (15 mL) was heated to 80° C. overnight, then cooled to room temperature. To this mixture was added NaBH₄ (170 mg, 4.49 mmol) and the mixture was slowly warmed up to room temperature overnight. MeOH was then added to quench any excess NaBH₄, followed by the addition of water. The mixture was filtered to remove

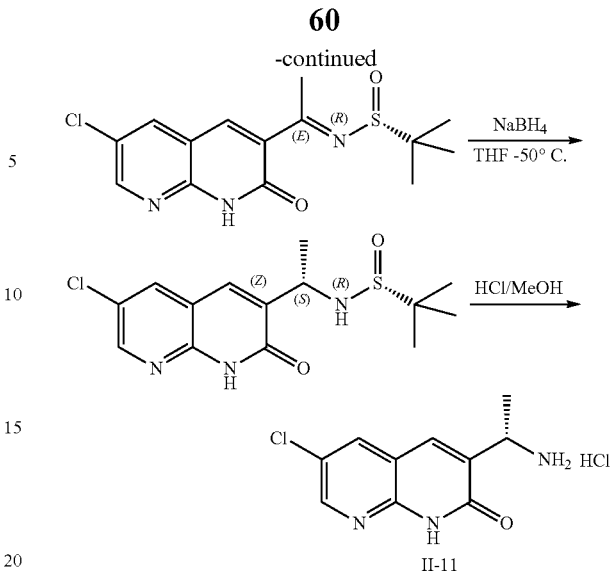

solids, then extracted with EtOAc twice, dried over Na$_2$SO$_4$, and concentrated. The residue was purified on a Biotage® chromatography system using a 25 g SiO$_2$ column eluted on a gradient (first 20% to 100% EtOAc/Hexanes, then 0-5% MeOH/DCM) to afford (S)—N—((S)-1-(2,6-dichloroquinolin-3-yl)ethyl)-2-methylpropane-2-sulfinamide (123 mg, 42% yield). $^1$H NMR (300 MHz, DMSO-d$_6$): δ 8.40 (s, 1H), 7.74 (s, 1H), 7.75 (s, 1H), 7.24 (s, 1H), 5.24 (d, J=9.45 Hz, 1H), 4.42 (m, 3H), 1.54 (d, J=6.93 Hz, 3H), 1.20 (s, 9H). LCMS (Method 1): Rt 2.07 min, m/z 328.98 [M+H]$^+$.

Step-3: (S)-3-(1-aminoethyl)-6-chloro-1,8-naphthyridin-2(1H)-one (II-11)

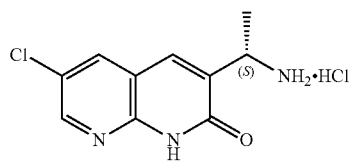

To a solution of ((S)—N—((S)-1-(6-chloro-2-oxo-1,2-dihydro-1,8-naphthyridin-3-yl)ethyl)-2-methylpropane-2-sulfinamide (123 mg, 0.375 mmol) in MeOH (5 mL) was added HCl (2 mL, 8.00 mmol, 4M in 1,4-dioxane). The mixture was then stirred at room temperature overnight. To this mixture was added 6 mL of ethyl ether and the resulting precipitate was filtered, washed with ethyl ether (2×), dried and concentrated to afford (S)-3-(1-aminoethyl)-6-chloro-1,8-naphthyridin-2(1H)-one, HCl (96 mg, 98% yield). $^1$H NMR (300 MHz, DMSO-d$_6$): δ 12.75 (br s, 1H), 8.60-8.35 (s, 1H), 8.26 (br, 1H) 8.07 (s, 1H), 4.40-4.50 (m, 1H), 1.51 (d, J=6.78 Hz, 3H). LCMS (Method 1): Rt 0.87 min, m/z 224.99 [M+H]$^+$.

Example 14—Intermediate II-12: (R)-3-(1-aminoethyl)-6-chloroquinoxalin-2(1H)-one

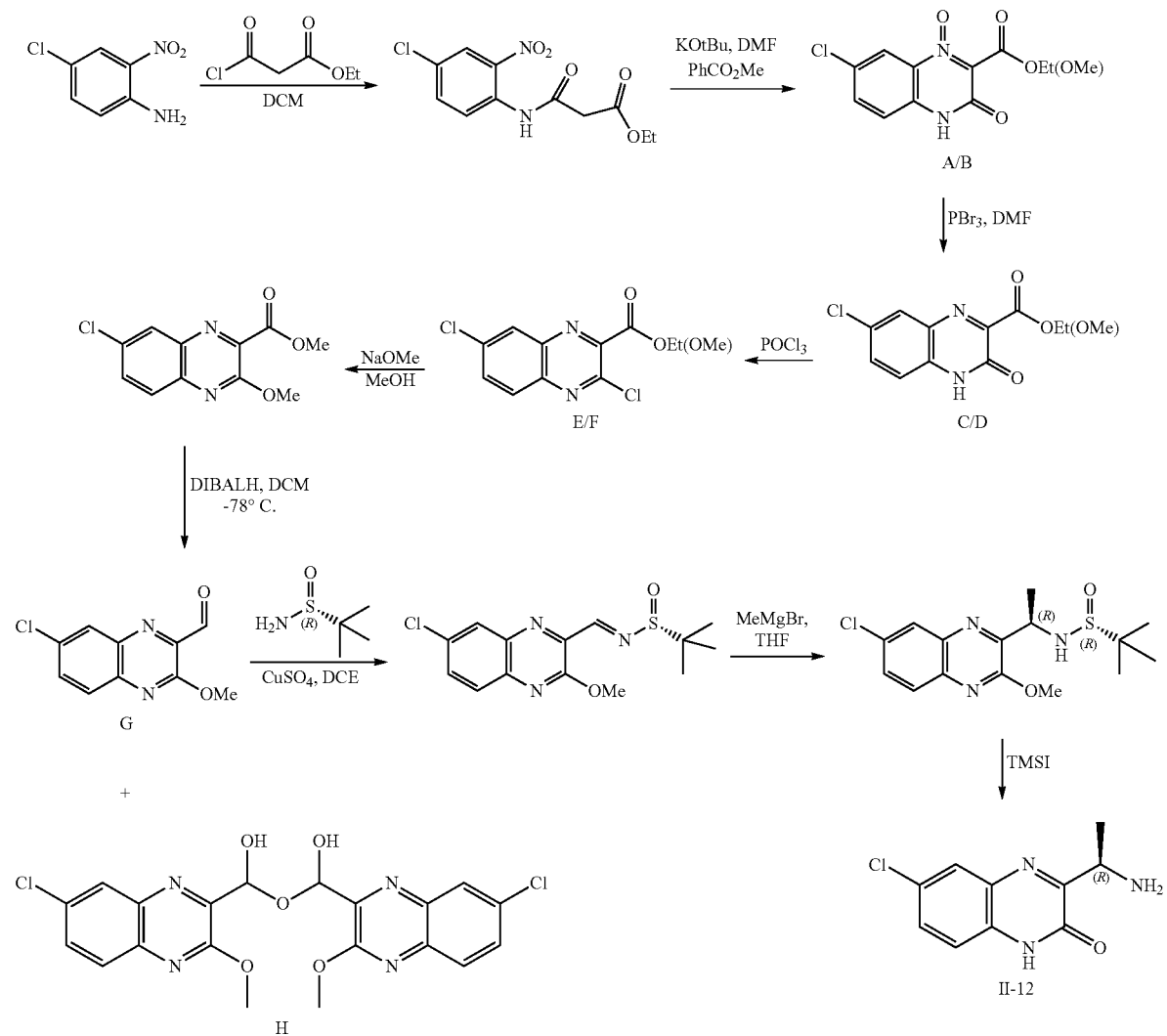

Step-1: Ethyl 3-((4-chloro-2-nitrophenyl)amino)-3-oxopropanoate

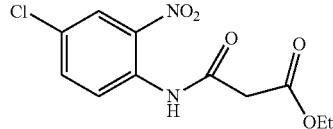 [SMILES: CCOC(=O)CC(=O)Nc1ccc(Cl)cc1[N+](=O)[O-]]

To a solution of 4-chloro-2-nitroaniline (42.3 g, 245 mmol) in CH$_2$Cl$_2$ (1 L) was added ethyl 3-chloro-3-oxopropanoate (48 g, 319 mmol) dropwise and the reaction mixture was stirred at room temperature overnight. The solvent was removed under vacuum and the resulting residue was dissolved in a minimum amount of MTBE (200 mL) and hexanes (800 mL) which was slowly added. Any product that precipitated out from solution was filtered and the filtrate was concentrated and purified by column chromatography ISCO® chromatography system with hexanes/ethyl acetate gradient elution to afford additional desired product. The title compound was obtained in 98% yield (69.85 g).

Step-2: 7-Chloro-2-(ethoxycarbonyl)-3-oxo-3,4-dihydroquinoxaline 1-oxide (A) and 7-Chloro-2-(methoxycarbonyl)-3-oxo-3,4-dihydroquinoxaline 1-oxide (B)

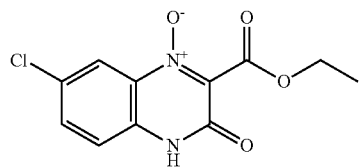

A

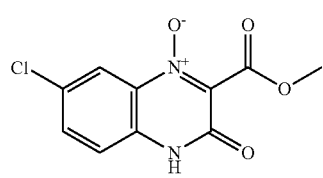

B

To a solution of ethyl 3-((4-chloro-2-nitrophenyl)amino)-3-oxopropanoate (68 g, 238 mmol) and methyl benzoate (150 mL) in anhydrous DMF (500 mL) at 0° C. was added dropwise KO$^t$Bu (1M solution in THF, 500 mL, 500 mmol). The reaction mixture was stirred at 0° C. for 4 hours and then quenched with saturated NH$_4$Cl aqueous solution. The mixture was extracted with CH$_2$Cl$_2$ (300 mL×3). The combined organic layers were dried (Na$_2$SO$_4$), concentrated, and purified by SiO$_2$ flash chromatography and eluted with CH$_2$Cl$_2$/MeOH to afford a mixture of A/B (42.54 g, 67% yield, A/B ratio 1:2) as a solid. This was used in the next step without further purification.

Step 3: Ethyl 7-chloro-3-oxo-3,4-dihydroquinoxaline-2-carboxylate (D) and methyl 7-chloro-3-oxo-3,4-dihydroquinoxaline-2-carboxylate (C)

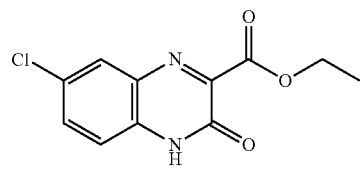

C

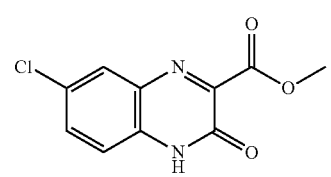

D

To a mixture of compounds A and B (42.54 g, 159 mmol) in DMF (200 mL) was added PBr$_3$ (85.9 g, 318 mmol) dropwise at room temperature. The reaction mixture was stirred at room temperature for 3 hours and was then quenched with ice water and extracted with CH$_2$Cl$_2$ (200 mL×3). The combined organic layers were dried (Na$_2$SO$_4$), concentrated, and purified by flash chromatography using CH$_2$Cl$_2$/MeOH (9:1) as eluent to afford C/D (36.6 g, 91% yield) as a solid. This was used in the next step without further purification.

Step-4: Ethyl 3,7-dichloroquinoxaline-2-carboxylate (E) and methyl 3,7-dichloro quinoxaline-2-carboxylate (F)

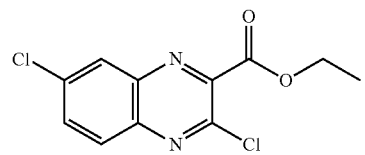

E

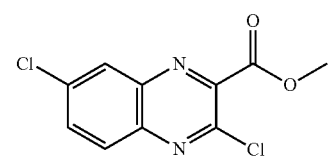

F

To a mixture of compounds C/D (36.6 g, 145 mmol) in a 1 L flask was added POCl$_3$ (150 mL) in one portion and the resulting mixture was refluxed for 3 hours. The mixture was then cooled to room temperature and carefully quenched with aqueous NaHCO$_3$ solution. The mixture was extracted with CH$_2$Cl$_2$ (200 mL×3). The combined organic layer was dried (Na$_2$SO$_4$), concentrated, and purified by SiO$_2$ flash chromatography using hexane/ethyl acetate (9:1) as eluent to afford E/F (23.7 g, 61% yield) as a solid. This mixture was used in the next step without further purification.

Step-5: Methyl 7-chloro-3-methoxyquinoxaline-2-carboxylate

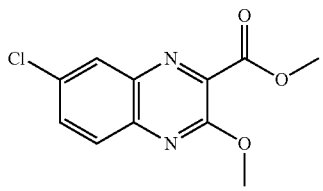 [SMILES: COC(=O)c1nc2cc(Cl)ccc2nc1OC]

To a mixture of compounds E/F (22.11 g, 81.9 mmol) in THF/MeOH (9:1, 300 mL) was added NaOMe (0.5 M, 360 mL) dropwise at 0° C. The resulting mixture was stirred at room temperature for 3 hours and quenched with solid NH$_4$Cl (20 g). The solvent was removed under vacuum and water was added (200 mL). The mixture was extracted with CH$_2$Cl$_2$ (150 mL×3) and the combined organic layers were dried (Na$_2$SO$_4$), concentrated, and purified by SiO$_2$ flash chromatography using hexanes/ethyl acetate (9:1) as eluent to afford the title compound (19.1 g, 88% yield) as a solid.

Step-6: 7-Chloro-3-methoxyquinoxaline-2-carbaldehyde (G) and oxybis((7-chloro-3-methoxyquinoxalin-2-yl)methanol) (H)

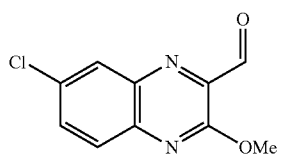

G

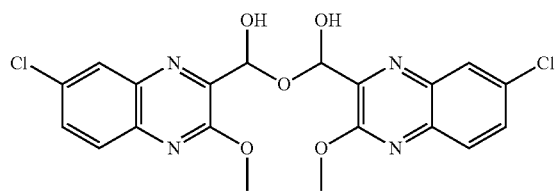

H

To methyl 7-chloro-3-methoxyquinoxaline-2-carboxylate (5.3 g, 20 mmol) in CH$_2$Cl$_2$ (250 mL) was added diisobutylaluminum hydride (1 M, 30 mL) drop-wise at −78° C. The resulting mixture was stirred at −78° C. for 3 hours and was then quenched with MeOH (at −78° C., 20 mL). After stirring for 0.5 hours, the mixture was warmed to room temperature and potassium sodium L-tartrate aqueous solution (100 mL) was added. The organic layer was then separated, and the aqueous layer was extracted with CH$_2$Cl$_2$ (50 mL×3). The combined organic layers were dried (Na$_2$SO$_4$), concentrated, and purified by SiO$_2$ flash chromatography using hexanes/ethyl acetate (1:1) as eluent to afford G (1.02 g, 23% yield) and H (2.24 g, 50% yield). The structure of H was assigned based on MS and $^1$H NMR.

Step-7: (R,E)-N-((7-chloro-3-methoxyquinoxalin-2-yl)methylene)-2-methylpropane-2-sulfinamide

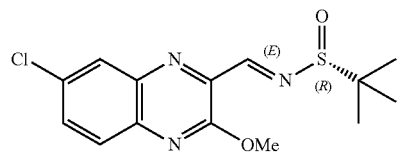

To compound H (2.24 g, 5.1 mmol) in DCE (300 mL) at room temperature was added (R)-2-methylpropane-2-sulfinamide (2.44 g, 20.1 mmol) and CuSO$_4$ (4.85 g, 30.3 mmol). The reaction was heated to 60° C. and stirred for 4 hours. The reaction mixture was then cooled to room temperature and quenched with 50 mL of saturated aqueous NaHCO$_3$ solution. After stirring for 10 minutes, the reaction mixture was filtered through a pad of Celite®. The filtrate was extracted with CH$_2$Cl$_2$ (50 mL×3), dried (Na$_2$SO$_4$), concentrated, and purified by column chromatography on an ISCO® chromatography system using hexanes/ethyl acetate as eluent to afford the title compound (2.21 g, 67% yield).

Step-8: (R)—N—((R) 1-(7-chloro-3-methoxyquinoxalin-2-yl)ethyl)-2-methylpropane-2-sulfinamide

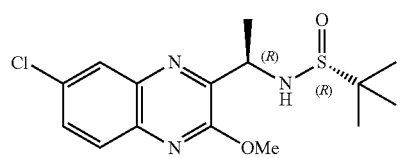

To (R,E)-N-((7-chloro-3-methoxyquinoxalin-2-yl)methylene)-2-methylpropane-2-sulfinamide (2.21 g, 6.8 mmol) in CH$_2$Cl$_2$ (150 mL) was added methyl magnesium chloride (MeMgCl) (3M in THF, 3.4 mL) dropwise at −78° C. The resulting mixture was stirred at −78° C. for 2 hours and was then quenched with aqueous NH$_4$Cl solution (20 mL). After stirring for 10 minutes, the organic layer was separated, and the aqueous layer was extracted with CH$_2$Cl$_2$ (25 mL×3). The combined organic layers were dried (Na$_2$SO$_4$), concentrated, and purified by column chromatography on an ISCO® chromatography system using hexanes/ethyl acetate as eluent to afford the title compound (1.18 g, 51% yield).

Step-9: (R)-3-(I-aminoethyl)-6-chloroquinoxalin-2 (1H)-one (II-12)

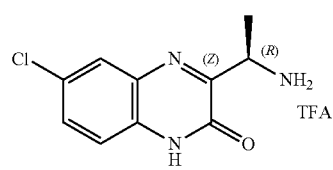

To the compound (R)—N—((R)-1-(7-chloro-3-methoxyquinoxalin-2-yl)ethyl)-2-methylpropane-2-sulfinamide (1.29 g, 3.46 mmol) in CH$_3$CN (100 mL) was added iodotrimethylsilane (3.46 g, 17.3 mmol) dropwise at 0° C.

The mixture was then refluxed for 2 hours, cooled to room temperature, and quenched with MeOH (10 mL). The solvent was removed under vacuum, and the residue was purified by reverse C-18 chromatography on an ISCO® chromatography system using water (0.1% TFA)/CH₃CN (0.1% TFA) as eluent to afford the compound II-12 (1.22 g, 95% yield) as a TFA salt.

Example 15—Intermediate II-13: (S)-3-(1-aminoethyl)-6-chloroquinoxalin-2(1H)-one

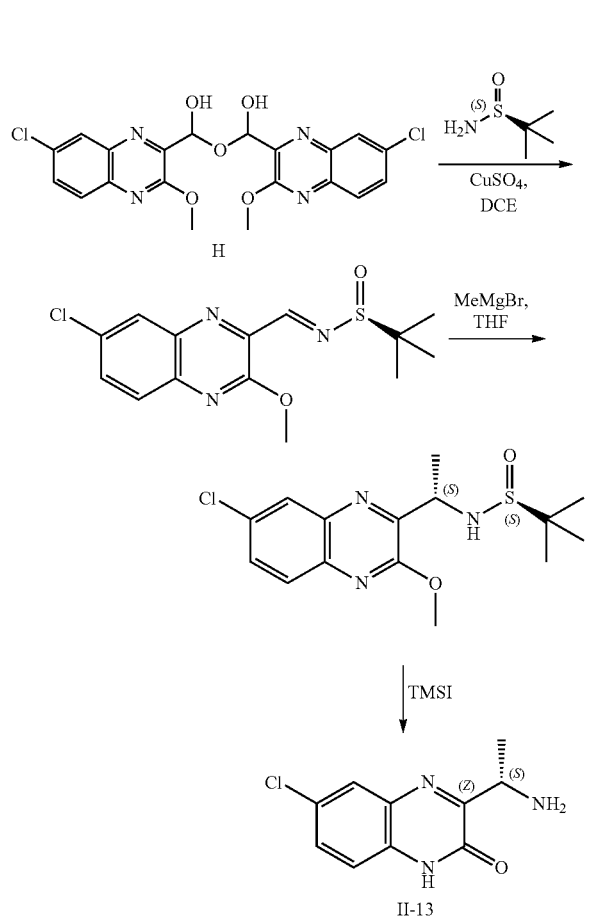

Step-1: (S,E)-N-((7-chloro-3-methoxyquinoxalin-2-yl)methylene)-2-methylpropane-2-sulfinamide To compound H (2.31 g, 5.2 mmol) in DCE (300 mL) at room temperature was added (S)-2-methylpropane-2-sulfinamide (2.52 g, 20.8 mmol) and CuSO₄ (5.0 g, 31.2 mmol). The resulting reaction mixture was heated to 60° C. and stirred for 4 hours. The reaction mixture was then cooled to room temperature and quenched with 50 mL of saturated aqueous NaHCO₃ solution. After stirring for 10 minutes, the mixture was filtered through a pad of Celite®. The filtrate was extracted with CH₂Cl₂ (50 mL×3), dried (Na₂SO₄), concentrated, and purified by column chromatography on an ISCO® chromatography system using hexanes/ethyl acetate as eluent to afford the title compound (2.62 g, 78% yield).

Step-2: (S)—N—((S)-1-(7-chloro-3-methoxyquinoxalin-2-yl)ethyl)-2-methylpropane-2-sulfinamide

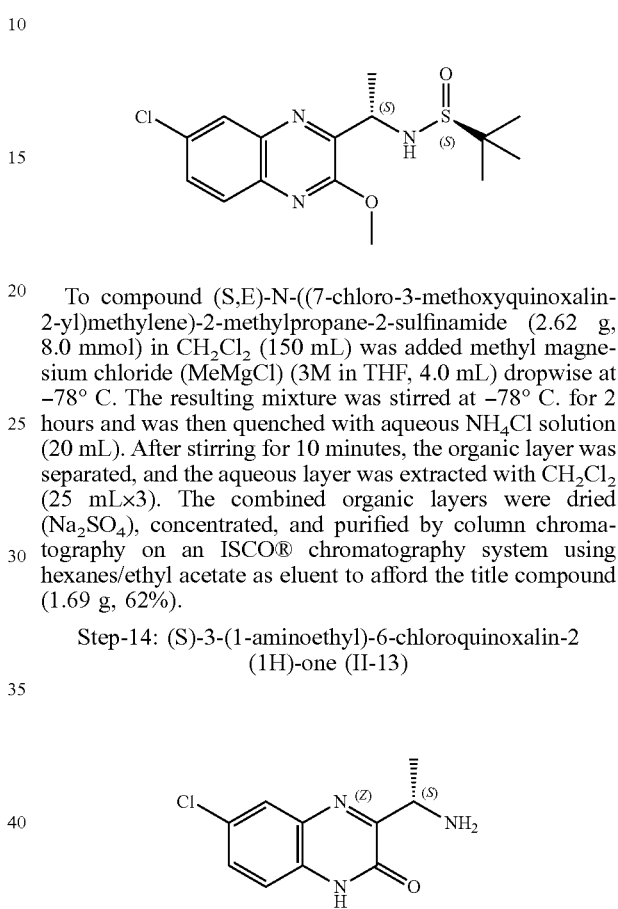

To compound (S,E)-N-((7-chloro-3-methoxyquinoxalin-2-yl)methylene)-2-methylpropane-2-sulfinamide (2.62 g, 8.0 mmol) in CH₂Cl₂ (150 mL) was added methyl magnesium chloride (MeMgCl) (3M in THF, 4.0 mL) dropwise at −78° C. The resulting mixture was stirred at −78° C. for 2 hours and was then quenched with aqueous NH₄Cl solution (20 mL). After stirring for 10 minutes, the organic layer was separated, and the aqueous layer was extracted with CH₂Cl₂ (25 mL×3). The combined organic layers were dried (Na₂SO₄), concentrated, and purified by column chromatography on an ISCO® chromatography system using hexanes/ethyl acetate as eluent to afford the title compound (1.69 g, 62%).

Step-14: (S)-3-(1-aminoethyl)-6-chloroquinoxalin-2(1H)-one (II-13)

To the compound (S)—N—((S)-1-(7-chloro-3-methoxyquinoxalin-2-yl)ethyl)-2-methylpropane-2-sulfinamide (350 mg, 1.03 mmol) in CH₃CN (40 mL) was added iodotrimethylsilane (1.03 g, 5.15 mmol) dropwise at 0° C. The mixture was then refluxed for 2 hours. After it was cooled to room temperature, the reaction was quenched with MeOH (2 mL). The solvent was removed under vacuum, and the residue was purified by reverse C-18 chromatography on an ISCO® chromatography system using water (0.1% TFA)/CH₃CN (0.1% TFA) as eluent to afford the title compound (267 mg, 79% yield) as a TFA salt.

Example 16—Intermediate II-14: (3-((S)-1-aminoethyl)-6-chloro-7-((R)-1-(pyridin-2-yl)ethoxy)quinolin-2(1H)-one

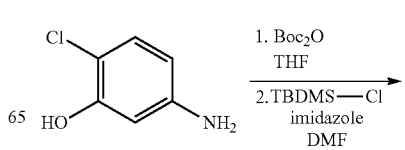

-continued

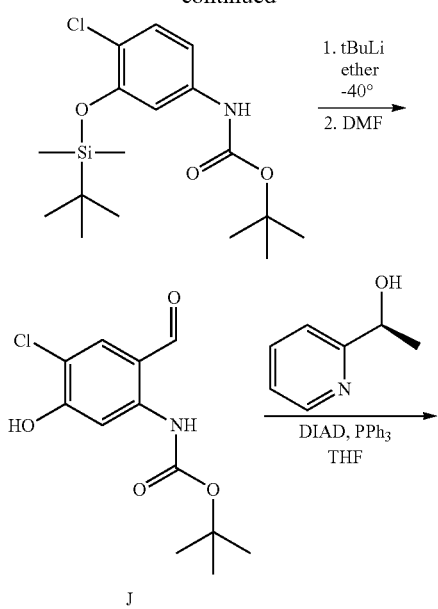

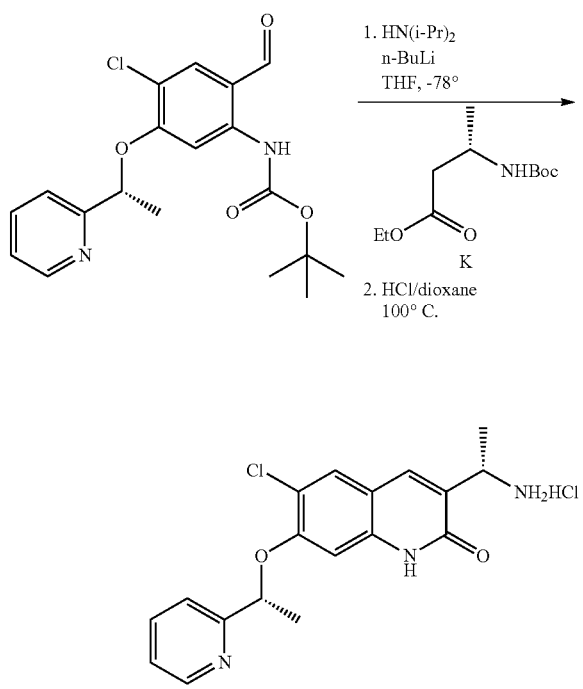

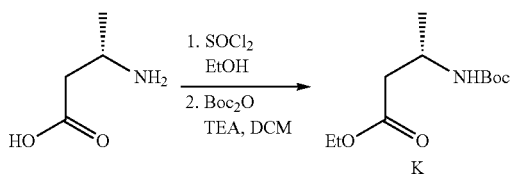

Step-1: tert-butyl (3-((tert-butyldimethylsilyl)oxy)-4-chlorophenyl)carbamate

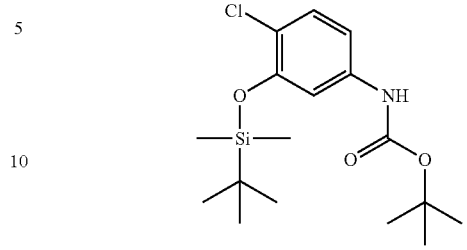

A solution of 5-amino-2-chlorophenol (10.00 g, 69.7 mmol) in THF (350 mL) was treated with di-tert-butyl dicarbonate (20 mL, 86 mmol) and stirred at reflux overnight. The solvent was evaporated under reduced pressure to provide a brown oil. The oil was then dissolved in EtOAc (300 mL), washed with water, saturated aqueous $NaHCO_3$, and brine (300 mL each), dried ($Na_2SO_4$), filtered, and evaporated under reduced pressure to provide 21.01 g of impure tert-butyl (4-chloro-3-hydroxyphenyl)carbamate as a brown oil (LCMS: m/z 244 $[M+H]^+$). This material was dissolved in DMF (130 mL) and cooled on an ice bath. Imidazole (11.74 g, 172 mmol) was then added slowly (over ~10 minutes). A solution of TBDMS-Cl (14.98 g, 99 mmol) in DMF (45 mL) was added (over ~2 minutes). The ice bath was removed and the solution was stirred at room temperature overnight. Once LCMS indicated the reaction had gone to completion, the solution was diluted with EtOAc (1 L) and washed with water (2×600 mL), half-saturated aqueous $NaHCO_3$ (600 mL), half-saturated aqueous $NH_4Cl$ (600 mL), saturated $NaHCO_3$ (600 mL), and brine (600 mL). The organic layer was dried ($MgSO_4$), filtered, and evaporated under reduced pressure to provide 28.00 g of a brown solid. The sample was dissolved in EtOAc, silica gel (33 g) was added, and the solvent was evaporated under reduced pressure. The material was divided into two batches, each of which was purified by column chromatography on a Biotage® MPLC chromatography system using a 330 g silica gel column eluted with 0 to 5% EtOAc in hexanes and with isocratic elution at 4.5% or 5% EtOAc when the product eluted. The product fractions were collected and provided 21.76 g of tert-butyl (3-((tert-butyldimethylsilyl) oxy)-4-chlorophenyl)carbamate (21.76 g, 60.8 mmol, 88% yield) as a peach-colored solid. $^1$H NMR (300 MHz, DMSO-$d_6$): δ ppm 9.43 (s, 1H), 7.23-7.28 (m, 1H), 7.22 (d, J=2.35 Hz, 1H), 7.09-7.16 (m, 1H), 1.46 (s, 9H), 0.99 (s, 9H), 0.21 (s, 6H). LCMS (Method 1): m/z 358 $[M+H]^+$.

Step-2: tert-butyl (4-chloro-2-formyl-5-hydroxyphenyl)carbamate (J)

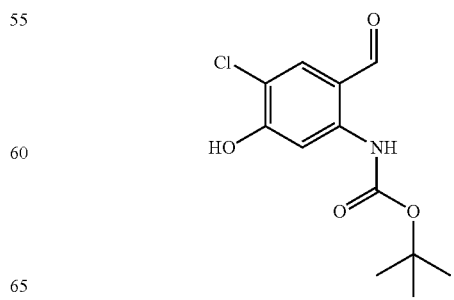

An oven-dried 3-necked 500 mL round bottom flask was charged with tert-butyl (3-((tert-butyldimethylsilyl)oxy)-4-chlorophenyl)carbamate (10 g, 27.9 mmol) An oven-dried addition funnel was attached, and the system was flushed with nitrogen. Ethyl ether (113 mL) was added by syringe. The resulting yellow solution was cooled on an acetonitrile/dry ice bath (to approximately −40° C.). t-BuLi (1.7 M in pentane, 40 mL, 68.0 mmol) was then added to the addition funnel by cannula. The t-BuLi solution was added dropwise to the ether solution (over ~10 minutes), during which time the ether solution gradually became cloudy with a precipitate. The mixture was stirred at about −40° C. for 2.5 hours, then DMF (11 mL) was added dropwise by syringe (over ~10 minutes), during which time the solids went back into solution. The acetonitrile/dry ice bath was replaced with an ice bath, and the yellow solution was stirred at 0° C. for 1.75 hours. The reaction was then quenched by dropwise addition of water (25 mL), resulting in formation of an orange precipitate. The ice bath was removed and the sample was diluted with water (125 mL), resulting in dissolution of the precipitate. The mixture was shaken, and the layers were separated. The aqueous layer was acidified to pH ~4-5 with AcOH. The resulting precipitate was extracted with EtOAc (200 mL), washed with water (2×100 mL), dried (Na$_2$SO$_4$), filtered, and evaporated under reduced pressure to provide tert-butyl (4-chloro-2-formyl-5-hydroxyphenyl)carbamate as a yellow solid (4.79 g, 17.63 mmol, 63% yield). $^1$H NMR (300 MHz, DMSO-d$_6$): δ ppm 11.72 (s, 1H), 10.50 (s, 1H), 9.68 (br s, 1H), 7.99 (s, 1H), 7.88-7.91 (m, 1H), 1.48 (s, 9H). LCMS (Method 1): m/z 216 (M-56, loss of t-Bu).

Step-3: (R)-tert-butyl (4-chloro-2-formyl-5-(1-(pyridin-2-yl)ethoxy)phenyl)carbamate

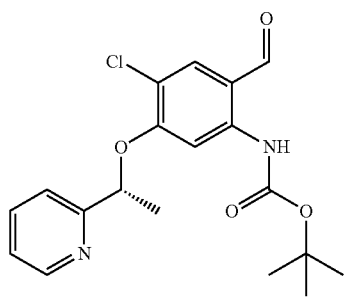 [SMILES: C[C@@H](Oc1cc(NC(=O)OC(C)(C)C)c(C=O)cc1Cl)c1ccccn1]

A mixture of (S)-1-(pyridin-2-yl)ethanol (454.3 mg, 3.69 mmol) tert-butyl (4-chloro-2-formyl-5-hydroxyphenyl)carbamate (1 g, 3.68 mmol) and triphenylphosphine (1.158 g, 4.42 mmol) was placed in a 100 mL round bottom flask under an atmosphere of nitrogen. THF (40 mL) was added by syringe. The resulting yellow solution was cooled on an ice bath and then DIAD (0.86 mL, 4.42 mmol) was added dropwise. The ice bath was removed and the solution was stirred at room temperature overnight. Once LCMS indicated the reaction had gone to completion, silica gel was added and the solvent was evaporated under reduced pressure. The sample was purified by column chromatography on a Biotage® MPLC chromatography system (using a 50 g silica gel column eluted with 0 to 13% EtOAc in hexanes) to provide 473.7 mg of a white solid. LCMS and NMR are consistent with (R)-tert-butyl (4-chloro-2-formyl-5-(1-(pyridin-2-yl)ethoxy)phenyl)carbamate contaminated with phenolic starting material (~5:1 product to starting material by NMR). The material was used for next step without further purification. $^1$H NMR (300 MHz, DMSO-d$_6$): δ ppm 10.42 (s, 1H), 9.73 (s, 1H), 8.54-8.60 (m, 1H), 7.98 (s, 1H), 7.92 (s, 1H), 7.82 (ddd, J=7.80, 7.80, 1.80 Hz, 1H), 7.44 (br d, J=7.90 Hz, 1H), 7.30-7.36 (m, 1H), 5.64 (q, J=6.35 Hz, 1H), 1.67 (d, J=6.45 Hz, 3H), 1.46 (s, 9H). LCMS (Method 1): m/z 377 [M+H]$^+$.

Step-4: (S)-ethyl 3-((tert-butoxycarbonyl)amino)butanoate (K)

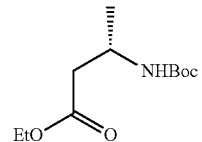

A suspension of (S)-3-aminobutanoic acid (6.25 g, 60.6 mmol) in EtOH (27.5 mL) was cooled on an ice bath. Thionyl chloride (7.5 mL, 103 mmol) was then added dropwise over 40 minutes, during which time the amino acid went into solution. The ice bath was allowed to melt, and the solution was stirred at room temperature overnight. The mixture was evaporated under reduced pressure, and the residue was mixed with more EtOH (60 mL) and again evaporated under reduced pressure to provide an oil. The oil was dissolved in DCM (55 mL) and cooled on an ice bath. TEA (25 mL, 179 mmol) was added dropwise over 15 minutes with stirring, resulting in a milky mixture. Di-tert-butyl dicarbonate (17 mL, 73.2 mmol) was then added. The ice bath was allowed to melt, and the mixture was stirred at room temperature for five days. The resulting mixture was filtered through Celite® 545 on a Buchner funnel, and the filter cake was washed with DCM (50 mL). The filtrate was washed with saturated aqueous citric acid (20 mL) and water (2×100 mL), dried (MgSO$_4$), filtered, and evaporated under reduced pressure to provide the title compound as a clear oil. $^1$H NMR is consistent with (S)-ethyl 3-((tert-butoxycarbonyl)amino)butanoate (13.47 g, 58.2 mmol, 96% yield). $^1$H NMR (300 MHz, CDCl$_3$): δ ppm 4.95 (br s, 1H), 4.15 (q, J=7.13, 2H), 3.98-4.10 (m, 1H), 2.40-2.57 (m, 2H), 1.44 (s, 9H), 1.27 (t, J=7.18, 3H), 1.22 (d, J=6.74, Hz, 3H).

Step-5 & 6: 3-((S)-1-aminoethyl)-6-chloro-7-((R)-1-(pyridin-2-yl)ethoxy)quinolin-2(1H)-one hydrochloride (II-14)

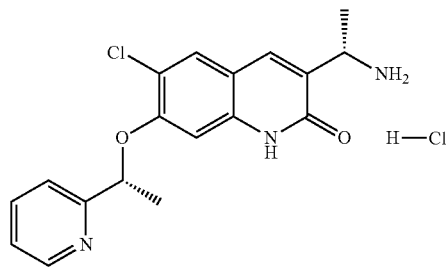

An oven-dried 25 mL round bottom flask and stir bar were placed under an atmosphere of nitrogen. THF (2.25 mL) and diisopropylamine (0.27 mL, 1.894 mmol) were then added by syringe. The solution was cooled using a dry ice/acetone bath (−78° C.) and n-BuLi (1.6 M in hexane, 1.15 mL, 1.84 mmol) was added dropwise over 5 minutes. After stirring for 10 minutes, a solution of (S)-ethyl 3-((tert-butoxycarbonyl)amino)butanoate K (115.3 mg, 0.499 mmol) in THF (0.5 mL) was added dropwise (over 5 minutes). The solution was stirred for 75 minutes at −78° C. and then a solution of (R)-tert-butyl (4-chloro-2-formyl-5-(1-(pyridin-2-yl)ethoxy)phenyl)carbamate (188.7 mg, 0.501 mmol) in THF (1.0 mL) was added dropwise by syringe. The reaction solution became yellow when the aldehyde was added. The reaction was stirred at −78° C. for 13 minutes and then quenched by the addition of saturated aqueous NH$_4$Cl solution (2.5 mL). The mixture was partitioned between EtOAc and water (10 mL each). The organic layer was dried (MgSO$_4$), filtered, and evaporated under reduced pressure to provide an impure mixture of isomers of (3S)-ethyl 3-((tert-butoxycarbonyl)amino)-2-((2-((tert-butoxycarbonyl)amino)-5-chloro-4-((R)-1-(pyridin-2-yl)ethoxy)phenyl)(hydroxy) methyl)butanoate as a yellow oil (344.8 mg; LCMS: m/z+608 [M+H]$^+$). The crude material (334 mg) was dissolved in 1,4-dioxane (5 mL) treated with 12M aqueous HCl (0.125 mL), and stirred at 110° C. for 90 minutes, during which time a red material precipitated. The mixture was allowed to cool and the supernatant was decanted and discarded. Heptane (~4 mL) was added to the red precipitate remaining in the round bottom and then evaporated under reduced pressure to provide 161.8 mg of a red solid. The material was triturated with $^i$PrOH (5 mL) and the resulting precipitate was collected on a Hirsch funnel and washed with $^i$PrOH (1 mL) and ethyl ether (~20 mL) to provide 3-((S)-1-aminoethyl)-6-chloro-7-((R)-1-(pyridin-2-yl)ethoxy)quinolin-2(1H)-one hydrochloride (104.2 mg, 0.274 mmol, 55% yield) as a red solid, impure but suitable for use as it is. $^1$H NMR (300 MHz, Methanol-d$_4$): δ ppm 8.81-8.87 (m, 1H), 8.55-8.64 (m, 1H), 8.18 (d, J=7.92 Hz, 1H), 7.96-8.04 (m, 1H), 7.95 (s, 1H), 7.85 (s, 1H), 6.99 (s, 1H), 5.98 (q, J=6.84 Hz, 1H), 4.48 (q, J=6.84 Hz, 1H), 1.86 (d, J=6.45 Hz, 3H), 1.64 (d, J=6.74 Hz, 3H). LCMS (Method 1): m/z 344 [M+H]$^+$.

Example 17—Intermediate II-15: (S)-3-(1-aminoethyl)-6-chloro-7-(cyclopropylmethoxy) quinolin-2(1H)one

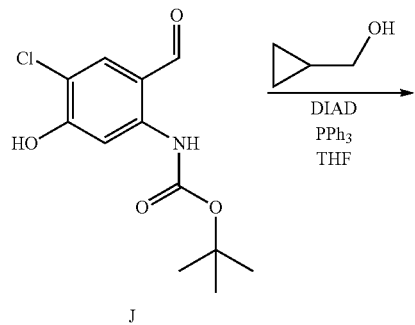

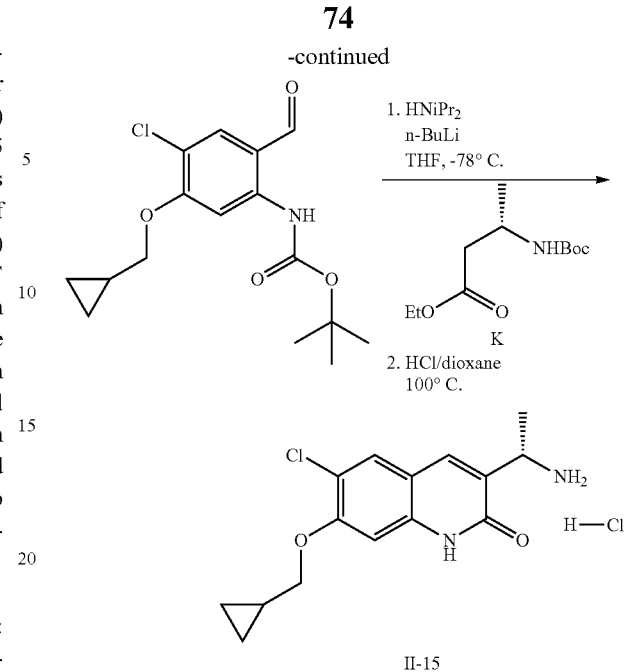

Step-1: tert-butyl (4-chloro-5-(cyclopropylmethoxy)-2-formylphenyl)carbamate

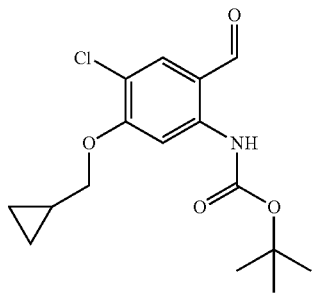 [SMILES: CC(C)(C)OC(=O)Nc1cc(OCC2CC2)c(Cl)cc1C=O]

A mixture of cyclopropylmethanol (0.145 mL, 1.838 mmol) tert-butyl (4-chloro-2-formyl-5-hydroxyphenyl)carbamate J (499.4 mg, 1.838 mmol) and triphenylphosphine (579.4 mg, 2.209 mmol) was placed in a 100 mL round bottom flask under an atmosphere of nitrogen and THF (20 mL) was then added by syringe. The resulting orange solution was cooled on an ice bath and DIAD (0.43 mL, 2.184 mmol) was added dropwise. The ice bath was removed and the solution was stirred at room temperature for 48 hours. Once LCMS indicated the reaction had gone to completion, silica gel was added and the solvent was evaporated under reduced pressure. The sample was purified by column chromatography on a Biotage® MPLC chromatography system using a 25 g silica gel column eluted with 0 to 3% EtOAc in hexanes to provide tert-butyl (4-chloro-5-(cyclopropylmethoxy)-2-formylphenyl)carbamate (410.6 mg, 1.260 mmol, 68.6% yield) as a yellowish solid. $^1$H NMR (300 MHz, DMSO-d$_6$): δ ppm 10.57 (s, 1H), 9.75 (s, 1H), 7.95-8.00 (m, 2H), 4.02 (d, J=7.04 Hz, 2H), 1.49 (s, 9H), 1.23-1.31 (m, 1H), 0.57-0.66 (m, 2H), 0.38-0.46 (m, 2H). LCMS (Method 1): m/z 270 (loss of t-Bu).

Step-2 & 3: (S)-3-(1-aminoethyl)-6-chloro-7-(cyclo-propylmethoxy)quinolin-2(1H)-one hydrochloride (II-15)

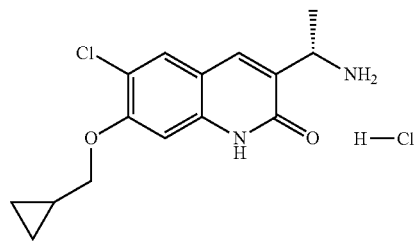

An oven-dried 25 mL round bottom flask and stir bar were placed under an atmosphere of nitrogen and THF (5.6 mL) and diisopropylamine (0.53 mL, 3.72 mmol) were added by syringe. The solution was cooled on a dry ice/acetone bath (to −78° C.) and n-BuLi (1.6 M in hexane, 2.35 mL, 3.76 mmol) was added dropwise over a 5 minute period. After stirring for 15 minutes, a solution of (S)-ethyl 3-((tert-butoxycarbonyl)amino)butanoate K (286 mg, 1.238 mmol) in THF (1.25 mL) was added dropwise (over 5 minutes). The solution was stirred for 80 minutes at −78° C. and a solution of tert-butyl (4-chloro-5-(cyclopropylmethoxy)-2-formyl-phenyl)carbamate (403.2 mg, 1.238 mmol) in THF (2.5 mL) was added dropwise by syringe. The reaction solution became yellow when the aldehyde was added. The reaction was stirred at −78° C. for 12 minutes and then quenched by addition of saturated aqueous NH$_4$Cl solution (6 mL). The mixture was partitioned between EtOAc and water (25 mL each) and the organic layer was dried (MgSO$_4$), filtered, and evaporated under reduced pressure to provide 724.5 g of a yellowish oil. The material was dissolved in 1,4-dioxane (12.5 mL) treated with 12M HCl (aqueous; 0.32 mL), and stirred at 110° C. for 70 minutes during which time the solution became thick with a pink precipitate. The sample was allowed to cool and the solvent was evaporated under reduced pressure to provide 1.13 g of a fibrous red solid. The material was triturated with i-PrOH (15 mL) and the resulting precipitate was collected on a Buchner funnel and washed with i-PrOH (20 mL) and ethyl ether (~60 mL) to provide (S)-3-(1-aminoethyl)-6-chloro-7-(cyclopropyl-methoxy)quinolin-2(1H)-one hydrochloride (146.1 mg, 0.444 mmol, 36% yield) as a papery white solid. $^1$H NMR (300 MHz, DMSO-d$_6$): δ ppm 12.13 (br s, 1H), 8.21 (br s, 3H), 7.98 (s, 1H), 7.86 (s, 1H), 6.98 (s, 1H), 4.32-4.46 (m, 1H), 3.96 (d, J=6.40 Hz, 2H), 1.51 (d, J=6.70 Hz, 3H), 1.21-1.35 (m, 1H), 0.55-0.68 (m, 2H), 0.35-0.46 (m, 2H). LCMS (Method 1): m/z 293 [M+H]$^+$.

Example 18—Intermediate II-16: 3-(1-Aminoethyl)-6-chloro-7-((3,3-difluorocyclobutyl) methoxy)quino-lin-2(1H)-one

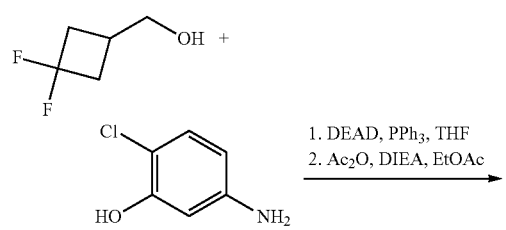

Step-1: N-(4-Chloro-3-((3,3-difluorocyclobutyl)methoxy)phenyl)acetamide

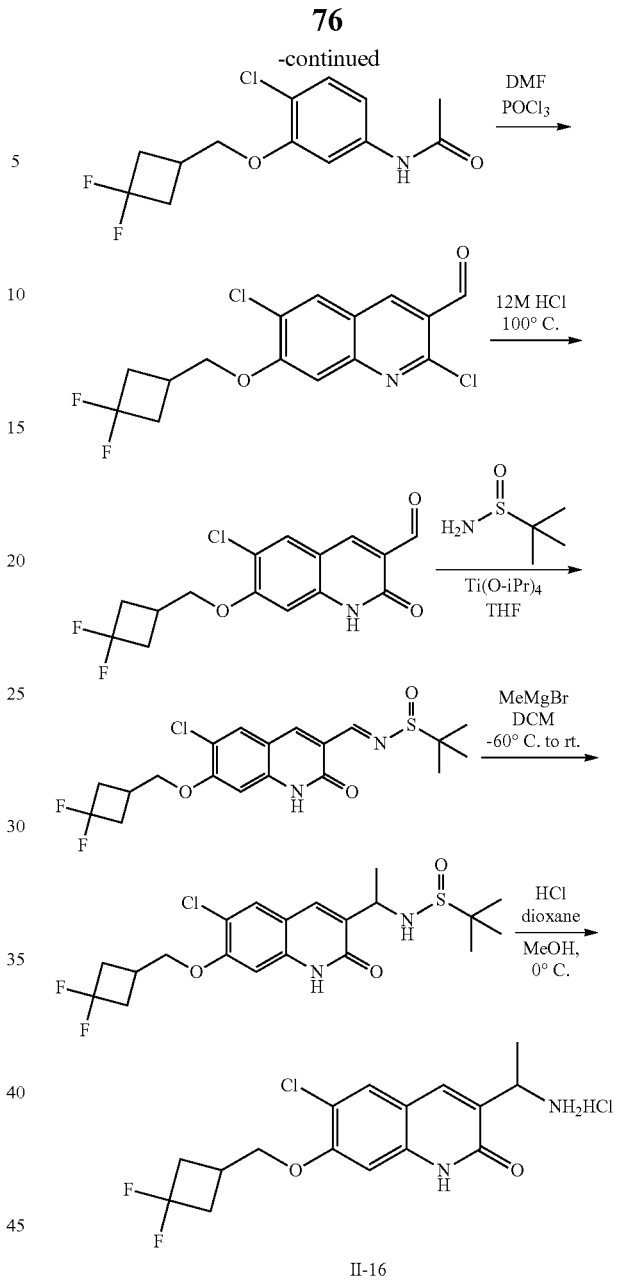

A solution of 5-amino-2-chlorophenol (3 g, 20.90 mmol) (3,3-difluorocyclobutyl)methanol (2.66 g, 21.78 mmol) in THF (375 mL) was placed under an atmosphere of nitrogen and treated with DEAD (3.90 mL, 24.63 mmol). The solution was stirred at room temperature for 48 hours. Once LCMS indicated adequate progression of the reaction, the silica gel was added to the solution and evaporated under reduced pressure. The material was purified by column chromatography on a Biotage® MPLC chromatography system (using a 340 g silica gel column eluted with 0 to 100% EtOAc in hexanes with isocratic elution when peaks eluted) to provide 3.89 g of the title compound as a brown liquid. LCMS was consistent with impure 4-chloro-3-((3,3-difluorocyclobutyl)methoxy)aniline (m/z 248 [M+H]$^+$). The sample was dissolved in EtOAc (80 mL) and treated with DIEA (3.00 mL, 17.18 mmol) and Ac$_2$O (1.60 mL, 16.96 mmol). The solution was stirred at room temperature overnight. The solution was then washed with water and brine (50 mL each), dried (Na$_2$SO$_4$), filtered, and evaporated under reduced pressure. The residue was purified by column chromatography on a Biotage® MPLC chromatography system (using a 50 g silica gel column, eluted with 0 to 50% EtOAc in hexanes with isocratic elution when peaks eluted) to provide 3.16 g of the title compound as a light brown oil, which slowly crystallized on standing. LCMS and $^1$H NMR are consistent with N-(4-chloro-3-((3,3-difluorocyclobutyl)methoxy)phenyl)acetamide (3.16 g, 10.91 mmol, 52% yield) In the NMR one proton is obscured by the solvent signal. $^1$H NMR (300 MHz, DMSO-d$_6$): δ ppm 11.91 (s, 1H), 8.54-8.67 (m, 1H), 7.80-7.95 (m, 2H), 7.68 (s, 1H), 7.56 (d, J=7.30 Hz, 1H), 7.34-7.44 (m, 1H), 7.29 (d, J=9.10 Hz, 1H), 7.13-7.22 (m, 1H), 7.03 (s, 1H), 6.31 (br s, 1H), 6.22 (d, J=7.90 Hz, 1H), 5.30 (s, 2H), 4.10-4.26 (m, 2H), 3.78 (s, 3H). LCMS (Method 1): m/z 290 [M+H]$^+$.

Step-2: 2,6-Dichloro-7-((3,3-difluorocyclobutyl)methoxy)quinoline-3-carbaldehyde

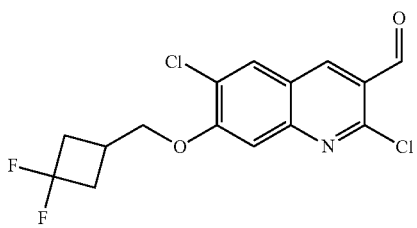 [SMILES: O=Cc1cc2cc(Cl)c(OCC3CC(F)(F)C3)cc2nc1Cl]

A tube was capped with a septum and placed under an atmosphere of nitrogen. DMF (2.15 mL, 27.8 mmol) was then added by syringe and the resulting reaction mixture was cooled on an ice bath. POCl$_3$ (8.40 mL, 90 mmol) was added dropwise by syringe (10 minutes) during which time a white material precipitated. The solution was then allowed to warm to room temperature over 10 minutes and the mixture was treated with N-(4-chloro-3-((3,3-difluorocyclobutyl)methoxy)phenyl)acetamide (2.44 g, 8.42 mmol) The mixture was stirred at 80° C. for two days. The resulting thick red solution was pipetted onto ice, resulting in a yellow precipitate. The precipitate was collected on a Buchner funnel, washed with water (~500 mL), and dried to provide 2.38 g of the title compound as a pale yellow solid. LCMS and $^1$H NMR are consistent with 2,6-dichloro-7-((3,3-difluorocyclobutyl)methoxy)quinoline-3-carbaldehyde (2.38 g, 6.88 mmol, 82% yield) $^1$H NMR (300 MHz, DMSO-d$_6$): δ ppm 10.31-10.36 (m, 1H), 8.88 (s, 1H), 8.48 (s, 1H), 7.65 (s, 1H), 4.37 (d, J=4.69 Hz, 2H), 2.53-2.84 (m, 5H). LCMS (Method 1): m/z 346 [M+H]$^+$.

Step-3: 6-Chloro-7-((3,3-difluorocyclobutyl)methoxy)-2-oxo-1,2-dihydroquinoline-3-carbaldehyde

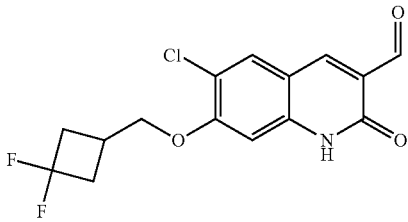 [SMILES: O=Cc1cc2cc(Cl)c(OCC3CC(F)(F)C3)cc2[nH]c1=O]

A solution of 2,6-dichloro-7-((3,3-difluorocyclobutyl)methoxy)quinoline-3-carbaldehyde (2.66 g, 7.68 mmol) in concentrated HCl (75 mL) was stirred at 100° C. for one day during which time a red crust formed on the surface of the flask. The mixture was diluted with water (800 mL), resulting in formation of a red precipitate. The mixture was allowed to stand at room temperature for 4 days. The precipitate was then collected on a Buchner funnel, washed with water (1 L), and dried under vacuum at 50° C. to provide 2.16 g of the title compound as a red solid. LCMS and $^1$H NMR are consistent with 6-chloro-7-((3,3-difluorocyclobutyl)methoxy)-2-oxo-1,2-dihydroquinoline-3-carbaldehyde (2.16 g, 6.59 mmol, 86% yield) $^1$H NMR (300 MHz, DMSO-d$_6$): δ ppm 12.21 (s, 1H), 10.16-10.18 (m, 1H), 8.43 (s, 1H), 8.09 (s, 1H), 6.94 (s, 1H), 4.20 (d, J=4.10 Hz, 2H), 2.54-2.80 (m, 5H). LCMS (Method 1): m/z+328 [M+H]$^+$.

Step-4: (E)-N-((6-Chloro-7-((3,3-difluorocyclobutyl)methoxy)-2-oxo-1,2-dihydroquinolin-3-yl)methylene)-2-methylpropane-2-sulfinamide

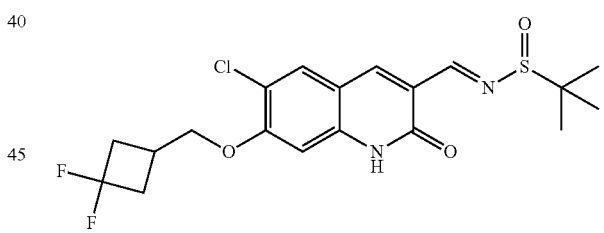

A mixture of 6-chloro-7-((3,3-difluorocyclobutyl)methoxy)-2-oxo-1,2-dihydroquinoline-3-carbaldehyde (499.6 mg, 1.525 mmol) and 2-methylpropane-2-sulfinamide (222.1 mg, 1.832 mmol) was placed in a 25 mL round bottom flask under an atmosphere of nitrogen. THF (3.0 mL) and titanium (IV) isopropoxide (Ti(O$^i$Pr)$_4$) (0.90 mL, 3.07 mmol) were added by syringe, and the suspension was stirred at room temperature overnight. Once LCMS indicated near completion of reaction, the reaction was quenched by dropwise addition of saturated aqueous NH$_4$Cl solution (2 mL). The material was then triturated with EtOAc (100 mL) and the resulting precipitate was filtered through Celite®. The filter cake was washed with EtOAc (50 mL), sonicated in EtOAc for 15 minutes and filtered using a Buchner funnel. The filtrates were combined and washed with brine (100 mL), dried (Na$_2$SO$_4$), filtered, and evaporated under reduced pressure to provide 413 mg of the title compound as a yellow solid. LCMS and $^1$H NMR are consistent with (E)-N-((6-chloro-7-((3,3-difluorocyclobutyl)methoxy)-2-oxo-1,2-dihydroquinolin-3-yl)methylene)-2-methylpropane-2-sulfinamide (413 mg, 0.958 mmol, 62.9% yield) $^1$H NMR (300 MHz, DMSO-$d_6$): δ ppm 12.21 (s, 1H), 8.74 (s, 1H), 8.59 (s, 1H), 8.09 (s, 1H), 6.95 (s, 1H), 4.19 (d, J=4.40 Hz, 2H), 2.55-2.79 (m, 5H), 1.19 (s, 9H). LCMS (Method 1): m/z 431 [M+H]$^+$.

Step-5: N-(1-(6-Chloro-7-((3,3-difluorocyclobutyl)methoxy)-2-oxo-1,2-dihydroquinolin-3-yl)ethyl)-2-methylpropane-2-sulfinamide

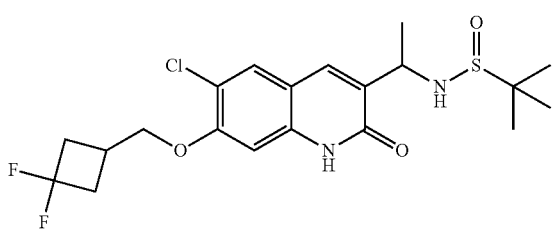 [SMILES: CC(NS(=O)C(C)(C)C)c1cc2cc(Cl)c(OCC3CC(F)(F)C3)cc2[nH]c1=O]

(E)-N-((6-Chloro-7-((3,3-difluorocyclobutyl)methoxy)-2-oxo-1,2-dihydroquinolin-3-yl) methylene)-2-methylpropane-2-sulfinamide (411.3 mg, 0.955 mmol) was placed in a 100 mL round-bottom flask under an atmosphere of nitrogen. DCM (7.6 mL) was added, and the suspension was cooled on a dry ice/chloroform bath (to approx. −60° C.). Methylmagnesium bromide (MeMgBr, 3M in ether) (0.95 mL, 2.85 mmol) was added dropwise. The cold bath was then allowed to warm to room temperature overnight, resulting in an orange solution. Once LCMS indicated reaction completion, the solution was cooled on an ice bath and treated dropwise with water (5 mL), resulting in precipitation. The mixture was diluted with EtOAc (100 mL) and washed with water (100 mL). Silica gel was added to the organic layer and the solvent was evaporated under reduced pressure. The material was purified by column chromatography on a Biotage® MPLC chromatography system (eluted with 0 to 5% MeOH in DCM with isocratic elution at 3.2% MeOH) to provide 345.5 mg of the title compound as a brown brittle foam. LCMS and $^1$H NMR are consistent with N-(1-(6-chloro-7-((3,3-difluorocyclobutyl)methoxy)-2-oxo-1,2-dihydroquinolin-3-yl)ethyl)-2-methylpropane-2-sulfinamide (345.5 mg, 0.773 mmol, 81% yield). NMR shows a ~1:1 mixture of diastereomers. LCMS (Method 1): m/z 447 [M+H]$^+$.

Step-6: 3-(1-Aminoethyl)-6-chloro-7-((3,3-difluorocyclobutyl)methoxy)quinolin-2(1H)-one hydrochloride (II-16)

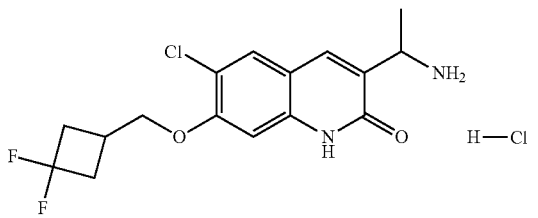 [SMILES: CC(N)c1cc2cc(Cl)c(OCC3CC(F)(F)C3)cc2[nH]c1=O ; Cl]

A solution of N-(1-(6-chloro-7-((3,3-difluorocyclobutyl)methoxy)-2-oxo-1,2-dihydroquinolin-3-yl)ethyl)-2-methylpropane-2-sulfinamide (342.7 mg, 0.767 mmol) in MeOH (7.0 mL) was cooled on an ice bath and treated dropwise with 4M HCl in 1,4-dioxane (4 mL). The solution was then stirred for 25 minutes. The solvents were evaporated under reduced pressure at room temperature. The residue was triturated with 20 mL ethyl ether and the resulting precipitate was collected on a Hirsch funnel and washed with more ethyl ether to provide 271.4 mg of a pink solid. LCMS and $^1$H NMR are consistent with 3-(1-aminoethyl)-6-chloro-7-((3,3-difluorocyclobutyl)methoxy)quinolin-2(1H)-one hydrochloride (271.4 mg, 0.716 mmol, 93% yield) $^1$H NMR (300 MHz, Methanol-$d_4$): δ ppm 7.95 (s, 1H), 7.79 (s, 1H), 6.96 (s, 1H), 4.48-4.55 (m, 1H), 4.20 (d, J=4.10 Hz, 2H), 2.56-2.79 (m, 5H), 1.68 (d, J=7.04 Hz, 3H). LCMS (Method 1): m/z 343 [M+H]$^+$.

Example 19—Intermediate II-17: (S)-3-(1-Aminoethyl)-6-chloro-8-fluoroquinolin-2(1H)-one

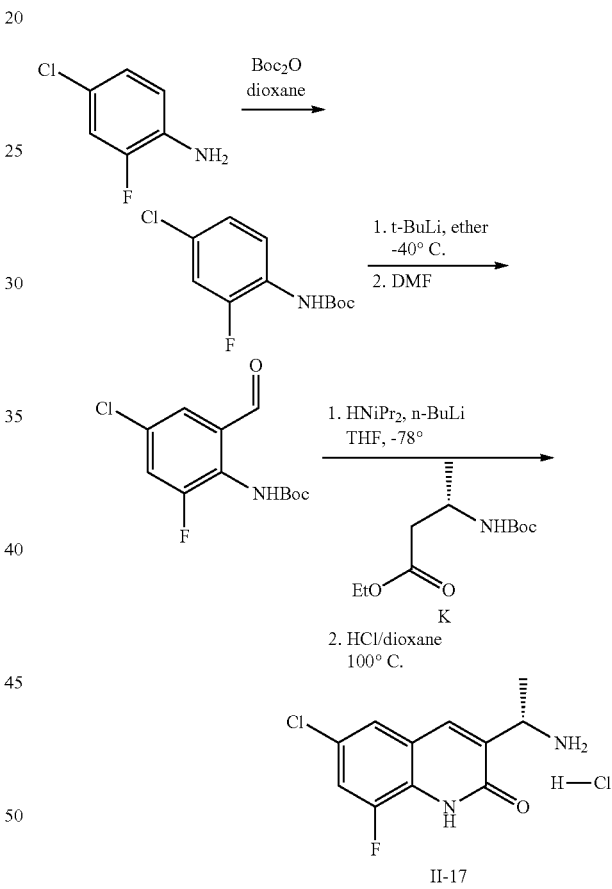

Step-1: tert-Butyl (4-chloro-2-fluorophenyl)carbamate

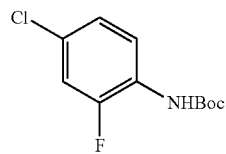 [SMILES: CC(C)(C)OC(=O)Nc1ccc(Cl)cc1F]

A solution of 4-chloro-2-fluoroaniline (2 g, 13.74 mmol) and di-tert-butyl dicarbonate (6.4 mL, 27.6 mmol) in 1,4-dioxane (50 mL) was stirred at reflux for 2 days. The solvent was then evaporated. The resulting oil was diluted with MeOH, water, and aqueous ammonium hydroxide solution (10 mL each) and vigorously stirred for 45 minutes. The organic lower layer was separated. The organic material was diluted with EtOAc (50 mL), and washed with water (50 mL), 3.6% aqueous HCl solution (2×50 mL), saturated aqueous NaHCO$_3$ solution (50 mL), and then again with water (2×50 mL). The organic layer was dried (MgSO$_4$), filtered, and evaporated under reduced pressure to provide tert-butyl (4-chloro-2-fluorophenyl)carbamate (3.0011 g, 12.22 mmol, 89% yield) as a reddish liquid that solidified on standing. $^1$H NMR (300 MHz, DMSO-d$_6$): δ ppm 9.12 (s, 1H), 7.63 (t, J=8.65 Hz, 1H), 7.42 (dd, J=10.85, 2.35 Hz, 1H), 7.18-7.24 (m, 1H), 1.45 (s, 9H). LCMS (Method 1): m/z 246 [M+H]$^+$.

Step-2: tert-Butyl (4-chloro-2-fluoro-6-formylphenyl)carbamate

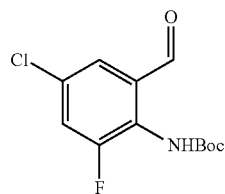 [SMILES: CC(C)(C)OC(=O)Nc1c(F)cc(Cl)cc1C=O]

An oven-dried 3-necked 500 mL round bottom flask was fitted with an oven-dried addition funnel and placed under an atmosphere of nitrogen. tert-Butyl (4-chloro-2-fluorophenyl)carbamate (5.44 g, 22.14 mmol) and ethyl ether (91 mL) were added by syringe. The clear solution was cooled on an acetonitrile/dry ice bath (to approximately −40° C.). tert-Butyllithium (1.7M in pentane, 33 mL, 22.14 mmol) was added to the addition funnel by cannula. The t-BuLi solution was added dropwise to the ether solution (over ~10 minutes), during which time the ether solution began to turn orange. The solution was stirred at about −40° C. for 2 hours, during which time it progressively became more orange. DMF (8.7 mL, 112 mmol) was added dropwise (over ~10 minutes), resulting in precipitation of a yellow solid. The MeCN/dry ice bath was replaced with an ice bath and the mixture was stirred for an additional 2 hours. The reaction was then quenched by dropwise addition of water (20 mL), resulting in a brown mixture and the ice bath was removed. The mixture was diluted with EtOAc (100 mL), washed with water (2×100 mL), dried (Na$_2$SO$_4$), filtered, and evaporated under reduced pressure to provide 5.45 g of an oily black solid. The material was triturated with hexanes (50 mL), collected on a Buchner funnel and washed with more hexanes to provide 2.73 g tert-butyl (4-chloro-2-fluoro-6-formylphenyl)carbamate as a yellow powder. The filtrate was evaporated under reduced pressure, the residue was triturated in hexanes (~15 mL), and the resulting yellow solid was collected on a Hirsch funnel to provide a second crop of the title compound (0.66 g). A total of 3.39 g (12.4 mmol, 56% yield) of tert-butyl (4-chloro-2-fluoro-6-formylphenyl)carbamate was recovered. $^1$H NMR (300 MHz, DMSO-d$_6$): δ ppm 9.93 (d, J=0.88 Hz, 1H), 9.47 (s, 1H), 7.81-7.90 (m, 1H), 7.55-7.61 (m, 1H), 1.44 (s, 9H). LCMS (Method 1): m/z 296 [M+Na].

Steps-3 & 4: (S)-3-(1-Aminoethyl)-6-chloro-8-fluoroquinolin-2(1H)-one hydrochloride (II-17)

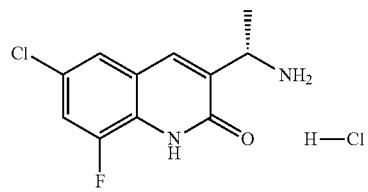 [SMILES: C[C@H](N)c1cc2cc(Cl)cc(F)c2[nH]c1=O ; Cl]

An oven-dried 200 mL round bottom flask and stir bar were placed under an atmosphere of nitrogen. THF (17 mL) and diisopropylamine (1.59 mL, 11.16 mmol) were added by syringe. The resulting solution was cooled on a dry ice/acetone bath (to approximately −78° C.) and then n-butyllithium (1.6M in hexane, 7.1 mL, 11.36 mmol) was added dropwise over a 5 minute period. After stirring for 15 minutes, a solution of (S)-ethyl 3-((tert-butoxycarbonyl)amino)butanoate K (860.7 mg, 3.72 mmol) in THF (3.75 mL) was added dropwise over 5 minutes. The solution was stirred for 80 minutes at −78° C., and a solution of tert-butyl (4-chloro-2-fluoro-6-formylphenyl)carbamate (1016.4 mg, 3.71 mmol) in THF (7.5 mL) was then added dropwise by syringe. The reaction was stirred at −78° C. for another 22 minutes and then quenched by addition of saturated aqueous NH$_4$Cl solution (17 mL). The mixture was partitioned between EtOAc and water (100 mL each). The organic layer was dried (MgSO$_4$), filtered, and evaporated under reduced pressure to provide 1.88 g of the title compound as an orange gum. The material was dissolved in 1,4-dioxane (38 mL) treated with 12M aqueous HCl (0.96 mL), and stirred at 110° C. for 50 minutes. The sample was then allowed to cool. The solvent was evaporated under reduced pressure to provide 1.24 g of a red solid. The material was triturated in IPA (25 mL), collected on a Hirsch funnel and washed sequentially with IPA (5 mL) and ethyl ether (~20 mL) to provide (S)-3-(1-aminoethyl)-6-chloro-8-fluoroquinolin-2(1H)-one hydrochloride (370.4 mg, 1.337 mmol, 36% yield) as a red solid. $^1$H NMR (300 MHz, DMSO-d$_6$): δ ppm 12.41 (s, 1H), 8.33 (br s, 3H), 8.10 (s, 1H), 7.67-7.76 (m, 2H), 4.38-4.53 (m, 1H), 1.52 (d, J=7.04 Hz, 3H). LCMS (Method 1): m/z 241 [M+H]$^+$.

Example 20—Intermediate II-18: (S)-3-(1-aminoethyl)-6-chloro-7-isopropoxy quinolin-2(1H)-one

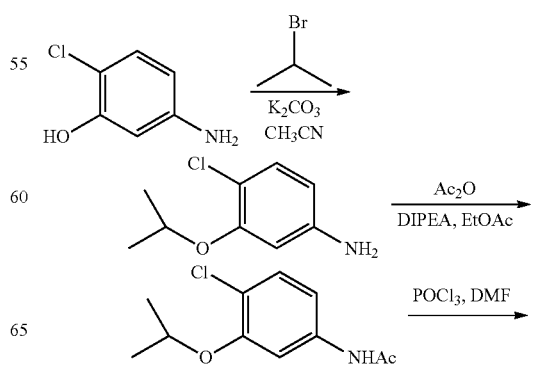

-continued

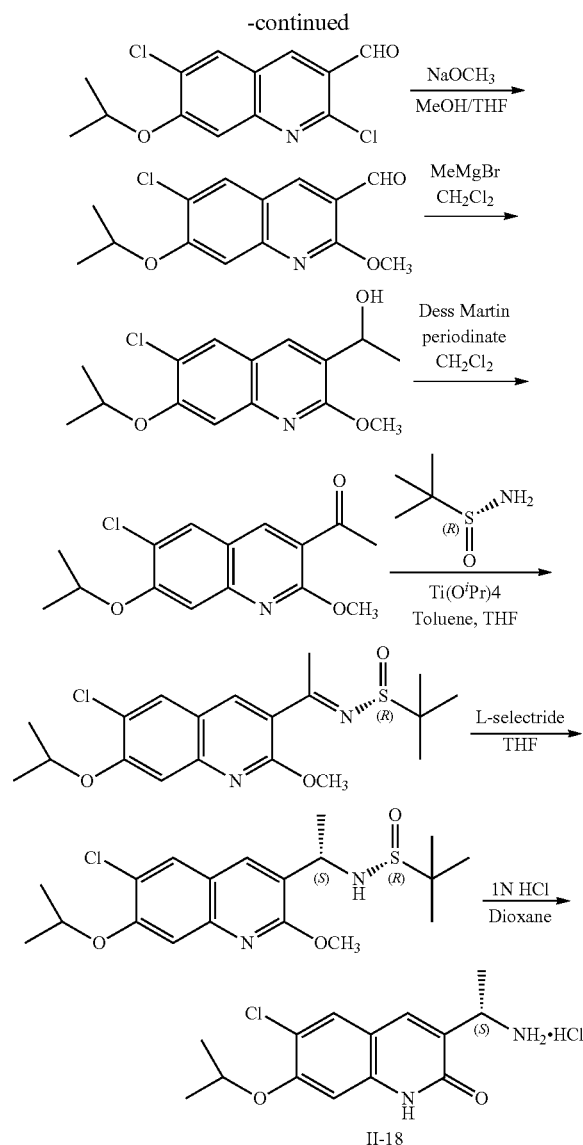

Step-1: 4-Chloro-3-isopropoxyaniline

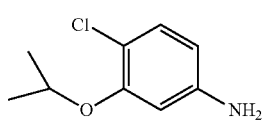

A mixture of 5-amino-2-chlorophenol (20 g, 139 mmol) and 2-bromopropane (26 mL, 278 mmol) and K₂CO₃ (38.4 g, 278 mmol) in CH₃CN (300 mL) was refluxed for 24 h. The reaction mixture was cooled to room temperature, filtered and the solid was washed with ethyl acetate (150 mL). The filtrate was concentrated and the residue was purified by ISCO (SiO₂: Hex/EtOAc 0 to 40%) to give the title compound, 4-Chloro-3-isopropoxyaniline (22.6 g, 87%). Step 2: N-(4-Chloro-3-isopropoxyphenyl)acetamide

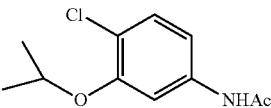

To a mixture of 4-chloro-3-isopropoxyaniline (22.5 g, 121 mmol) in CH₂Cl₂ (200 mL) was added DIPEA (42 mL, 242 mmol) followed by acetic anhydride (17 mL, 181 mmol). The resultant mixture was stirred at room temperature for 3 h. Upon the completion of the reaction, water (100 mL) was added and stirred for 10 minutes. The organic layer was separated, washed with 1N HCl (aq, 200 mL), brine (150 mL) and dried over anhydrous Na₂SO₄. The solution was filtered and concentrated. The crude residue was recrystallized from CH₂Cl₂/hexanes to give desired compound N-(4-Chloro-3-isopropoxyphenyl)acetamide (19.6 g, 71%).

Step-3: 2,6-Dichloro-7-isopropoxyquinoline-3-carbaldehyde

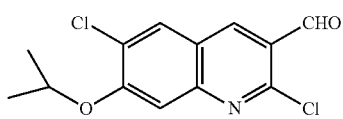 [SMILES: CC(C)Oc1cc2nc(Cl)c(C=O)cc2cc1Cl]

DMF (15 mL, 193.6 mmol) was added to a 350 mL seal tube and cooled to 0° C. To this solution was added phosphorous oxychloride (60.1 mL, 645.6 mmol) drop wise during 40-50 min. The resultant mixture was brought to room temperature followed by addition of N-(4-chloro-3-isopropoxyphenyl)acetamide (14.7 g, 64.5 mmol) in portions and heated at 80° C. overnight. The mixture was cooled to room temperature and carefully poured onto crushed ice. The yellow precipitate was filtered, washed with water and dried over P₂O₅ overnight to afford 2,6-Dichloro-7-isopropoxyquinoline-3-carbaldehyde as yellow solid (17.5 g, 95%).

Step-4: 6-Chloro-7-isopropoxy-2-methoxyquinoline-3-carbaldehyde

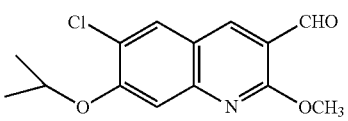 [SMILES: COc1nc2cc(OC(C)C)c(Cl)cc2cc1C=O]

To 2,6-dichloro-7-isopropoxyquinoline-3-carbaldehyde (5.8 g, 20.4 mmol) in a co-solvent of MeOH:THF (1:1, 100 mL) was added NaOMe (2.2 g, 40.8 mmol) portion wise at rt. The reaction mixture was refluxed for 3 h. After cooling to room temperature (rt), the reaction was quenched with aqueous NH₄Cl solution (20 mL). The mixture was extracted with EtOAc (25 mL×3). The combined organic layer was dried (Na₂SO₄), concentrated and purified by flash chromatography with Hexane/EA (3:1) to give 6-Chloro-7-isopropoxy-2-methoxyquinoline-3-carbaldehyde (5.07 g, 89%) as a yellow solid.

Step-5: 1-(6-Chloro-7-isopropoxy-2-methoxyquinolin-3-yl)ethanol

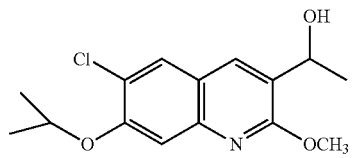 [SMILES: COc1nc2cc(OC(C)C)c(Cl)cc2cc1C(C)O]

To 6-chloro-7-isopropoxy-2-methoxyquinoline-3-carbaldehyde (5.07 g, 18.17 mmol) in THF (100 mL) at −78° C. was added a solution of MeMgCl in THF (3 M, 9.1 mL, 27.2 mmol) drop wise. The reaction was stirred at rt for 3 h and then quenched with aqueous NH$_4$Cl solution (50 mL). The organic layer was separated and the aqueous layer was extracted with EtOAc (25 mL×3). The combined organic layers were dried (Na$_2$SO$_4$), concentrated, and purified by silica gel chromatography with hexane/EA (3:1) to give compound I-(6-Chloro-7-isopropoxy-2-methoxyquinolin-3-yl)ethanol (4.06 g, 76%).

Step-6: 1-(6-Chloro-7-isopropoxy-2-methoxyquinolin-3-yl)ethanone

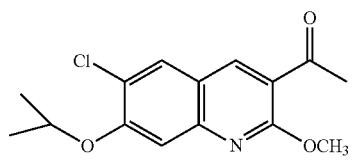

To 1-(6-chloro-7-isopropoxy-2-methoxyquinolin-3-yl)ethanol (4.06 g, 13.8 mmol) in CH$_2$Cl$_2$ (50 mL) at rt was added DMP (7.0 g, 16.5 mmol) portion wise. The reaction was stirred at rt for 2 h, and then was quenched with an aqueous solution of NaHCO$_3$ and Na$_2$S$_2$O$_3$. After stirring for 15 min, both layers became clear. The organic layer was separated and the aqueous layer was extracted with CH$_2$Cl$_2$ (30 mL×2). The combined organic layers were dried (Na$_2$SO$_4$), concentrated and purified by silica gel chromatography with hexane/EA (4:1) to give 1-(6-Chloro-7-isopropoxy-2-methoxyquinolin-3-yl)ethanone (3.67 g, 72%) as a white solid.

Step-7: (R,E)-N-(1-(6-chloro-7-isopropoxy-2-methoxyquinolin-3-yl)ethylidene)-2-methyl propane-2-sulfinamide

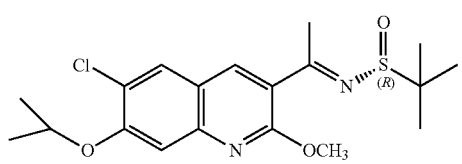

To 1-(6-chloro-7-isopropoxy-2-methoxyquinolin-3-yl)ethanone (3.67 g, 12.5 mmol) in THF/toluene (20 mL: 400 mL) at rt was added (R)-2-methylpropane-2-sulfinamide (3.03 g, 25 mmol) and Ti(O$^i$Pr)$_4$ (11 mL, 37.5 mmol,). The reaction was refluxed with a Dean-Stark apparatus. After the reaction was refluxed for 4 h and 150 mL of solvent was removed, the reaction was cooled to rt. The solvent was removed under vacuum, and 50 mL of EtOAc was added to the residue, followed by addition of 20 mL of saturated aqueous NaHCO$_3$ solution. After stirring for 10 min, the solid was removed through a pad of celite. The filtrate was extracted with EtOAc (200 mL×2), dried (Na$_2$SO$_4$), concentrated and purified by silica gel chromatography with hexane/EA (1:1) to give the title compound (4.32 g, 87%).

Step-8: (R)—N—((S)-1-(6-chloro-7-isopropoxy-2-methoxyquinolin-3-yl)ethyl)-2-methyl propane-2-sulfinamide

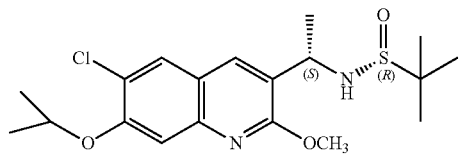

To (R,E)-N-(1-(6-chloro-7-isopropoxy-2-methoxyquinolin-3-yl)ethylidene)-2-methyl propane-2-sulfinamide (4.32 g, 10.9 mmol) in THF (100 mL) at −78° C., was added 1 M L-selectride (14.2 mL, 14.2 mmol) in THF drop wise. The reaction mixture was warmed to rt and stirred for 3 h. The reaction was quenched with aqueous saturated NH$_4$Cl (30 mL) solution and then extracted with EtOAc (20 mL×3). The combined organic layers were dried (Na$_2$SO$_4$), concentrated and purified by silica gel chromatography with hexane/EA (1:1) to give the desired compound (3.58 g, 82%).

Step-9: (S)-3-(1-aminoethyl)-6-chloro-7-isopropoxyquinolin-2(1H)-one hydrochloride salt (II-18)

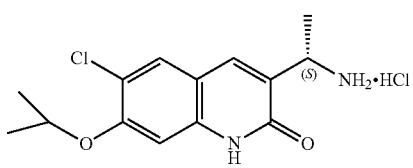

To (R)—N—((S)-1-(6-chloro-7-isopropoxy-2-methoxyquinolin-3-yl)ethyl)-2-methyl propane-2-sulfinamide (3.58 g, 8.99 mmol) in dioxane (50 mL) was added 2 N HCl (50 mL) at rt. The reaction was refluxed for 3 h. The solvent was removed under vacuum and the residue was dried under vacuum to afford crude II-18, which was further purified by trituration (CH$_2$Cl$_2$/MeOH/hexane) to give pure compound II-18 (2.44 g, 86%) as a white solid. $^1$H NMR (300 MHz, DMSO-d$_6$): δ 12.10 (s, 1H), 8.29 (br, s, 3H), 7.98 (s, 1H), 7.83 (s, 1H), 7.08 (s, 1H), 4.66 (m, 1H), 4.38 (m, 1H), 3.91 (s, 3H), 1.52 (d, J=6.87 Hz, 3H), 1.37 (d, J=6.03 Hz, 6H). LCMS (Method 3, APCI): RT=8.06 min, m/z=281.1 [M+H]$^+$.

Example 21—Intermediate IV-1: (S)-6-chloro-3-(1-(4-iodopyridin-2-ylamino) ethyl)quinolin-2(1H)-one

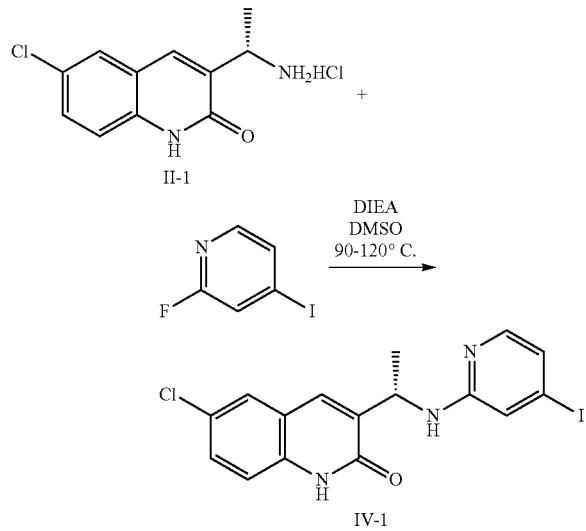

A mixture of (S)-3-(1-aminoethyl)-6-chloroquinolin-2(1H)-one hydrochloride II-1 (99.4 mg, 0.384 mmol) and 2-fluoro-4-iodopyridine (90.8 mg, 0.407 mmol) was treated with DMSO (1.3 ml) and DIEA (0.20 mL, 1.145 mmol) The solution was stirred at 90° C. for six hours, then 100° C. for two days, then 120° C. for one day. The sample was mixed with water (20 mL) and extracted with DCM (3×15 mL). The extracts were dried (Na$_2$SO$_4$), filtered, treated with silica gel, and evaporated under reduced pressure. The material was chromatographed by Biotage MPLC (10 g silica gel column, 0 to 50% EtOAc in hexanes, with isocratic elution at 42% EtOAc) to provide (S)-6-chloro-3-(1-(4-iodopyridin-2-ylamino)ethyl)quinolin-2(1H)-one IV-1 (50.7 mg, 0.119 mmol, 31.1% yield) as a yellowish solid. $^1$H NMR (300 MHz, DMSO-d$_6$): δ ppm 11.94 (s, 1H), 7.76 (d, J=2.35 Hz, 1H), 7.70 (s, 1H), 7.59 (d, J=5.28 Hz, 1H), 7.47 (dd, J=8.79, 2.05 Hz, 1H), 7.29 (d, J=8.50 Hz, 1H), 7.15 (d, J=7.04 Hz, 1H), 7.01 (s, 1H), 6.79 (dd, J=5.42, 1.32 Hz, 1H), 4.99-5.13 (m, 1H), 1.38 (d, J=6.74 Hz, 3H). LCMS (Method 1): Rt 2.15 min., m/z 425.8 [M+H]$^+$.

Example 22—Intermediate IV-2: (S)-3-(1-((4-bromopyridin-2-yl)amino)ethyl)-6-chloroquinolin-2(1H)-one

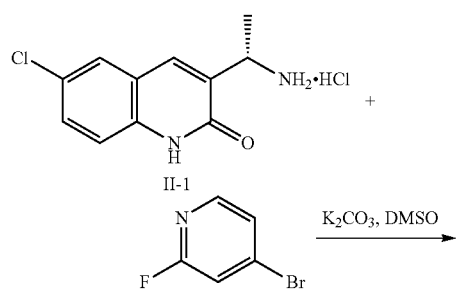

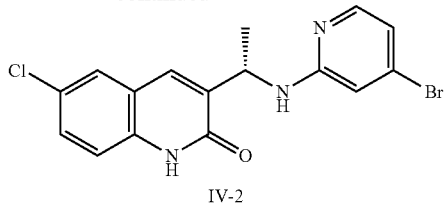

In a sealed tube under nitrogen flow were combined 4-bromo-2-fluoropyridine (1.0 g, 5.7 mmol), (S)-3-(1-aminoethyl)-6-chloroquinolin-2(1H)-one hydrochloride II-1 (500 mg, 1.9 mmol) and K$_2$CO$_3$ (0.54 g, 4.0 mmol) in 4 mL of anhydrous DMSO. The reaction mixture was stirred at 110-115° C. for 3.5 h in a sealed tube, cooled to a room temperature, diluted with EtOAc, washed with water and brine. Organic phase was dried over Na$_2$SO$_4$, filtered and concentrated to dryness under reduced pressure. The crude was purified by ISCO, using 40 g SiO$_2$-column with a gradient elution of EtOAc in CH$_2$Cl$_2$, to provide 175 mg (24% yield) of the title compound IV-2. $^1$H NMR (300 MHz, CDCl$_3$): δ ppm: 11.66 (br s 1H), 7.89 (d, J=5.5 Hz, 1H), 7.71 (s, 1H), 7.51 (d, J=2.2 Hz, 1H), 7.44 (dd, J1=8.8 Hz, J2=2.2 Hz, 1H), 7.28 (d, J=8.8 Hz, 1H), 6.70 (dd, J1=5.5 Hz, J2=1.6 Hz, 1H), 6.50 (d, J=1.6 Hz, 1H), 5.55 (br d, 1H), 5.05-5.15 (m, 1H), 1.61 (d, J=6.6 Hz, 3H). LCMS (Method 3), Rt 3.70 min. m/z 378.0/380.0 [M+H]+. MP=124-125° C.

Example 23—Intermediate IV-3: (S)-3-(1-(6-bromopyridin-2-ylamino)ethyl)-6-chloroquinolin-2(1H)-one

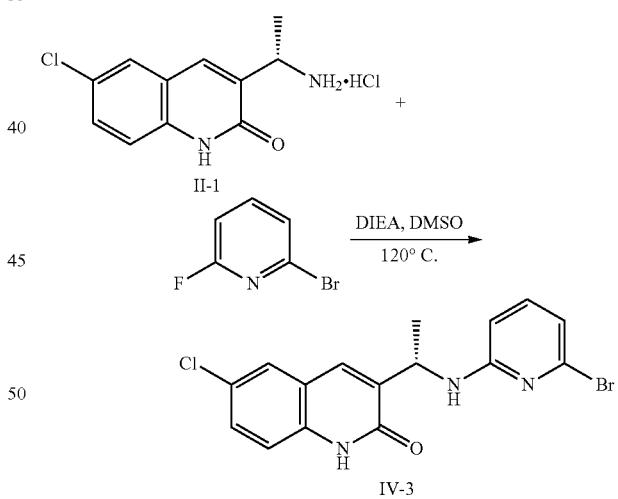

A mixture of (S)-3-(1-aminoethyl)-6-chloroquinolin-2(1H)-one hydrochloride II-1 (59.8 mg, 0.231 mmol) and 2-bromo-6-fluoropyridine (41.2 mg, 0.234 mmol) in DMSO (0.60 ml) was treated with DIEA (0.12 mL, 0.687 mmol) and stirred at 90° C. for twenty hours, then at 120° C. for one day. The sample was mixed with water (20 mL) and extracted with DCM (3×15 mL). The extracts were dried (Na$_2$SO$_4$), filtered, treated with silica gel, and evaporated under reduced pressure. The material was chromatographed by Biotage MPLC (10 g silica gel column, 0 to 50% EtOAc in hexanes, with isocratic elution at 42% EtOAc) to provide (S)-3-(1-(6-bromopyridin-2-ylamino)ethyl)-6-chloroquinolin-2(1H)-one IV-3 (56.2 mg, 0.148 mmol, 64.3% yield) as a white solid. ¹H NMR (300 MHz, DMSO-d₆): δ ppm 11.98 (s, 1H), 7.76 (d, J=2.05 Hz, 1H), 7.74 (s, 1H), 7.49 (dd, J=8.79, 2.05 Hz, 1H), 7.40 (d, J=7.33 Hz, 1H), 7.24-7.35 (m, 2H), 6.63 (d, J=7.04 Hz, 1H), 6.44 (d, J=8.20 Hz, 1H), 4.91-5.05 (m, 1H), 1.40 (d, J=6.74 Hz, 3H). LCMS (Method 1): Rt 2.59 min., m/z 378, 380 [M+H]⁺.

Example 24—Intermediate IV-4: (S)-6-chloro-3-(1-((3-fluoro-4-iodopyridin-2-yl)amino) ethyl)quinolin-2(1H)-one

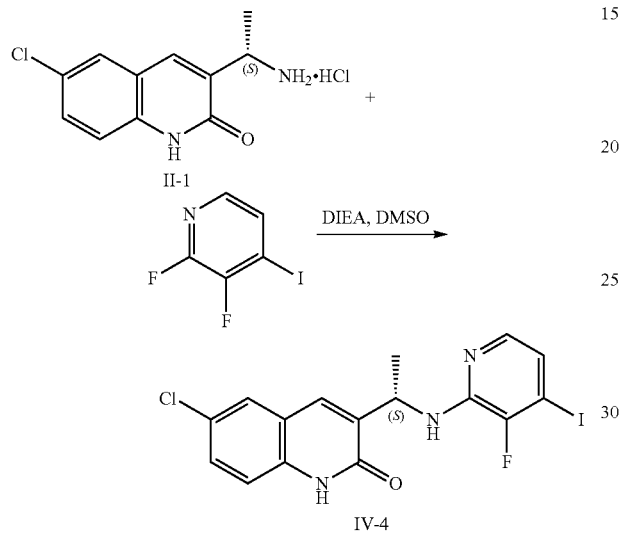

A mixture of (S)-3-(1-aminoethyl)-6-chloroquinolin-2 (1H)-one hydrochloride II-1 (6.93 g, 26.74 mmol), 2,3-difluoro-4-iodopyridine (6.5 g, 26.97 mmol) and K₂CO₃ (11.1 g, 80.31 mmol) in DMSO (70 mL) was heated at 110° C. for 4 h. The mixture was cooled to room temperature and poured onto crushed ice. The mixture was extracted with CH₂Cl₂ (3×100 mL), dried over anhydrous Na₂SO₄, filtered and evaporated to dryness. The resulting residue was purified by ISCO (SiO₂: hexanes/EtOAc 0 to 100%) followed by trituration with hexanes-isopropanol to give the title compound as an off-white solid (3.27 g, 28%). ¹H NMR (300 MHz, DMSO-d₆): δ 11.95 (br s, 1H), 7.75-7.73 (m, 1H), 7.49-7.39 (m, 2H), 7.29 (d, J=8.8 Hz, 1H), 7.15 (d, J=8.8 Hz, 1H), 6.89-6.86 (m, 1H), 5.25-5.18 (m, 1H), 1.44 (d, J=6.9 Hz, 3H). LCMS (method 3): Rt 5.14 min, m/z 444 [M+H]⁺.

Example 25—Intermediate VII-1: 6-(((6-chloro-7-hydroxy-2-oxo-1,2-dihydroquinolin-3-yl)methyl) amino)-2-methylnicotinonitrile

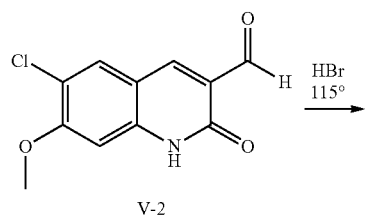

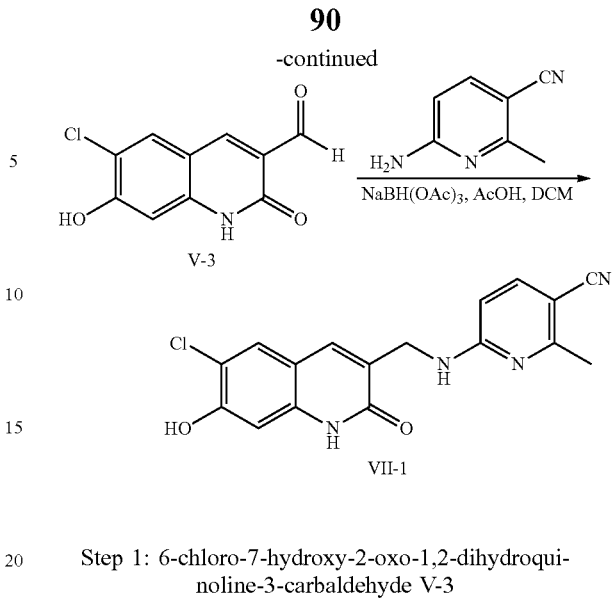

Step 1: 6-chloro-7-hydroxy-2-oxo-1,2-dihydroquinoline-3-carbaldehyde V-3

A suspension of 6-chloro-7-methoxy-2-oxo-1,2-dihydroquinoline-3-carbaldehyde V-2 (see Step 2, in preparation of II-6; maximum 39.0 mmol) in 48% hydrobromic acid (210 ml) was heated on a 110° C. bath. After an hour the bath temperature was raised to 115° C., and after another ~30 minutes the suspension went into solution. The solution was heated at 115° C. for four days, during which time a small quantity of brown precipitate formed. The mixture was poured into water and diluted to 2 L, resulting in more precipitation. The precipitate was collected on a Buchner funnel, washed with water (800 mL), and dried in a vacuum oven to provide 6-chloro-7-hydroxy-2-oxo-1,2-dihydroquinoline-3-carbaldehyde (6.47 g, 28.9 mmol, 74.2% yield) as a brown solid, impure but suitable for use. ¹H NMR (300 MHz, DMSO-d₆): δ ppm 12.11 (s, 1H), 11.67 (s, 1H), 10.13-10.18 (m, 1H), 8.38 (s, 1H), 8.01 (s, 1H), 6.93 (s, 1H). LCMS (Method 1): Rt 1.74 min., m/z 224.0 [M+H]⁺.

Step 2: 6-(((6-chloro-7-hydroxy-2-oxo-1,2-dihydroquinolin-3-yl)methyl)amino)-2-methylnicotinonitrile (VII-1)

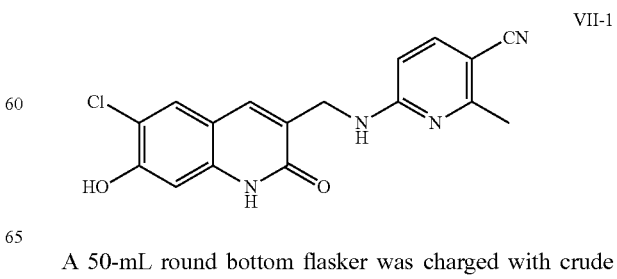

A 50-mL round bottom flasker was charged with crude 6-chloro-7-hydroxy-2-oxo-1,2-dihydroquinoline-3-carbaldehyde V-3 (0.333 g, 0.671 mmol), 6-amino-2-methylnicotinonitrile (0.089 g, 0.671 mmol), MeOH (ca 4 mL) and toluene (ca 10 mL). The suspension was heated briefly with a heat gun, then concentrated under reduced pressure. The residue was suspended in fresh toluene (ca 10 mL), which was also removed under reduced pressure. The resulting yellow-orange solid residue was taken up in DMA (2 ml) and treated with sodium triacetoxyborohydride (0.384 g, 1.811 mmol) in one portion. The reaction mixture was then heated to 50° C. LCMS analysis after 16 h showed complete consumption of aldehyde. Additional sodium triacetoxyborohydride (0.16 g, 0.755 mmol) was added. Heating was continued for four more hours. After cooling, the reaction mixture was carefully diluted with sat. aq NaHCO$_3$ (ca 10 mL). The mixture was stirred for 30 min at rt. A slight precipitate formed. The mixture was filtered, and the solid washed with water. LCMS of the solid and mother liquors showed that the product is in the mother liquors. The mother liquors were extracted twice with EtOAc. The combined extracts were concentrated under reduce pressure. The residual solvent DMA was removed under a stream of nitrogen. The residue was then triturated with 1 N HCl. The slurry was filtered. The solid was rinsed with 1 N HCl followed by water. LCMS confirms that the unreacted aminopyridine was removed in this manner and that the solid is reasonably pure desired product VII-1 (35 mg, 15.3% yield) for next step without further purification. $^1$H NMR (300 MHz, DMSO-d$_6$): δ ppm 11.76 (s, 1H), 10.88 (s, 1H), 7.85 (s, 1H), 7.73 (s, 1H), 7.65 (bs, 2H), 6.91 (s, 1H), 6.45 (bs, 1H), 4.30 (bs, 2H), 2.42 (s, 3H). LCMS (Method 4): Rt 1.49 min., m/z 341.11 [M+H]$^+$.

TABLE 1

The Intermediates listed in Table 1 were either prepared using the methods described above or obtained from commercial sources.

| Intermediate No. | Chemical names | Structure |
| --- | --- | --- |
| II-1 | (S)-3-(1-aminoethyl)-6-chloroquinolin-2(1H)-one | 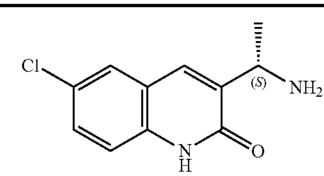 |
| II-2 | (R)-3-(1-aminoethyl)-6-chloroquinolin-2(1H)-one | 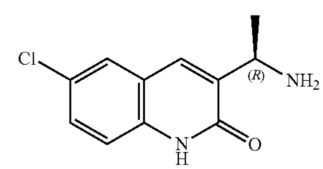 |
| II-3 | 3-(1-aminoethyl)-6-chloro-7-fluoroquinolin-2(1H)-one | 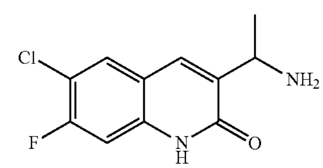 [SMILES: CC(N)c1cc2cc(Cl)c(F)cc2[nH]c1=O] |
| II-4 | (S)-3-(1-aminoethyl)-6-chloro-7-fluoroquinolin-2(1H)-one | 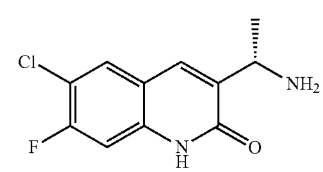 [SMILES: C[C@H](N)c1cc2cc(Cl)c(F)cc2[nH]c1=O] |
| II-5 | (R)-3-(1-aminoethyl)-6-chloro-7-flurooquinolin-2(1H)-one | 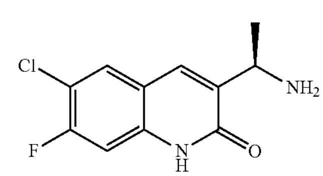 [SMILES: C[C@@H](N)c1cc2cc(Cl)c(F)cc2[nH]c1=O] |
| II-6 | 3-(1-aminoethyl)-6-chloro-7-methoxyquinolin-2(1H)-one | 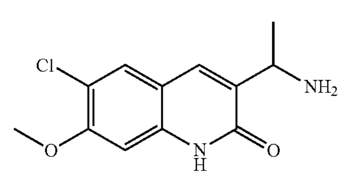 [SMILES: COc1cc2[nH]c(=O)c(C(C)N)cc2cc1Cl] |

TABLE 1-continued

The Intermediates listed in Table 1 were either prepared using the methods described above or obtained from commercial sources.

| Intermediate No. | Chemical names | Structure |
|---|---|---|
| II-7 | (S)-3-(1-aminoethyl)-6-chloro-7-methoxyquinolin-2(1H)-one | 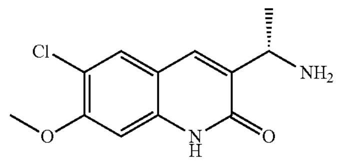 [SMILES: COc1cc2[nH]c(=O)c([C@H](C)N)cc2cc1Cl] |
| II-8 | (R)-3-(1-aminoethyl)-6-chloro-7-methoxyquinolin-2(1H)-one | 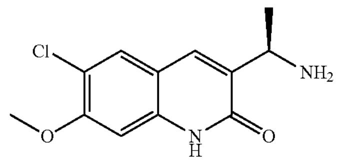 [SMILES: COc1cc2[nH]c(=O)c([C@@H](C)N)cc2cc1Cl] |
| II-9 | 3-(1-aminoethyl)-6-chloro-7-(pyridin-2-ylmethoxy)quinolin-2(1H)-one | 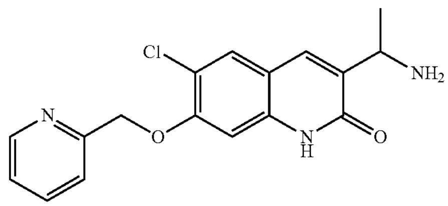 [SMILES: CC(N)c1cc2cc(Cl)c(OCc3ccccn3)cc2[nH]c1=O] |
| II-10 | (S)-3-(1-aminoethyl)-6-chloro-7-(pyridin-2-ylmethoxy)quinolin-2(1H)-one | 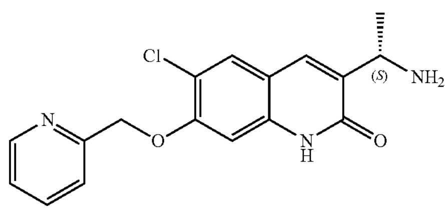 |
| II-11 | (S)-3-(1-aminoethyl)-6-chloro-1,8-naphthyridin-2(1H)-one | 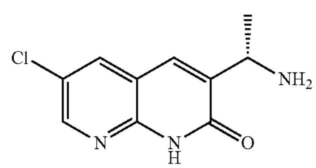 |
| II-12 | (R)-3-(1-aminoethyl)-6-chloroquinoxalin-2(1H)-one | 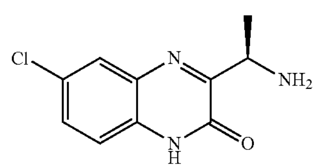 |
| II-13 | (S)-3-(1-aminoethyl)-6-chloroquinoxalin-2(1H)-one | 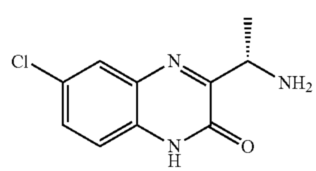 |
| II-14 | (3-((S)-1-aminoethyl)-6-chloro-7-((R)-1-(pyridin-2-yl)ethoxy)quinolin-2(1H)-one | 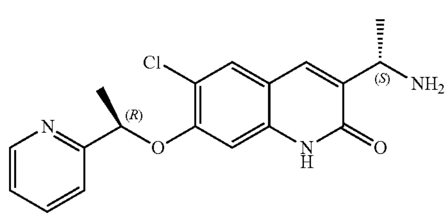 |

TABLE 1-continued

The Intermediates listed in Table 1 were either prepared using the methods described above or obtained from commercial sources.

| Intermediate No. | Chemical names | Structure |
|---|---|---|
| II-15 | (S)-3-(1-aminoethyl)-6-chloro-7-(cyclopropylmethoxy)quinolin-2(1H)-one | 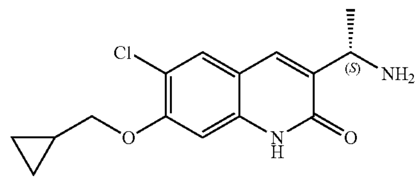 |
| II-16 | 3-(1-aminoethyl)-6-chloro-7-((3,3-difluorocyclobutyl)methoxy)quinolin-2(1H)-one | 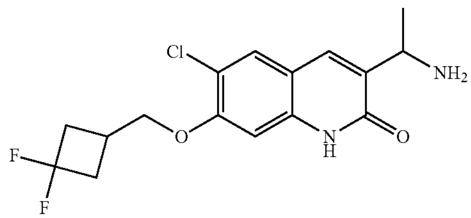 [SMILES: CC(N)c1cc2cc(Cl)c(OCC3CC(F)(F)C3)cc2[nH]c1=O] |
| II-17 | (S)-3-(1-aminoethyl)-6-chloro-8-fluoroquinolin-2(1H)-one | 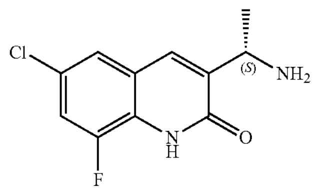 |
| II-18 | (S)-3-(1-aminoethyl)-6-chloro-7-isopropoxy-quinolin-2(1H)-one | 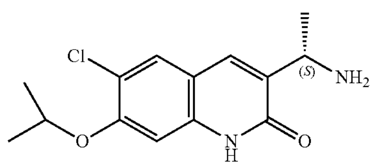 |
| III-1 | 6-chloro-4-methoxynicotinonitrile | 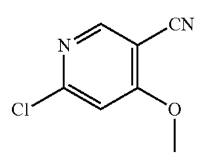 |
| III-2 | 6-fluoro-2-methylnicotinonitrile | 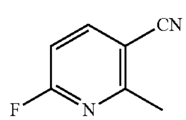 |
| III-3 | 6-fluoro-4-methylnicotinonitrile | 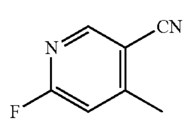 |
| III-4 | 6-chloro-2-methoxynicotinonitrile | 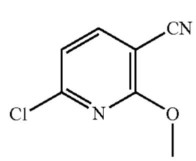 |

TABLE 1-continued

The Intermediates listed in Table 1 were either prepared using the methods described above or obtained from commercial sources.

| Intermediate No. | Chemical names | Structure |
|---|---|---|
| III-5 | 3-(4,6-difluoropyridin-2-yl)oxazolidin-2-one | 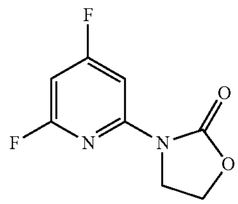 [SMILES: O=C1OCCN1c1cc(F)cc(F)n1] |
| IV-1 | (S)-6-chloro-3-(1-((4-iodopyridin-2-yl)amino)ethyl)quinolin-2(1H)-one | 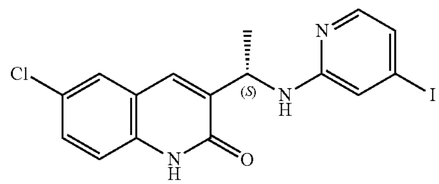 |
| IV-2 | (S)-3-(1-((4-bromopyridin-2-yl)amino)ethyl)-6-chloroquinolin-2(1H)-one | 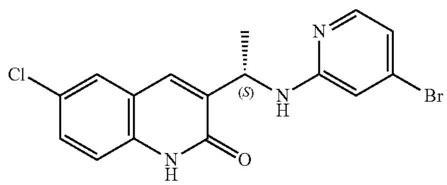 |
| IV-3 | (S)-3-(1-((6-bromopyridin-2-yl)amino)ethyl)-6-chloroquinolin-2(1H)-one | 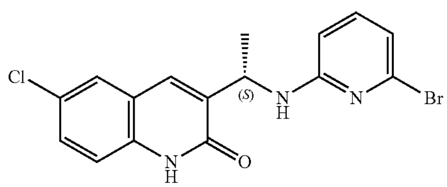 |
| IV-4 | (S)-6-chloro-3-(1-((3-fluoro-4-iodopyridin-2-yl)amino)ethyl)quinolin-2(1H)-one | 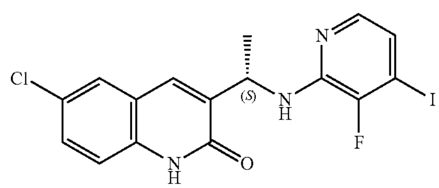 |
| V-1 | 6-chloro-2-oxo-1,2-dihydroquinoline-3-carbaldehyde | 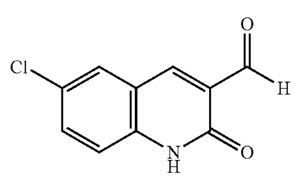 [SMILES: O=Cc1cc2cc(Cl)ccc2[nH]c1=O] |
| V-2 | 6-chloro-7-methoxy-2-oxo-1,2-dihydroquinoline-3-carbaldehyde | 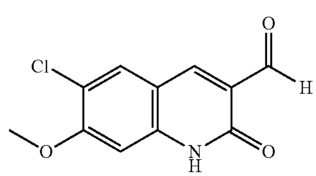 [SMILES: COc1cc2[nH]c(=O)c(C=O)cc2cc1Cl] |
| V-3 | 6-chloro-7-hydroxy-2-oxo-1,2-dihydorquinoline-3-carbaldehyde | 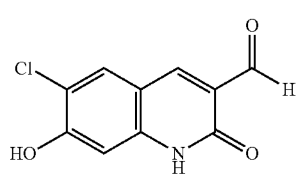 [SMILES: O=Cc1cc2cc(Cl)c(O)cc2[nH]c1=O] |

TABLE 1-continued

The Intermediates listed in Table 1 were either prepared using the methods described above or obtained from commercial sources.

| Intermediate No. | Chemical names | Structure |
|---|---|---|
| V-4 | 7-chloro-2-oxo-1,2-dihydroquinoline-3-carbaldehyde | 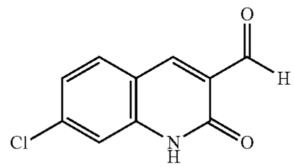 [SMILES: O=Cc1cc2ccc(Cl)cc2[nH]c1=O] |
| V-5 | 6-methoxy-2-oxo-1,2-dihydroquinoline-3-carbaldehyde | 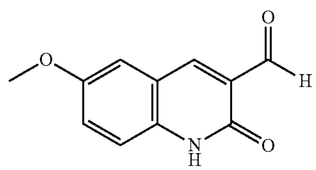 |
| V-6 | 7-methoxy-2-oxo-1,2-dihydroquinoline-3-carbaldehyde | 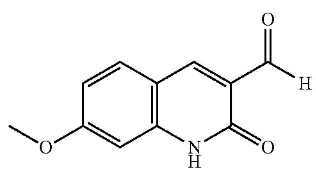 |
| V-7 | 6,7-dimethyl-2-oxo-1,2-dihydroquinoline-3-carbaldehyde | 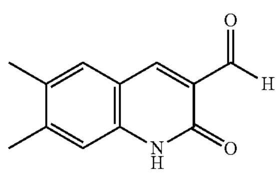 |
| V-8 | 6-(tert-butyl)-2-oxo-1,2-dihydroquinoline-3-carbaldehyde | 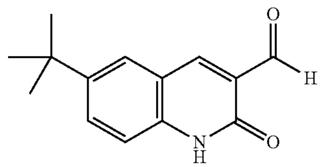 [SMILES: CC(C)(C)c1ccc2[nH]c(=O)c(C=O)cc2c1] |
| VI-1 | 6-amino-2-methylnicotinonitrile | 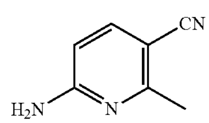 |
| VI-2 | 6-amino-2-methoxynicotinonitrile | 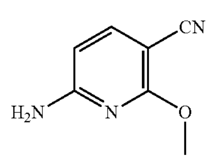 |
| VII-1 | 6-(((6-chloro-7-hydroxy-2-oxo-1,2-dihydroquinolin-3-yl)methyl)amino)-2-methylnicotinonitrile | 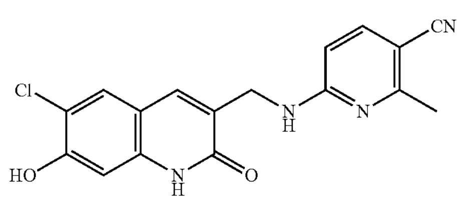 [SMILES: Cc1nc(NCc2cc3cc(Cl)c(O)cc3[nH]c2=O)ccc1C#N] |

Note: All amines are hydrochloride salts, except that II-5a is TFA salt

Example 26—6-{[(1S)-1-(6-chloro-2-oxo-1,2-dihydroquinolin-3-yl)ethyl]amino}-4-methoxypyridine-3-carbonitrile (I-1)

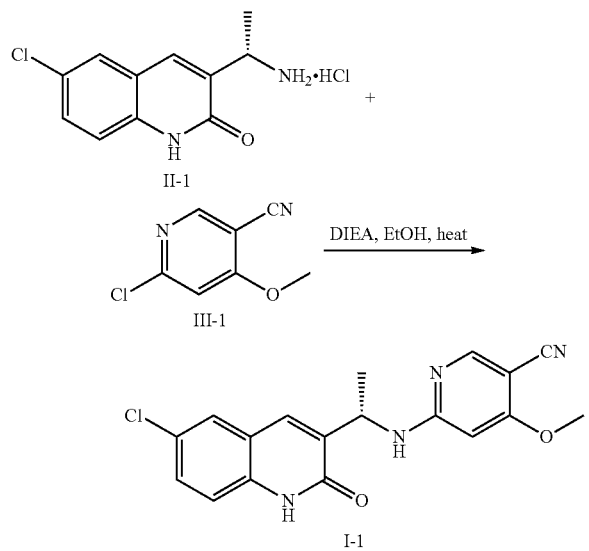

In a 80 mL microwave vessel were combined 6-chloro-4-methoxynicotinonitrile III-1 (1 g, 60 mmol), (S)-3-(1-aminoethyl)-6-chloroquinolin-2(1H)-one hydrochloride II-1 (1.34 g, 53 mmol) and DIEA (1.98 mL, 11.4 mmol) in 21 mL of EtOH (200 proof). The reaction mixture was microwaved at 140° C. for 4 h 30 min, cooled to a room temperature, concentrated to dryness under reduced pressure and purified twice by ISCO, using 40 g "gold" column with a gradient elution of EtOAc in CH$_2$Cl$_2$, providing the title compound I-1 (478 mg, 24% yield). $^1$H NMR (300 MHz, DMSO-d$_6$): δ ppm: 11.99 (br s 1H), 8.16 (s, 1H), 7.90 (d, J=7.41 Hz, 1H), 7.75 (d, J=2.46 Hz, 1H), 7.72 (s, 1H), 7.48 (dd, J1=8.52 Hz, J2=2.46 Hz, 1H), 7.29 (d, J=8.52 Hz, 1H), 6.25 (br s, 1H), 5.22 (br s, 1H), 3.85 (s, 3H), 1.41 (d, J=6.6 Hz, 3H). LCMS (Method 3): Rt 4.38 min, m/z 355.1 [M+H]$^+$. MP: 248-249° C.

Example 27—(S)-6-(1-(6-chloro-2-oxo-1,2-dihydroquinolin-3-yl)ethylamino)-2-methyl nicotinonitrile. (I-4)

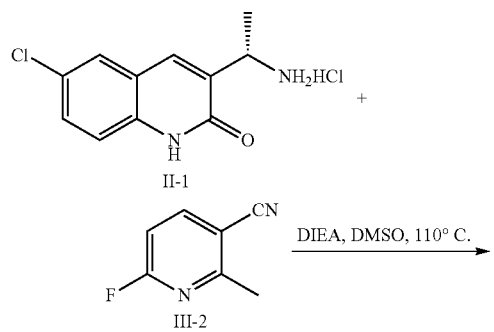

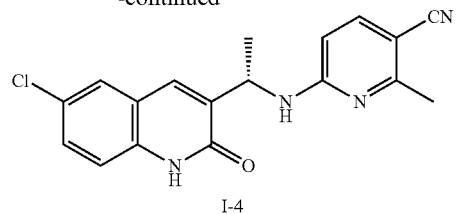

A mixture of 6-fluoro-2-methylnicotinonitrile III-2 (28.6 mg, 0.210 mmol) and (S)-3-(1-aminoethyl)-6-chloroquinolin-2(1H)-one hydrochloride II-1 (49.6 mg, 0.191 mmol) was treated with DMSO (1.4 ml) and DIEA (0.10 mL, 0.573 mmol). The solution was stirred at 110° C. for two hours. LCMS indicated the reaction had gone to completion. The sample was mixed with water (20 mL) and extracted with DCM (3×15 mL). The extracts were dried (Na$_2$SO$_4$), filtered, treated with silica gel, and evaporated under reduced pressure. The material was chromatographed by Biotage MPLC (10 g silica gel column, 0 to 50% EtOAc in hexanes) to provide the title compound I-4 (51.5 mg, 0.145 mmol, 76% yield, HPLC purity >95% at 220 nm) as a solid. $^1$H NMR (300 MHz, DMSO-d$_6$): δ ppm 11.99 (s, 1H), 7.91 (d, J=7.30 Hz, 1H), 7.72-7.80 (m, 2H), 7.62 (d, J=8.80 Hz, 1H), 7.45-7.53 (m, 1H), 7.30 (d, J=8.79 Hz, 1H), 6.35-6.55 (m, 1H), 5.12-5.34 (m, 1H), 2.36 (s, 3H), 1.42 (d, J=6.70 Hz, 3H). LCMS (Method 1): Rt 2.40 min., m/z 339.0 [M+H]$^+$.

Example 28—(S)-6-((1-(6-chloro-2-oxo-1,2-dihydroquinolin-3-yl)ethyl)amino)-4-methyl nicotinonitrile (I-5)

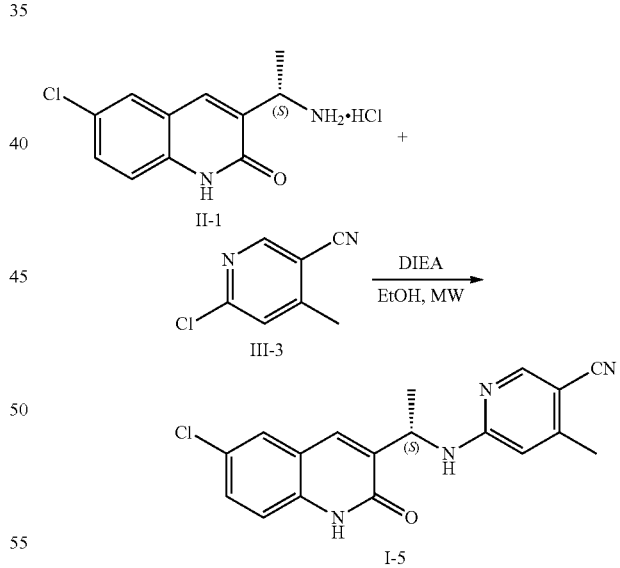

A mixture of (S)-3-(1-aminoethyl)-6-chloroquinolin-2 (1H)-one hydrochloride II-1 (90 mg, 0.35 mmol), 6-chloro-4-methylnicotinonitrile III-3 (66 mg, 0.43 mmol) and N,N-diisopropylethylamine (200 μL, 1.15 mmol) in EtOH (2 mL) was heated in the microwave at 150° C. for six hours. Two more batches were carried out under the same condition. They were then combined and concentrated in vacuum. The residue was purified on ISCO (40 g silica gel column, EtOAc/dichloromethane 0-80%) to afford the title compound I-5 as a pale yellow solid (160 mg, 45%). m.p.

241-243° C. $^1$H NMR (300 MHz, DMSO-d$_6$) δ: 11.98 (s, 1H), 8.25 (s, 1H), 7.90 (d, J=6.8 Hz, 1H), 7.76 (d, J=2.2 Hz, 1H), 7.69 (s, 1H), 7.49 (dd, J=8.8, 2.5 Hz, 1H), 7.30 (d, J=8.9 Hz, 1H), 6.53 (br.s, 1H), 5.13 (m, 1H), 2.27 (s, 3H), 1.42 (d, J=6.6 Hz, 3H). LCMS m/z 339, 341 [M+H]$^+$.

Example 29—(S)-6-((1-(6-chloro-2-oxo-1,2-dihydroquinolin-3-yl)ethyl)amino)-2-methoxynicotinonitrile (I-8)

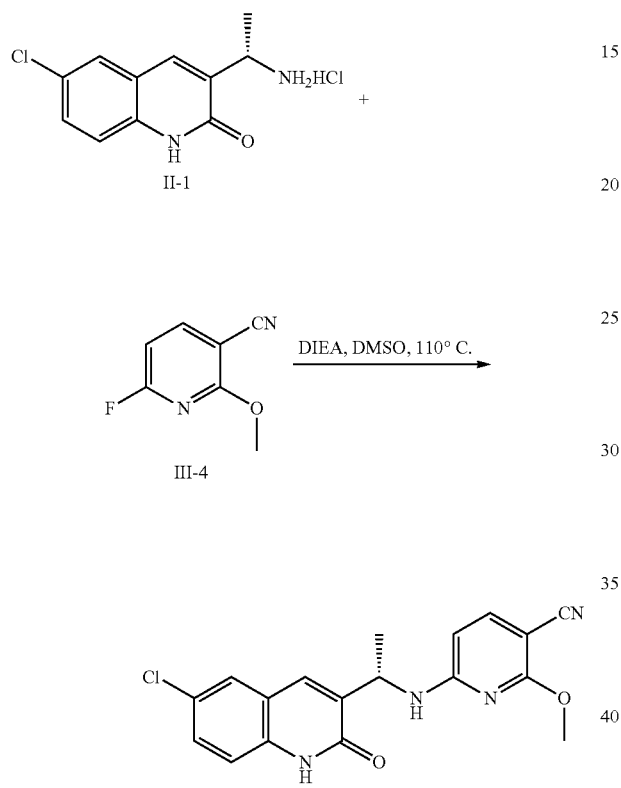

A solution of (S)-3-(1-aminoethyl)-6-chloroquinolin-2(1H)-one hydrochloride II-1 (69.7 mg, 0.269 mmol) and 6-fluoro-2-methoxynicotinonitrile III-4 (45.2 mg, 0.297 mmol) in DMSO (1.5 ml) was treated with DIEA (141 μL, 0.807 mmol) and stirred at 110° C. one hour. LCMS at 45 minutes showed the reaction had gone to completion. The sample was pipetted onto water (20 mL), resulting in formation of a white precipitate. The precipitate was extracted with EtOAc (2×15 mL), dried (Na$_2$SO$_4$), and filtered. Silica gel was added and the solvent was evaporated under reduced pressure. The material was chromatographed by Biotage MPLC (10 g silica gel column) with 0 to 75% EtOAc in hexanes, with isocratic elution when peaks came off to provide the title compound I-8 (68.8 mg, 0.194 mmol, 72.1% yield, HPLC purity 100% at 220 nm) as a white solid. $^1$H NMR (300 MHz, DMSO-d$_6$) δ ppm 11.97 (br s, 1H), 8.13 (br s, 1H), 7.77 (d, J=2.35 Hz, 1H), 7.73 (s, 1H), 7.60 (d, J=8.50 Hz, 1H), 7.48 (dd, J=8.79, 2.35 Hz, 1H), 7.29 (d, J=9.09 Hz, 1H), 6.26 (br s, 1H), 5.20 (br s, 1H), 3.72 (br s, 3H), 1.44 (d, J=7.04 Hz, 3H). LCMS (Method 1): Rt 2.38 min., m/z 355.0 [M+H]$^+$.

TABLE 1

The compounds listed in Table 1 were prepared using methods similar to those described for the preparation of I-1, I-4, I-5 and I-8.

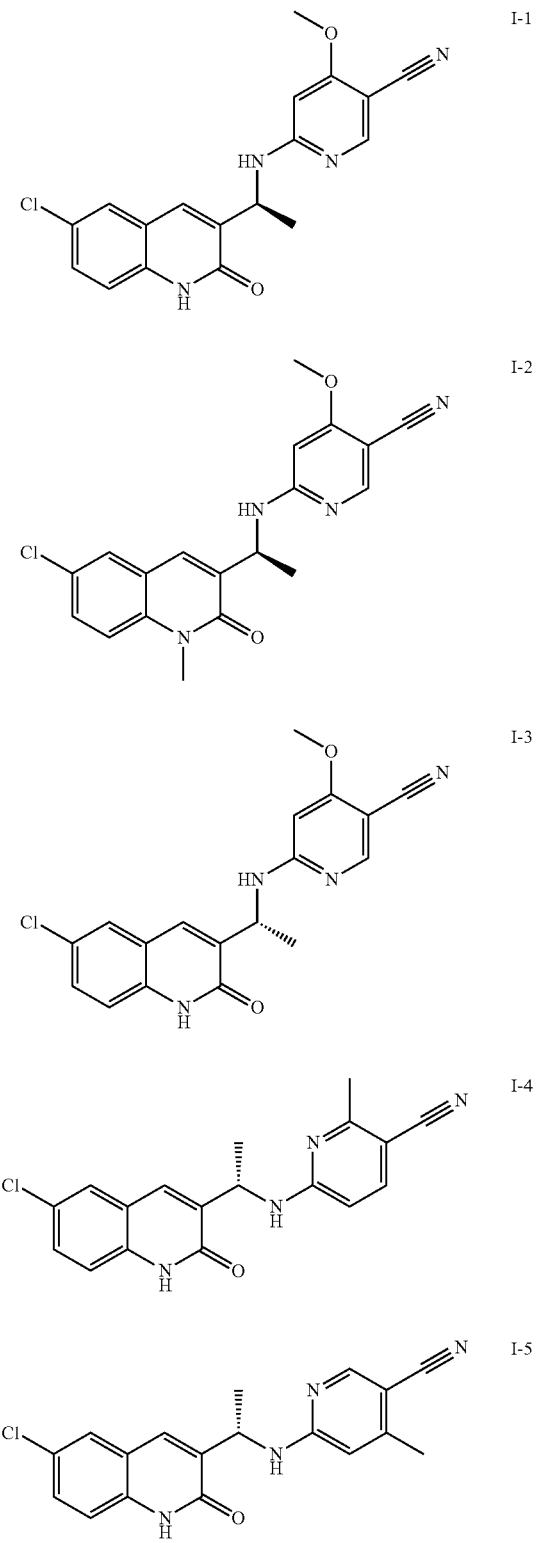

TABLE 1-continued

The compounds listed in Table 1 were prepared using methods similar to those described for the preparation of I-1, I-4, I-5 and I-8.

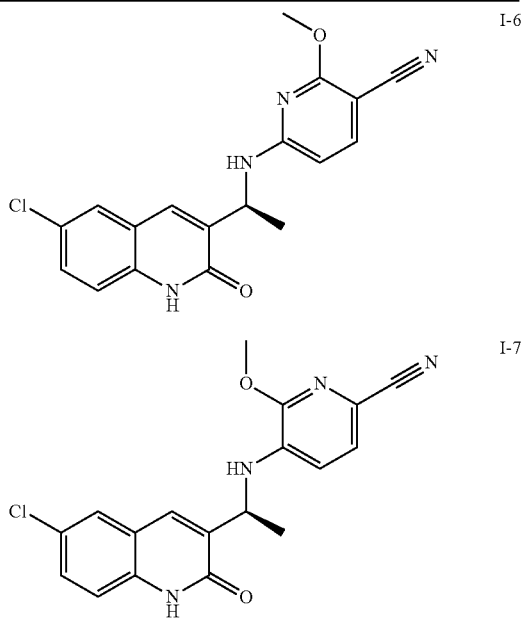

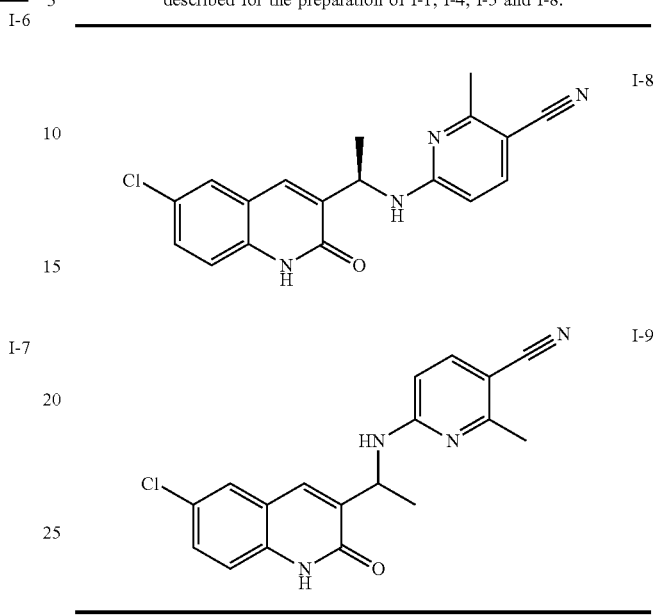

TABLE 2

LCMS signal and NMR chemical shifts of each Compound listed in Table 1.

| Compound | LCMS | 1H NMR (300 MHz) δ ppm | Chemical Name |
|---|---|---|---|
| I-1 | m/z: 355.03 (M + H)+<br>Rt (min): 1.24 | 1H NMR (300 MHz, DMSO-d6): δ ppm: 11.99 (br s 1H), 8.16 (s, 1H), 7.90 (d, J = 7.41 Hz, 1H), 7.75 (d, J = 2.46 Hz, 1H), 7.72 (s, 1H), 7.48 (dd, J1 = 8.52 Hz, J2 = 2.46 Hz, 1H), 7.29 (d, J = 8.52 Hz, 1H), 6.25 (br s, 1H), 5.22 (br s, 1H), 3.85 (s, 3H), 1.41 (d, J = 6.6 Hz, 3H). | 6-{[(1S)-1-(6-chloro-2-oxo-1,2-dihydroquinolin-3-yl)ethyl]amino}-4-methoxypyridine-3-carbonitrile |
| I-2 | m/z: 369.19 (M + H)+<br>Rt (min): 1.43 | 1H NMR (300 MHz, DMSO-d6): δ 8.15 ppm (s, 1H), 7.91 ppm (d, J = 7.41 Hz, 1H), 7.82 ppm (d, J = 2.56 Hz, 1H), 7.72 (s, 1H), 7.61 (dd, J1 = 8.8 Hz, J2 = 2.2 Hz, 1H), 7.53 (J = 8.8 Hz, 1H), 6.26 (br s, 1H), 5.23 (br.s), 3.85 (s, 3H), 3.66 (s, 3H), 1.42 (d, J = 6.8 Hz, 3H) | 6-{[(1S)-1-(6-chloro-1-methyl-2-oxo-1,2-dihydroquinolin-3-yl)ethyl]amino}-4-methoxypyridine-3-carbonitrile |
| I-3 | m/z: 355.20 (M + H)+<br>Rt (min): 1.24 | 1H NMR (300 MHz, CHLOROFORM-d) δ ppm 11.70 (br s, 1 H), 8.17 (s, 1 H), 7.71 (s, 1 H), 7.53 (d, J = 2.05 Hz, 1 H), 7.36-7.48 (m, 1 H), 7.15-7.31 (m, 1 H), 6.28 (br d, J = 7.92 Hz, 1 H), 5.81 (s, 1 H), 5.12-5.43 (m, 1 H), 3.80 (s, 3 H), 1.64 (d, H = 7.04 Hz, 3H) | 6-{[(1R)-1-(6-chloro-2-oxo-1,2-dihydroquinolin-3-yl)ethyl]amino}-4-methoxypyridine-3-carbonitrile |
| I-4 | m/z: 339.18 (M + H)+<br>Rt (min): 1.35 | 1H NMR (300 MHz, DMSO-d6): δ ppm 11.99 (s, 1 H), 7.91 (d, J = 7.30 Hz, 1 H), 7.72-7.80 (m, 2 H), 7.62 (d, J = 8.80 Hz, 1 H), 7.45-7.53 (m, 1 H), 7.30 (d, J = 8.79 Hz, 1 H), 6.35-6.55 (m, 1 H), 5.12-5.34 (m, 1 H), 2.36 (s, 3 H), 1.42 (d, J = 6.70 Hz, 3 H). | 6-{[(1S)-1-(6-chloro-2-oxo-1,2-dihydroquinolin-3-yl)ethyl]amino}-2-methylpyridine-3-carbonitrile |
| I-5 | m/z: 339.19 (M + H)+<br>Rt (min): 1.29 | 1H NMR (300 MHz, DMSO-d6) δ: 11.98 (s, 1H), 8.25 (s, 1H), 7.90 (d, J = 6.8 Hz, 1H), 7.76 (d, J = 2.2 Hz, 1H), 7.69 (s, 1H), 7.49 (dd, J = 8.8, 2.5 Hz, 1H), 7.30 (d, J = 8.9 Hz, 1H), 6.53 (br.s, 1H), 5.13 (m, 1H), 2.27 (s, 3H), 1.42 (d, J = 6.6 Hz, 3H) | 6-{[(1S)-1-(6-chloro-2-oxo-1,2-dihydroquinolin-3-yl)ethyl]amino}-4-methylpyridine-3-carbonitrile |
| I-6 | m/z: 355.17 (M + H)+<br>Rt (min): 1.36 | 1H NMR (300 MHz, DMSO-d6) δ ppm 11.97 (br s, 1 H), 8.13 (br s, 1 H), 7.77 (d, J = 2.35 Hz, 1 H), 7.73 (s, 1 H), 7.60 (d, J = 8.50 Hz, 1 H), 7.48 (dd, J = 8.79, 2.35 Hz, | 6-{[(1S)-1-(6-chloro-2-oxo-1,2-dihydroquinolin-3-yl)ethyl]amino}-2-methoxypyridine-3- |

TABLE 2-continued

LCMS signal and NMR chemical shifts of each Compound listed in Table 1.

| Compound | LCMS | 1H NMR (300 MHz) δ ppm | Chemical Name |
|---|---|---|---|
| I-7 | m/z: 355.06 (M + H)+<br>Rt (min): 1.44 | 1 H), 7.29 (d, J = 9.09 Hz, 1 H),<br>6.26 (br s, 1 H), 5.20 (br s, 1 H), 3.72 (br s, 3 H), 1.44 (d, J = 7.04 Hz, 3 H).<br>1H NMR (300 MHz, DMSO-d6): δ ppm 12.07 (s, 1 H), 7.72-7.79 (m, 2 H), 7.50 (dd, J = 8.79, 2.35 Hz, 1 H), 7.33 (m, 2 H), 6.65 (d, J = 7.62 Hz, 1 H), 6.48 (d, J = 7.92 Hz, 1 H), 4.72 (quin, J = 6.82 Hz, 1 H), 3.97 (s, 3 H), 1.50 (d, J = 6.74 Hz, 3 H). | carbonitrile<br>5-{[(1S)-1-(6-chloro-2-oxo-1,2-dihydroquinolin-3-yl)ethyl]amino}-6-methoxypyridine-2-carbonitrile |
| I-8 | m/z: 339.18 (M + H)+<br>Rt (min): 1.35 | | 6-{[(1R)-1-(6-chloro-2-oxo-1,2-dihydroquinolin-3-yl)ethyl]amino}-2-methylpyridine-3-carbonitrile |
| I-9 | m/z: 339.08 (M + H)+<br>Rt (min): 1.30 | 1H NMR (300 MHz, DMSO-d6): δ ppm 11.99 (s, 1 H), 7.92 (d, J = 7.60 Hz, 1 H), 7.77 (d, J = 2.35 Hz, 1 H), 7.74 (s, 1 H), 7.62 (d, J = 8.50 Hz, 1 H), 7.49 (dd, J = 8.79, 2.05 Hz, 1 H), 7.30 (d, J = 8.79 Hz, 1 H), 6.44 (br s, 1 H), 5.07-5.37 (m, 1 H), 2.36 (s, 3 H), 1.42 (d, J = 7.04 Hz, 3 H). | 6-{[1-(6-chloro-2-oxo-1,2-dihydroquinolin-3-yl)ethyl]amino}-2-methylpyridine-3-carbonitrile |

Example 30—(S)-3-(2-(1-(6-chloro-2-oxo-1,2-dihydroquinolin-3-yl)ethylamino)pyridin-4-yl)oxazolidin-2-one (I-10)

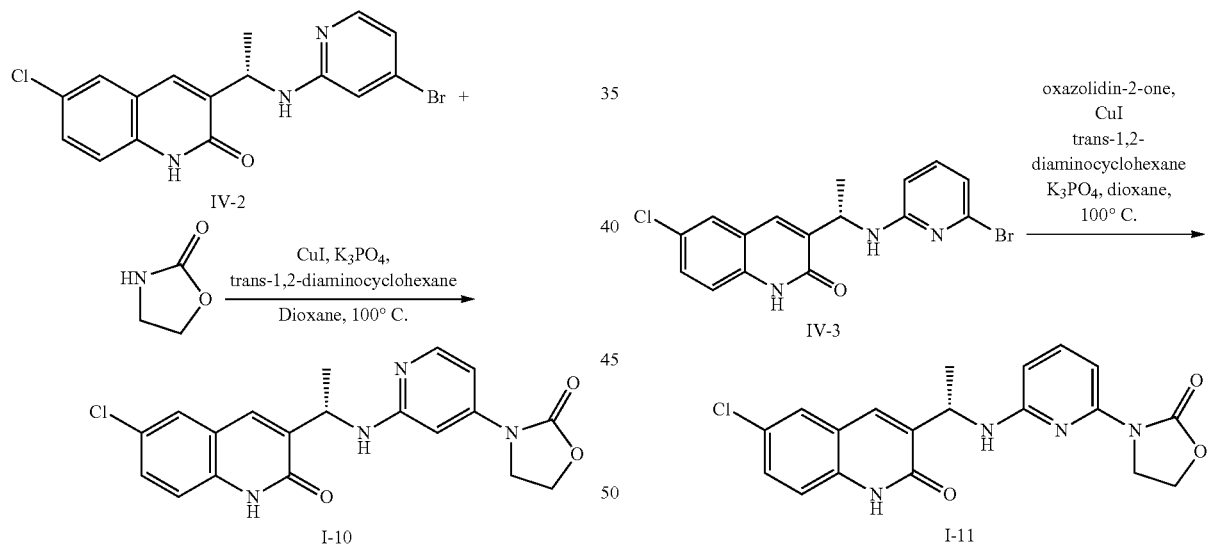

A 2 dram vial was charged with (S)-3-(1-(4-bromopyridin-2-ylamino)ethyl)-6-chloroquinolin-2(1H)-one IV-2 (21.4 mg, 0.057 mmol), copper(I) iodide (24.3 mg, 0.128 mmol), oxazolidin-2-one (13.0 mg, 0.149 mmol) and tripotassium phosphate (111.4 mg, 0.525 mmol) and placed under nitrogen. A solution of trans-cyclohexane-1,2-diamine (16 μl, 0.133 mmol) in dioxane (3 ml) was added by syringe and the mixture was stirred at 100° overnight. LCMS indicated the reaction had gone to completion. The sample was diluted with MeOH and DCM, filtered through a syringe filter, treated with silica gel, and evaporated under reduced pressure. The material was chromatographed by Biotage MPLC (10 g silica gel column, 0 to 5% MeOH in DCM) to provide the title compound I-10 (16.9 mg). LCMS (Method 4): Rt 0.89 min., m/z 385.1 [M+H]+.

Example 31—(S)-3-(6-((1-(6-chloro-2-oxo-1,2-dihydroquinolin-3-yl)ethyl)amino)pyridin-2-yl)oxazolidin-2-one (I-11)

A 2 dram vial was charged with (S)-3-(1-(6-bromopyridin-2-ylamino)ethyl)-6-chloroquinolin-2(1H)-one IV-3 (30.2 mg, 0.080 mmol), CuI (27.4 mg, 0.144 mmol), oxazolidin-2-one (11.9 mg, 0.137 mmol), and tripotassium phosphate (139.1 mg, 0.655 mmol) and placed under nitrogen. A solution of trans-1,2-diaminocyclohexane (16.0 μl, 0.133 mmol) in dioxane (2.3 ml) was added by syringe and the mixture was stirred at 100° C. five hours. The sample was diluted with MeOH, treated with silica gel, and evaporated under reduced pressure. The material was chromatographed by Biotage MPLC (10 g silica gel column, 0 to 80% EtOAc in hexanes, with isocratic elution when peaks came off) to provide I-11 (21.6 mg). LCMS (Method 4): Rt 1.29 min., m/z 385.1 [M+H]+.

Example 32—(S)-3-(2-(1-(6-chloro-2-oxo-1,2-dihydroquinolin-3-yl)ethylamino)-6-methyl pyridin-4-yl)oxazolidin-2-one (I-12)

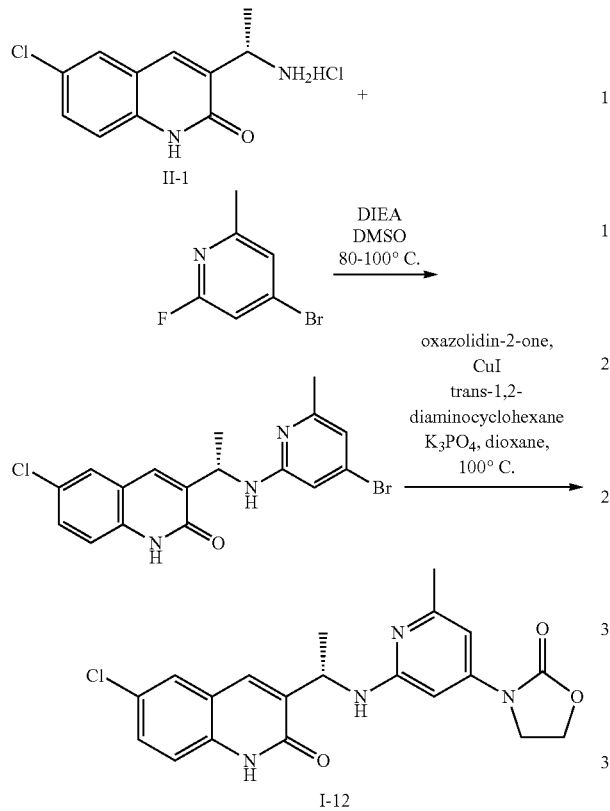

Step-1: (S)-3-(1-((4-bromo-6-methylpyridin-2-yl)amino)ethyl)-6-chloroquinolin-2(1H)-one A mixture of 4-bromo-2-fluoro-6-methylpyridine (62.6 mg, 0.329 mmol) and (S)-3-(1-aminoethyl)-6-chloroquinolin-2(1H)-one hydrochloride II-1 (80.6 mg, 0.311 mmol) was treated with DMSO (2.2 ml) and DIEA (0.16 ml, 0.916 mmol). The solution was stirred at 80° C. overnight, then at 90° C. over the weekend, then at 100° C. for two days. The sample was mixed with water (30 mL) and extracted with DCM (3×15 mL). The extracts were dried (Na2SO4), filtered, treated with silica gel, and evaporated under reduced pressure. The material was chromatographed by Biotage MPLC (10 g silica gel snap column, 0 to 8% MeOH in DCM, with isocratic elution at 3.2% MeOH) to provide 38.4 mg crude (S)-3-(1-(4-bromo-6-methylpyridin-2-ylamino)ethyl)-6-chloroquinolin-2(1H)-one. LCMS (Method 1): Rt 2.18 min., m/z 393.9 [M+H]+.

Step-2: (S)-3-(2-(1-(6-chloro-2-oxo-1,2-dihydroquinolin-3-yl)ethylamino)-6-methyl pyridin-4-yl)oxazolidin-2-one (I-12)

The crude material of (S)-3-(1-(4-bromo-6-methylpyridin-2-ylamino)ethyl)-6-chloroquinolin-2(1H)-one was treated with copper(I) iodide (19.1 mg, 0.100 mmol), oxazolidin-2-one (14.3 mg, 0.164 mmol), and tripotassium phosphate (167.8 mg, 0.791 mmol) and placed under nitrogen. A solution of trans-1,2-diaminocyclohexane (12 μL, 0.100 mmol) in dioxane (2.8 ml) was added by syringe and the mixture was stirred at 100° C. for 6.5 hours. More trans-1,2-diaminocyclohexane (15 μL), CuI (18.9 mg), and oxazolidinone (9.8 mg) were added, and the sample was placed back under nitrogen and stirred at 100° C. overnight. The sample was diluted with MeOH and DCM and filtered. The filtrate was treated with silica gel and evaporated under reduced pressure. The material was chromatographed by Biotage MPLC (10 g silica gel cartridge, 0 to 8% MeOH in DCM, with isocratic elution at ~4.5% MeOH) to yield 22.1 mg residue. The crude was further purified by reverse phase HPLC to provide the title compound I-12 (5.6 mg, 0.014 mmol, 4.5% yield, HPLC purity 100% at 220 nm) as a white solid. LCMS (Method 4): Rt 0.91 min., m/z 399.1 [M+H]+

Example 33—(S)-3-(2-((1-(6-chloro-2-oxo-1,2-dihydroquinolin-3-yl)ethyl)amino)-3-fluoropyridin-4-yl)oxazolidin-2-one (I-14)

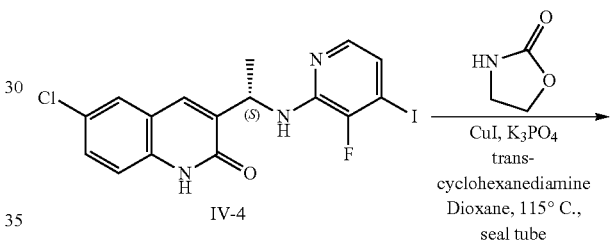

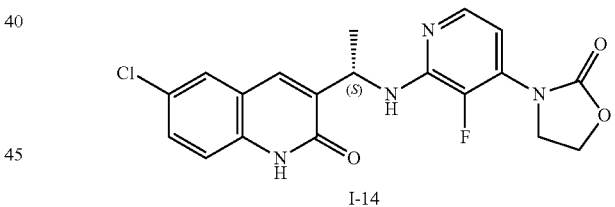

To a mixture of (S)-6-chloro-3-(1-((3-fluoro-4-iodopyridin-2-yl)amino)ethyl) quinolin-2(1H)-one IV-4 (200 mg, 0.45 mmol), oxazolidin-2-one (38 mg, 0.437 mmol), K3PO4 (805 mg, 3.79 mmol) and CuI (98 mg, 0.51 mmol) in dioxane (13 mL) was added trans-cyclohexanediamine (67 uL, 0.55 mmol). The resultant mixture was heated at 115° C. for 2 h in a sealed tube. The mixture was diluted with MeOH and filtered through sintered funnel. The filtrate was evaporated with silica gel and purified by ISCO (SiO2: hexanes/EtOAc 0 to 100%) to give the title compound I-14 (82 mg, 45%) as white solid. 1H NMR (300 MHz, DMSO-d6): δ 11.96 (br s, 1H), 7.75-7.73 (m, 2H), 7.69 (d, J=5.49 Hz, 1H), 7.49-7.45 (m, 1H), 7.30 (d, J=8.8 Hz, 1H), 7.05 (d, J=8.8 Hz, 1H), 6.79-6.75 (m, 1H), 5.30-5.25 (m, 1H), 4.49-4.44 (m, 2H), 4.12-4.06 (m, 1H), 1.44 (d, J=6.9 Hz, 3H). LCMS (method 3): Rt 4.02 min, m/z 403.1[M+H]+.

Example 34—(S)-3-(6-((1-(6-chloro-2-oxo-1,2-dihydroquinolin-3-yl)ethyl)amino)-4-fluoro pyridin-2-yl)oxazolidin-2-one (I-16) and (S)-3-(2-((1-(6-chloro-2-oxo-1,2-dihydroquinolin-3-yl)ethyl)amino)-6-fluoropyridin-4-yl)oxazolidin-2-one (I-17)

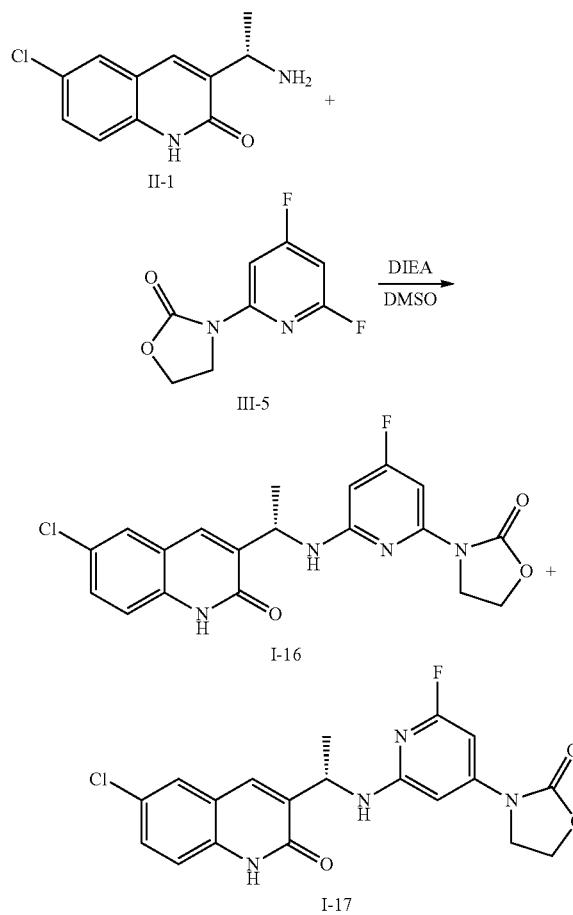

In a 4 mL vial was added (S)-3-(1-aminoethyl)-6-chloroquinolin-2(1H)-one II-1 (80 mg, 0.359 mmol) and 3-(4,6-difluoropyridin-2-yl)oxazolidin-2-one (71.9 mg, 0.359 mmol) in DMSO (0.8 ml), To this solution was then added DIEA (0.314 ml, 1.796 mmol). The reaction mixture was stirred at 120° C. over weekend. The mixture was diluted with EtOAc and washed with brine (×2). The organic extract was dried over Na$_2$SO$_4$, filtered, concentrated under reduced pressure to give a crude product. This crude was purified by column chromatography (Biotage, using 0-100% EtOAc in hexanes) to yield a mixture of I-16 (18.8 mg, minor) and I-17 (39.7 mg, major):

(S)-3-(6-((1-(6-chloro-2-oxo-1,2-dihydroquinolin-3-yl)ethyl)amino)-4-fluoropyridin-2-yl)oxazolidin-2-one (I-16); $^1$H NMR (300 MHz, CHLOROFORM-d) δ ppm 11.64 (br s, 1H), 7.61 (s, 1H), 7.45 (m, 1H), 7.33-7.40 (m, 1H), 7.21-7.25 (m, 1H), 7.17 (m, 1H), 5.76 (dd, J=9.97, 1.17 Hz, 1H), 5.02 (br s, 1H), 4.24-4.38 (m, 2H), 3.93-4.22 (m, 2H), 1.55 (d, J=6.45 Hz, 3H). LCMS (method 1): Rt 2.41 min, m/z 402.88 [M+H]$^+$.

(S)-3-(2-((1-(6-chloro-2-oxo-1,2-dihydroquinolin-3-yl)ethyl)amino)-6-fluoropyridin-4-yl)oxazolidin-2-one (I-17); $^1$H NMR (300 MHz, CHLOROFORM-d) δ ppm 10.95-11.50 (m, 1H), 7.68 (s, 1H), 7.38-7.57 (m, 2H), 7.29 (s, 1H), 5.74 (s, 1H), 4.81 (br d, J=6.16 Hz, 1H), 4.38-4.49 (m, 2H), 4.10-4.24 (m, 2H), 1.65 (br s, 3H). LCMS (method 1): Rt 2.30 min, m/z 402.88 [M+H]$^+$.

TABLE 3

The compounds listed in Table 3 were prepared using methods similar to those described for the preparation of I-10 to I-12, I-14, I-16 to I-17.

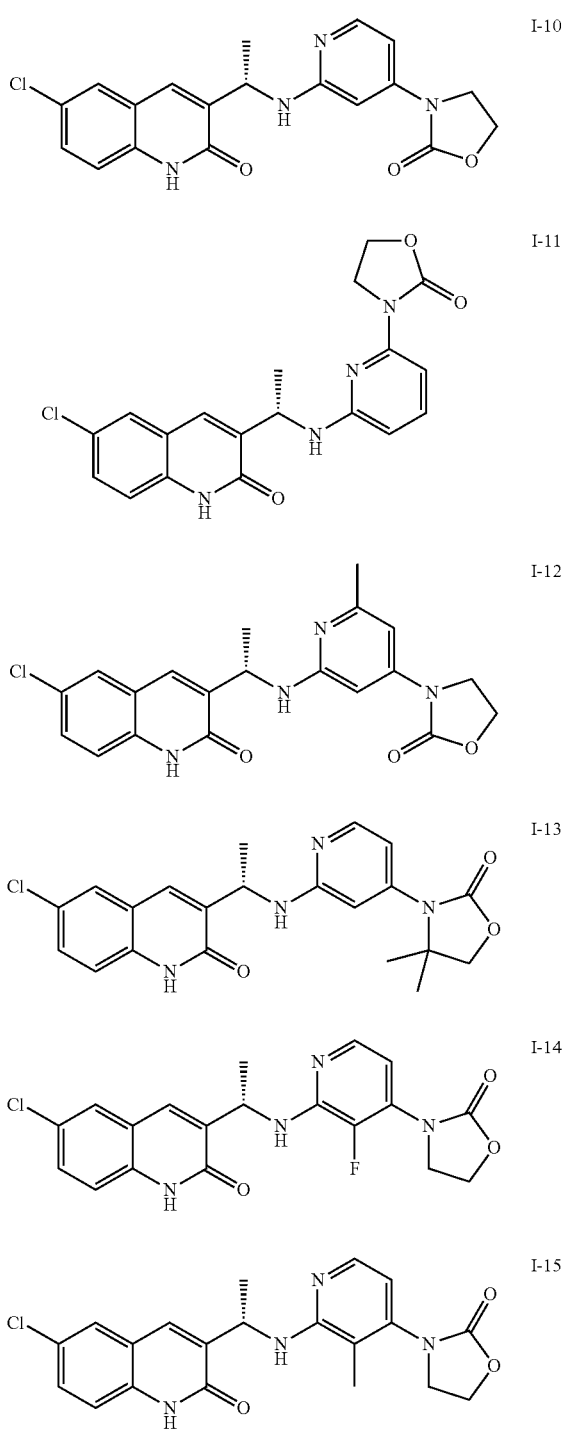

TABLE 3-continued

The compounds listed in Table 3 were prepared using methods similar to those described for the preparation of I-10 to I-12, I-14, I-16 to I-17.

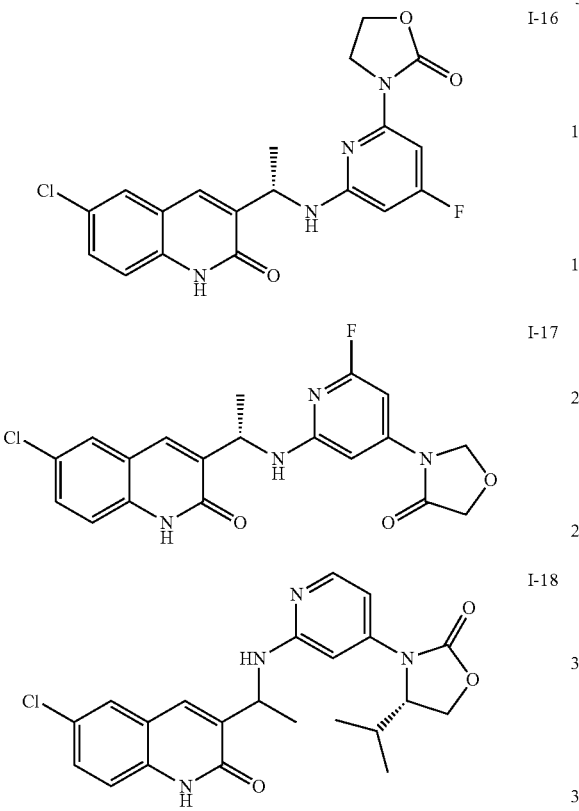

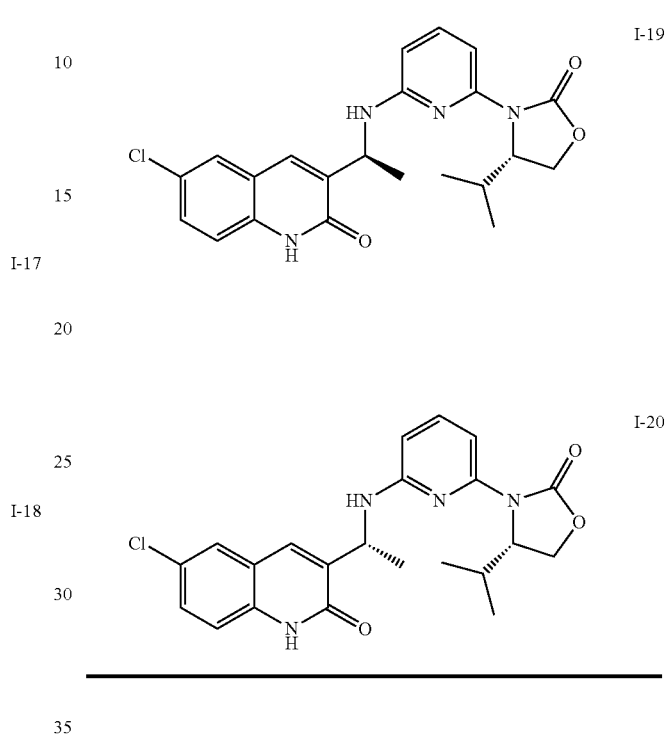

TABLE 4

| Compound | LCMS | 1H NMR (300 MHz) δ ppm | Chemical Name |
|---|---|---|---|
| I-10 | m/z: 385.10 (M + H)+<br>Rt (min): 0.89 | | 6-chloro-3-[(1S)-1-{[4-(2-oxo-1,3-oxazolidin-3-yl)pyridin-2-yl]amino}ethyl]-1,2-dihydroquinolin-2-one |
| I-11 | m/z: 385.12 (M + H)+<br>Rt (min): 1.29 | | 6-chloro-3-[(1S)-1-{[6-(2-oxo-1,3-oxazolidin-3-yl)pyridin-2-yl]amino}ethyl]-1,2-dihydroquinolin-2-one |
| I-12 | m/z: 399.10 (M + H)+<br>Rt (min): 0.91 | | 6-chloro-3-[(1S)-1-{[6-methyl-4-(2-oxo-1,3-oxazolidin-3-yl)pyridin-2-yl]amino}ethyl]-1,2-dihydroquinolin-2-one |
| I-13 | m/z: 413.14 (M + H)+<br>Rt (min): 0.96 | | 6-chloro-3-[(1S)-1-{[4-(4,4-dimethyl-2-oxo-1,3-oxazolidin-3-yl)pyridin-2-yl]amino}ethyl]-1,2-dihydroquinolin-2-one |
| I-14 | m/z: 403.12 (M + H)+<br>Rt (min): 1.19 | 1H NMR (300 MHz, DMSO-d6): δ ppm 11.97 (s, 1 H), 7.72-7.78 (m, 2 H), 7.69 (d, J = 5.57 Hz, 1 H), 7.48 (dd, J = 8.79, 2.35 Hz, 1 H), 7.30 (d, J = 8.79 Hz, 1 H), 7.08 (d, J = 7.60 Hz, 1 H), 6.78 (dd, J = 5.30, 5.30 Hz, 1 H), 5.20-5.37 (m, 1 H), 4.42-4.52 (m, 2 H), 4.02-4.18 (m, 2 H), 1.44 (d, J = 7.04 Hz, 3 H). | 6-chloro-3-[(1S)-1-{[3-fluoro-4-(2-oxo-1,3-oxazolidin-3-yl)pyridin-2-yl]amino}ethyl]-1,2-dihydroquinolin-2-one |

TABLE 4-continued

LCMS signal and NMR chemical shifts of each Compound listed in Table 3

| Compound | LCMS | 1H NMR (300 MHz) δ ppm | Chemical Name |
|---|---|---|---|
| I-15 | m/z: 399.04 (M + H)+<br>Rt (min): 0.91 | | 6-chloro-3-[(1S)-1-{[3-methyl-4-(2-oxo-1,3-oxazolidin-3-yl)pyridin-2-yl]amino}ethyl]-1,2-dihydroquinolin-2-one |
| I-16 | m/z: 403.06 (M + H)+<br>Rt (min): 1.38 | 1H NMR (300 MHz, CHLOROFORM-d) δ ppm 11.64 (br s, 1 H), 7.61 (s, 1 H), 7.45 (m, 1 H), 7.33-7.40 (m, 1 H), 7.21-7.25 (m, 1H), 7.17 (m, 1 H), 5.76 (dd, J = 9.97, 1.17 Hz, 1 H), 5.02 (br s, 1 H), 4.24-4.38 (m, 2 H), 3.93-4.22 (m, 2 H), 1.55 (d, J = 6.45 Hz, 3 H). | 6-chloro-3-[(1S)-1-{[4-fluoro-6-(2-oxo-1,3-oxazolidin-3-yl)pyridin-2-yl]amino}ethyl]-1,2-dihydroquinolin-2-one |
| I-17 | m/z: 403.08 (M + H)+<br>Rt (min): 1.28 | 1H NMR (300 MHz, CHLOROFORM-d) δ ppm 10.95-11.50 (m, 1 H), 7.68 (s, 1 H), 7.38-7.57 (m, 2 H), 7.29 (s, 1 H), 5.74 (s, 1 H), 4.81 (br d, J = 6.16 Hz, 1 H), 4.38-4.49 (m, 2 H), 4.10-4.24 (m, 2 H), 1.65 (br s, 3 H). | 6-chloro-3-[(1S)-1-{[6-fluoro-4-(2-oxo-1,3-oxazolidin-3-yl)pyridin-2-yl]amino}ethyl]-1,2-dihydroquinolin-2-one |
| I-18 | m/z: 427.19 (M + H)+<br>Rt (min): 1.04 | 1H NMR (300 MHz, CHLOROFORM-d) δ ppm 11.27-11.82 (m, 1 H), 7.74-7.95 (m, 3 H), 7.24-7.54 (m, 3 H), 6.72-7.00 (m, 2 H), 4.94-5.13 (m, 1 H), 4.04-4.35 (m, 2 H), 2.17-2.32 (m, 1 H), 1.94 (br s, 1 H), 1.49-1.68 (m, 3 H), 0.89 (br d, J = 7.04 Hz, 2 H), 0.65-0.76 (m, 4 H). | 6-chloro-3-[1-({4-[(4S)-2-oxo-4-(propan-2-yl)-1,3-oxazolidin-3-yl]pyridin-2-yl}amino)ethyl]-1,2-dihydroquinolin-2-one |
| I-19 | m/z: 427.12 (M + H)+<br>Rt (min): 1.43 | | 6-chloro-3-[(1S)-1-({6-[(4S)-2-oxo-4-(propan-2-yl)-1,3-oxazolidin-3-yl]pyridin-2-yl}amino)ethyl]-1,2-dihydroquinolin-2-one |
| I-20 | m/z: 427.09 (M + H)+<br>Rt (min): 1.46 | | 6-chloro-3-[(1R)-1-({6-[(4S)-2-oxo-4-(propan-2-yl)-1,3-oxazolidin-3-yl]pyridin-2-yl}amino)ethyl]-1,2-dihydroquinolin-2-one |

Example 35—(S)-6-((1-(6-Chloro-7-fluoro-2-oxo-1,2-dihydroquinolin-3-yl)ethyl)amino)-2-methyl nicotinonitrile (I-22)

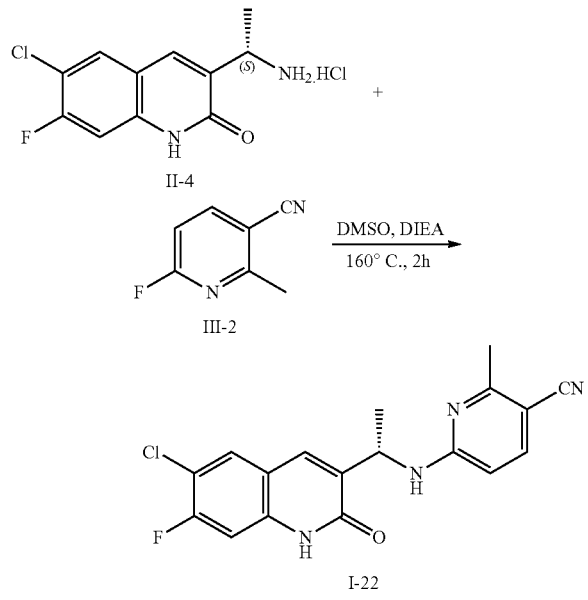

A mixture of (S)-3-(1-aminoethyl)-6-chloro-7-fluoroquinolin-2(1H)-one hydrochloride II-4 (84 mg, 0.30 mmol, 1 eq.), 6-fluoro-2-methylnicotinonitrile (45 mg, 0.33 mmol, 1.1 eq.) and DIEA (111 mg, 0.9 mmol, 3 eq.) in 1.2 mL DMSO was heated in the microwave at 160° C. for 2 hours. The reaction was then poured into water and the precipitate collected and rinsed with water. The beige solid (111 mg) was chromatographed over 3.5 g silica gel, eluting with DCM/2% EtOH. After evaporation of the pure fractions, the resulting solid was triturated with cold MeOH to provide I-22 as a gold solid (55 mg, 51%). $^1$H-NMR (300 MHz, DMSO-d$_6$, 120° C.) δ: 11.60 (broad s, 0.6H), 7.81 (d, J=7.95, 1H), 7.76 (s, 1H), 7.54 (d, J=8.79, 1H), 7.35 (broad d, 1H), 7.21 (d, J=10.44, 1H), 6.44 (d, J=8.52, 1H), 2.40 (s, 3H), 1.47 (d, J=6.60, 3H).

$^1$H-NMR (300 MHz, CDCl$_3$) δ: 11.01 broad s, 0.75H), 7.66 (s, 1H), 7.58 (d, J=7.41, 1H), 7.45 (d, J=8.49, 1H), 7.06 (d, J=9.33, 1H), 6.13 (d, J=8.52, 1H), 5.82 (broad d, 1H), 5.18 (broad m, 1H), 2.55 (s, 3H), 1.61 (d, J=6.87, 3H). LC/MS(Method 3): Rt 4.6 min., m/z 357 [M+H]$^+$.

Example 36—(S)-6-((1-(6-Chloro-7-methoxy-2-oxo-1,2-dihydroquinolin-3-yl)ethyl)amino)-4-methoxy nicotinonitrile (I-25)

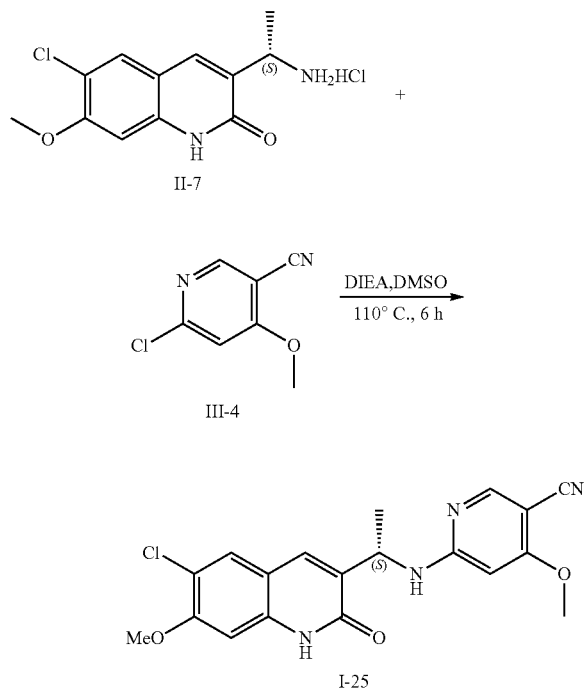

A mixture of (S)-3-(1-aminoethyl)-6-chloro-7-methoxyquinolin-2(1H)-one hydrochloride II-7 (2.89 g, 10.0 mmol), 6-chloro-4-methoxynicotinonitrile 1 (3.37 g, 20.0 mmol), N,N-diisopropylethylamine (5.20 mL, 30.0 mmol) in DMSO (30 mL) was heated at 110° C. in microwave for 6 h. MS and TLC showed clean conversion. The reaction mixture was poured into water (300 mL) with vigorous stirring. The solid was filtered and washed by water, and then dissolved in EtOAc and dried over sodium sulfate. After filtration, the solution was concentrated with silica gel and purified by ISCO (SiO$_2$: dichloromethane/EtOAc 0 to 60%) to afford the title compound I-25 as a pale yellow solid (670 mg, 17%). $^1$H NMR (300 MHz, DMSO-d$_6$) δ 11.84 (s, 1H), 8.16 (s, 1H), 8.09 (d, J=7.4 Hz, 1H), 7.76 (s, 1H), 7.65 (s, 1H), 6.94 (s, 1H), 6.24 (bs, 1H), 5.19 (bs, 1H), 3.88 (s, 3H), 3.84 (s, 3H), 1.50 (d, J=6.9 Hz, 3H); LCMS (Method 3): Rt 4.22 min, m/z 385.1[M+H]$^+$.

Example 37—(S)-6-((1-(6-chloro-7-methoxy-2-oxo-1,2-dihydroquinolin-3-yl)ethyl)amino)-4-methylnicotino-nitrile (I-27)

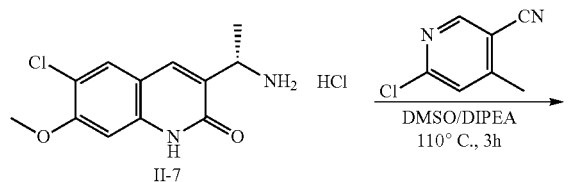

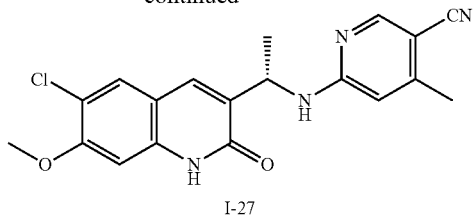

To a solution of (S)-3-(1-aminoethyl)-6-chloro-7-methoxyquinolin-2(1H)-one HCl salt, II-7 (400 mg, 1.39 mmol) in DMSO (5 ml) was added 6-chloro-4-methylnicotinonitrile (320 mg, 2.35 mmol) and DIEA (0.56 ml, 2.96 mmol). The reaction was heated at 110° C. for 3 h, MS and TLC showed completed reaction. The reaction mixture was allowed to cool, quenched with water and extracted with EtOAc. The organic layer was separated and washed with water, brine and dried over magnesium sulfate. The organic layer was filtered and concentrated and the residue obtained was purified by column (SiO$_2$: 0-10%/MeOH/DCM) to get a foam 160 mg, which was triturated with MeOH to give the title compound I-27 as pale yellow solid (150 mg). $^1$H NMR (300 MHz, DMSO-d$_6$, 120° C.) δ 11.38 (s, 1H), 8.22 (s, 1H), 7.68 (s, 1H), 7.64 (s, 1H), 7.31 (d, J=7.4 Hz, 1H), 7.02 (s, 1H), 6.52 (s, 1H), 5.17-5.22 (m, 1H), 3.91 (s, 3H), 2.29 (s, 3H), 1.47 (d, J=6.9 Hz, 3H), LCMS (Method 2): Rt 4.39 min, m/z 369.1 [M+H]$^+$.

Example 38—(S)-6-((1-(6-chloro-2-oxo-7-(pyridin-2-ylmethoxy)-1,2-dihydroquinolin-3-yl)ethyl)amino)-2-methylnicotinonitrile (I-29)

A mixture of (S)-3-(1-aminoethyl)-6-chloro-7-(pyridine-2-ylmethoxy)quinolin-2-(1H)-one II-9 (60 mg, 0.135 mmol), 6-fluoro-2-methylnicotinonitrile II-2 (28 mg, 0.202 mmol) and DIPEA (46 uL, 0.27 mmol) in DMSO (1 mL) was heated at 110° C. for 2.5 h. After TLC and MS showed completed reaction, the mixture was cooled to room temperature and poured onto crushed ice. The mixture was extracted with CH$_2$Cl$_2$ (3×10 mL), dried over anhydrous Na$_2$SO$_4$, filtered and evaporated to dryness. The resulting residue was purified by ISCO (SiO$_2$: CH$_2$Cl$_2$/MeOH 0 to 10%) to afford the title compound (I-29) (45 mg, 75%) as white solid. $^1$H NMR (300 MHz, DMSO-d$_6$): δ 11.81 (br s, 1H), 8.61 (d, J=4.6 Hz, 1H), 7.88-7.82 (m, 3H), 7.67-7.53 (m, 3H), 7.40-7.35 (m, 1H), 7.02 (s, 1H), 6.45 (br m, 1H), 5.29-5.10 (m, 3H), 2.37 (s, 3H), 1.41 (d, J=6.6 Hz, 3H). LCMS (Method 3): Rt 4.0 min, m/z 446.1[M+H]⁺.

Example 39—6-((1-(6-chloro-7-((3,3-difluorocyclobutyl)methoxy)-2-oxo-1,2-dihydro quinolin-3-yl)ethyl)amino)-2-methylnicotinonitrile (I-30)

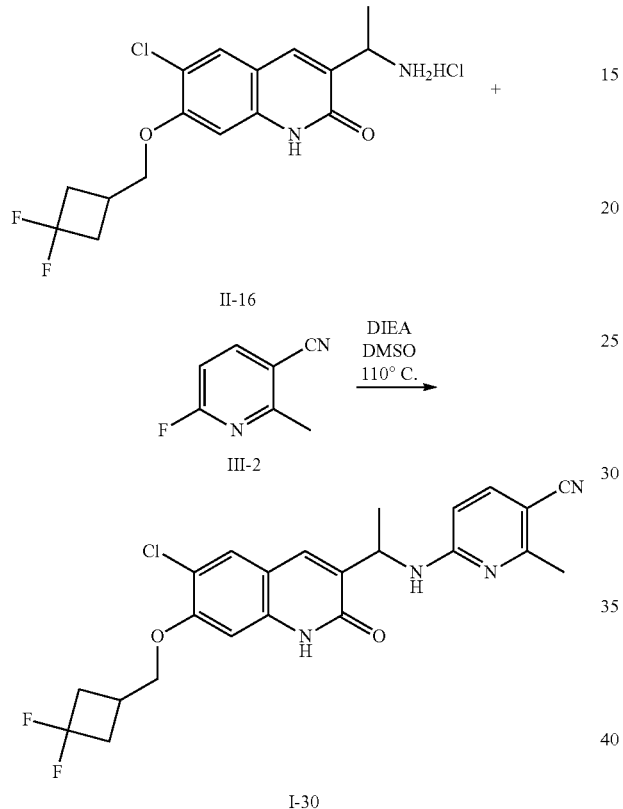

A mixture of 6-fluoro-2-methylnicotinonitrile III-2 (23.6 mg, 0.173 mmol) and 3-(1-aminoethyl)-6-chloro-7-((3,3-difluorocyclobutyl)methoxy)quinolin-2(1H)-one hydrochloride II-16 (59.5 mg, 0.157 mmol) was treated with DMSO (1 ml) and DIEA (84 μL, 0.481 mmol). The solution was stirred at 110° C. for three hours. LCMS indicated the reaction had gone to completion. The sample was mixed with water (15 mL) and extracted with DCM (3×10 mL). The extracts were dried (Na₂SO₄), filtered, treated with silica gel, and evaporated under reduced pressure. The material was chromatographed by Biotage MPLC (10 g silica gel snap column) with 0 to 70% in EtOAc in hexanes to provide the title compound (I-30) (49.1 mg, 0.107 mmol, 68.2% yield, HPLC purity 100% at 220 nm) as an off-white brittle foam. ¹H NMR (300 MHz, DMSO-d₆): δ ppm 11.84 (s, 1H), 7.88 (d, J=7.30 Hz, 1H), 7.79 (s, 1H), 7.68 (s, 1H), 7.62 (d, J=9.09 Hz, 1H), 6.93 (s, 1H), 6.44 (br s, 1H), 5.20 (br s, 1H), 4.12 (d, J=4.10 Hz, 2H), 2.52-2.80 (m, 5H), 2.36 (s, 3H), 1.41 (d, J=6.74 Hz, 3H). LCMS (Method 4): Rt 1.6 min., m/z 459.1 [M+H]⁺.

Example 40—6-(1-(6-Chloro-2-oxo-1,2-dihydroquinolin-3-yl)cyclopropylamino)-2-methyl nicotinonitrile (I-31)

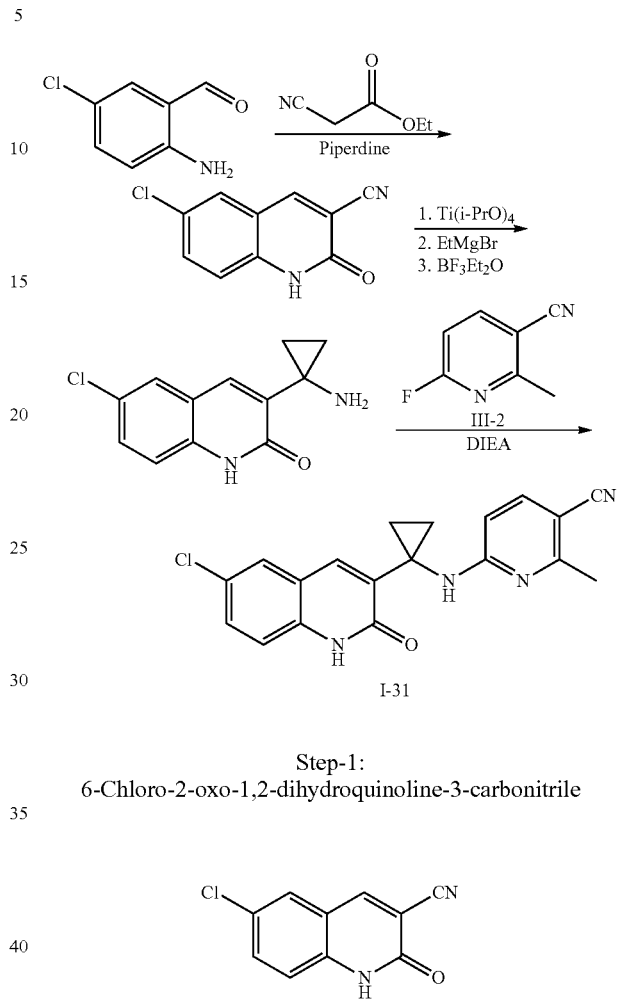

Step-1: 6-Chloro-2-oxo-1,2-dihydroquinoline-3-carbonitrile

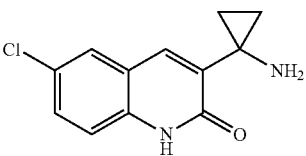 [SMILES: NC1(c2cc3cc(Cl)ccc3[nH]c2=O)CC1]

The mixture of piperidine (0.022 g, 0.257 mmol), 2-amino-5-chlorobenzaldehyde (2 g, 12.85 mmol), and ethyl 2-cyanoacetate (1.454 g, 12.85 mmol) in EtOH (30 ml) was stirred at room temperature for 30 minutes, then refluexed for 2 hours, cooled to room temperature again. The precipitate was filtered, washed with EtOH and dried to afford 1.84 g of 6-chloro-2-oxo-1,2-dihydroquinoline-3-carbonitrile (70%). ¹H NMR (300 MHz, DMSO-d₆) δ ppm 12.43-12.68 (s br, 1H), 8.50-8.78 (s, 1H), 7.54-7.96 (m, 1H), 7.33 (d, J=9.09 Hz, 1H). LCMS (Method 3): Rt 1.87 min, m/z 205.95[M+H]⁺.

Step-2: 3-(1-aminocyclopropyl)-6-chloroquinolin-2(1H)-one

121

To a solution of 6-chloro-2-oxo-1,2-dihydroquinoline-3-carbonitrile (800 mg, 3.91 mmol) in THF (15 ml) at −78° C. was added Ti(O$^i$Pr)$_4$ (1.333 g, 1.375 ml, 4.69 mmol), After 10 minutes of stirring, EtMgBr (1824 mg, 3N, 5 ml, 13.68 mmol) in ether was added. The solution was stirred at −78° C. for 30 minutes, then warmed up to room temperature, follow by addition of BF$_3$.OEt$_2$ (1.942 g, 1.734 ml, 13.68 mmol) After stirred at room temperature for additional two hours, the mixture was treated with NH$_4$Cl to quench the reaction, follow by 1 N NaOH to adjust pH to 11-12. The resulting mixture was extracted with EtOAc, dried and concentrated under reduced pressure. The Biotage purification to afford 140 mg of 3-(1-aminocyclopropyl)-6-chloroquinolin-2(1H)-one (15.26%). $^1$H NMR (300 MHz, CDCl$_3$) δ ppm 12.53 (br s, 1H), 8.20 (s, 1H), 7.65-7.82 (m, 1H), 7.50-7.59 (m, 1H), 7.35-7.49 (m, 1H), 3.04-3.22 (m, 1H), 1.21-1.45 (m, 1H), 1.09-1.26 (m, 1H), 0.76-1.01 (m, 1H). LCMS (Method 1): Rt 2.11 min, m/z 235.99 [M+H]$^+$.

Step-3: 6-(1-(6-Chloro-2-oxo-1,2-dihydroquinolin-3-yl)cyclopropylamino)-2-methyl nicotinonitrile (I-31)

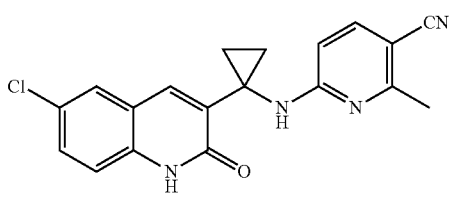 [SMILES: Cc1nc(NC2(c3cc4cc(Cl)ccc4[nH]c3=O)CC2)ccc1C#N]

The mixture 3-(1-aminocyclopropyl)-6-chloroquinolin-2(1H)-one (60 mg, 0.256 mmol) 6-fluoro-2-methylnicotinonitrile (34.8 mg, 0.256 mmol) and of DIEA (0.134 ml, 0.767 mmol) in DMSO (2 ml) was heated to 130° C. for overnight. The reaction mixture was extracted with EtOAc, washed with water and brine, then dried and concentrated under reduced pressure. The biotage purification afforded 6-(1-(6-chloro-2-oxo-1,2-dihydroquinolin-3-yl)cyclopropyl amino)-2-methylnicotinonitrile I-31 (10 mg, 11.1%). LCMS (Method 1): Rt 2.71 min, m/z 351.99[M+H]$^+$.

Example 41—4-((6-chloro-8-(2-morpholinoethoxy)-2-oxo-1,2-dihydroquinolin-3-yl)methyl amino)-2-methoxybenzonitrile (I-32)

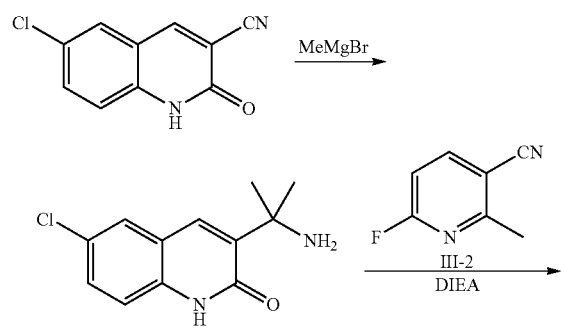

122

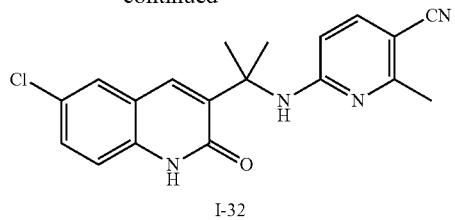

I-32

Step-1: 3-(2-aminopropan-2-yl)-6-chloroquinolin-2(1H)-one

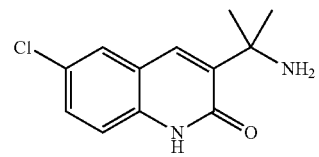 [SMILES: CC(C)(N)c1cc2cc(Cl)ccc2[nH]c1=O]

To a solution of 6-chloro-2-oxo-1,2-dihydroquinoline-3-carbonitrile (500 mg, 2.444 mmol) in THF (15 ml) at −78° C. was added Ti(O$^i$Pr)$_4$ (2.148 ml, 7.33 mmol). After stirring for 10 minutes at −78° C., methylmagnesium bromide (6.52 ml, 19.55 mmol, 3M) was added dropwise. The resulting solution was stirred at −78° C. for 30 minutes, then warmed up to room temperature. The solution was continuously stirred at room temperature for two hours, follow by addition of a saturated NH$_4$Cl solution (10 ml) to quench the reaction, then a 1 N NaOH solution to adjust pH=11-12, The mixture was extracted with EtOAc, dried over sodium sulfate, and concentrated under reduced pressure. The biotage purification on a 25 g column with 0-10%/o MeOH/DCM afforded 140 mg of 3-(2-aminopropan-2-yl)-6-chloroquinolin-2(1H)-one (22.40%/a). $^1$H NMR (300 MHz, CDCl$_3$): δ 7.67 (s, 1H), 7.52 (d, J=2.19 Hz, 1H), 7.38 (d, J=2.23 Hz, 1H), 7.30 (s, 1H), 1.60 (s, 6H). LCMS (Method 1): Rt 1.37 min, m/z 237.03[M+H]$^+$.

Step-2: 6-(2-(6-Chloro-2-oxo-1,2-dihydroquinolin-3-yl)propan-2-ylamino)-2-methyl nicotinonitrile (I-32)

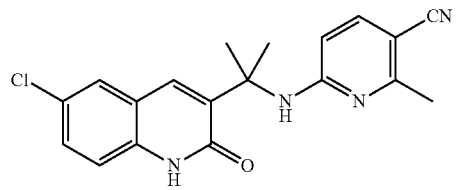 [SMILES: Cc1nc(NC(C)(C)c2cc3cc(Cl)ccc3[nH]c2=O)ccc1C#N]

The mixture of N,N-diisopropylethylamine (0.155 ml, 0.887 mmol), 3-(2-aminopropan-2-yl)-6-chloroquinolin-2(1H)-one (70 mg, 0.296 mmol) and 6-fluoro-2-methylnicotinonitrile III-2 (40.3 mg, 0.296 mmol) in DMSO (2 ml) was heated to 130° C. for overnight. The mixture was treated with EtOAc, washed with water, then brine, dried, and concentrated under reduced pressure. The biotage purification afforded 6-(2-(6-chloro-2-oxo-1,2-dihydroquinolin-3-yl)propan-2-ylamino)-2-methylnicotinonitrile (61 mg, 58.5%). $^1$H NMR (300 MHz, DMSO-d$_6$) δ ppm 11.69 (s, 1H), 7.73-7.88 (m, 2H), 7.57-7.68 (m, 1H), 7.39-7.57 (m, 2H), 7.22 (d, J=8.79 Hz, 1H), 6.41 (d, J=8.79 Hz, 1H), 2.15 (s, 3H), 1.75 (s, 6H). LCMS (Method 1): Rt 2.51 min, m/z 353.98[M+H]$^+$.
TABLE 5
The compounds listed in Table 5 were prepared using methods similar to those described for the preparation of Compounds I-22, I-25, I-27-I-32.
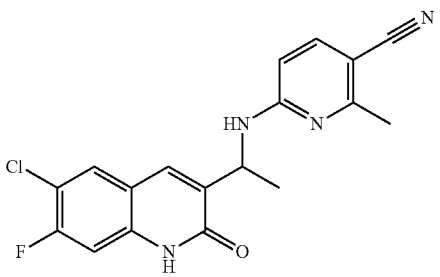 [SMILES: Cc1nc(NC(C)c2cc3cc(Cl)c(F)cc3[nH]c2=O)ccc1C#N]
I-21
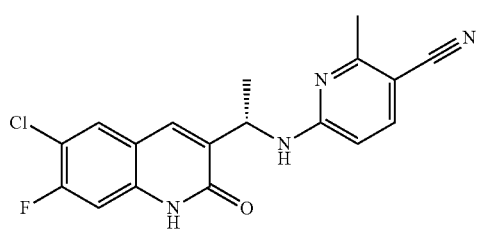 [SMILES: Cc1nc(N[C@@H](C)c2cc3cc(Cl)c(F)cc3[nH]c2=O)ccc1C#N]
I-22
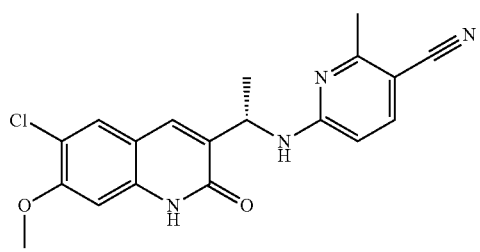 [SMILES: COc1cc2[nH]c(=O)c([C@H](C)Nc3ccc(C#N)c(C)n3)cc2cc1Cl]
I-23
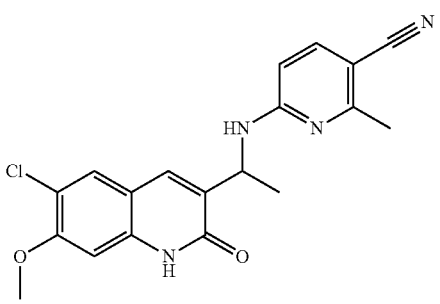 [SMILES: COc1cc2[nH]c(=O)c(C(C)Nc3ccc(C#N)c(C)n3)cc2cc1Cl]
I-24
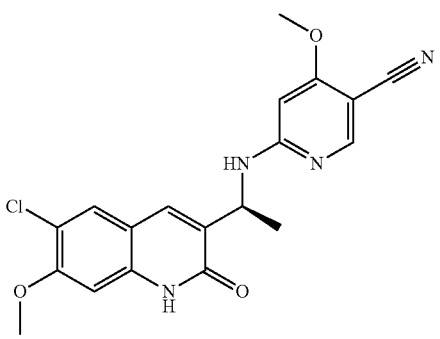 [SMILES: COc1cc2[nH]c(=O)c([C@H](C)Nc3cc(OC)c(C#N)cn3)cc2cc1Cl]
I-25

TABLE 5-continued
The compounds listed in Table 5 were prepared using methods similar to those described for the preparation of Compounds I-22, I-25, I-27-I-32.
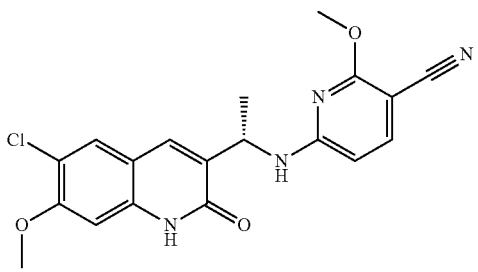 [SMILES: COc1cc2[nH]c(=O)c([C@H](C)Nc3ccc(C#N)c(OC)n3)cc2cc1Cl]
I-26
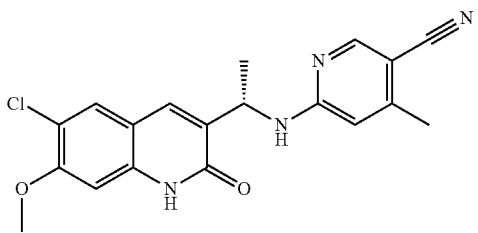 [SMILES: COc1cc2[nH]c(=O)c([C@H](C)Nc3cc(C)c(C#N)cn3)cc2cc1Cl]
I-27
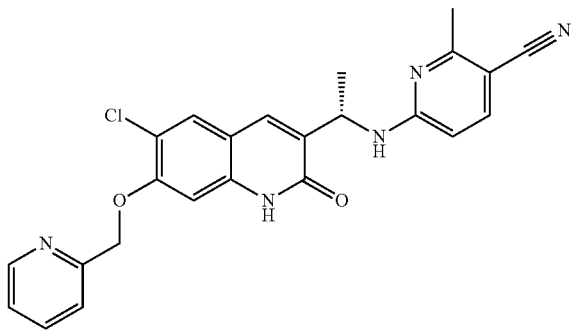 [SMILES: Cc1nc(N[C@@H](C)c2cc3cc(Cl)c(OCc4ccccn4)cc3[nH]c2=O)ccc1C#N]
I-28
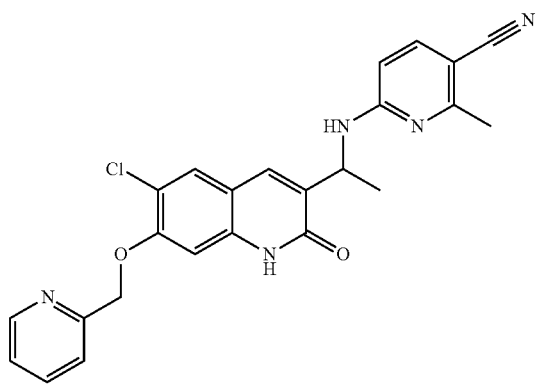 [SMILES: Cc1nc(NC(C)c2cc3cc(Cl)c(OCc4ccccn4)cc3[nH]c2=O)ccc1C#N]
I-29

TABLE 5-continued

The compounds listed in Table 5 were prepared using methods similar to those described for the preparation of Compounds I-22, I-25, I-27-I-32.

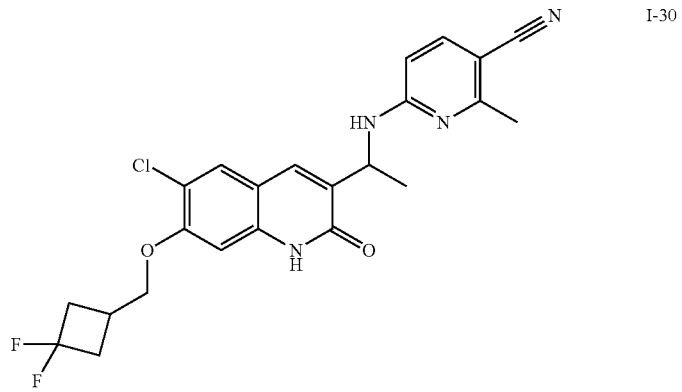

I-30

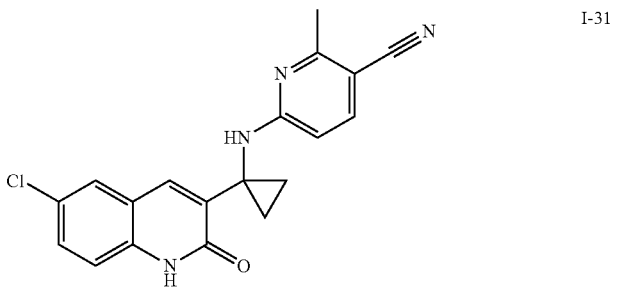

I-31

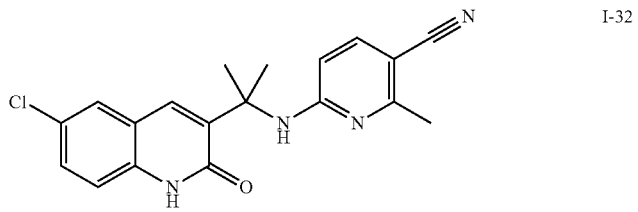

I-32

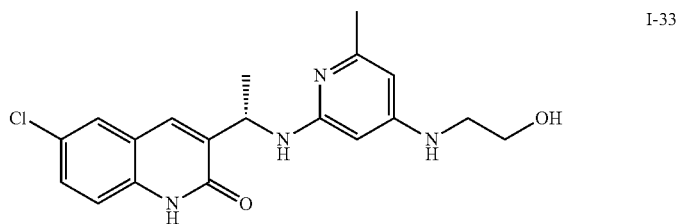

I-33

TABLE 6

LCMS signal and NMR chemical shifts of each Compound listed in Table 5.

| Compound | LCMS | 1H NMR (300 MHz) δ ppm | Chemical Name |
|---|---|---|---|
| I-21 | m/z: 357.04 (M + H)+ Rt (min): 1.38 | 1H NMR (300 MHz, DMSO-d6): δ ppm 12.04 (s, 1 H), 7.98 (d, J = 7.92 Hz, 1 H), 7.92 (d, J = 7.30 Hz, 1 H), 7.74 (s, 1 H), 7.62 (d, J = 9.09 Hz, 1 H), 7.20 (d, J = 10.26 Hz, 1 H), 6.47 (br s, 1 H), 5.07-5.30 (m, 1 H), 2.36 (s, 3 H), 1.42 (d, J = 7.04 Hz, 3 H). | 6-{[1-(6-chloro-7-fluoro-2-oxo-1,2-dihydroquinolin-3-yl)ethyl]amino}-2-methylpyridine-3-carbonitrile |

TABLE 6-continued

LCMS signal and NMR chemical shifts of each Compound listed in Table 5.

| Compound | LCMS | 1H NMR (300 MHz) δ ppm | Chemical Name |
|---|---|---|---|
| I-22 | m/z: 357.17 (M + H)+<br>Rt (min): 1.38 | 1H NMR (300 Hz, CDCl3) δppm:<br>11.01 broad s, 0.75H), 7.66 (s, 1H),<br>7.58 (d, J = 7.41, 1H), 7.45 (d, J = 8.49,<br>1H), 7.06 (d, J = 9.33, 1H),<br>6.13 (d, J = 8.52, 1H), 5.82 (broad d, 1H),<br>5.18 (broad m, 1H), 2.55 (s, 3H),<br>1.61 (d, J = 6.87, 3H). | 6-{[(1S)-1-(6-chloro-7-<br>fluoro-2-oxo-1,2-<br>dihydroquinolin-3-<br>yl)ethyl]amino}-2-<br>methylpyridine-3-<br>carbonitrile |
| I-23 | m/z: 369.19 (M + H)+<br>Rt (min): 1.32 | 1H-NMR (300 MHz, DMSO-d6, 120° C.)<br>δ: 11.42 (broad s, 0.71H),<br>7.70 (s, 1H), 7.66 (s, 1H), 7.55 (d, J = 8.79,<br>1H), 7.37 (bs, 1H), 7.02 (s, 1H),<br>6.42 (d, J = 8.70, 1H), 5.18 (m, 1H),<br>3.91 (s, 3H), 2.41 (s, 3H), 1.47 (d, J = 6.33,<br>3H) | 6-{[(1S)-1-(6-chloro-7-<br>methoxy-2-oxo-1,2-<br>dihydroquinolin-3-<br>yl)ethyl]amino}-2-<br>methylpyridine-3-<br>carbonitrile |
| I-24 | m/z: 369.06 (M + H)+<br>Rt (min): 1.33 | 1H NMR (300 MHz, DMSO-d6): δ<br>ppm 11.84 (s, 1 H), 7.87 (d, J = 7.30 Hz,<br>1 H), 7.78 (s, 1 H), 7.67 (s, 1 H),<br>7.61 (d, J = 8.79 Hz, 1 H), 6.94 (s, 1<br>H), 6.43 (br s, 1 H), 5.08-5.33 (m, 1<br>H), 3.87 (s, 3 H), 2.37 (s, 3 H),<br>1.41 (d, J = 6.74 Hz, 3 H). | 6-{[1-(6-chloro-7-methoxy-<br>2-oxo-1,2-dihydroquinolin-<br>3-yl)ethyl]amino}-2-<br>methylpyridine-3-<br>carbonitrile |
| I-25 | m/z: 385.19 (M + H)+<br>Rt (min): 1.25 | 1H NMR (300 MHz, DMSO-d6) δ<br>11.84 (s, 1H), 8.16 (s, 1H), 8.09 (d, J = 7.4 Hz,<br>1H), 7.76 (s, 1H), 7.65 (s,<br>1H), 6.94 (s, 1H), 6.24 (bs, 1H),<br>5.19 (bs, 1H), 3.88 (s, 3H), 3.84 (s, 3H),<br>1.50 (d, J = 6.9 Hz, 3H); LCMS<br>(method LCMS3, Cl): RT = 4.22 min,<br>m/z = 385.1, 387.1 [M +H]+ | 6-{[(1S)-1-(6-chloro-7-<br>methoxy-2-oxo-1,2-<br>dihydroquinolin-3-<br>yl)ethyl]amino}-4-<br>methoxypyridine-3-<br>carbonitrile |
| I-26 | m/z: 385.15 (M + H)+<br>Rt (min): 1.36 | 1H NMR (300 MHz, DMSO-d6): δ<br>ppm 11.82 (br s, 1 H), 8.07 (br s, 1<br>H), 7.77 (s, 1 H), 7.66 (s, 1 H),<br>7.59 (br d, J = 8.21 Hz, 1 H), 6.94 (s, 1 H),<br>6.24 (br s, 1 H), 5.17 (br s, 1 H),<br>3.87 (s, 3 H), 3.74 (br s, 3 H), 1.43 (d,<br>J = 6.74 Hz, 3 H). | 6-{[(1S)-1-(6-chloro-7-<br>methoxy-2-oxo-1,2-<br>dihydroquinolin-3-<br>yl)ethyl]amino}-2-<br>methoxypyridine-3-<br>carbonitrile |
| I-27 | m/z: 369.20 (M + H)+<br>Rt (min): 1.3 | 1H NMR (300 MHz, DMSO-d6, 120° C.)<br>δ 11.38 (s, 1H), 8.22 (s, 1H),<br>7.68 (s, 1H), 7.64 (s, 1H), 7.31 (d, J = 7.4 Hz,<br>1H), 7.02 (s, 1H), 6.52 (s,<br>1H), 5.17-5.22 (m, 1H), 3.91 (s, 3H),<br>2.29 (s, 3H), 1.47 (d, J = 6.9 Hz, 3H) | 6-{[(1S)-1-(6-chloro-7-<br>methoxy-2-oxo-1,2-<br>dihydroquinolin-3-<br>yl)ethyl]amino}-4-<br>methylpyridine-3-<br>carbonitrile |
| I-28 | m/z: 446.04 (M + H)+<br>Rt (min): 1.38 | 1H NMR (300 MHz, DMSO-d6): δ<br>11.81 (br s, 1H), 8.61 (d, J = 4.6 Hz,<br>1H), 7.88-7.82 (m, 3H),<br>7.67-7.53 (m, 3H), 7.40-7.35 (m, 1H), 7.02 (s,<br>1H), 6.45 (br m, 1H), 5.29-5.10 (m,<br>3H), 2.37 (s, 3H), 1.41 (d, J = 6.6 Hz,<br>3H). | 6-{[(1S)-1-[6-chloro-2-oxo-<br>7-(pyridin-2-ylmethoxy)-1,2-<br>dihydroquinolin-3-<br>yl]ethyl]amino}-2-<br>methylpyridine-3-<br>carbonitrile |
| I-29 | m/z: 446.10 (M + H)+<br>Rt (min): 1.3414 | 1H NMR (300 MHz, DMSO-d6): δ<br>ppm 11.82 (s, 1 H), 8.57-8.64 (m, 1<br>H), 7.88 (ddd, J = 7.62, 7.62, 1.76 Hz,<br>2 H), 7.83 (s, 1 H), 7.68 (s, 1 H),<br>7.62 (d, J = 8.79 Hz, 1 H), 7.55 (d, J = 7.92 Hz,<br>1 H), 7.38 (dd, J = 6.74, 4.69 Hz, 1<br>H), 7.02 (s, 1 H), 5.29 (s, 2 H),<br>2.36 (s, 3 H), 1.40 (d, J = 7.04 Hz, 3 H).<br>missing NH, one methyne H (buried<br>in baseline?) | 6-({1-[6-chloro-2-oxo-7-<br>(pyridin-2-ylmethoxy)-1,2-<br>dihydroquinolin-3-<br>yl]ethyl}amino)-2-<br>methylpyridine-3-<br>carbonitrile |
| I-30 | m/z: 459.05 (M + H)+<br>Rt (min): 1.6 | 1H NMR (300 MHz, DMSO-d6): δ<br>ppm 11.84 (s, 1 H), 7.88 (d, J = 7.30 Hz,<br>1 H), 7.79 (s, 1 H), 7.68 (s, 1 H),<br>7.62 (d, J = 9.09 Hz, 1 H), 6.93 (s, 1<br>H), 6.44 (br s, 1 H), 5.20 (br s, 1 H),<br>4.12 (d, J = 4.10 Hz, 2 H),<br>2.52-2.80 (m, 5 H), 2.36 (s, 3 H), 1.41 (d,<br>J = 6.74 Hz, 3 H). | 6-[(1-{6-chloro-7-[(3,3-<br>difluorocyclobutyl)methoxy]-<br>2-oxo-1,2-dihydroquinolin-<br>3-yl}ethyl)amino]-2-<br>methylpyridine-3-<br>carbonitrile |
| I-31 | m/z: 351.04 (M + H)+<br>Rt (min): 1.36 | | 6-{[1-(6-chloro-2-oxo-1,2-<br>dihydroquinolin-3-<br>yl)cyclopropyl]amino}-2-<br>methylpyridine-3-<br>carbonitrile |

TABLE 6-continued

LCMS signal and NMR chemical shifts of each Compound listed in Table 5.

| Compound | LCMS | 1H NMR (300 MHz) δ ppm | Chemical Name |
|---|---|---|---|
| I-32 | m/z: 353.10 (M + H)+ Rt (min): 1.54 | 1H NMR (300 MHz, DMSO-d6): δ 11.68 (br, 1H), 7.83 (s, 1H), 7.80 (d, J = 2.37 Hz, 1H), 7.47 (d, J = 8.92 Hz, 1H), 7.42 (d, J = 2.4 Hz, 1H)7.22 (d, J = 8.78 Hz, 1H), 6.41 (d, J=, 1H), 2.15 (s, 3H), 1.75 (s, 6H). | 6-{[2-(6-chloro-2-oxo-1,2-dihydroquinolin-3-yl)propan-2-yl]amino}-2-methylpyridine-3-carbonitrile |
| I-33 | m/z: 373.07 (M + H)+ Rt (min): 0.84 | | 6-chloro-3-[(1S)-1-({4-[(2-hydroxyethyl)amino]-6-methylpyridin-2-yl}amino)ethyl]-1,2-dihydroquinolin-2-one |

Example 42—(S)—N-(2-((1-(6-chloro-2-oxo-1,2-dihydroquinolin-3-yl)ethyl)amino)-3-fluoro pyridin-4-yl)acetamide (I-34)

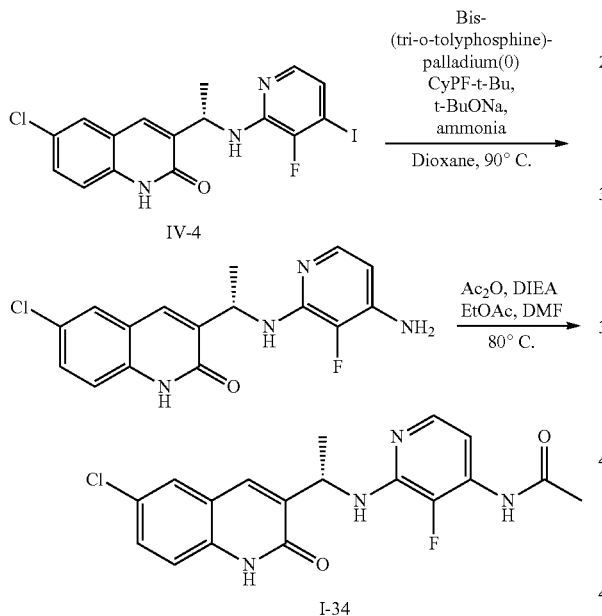

Step 1. (S)-3-(1-((4-amino-3-fluoropyridin-2-yl)amino)ethyl)-6-chloroquinolin-2(1H)-one

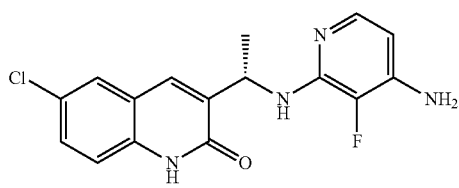 [SMILES: C[C@H](Nc1nccc(N)c1F)c1cc2cc(Cl)ccc2[nH]c1=O]

A mixture of (S)-6-chloro-3-(1-((3-fluoro-4-iodopyridin-2-yl)amino)ethyl)quinolin-2(1H)-one IV-4 (110.2 mg, 0.248 mmol), bis(tri-o-tolylphosphine)palladium(0) (9.5 mg, 0.013 mmol), (R)-(−)-1-[(S)-2-(Dicyclohexylphosphino)ferrocenyl]ethyldi-t-butylphosphine (CypF-t-Bu; 6.9 mg, 1.250 mmol), and sodium tert-butoxide (33.7 mg, 0.351 mmol) was placed under nitrogen in a 40 mL vial. Dioxane (4 ml) and ammonia (0.5M in dioxane, 2.5 ml, 1.250 mmol) were added by syringe and the mixture was stirred at 90° C. one day. The sample was diluted with MeOH, silica gel was added, and the solvent was evaporated under reduced pressure. The material was chromatographed by Biotage MPLC (10 g silica gel column, 0 to 8% MeOH in DCM, with isocratic elution at 4% MeOH) to provide (S)-3-(1-((4-amino-3-fluoropyridin-2-yl)amino)ethyl)-6-chloroquinolin-2(1H)-one (30 mg, 0.90 mmol, 36%) as a brown solid. $^1$H NMR (300 MHz, DMSO-d$_6$): δ ppm 11.93 (s, 1H), 7.73 (br s, 2H), 7.47 (dd, J=8.65, 2.49 Hz, 1H), 7.22-7.33 (m, 2H), 6.28 (d, J=7.90 Hz, 1H), 5.98 (dd, J=6.00, 6.00 Hz, 1H), 5.70 (s, 2H), 5.20 (quin, J=7.04 Hz, 1H), 1.40 (d, J=6.74 Hz, 3H). LCMS (Method 1): Rt 1.50 min., m/z 333.0 [M+H]$^+$.

Step 2: (S)—N-(2-((1-(6-chloro-2-oxo-1,2-dihydroquinolin-3-yl)ethyl)amino)-3-fluoropyridin-4-yl)acetamide (I-34)

A suspension of (S)-3-(1-((4-amino-3-fluoropyridin-2-yl)amino)ethyl)-6-chloroquinolin-2(1H)-one (26.6 mg, 0.080 mmol) in ethyl acetate (3 ml) was treated with acetic anhydride (7.8 µl, 0.083 mmol) and DIEA (15.4 µl, 0.088 mmol) and stirred at room temperature overnight. LCMS showed only starting material. The suspension was treated with DMF (1 mL) and the material went into solution. LCMS after 4 weeks showed 6% conversion to product. The EtOAc was evaporated under reduced pressure, more DMF (2 mL), Ac$_2$O (15.6 µL), and DIEA (30.8 µL) were added, and the solution was shaken at 80° C. six days. The solvent was evaporated under reduced pressure. The residue was dissolved in DCM (10 mL) and washed with water, and the aqueous wash was back-extracted with DCM (10 mL). The organics were combined, silica gel was added, and the mixture was evaporated under reduced pressure. The material was chromatographed by Biotage MPLC (10 g silica gel column, 0 to 10% MeOH in DCM, with isocratic elution when peaks came off) to provide the title compound I-34

(2.4 mg, 6.00 µmol, 7.5% yield, HPLC purity 93.6% at 220 nm). LCMS (Method 4): Rt 1.00 min., m/z 375.1 [M+H]⁺.

Example 43—(S)-6-chloro-3-(1-((6-(1,1-dioxidoiso-thiazolidin-2-yl)pyridin-2-yl)amino) ethyl)quinolin-2(1H)-one (I-35)

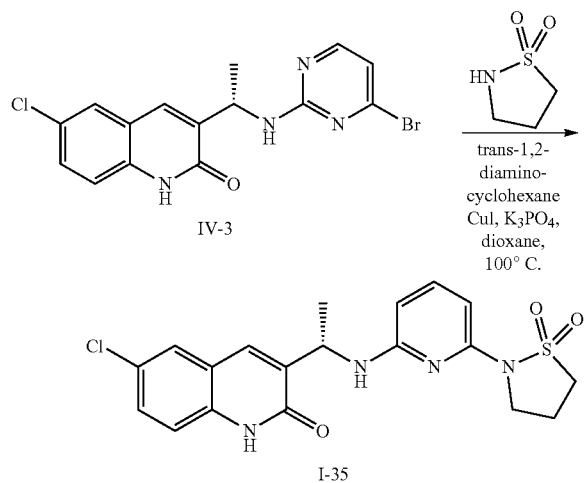

A 2 dram vial was charged with (S)-3-(1-(6-bromopyridin-2-ylamino)ethyl)-6-chloroquinolin-2(1H)-one IV-3 (30.3 mg, 0.080 mmol), CuI (17.1 mg, 0.090 mmol), 1,3-propanesultam (11.7 mg, 0.097 mmol), and tripotassium phosphate (136.3 mg, 0.642 mmol) and placed under nitrogen. A solution of trans-cyclohexane-1,2-diamine (9.5 µl, 0.079 mmol) in dioxane (2.4 ml) was added by syringe and the mixture was stirred at 100° C. for five hours. The sample was diluted with MeOH and DCM and filtered. The filtrate was treated with silica gel and evaporated under reduced pressure. The material was chromatographed by Biotage MPLC (10 g silica gel cartridge, 0 to 3.4% MeOH in DCM, with isocratic elution at 1.7% MeOH) to provide the title compound (I-35) (20.9 mg, 0.046 mmol, 57.5% yield, HPLC purity 92.25% at 220 nm) as a solid. ¹H NMR (300 MHz, DMSO-d₆): δ ppm 11.93 (s, 1H), 7.74 (s, 1H), 7.71 (d, J=2.35 Hz, 1H), 7.46 (dd, J=8.79, 2.35 Hz, 1H), 7.25-7.36 (m, 2H), 7.03 (d, J=6.74 Hz, 1H), 6.24 (d, J=7.62 Hz, 1H), 6.19 (d, J=7.92 Hz, 1H), 4.99-5.12 (m, 1H), 3.75-3.86 (m, 1H), 3.50-3.60 (m, 1H), 3.46 (t, J32 7.33 Hz, 2H), 2.18-2.32 (m, 2H), 1.40 (d, J=6.74 Hz, 3H). LCMS (Method 4): Rt 1.25 min., m/z 419.1 [M+H]⁺.

Example 44—(S)-6-chloro-3-(1-((3-fluoro-4-(1H-imidazol-1-yl)pyridin-2-yl)amino)ethyl) quinolin-2(1H)-one (I-37)

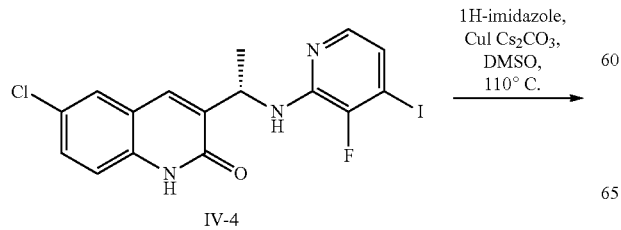

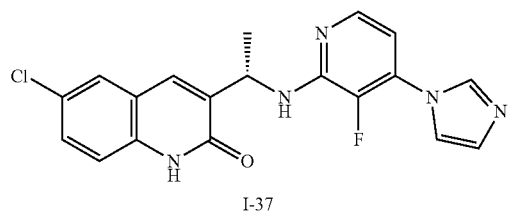

A suspension of (S)-6-chloro-3-(1-((3-fluoro-4-iodopyridin-2-yl)amino)ethyl) quinolin-2(1H)-one IV-4 (39.7 mg, 0.089 mmol), 1H-imidazole (8.9 mg, 0.131 mmol), copper (I) oxide (5.2 mg, 0.036 mmol), and Cs₂CO₃ (57.7 mg, 0.177 mmol) in DMSO (0.3 ml) was stirred at 110° C. overnight. LCMS showed a ~1.5:1 mixture of product and iodide starting material. The sample was diluted with MeOH, silica gel was added, and the solvent was evaporated under reduced pressure. The sample was chromatographed by Biotage MPLC (10 g silica gel column, 0 to 6% MeOH in DCM, with isocratic elution at 4% MeOH) to provide the title compound (I-37) (13.7 mg, 0.034 mmol, 38.3% yield, HPLC purity 96% at 220 nm) as a film. ¹H NMR (300 MHz, DMSO-d₆): δ ppm 11.99 (s, 1H), 7.83 (d, J=5.28 Hz, 1H), 7.77 (s, 1H), 7.74 (d, J=2.35 Hz, 1H), 7.48 (dd, J=8.79, 2.35 Hz, 1H), 7.37 (d, J=7.60 Hz, 1H), 7.30 (d, J=8.79 Hz, 1H), 6.86 (br s, 1H), 5.25-5.40 (m, 1H), 1.47 (d, J=7.04 Hz, 3H). LCMS (Method 4): Rt 1.05 min., m/z 384.0 [M+H]⁺.

TABLE 7

The compounds listed in Table 7 were prepared using methods similar to those described for the preparation of Compounds I-34 to I-37

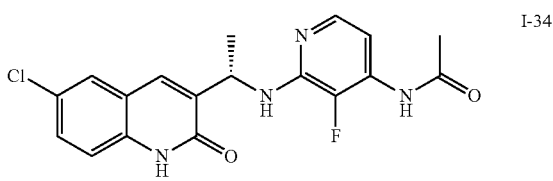

I-34

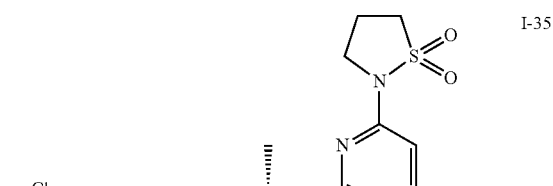

I-35

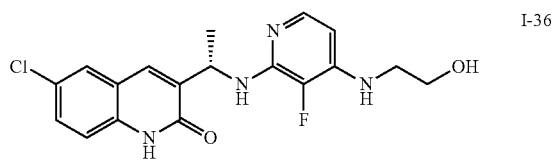

I-36

TABLE 7-continued

The compounds listed in Table 7 were prepared using methods similar to those described for the preparation of Compounds I-34 to I-37

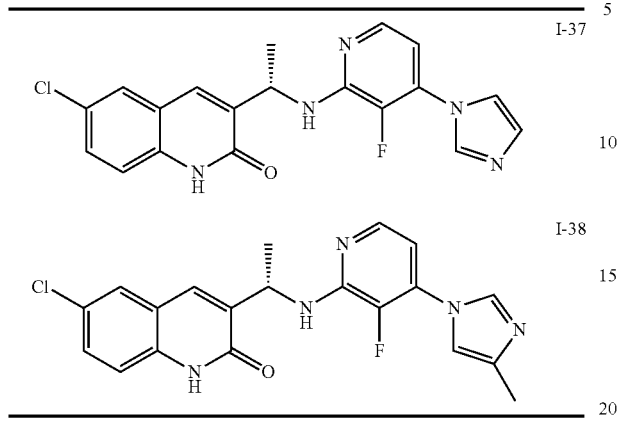

Example 45—Library synthesis protocol: (S)-6-chloro-3-(1-((4-(1,3-dimethyl-1H-pyrazol-5-yl)pyridin-2-yl)amino)ethyl) quinolin-2(1H)-one (I-39)

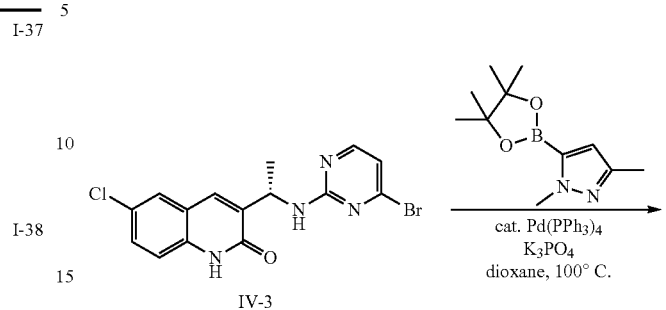

TABLE 8

LCMS signal and NMR chemical shifts of each Compound listed in Table 7.

| Compound | LCMS | 1H NMR (300 MHz) δ ppm | Chemical Name |
|---|---|---|---|
| I-34 | m/z: 375.07 (M + H)+ Rt (min): 1.0 | 1 1H NMR (300 MHz, DMSO-d6): δ ppm 11.96 (s, 1 H), 9.93 (s, 1 H), 7.69-7.77 (m, 2 H), 7.59 (d, J = 5.57 Hz, 1 H), 7.47 (dd, J = 8.50, 2.05 Hz, 1 H), 7.29 (d, J = 8.79 Hz, 1 H), 7.24 (dd, J = 5.10, 5.10 Hz, 1 H), 6.87 (d, J = 7.90 Hz, 1 H), 5.18-5.32 (m, 1 H), 2.12 (s, 3 H), 1.44 (d, J = 7.04 Hz, 3 H). | N-(2-{[(1S)-1-(6-chloro-2-oxo-1,2-dihydroquinolin-3-yl)ethyl]amino}-3-fluoropyridin-4-yl)acetamide |
| I-35 | m/z: 419.06 (M + H)+ Rt (min): 1.25 | 1H NMR (300 MHz, DMSO-d6): δ ppm 11.93 (s, 1 H), 7.74 (s, 1 H), 7.71 (d, J = 2.35 Hz, 1 H), 7.46 (dd, J = 8.79, 2.35 Hz, 1 H), 7.25-7.36 (m, 2 H), 7.03 (d, J = 6.74 Hz, 1 H), 6.24 (d, J = 7.62 Hz, 1 H), 6.19 (d, J = 7.92 Hz, 1 H), 4.99-5.12 (m, 1 H), 3.75-3.86 (m, 1 H), 3.50-3.60 (m, 1 H), 3.46 (t, J = 7.33 Hz, 2 H), 2.18-2.32 (m, 2 H), 1.40 (d, J = 6.74 Hz, 3 H). | 2-(6-{[(1S)-1-(6-chloro-2-oxo-1,2-dihydroquinolin-3-yl)ethyl]amino}pyridin-2-yl)-1$\lambda^6$,2-thiazolidine-1,1-dione |
| I-36 | m/z: 377.06 (M + H)+ Rt (min): 0.79 | | 6-chloro-3-[(1S)-1-({3-fluoro-4-[(2-hydroxyethyl)amino]pyridin-2-yl}amino)ethyl]-1,2-dihydroquinolin-2-one |
| I-37 | m/z: 384.02 (M + H)+ Rt (min): 1.0472 | 1H NMR (300 MHz, DMSO-d6): δ ppm 11.99 (s, 1 H), 7.83 (d, J = 5.28 Hz, 1 H), 7.77 (s, 1 H), 7.74 (d, J = 2.35 Hz, 1 H), 7.48 (dd, J = 8.79, 2.35 Hz, 1 H), 7.37 (d, J = 7.60 Hz, 1 H), 7.30 (d, J = 8.79 Hz, 1 H), 6.86 (br s, 1 H), 5.25-5.40 (m, 1 H), 1.47 (d, J = 7.04 Hz, 3 H). The three imidazole protons don't show up-we decided they are spread out in the baseline. | 6-chloro-3-[(1S)-1-{[3-fluoro-4-(1H-imidazol-1-yl)pyridin-2-yl]amino}ethyl]-1,2-dihydroquinolin-2-one |
| I-38 | m/z: 397.99 (M + H)+ Rt (min): 1.05 | 1H NMR (300 MHz, DMSO-d6): δ ppm 11.98 (s, 1 H), 7.80 (d, J = 5.57 Hz, 1 H), 7.77 (s, 1 H), 7.74 (d, J = 2.05 Hz, 1 H), 7.48 (dd, J = 8.79, 2.35 Hz, 1 H), 7.25-7.37 (m, 2 H), 6.81 (dd, J = 4.80, 4.80 Hz, 1 H), 5.32 (m, 1 H), 2.18 (br s, 3 H), 1.47 (d, J = 7.04 Hz, 3 H). | 6-chloro-3-[(1S)-1-{[3-fluoro-4-(4-methyl-1H-imidazol-1-yl)pyridin-2-yl]amino}ethyl]-1,2-dihydroquinolin-2-one |

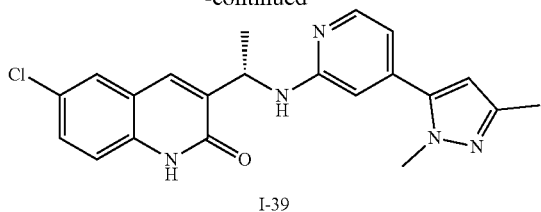

I-39

A 2 mL reaction vial was charged with 0.2M 1,4-dioxane solutions of (S)-3-(1-((4-bromopyridin-2-yl)amino)ethyl)-6-chloroquinolin-2(1H)-one IV-2 (100 uL, 20 umol) and 1,3-dimethyl-5-(4,4,5,5-tetramethyl-1,3,2-dioxaborolan-2-yl)-1H-pyrazole (150 uL, 30 umol, 1.5 equivalents). To the mixture was added 1M aqueous potassium phosphate tribasic solution (75 uL, 75 umol, 3.75 equivalents). Nitrogen gas was bubbled through the mixture for 3-5 seconds before a 0.01M solution of palladium tetrakis in 1,4-dioxane (50 uL, 0.5 umol) was added. Nitrogen gas was passed through the mixture once more, then the vial was sealed and heated at 100° C. overnight. LC-MS analysis confirmed the presence of the cross-coupled product. The mixture was diluted with brine (500 uL) and extracted with ethyl acetate (2×500 uL). The organic layers were dropped onto a 0.5 gram ion exchange column (benzenesulfonic acid on silica). The column was flushed with ethyl acetate (3 mL), then the title compound was released from the column by eluting with a 10:1:1 solution of ethyl acetate/methanol/triethylamine (3 mL). The eluent containing crude product was concentrated under a stream of nitrogen at 50° C., dissolved in DMSO (500 uL), and purified by mass-triggered preparatory HPLC to yield the title compound (4.5 mg, 57% yield).). LCMS (Method 4): Rt 0.99 min, m/z 394.08 [M+H]$^+$.

Example 46—(S)-6-chloro-3-(1-((3-fluoro-4-(1-methyl-1H-pyrrol-2-yl)pyridin-2-yl)amino) ethyl) quinolin-2(1H)-one (I-42)

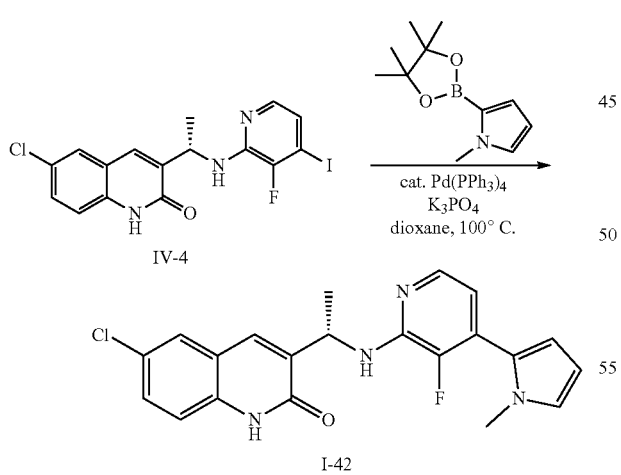

I-42

A 2 mL reaction vial was charged with 0.2M 1,4-dioxane solutions of (S)-6-chloro-3-(1-((3-fluoro-4-iodopyridin-2-yl)amino)ethyl)quinolin-2(1H)-one IV-4 (100 uL, 20 umol) and 1-methyl-2-(4,4,5,5-tetramethyl-1,3,2-dioxaborolan-2-yl)-1H-pyrrole (150 uL, 30 umol, 1.5 equivalents). To the mixture was added 1M aqueous potassium phosphate tribasic solution (75 uL, 75 umol, 3.75 equivalents). Nitrogen gas was bubbled through the mixture for 3-5 seconds before a 0.01M solution of palladium tetrakis in 1,4-dioxane (50 uL, 0.5 umol) was added. Nitrogen gas was passed through the mixture once more, then the vial was sealed and heated at 100° C. overnight. LC-MS analysis confirmed the presence of the cross-coupled product. The mixture was diluted with brine (500 uL) and extracted with ethyl acetate (2×500 uL). The organic layers were concentrated under a stream of nitrogen at 50° C., dissolved in DMSO (500 uL), and purified by mass-triggered preparatory HPLC to yield the title compound (4.3 mg, 54% yield). LCMS (Method 4): Rt 1.54 min, m/z 397.05 [M+H]$^+$.

TABLE 9

The compounds listed in Table 10 were prepared using methods similar to those described for the preparation of Compounds I-39 and I-42.

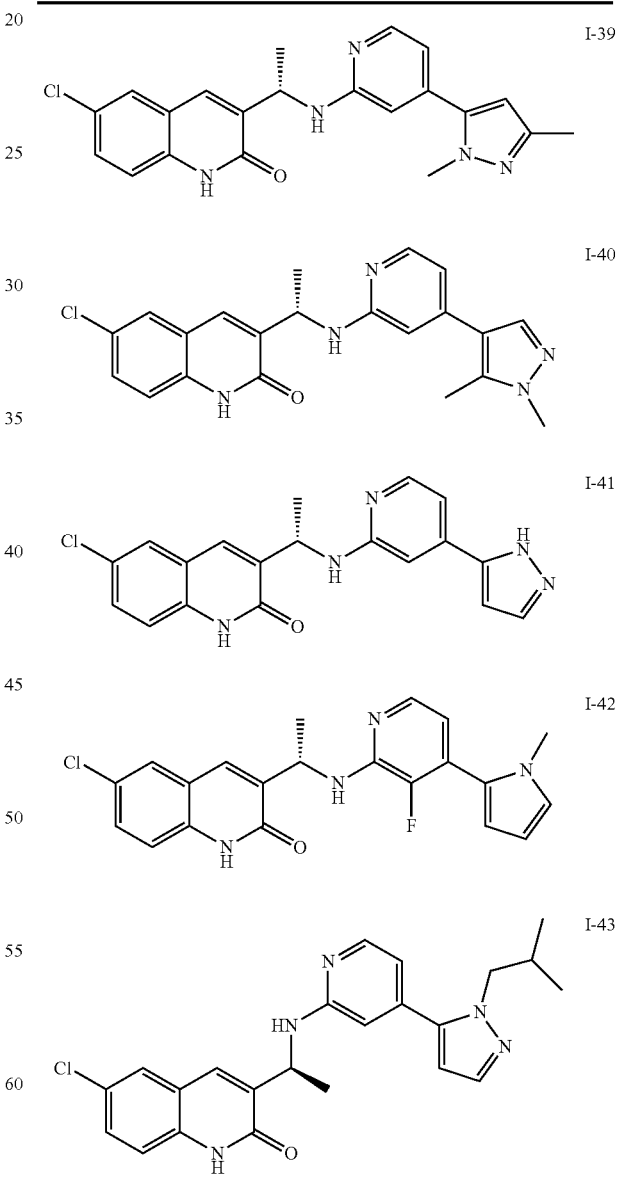

TABLE 9-continued
The compounds listed in Table 10 were prepared using methods similar to those described for the preparation of Compounds I-39 and I-42.
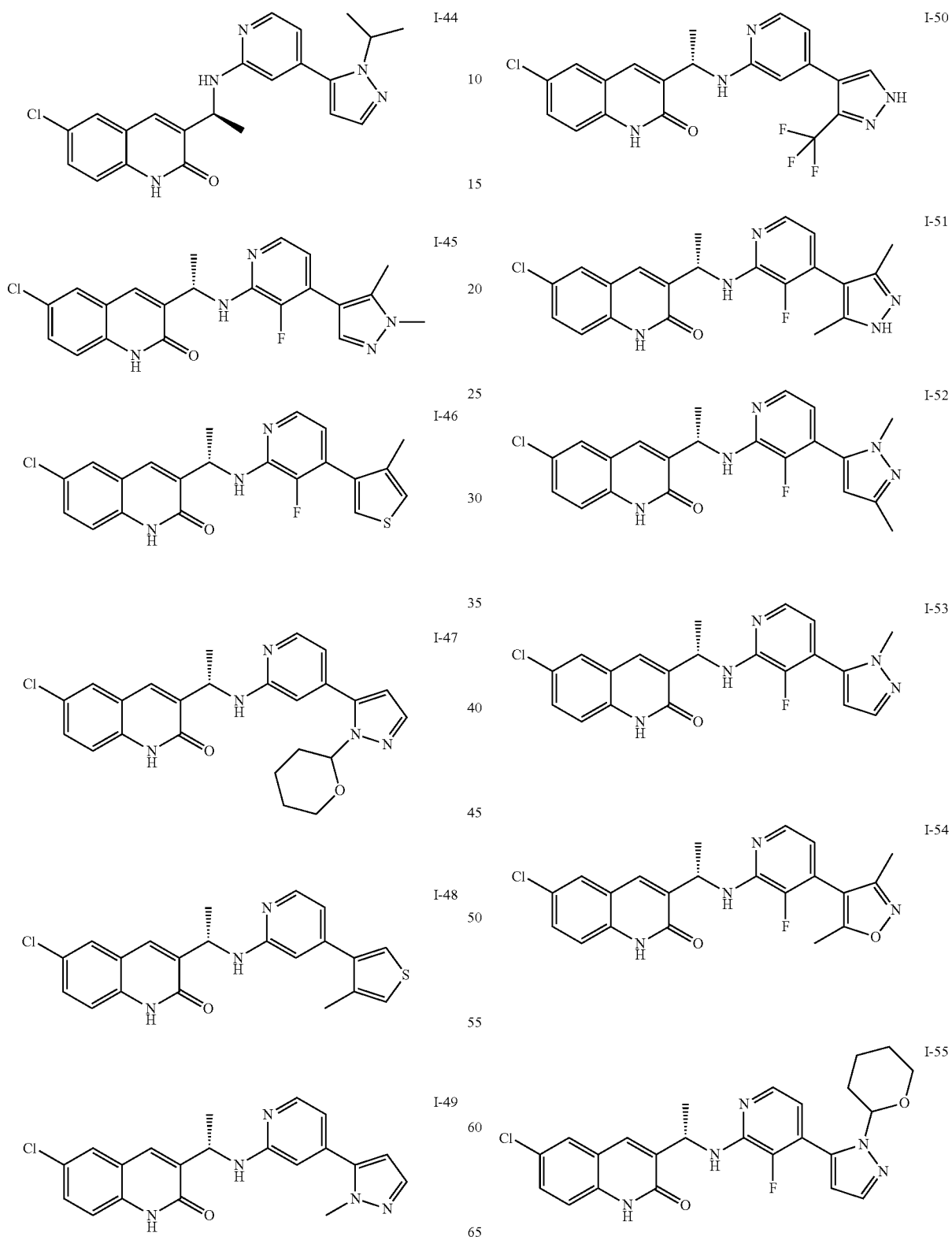

TABLE 9-continued

The compounds listed in Table 10 were prepared using methods similar to those described for the preparation of Compounds I-39 and I-42.

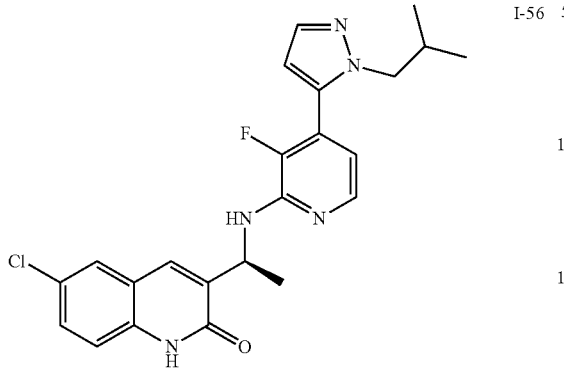

I-56

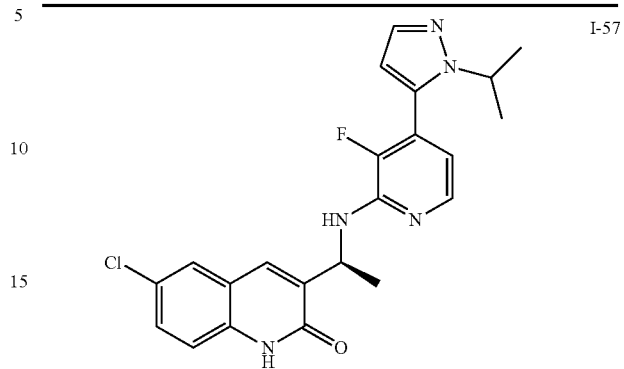

I-57

TABLE 10

LCMS signal and chemical names of each compound listed in Table 9.

| Compound | LCMS | Chemical Name |
| --- | --- | --- |
| I-39 | m/z: 394.08 (M + H)+<br>Rt (min): 0.98 | 6-chloro-3-[(1S)-1-{[4-(1,3-dimethyl-1H-pyrazol-5-yl)pyridin-2-yl]amino}ethyl]-1,2-dihydroquinolin-2-one |
| I-40 | m/z: 394.10 (M + H)+<br>Rt (min): 0.89 | 6-chloro-3-[(1S)-1-{[4-(1,5-dimethyl-1H-pyrazol-4-yl)pyridin-2-yl]amino}ethyl]-1,2-dihydroquinolin-2-one |
| I-41 | m/z: 366.06 (M + H)+<br>Rt (min): 0.85 | 6-chloro-3-[(1S)-1-{[4-(1H-pyrazol-5-yl)pyridin-2-yl]amino}ethyl]-1,2-dihydroquinolin-2-one |
| I-42 | m/z: 397.05 (M + H)+<br>Rt (min): 1.54 | 6-chloro-3-[(1S)-1-{[3-fluoro-4-(1-methyl-1H-pyrrol-2-yl)pyridin-2-yl]amino}ethyl]-1,2-dihydroquinolin-2-one |
| I-43 | m/z: 422.10 (M + H)+<br>Rt (min): 1.18 | 6-chloro-3-[(1S)-1-({4-[1-(2-methylpropyl)-1H-pyrazol-5-yl]pyridin-2-yl}amino)ethyl]-1,2-dihydroquinolin-2-one |
| I-44 | m/z: 408.16 (M + H)+<br>Rt (min): 1.1 | 6-chloro-3-[(1S)-1-({4-[1-(propan-2-yl)-1H-pyrazol-5-yl]pyridin-2-yl}amino)ethyl]-1,2-dihydroquinolin-2-one |
| I-45 | m/z: 412.03 (M + H)+<br>Rt (min): 1.23 | 6-chloro-3-[(1S)-1-{[4-(1,5-dimethyl-1H-pyrazol-4-yl)-3-fluoropyridin-2-yl]amino}ethyl]-1,2-dihydroquinolin-2-one |
| I-46 | m/z: 414.00 (M + H)+<br>Rt (min): 1.71 | 6-chloro-3-[(1S)-1-{[3-fluoro-4-(4-methylthiophen-3-yl)pyridin-2-yl]amino}ethyl]-1,2-dihydroquinolin-2-one |
| I-47 | m/z: 450.11 (M + H)+<br>Rt (min): 1.14 | 6-chloro-3-[(1S)-1-({4-[1-(oxan-2-yl)-1H-pyrazol-5-yl]pyridin-2-yl}amino)ethyl]-1,2-dihydroquinolin-2-one |
| I-48 | m/z: 396.02 (M + H)+<br>Rt (min): 1.17 | 6-chloro-3-[(1S)-1-{[4-(4-methylthiophen-3-yl)pyridin-2-yl]amino}ethyl]-1,2-dihydroquinolin-2-one |
| I-49 | m/z: 380.08 (M + H)+<br>Rt (min): 0.94 | 6-chloro-3-[(1S)-1-{[4-(1-methyl-1H-pyrazol-5-yl)pyridin-2-yl]amino}ethyl]-1,2-dihydroquinolin-2-one |
| I-50 | m/z: 434.03 (M + H)+<br>Rt (min): 1.0 | 6-chloro-3-[(1S)-1-({4-[3-(trifluoromethyl)-1H-pyrazol-4-yl]pyridin-2-yl}amino)ethyl]-1,2-dihydroquinolin-2-one |
| I-51 | m/z: 412.02 (M + H)+<br>Rt (min): 1.14 | 6-chloro-3-[(1S)-1-{[4-(3,5-dimethyl-1H-pyrazol-4-yl)-3-fluoropyridin-2-yl]amino}ethyl]-1,2-dihydroquinolin-2-one |
| I-52 | m/z: 412.09 (M + H)+<br>Rt (min): 1.37 | 6-chloro-3-[(1S)-1-{[4-(1,3-dimethyl-1H-pyrazol-5-yl)-3-fluoropyridin-2-yl]amino}ethyl]-1,2-dihydroquinolin-2-one |
| I-53 | m/z: 398.07 (M + H)+<br>Rt (min): 1.32 | 6-chloro-3-[(1S)-1-{[3-fluoro-4-(1-methyl-1H-pyrazol-5-yl)pyridin-2-yl]amino}ethyl]-1,2-dihydroquinolin-2-one |
| I-54 | m/z: 413.03 (M + H)+<br>Rt (min): 1.46 | 6-chloro-3-[(1S)-1-{[4-(dimethyl-1,2-oxazol-4-yl)-3-fluoropyridin-2-yl]amino}ethyl]-1,2-dihydroquinolin-2-one |
| I-55 | m/z: 468.07 (M + H)+<br>Rt (min): 1.48 | 6-chloro-3-[(1S)-1-({3-fluoro-4-[1-(oxan-2-yl)-1H-pyrazol-5-yl]pyridin-2-yl}amino)ethyl]-1,2-dihydroquinolin-2-one |

TABLE 10-continued

LCMS signal and chemical names of each compound listed in Table 9.

| Compound | LCMS | Chemical Name |
|---|---|---|
| I-56 | m/z: 440.11 (M + H)+<br>Rt (min): 1.58 | 6-chloro-3-[(1S)-1-({3-fluoro-4-[1-(2-methylpropyl)-1H-pyrazol-5-yl]pyridin-2-yl}amino)ethyl]-1,2-dihydroquinolin-2-one |
| I-57 | m/z: 426.04 (M + H)+<br>Rt (min): 1.51 | 6-chloro-3-[(1S)-1-({3-fluoro-4-[1-(propan-2-yl)-1H-pyrazol-5-yl]pyridin-2-yl}amino)ethyl]-1,2-dihydroquinolin-2-one |

Example 47—4-(((6-chloro-2-oxo-1,2-dihydroquinolin-3-yl)methyl)amino)-2-methoxybenzonitrile (I-58)

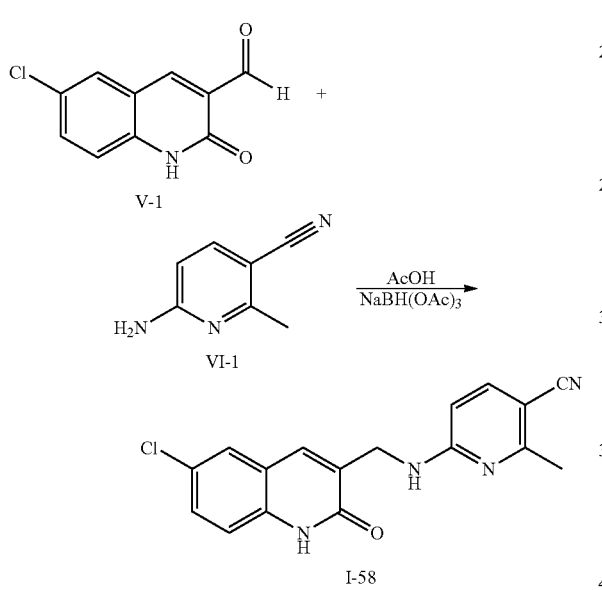

A suspension of 6-chloro-2-oxo-1,2-dihydroquinoline-3-carbaldehyde (150 mg, 0.722 mmol) and 6-amino-2-methylnicotinonitrile (115 mg, 0.867 mmol) in DCE (20 ml) was treated with AcOH (0.124 ml, 2.167 mmol) and stirred for 20 minutes. Sodium triacetoxyborohydride (459 mg, 2.167 mmol) was added. The mixture was placed under nitrogen and stirred at room temperature. After 30 minute, the suspension went into solution. The brown solution was stirred at RT over the weekend, during which time a material precipitated. The mixture was diluted with EtOAc (50 mL), washed with water (2×50 mL) and brine (50 mL), dried ($Na_2SO_4$), filtered, and evaporated. The residue (~0.13 g) was dissolved in methanol, treated with silica gel, and evaporated. The crude material was chromatographed by Biotage MPLC (25 g silica gel column) with 0 to 10% MeOH/DCM to yield 40 mg of 6-(((6-chloro-2-oxo-1,2-dihydroquinolin-3-yl)methylamino)-2-methylnicotinonitrile I-58 (17%). $^1$H NMR (300 MHz, DMSO-$d_6$): δ 12.02 (br, 1H), 7.72-7.79 ((m, 3H), 7.47 (dd, $J_1$=2.34 Hz, $J_2$=8.79 Hz, 1H), 7.29 (d, J=8.79 Hz, 1H), 6.75 (d, J=8.8 Hz, 1H), 4.31 (sd, J=5.57 Hz, 1H), 4.11 (s, 1H), 3.14 (d, J=5.27 Hz, 1H). LCMS (Method 4): Rt 1.31 min, m/z 325.00 [M+H]+.

TABLE 12

The compounds listed in Table 12 were prepared using methods similar to those described for the preparation of Compound I-58.

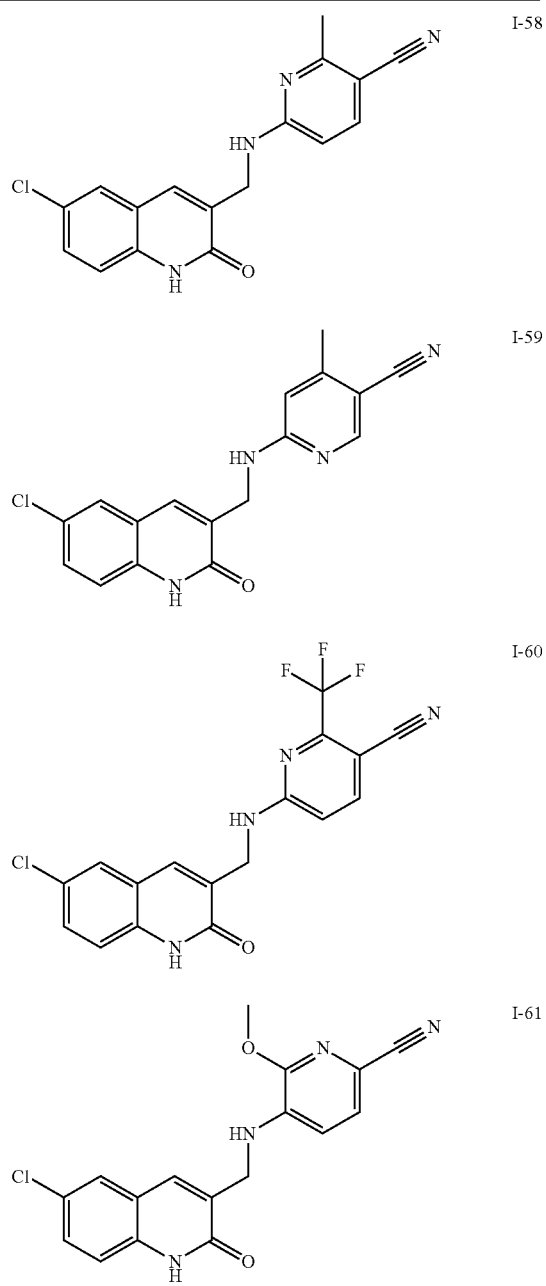

TABLE 12-continued

The compounds listed in Table 12 were prepared using methods similar to those described for the preparation of Compound I-58.

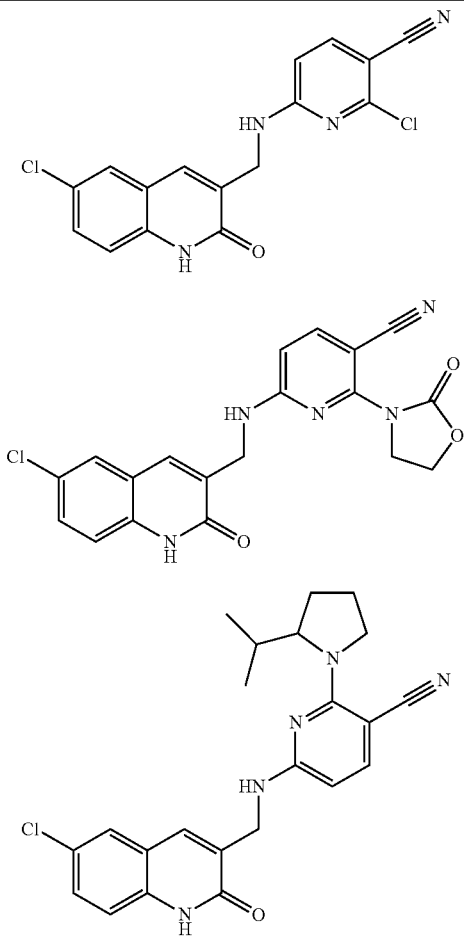

I-62

I-63

I-64

TABLE 12-continued

The compounds listed in Table 12 were prepared using methods similar to those described for the preparation of Compound I-58.

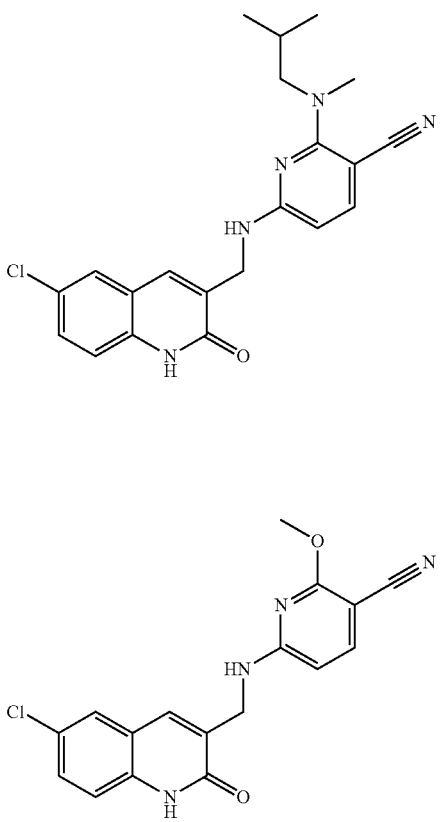

I-65

I-66

TABLE 13

LCMS signal and NMR chemical shifts of each compound listed in Table 12.

| Compound | LCMS | 1H NMR (300 MHz) δ ppm | Chemical Name |
|---|---|---|---|
| I-58 | m/z: 325.00 (M + H)+ Rt (min): 1.31 | 1H NMR (300 MHz, DMSO-d6): δ 12.02 (br, 1H), 7.72-7.79 ((m, 3H), 7.47 (dd, J1 = 2.34 Hz, J2 = 8.79 Hz, 1H), 7.29 (d, J = 8.79 Hz, 1H), 6.75 (d, J = 8.8 Hz, 1H),, 4.31 (sd, J = 5.57 Hz, 1H), 4.11 (s, 1H), 3.14 (d, J = 5.27 Hz, 1H) | 6-{[(6-chloro-2-oxo-1,2-dihydroquinolin-3-yl)methyl]amino}-2-methylpyridine-3-carbonitrile |
| I-59 | m/z: 325.00 (M + H)+ Rt (min): 1.24 | 1H NMR (300 MHz, DMSO-d6): δ 11.98 (br, 1H), 8.24 (s, 1H), 7.86 (s, 1H), 7.72 (d, J = 2.21 Hz, 1H), 7.59 (s 1H), 7.41 (d, J = 8.47 Hz, 1H), 7.25 (d, J = 8.78 Hz, 1H), 6.49 (s, 1H), 4.33 (s, 2H), 2.22 (s, 3H) | 6-{[(6-chloro-2-oxo-1,2-dihydroquinolin-3-yl)methyl]amino}-4-methylpyridine-3-carbonitrile |
| I-60 | m/z: 378.98 (M + H)+ Rt (min): 1.5 | 1H NMR (300 MHz, DMSO-d6): δ 12.02 (br, 1H), 8.54 (s, 1H), 7.90 (s, 1H), 7.70 (s, 2H), 7.45 (d, J = 7.05 Hz, 1H), 7.25 (d, J = 87.8 Hz, 1H),, 6.86 (s, 1H), 4.37 (s, 2H) | 6-{[(6-chloro-2-oxo-1,2-dihydroquinolin-3-yl)methyl]amino}-2-(trifluoromethyl)pyridine-3-carbonitrile |
| I-61 | m/z: 340.98 (M + H)+ Rt (min): 1.35 | 1H NMR (300 MHz, DMSO-d6): δ 12.01 (br, 1H), 7.75 (s, 1H), 7.56 (s, 1H), 7.45 (dd, J1 = 2.64 Hz, J2 = 8.79 Hz, 1H), 7.25-7.30 (m, 2H), 6.90 (m, 1H),, 6.57 (d, J = 7.91 Hz, 1H), 4.22 (d, J = 5.57 Hz, 2H), 3.94 (s, 3H) | 5-{[(6-chloro-2-oxo-1,2-dihydroquinolin-3-yl)methyl]amino}-6-methoxypyridine-2-carbonitrile |

TABLE 13-continued

LCMS signal and NMR chemical shifts of each compound listed in Table 12.

| Compound | LCMS | 1H NMR (300 MHz) δ ppm | Chemical Name |
|---|---|---|---|
| I-62 | m/z: 344.89 (M + H)+ Rt (min): 1.48 | 1H NMR (300 MHz, DMSO-d6): δ 12.03 (br, 1H), 8.00 (d, J = 7.95 Hz, 1H), 7.95 (m, 1H), 7.80 (s, 1H), 7.64 (s, 1H)), 7.45-7.48 (m, 1H) 7.29 (d, J = 8.79 Hz, 1H), 6.73 (d, J = 7.95 Hz, 1H), 4.37 (d, J = 5.26 Hz, 2H), 3.31 (s, 3H) | 2-chloro-6-{[(6-chloro-2-oxo-1,2-dihydroquinolin-3-yl)methyl]amino}pyridine-3-carbonitrile |
| I-63 | m/z: 396.12 (M + H)+ Rt (min): 1.26 | | 6-{[(6-chloro-2-oxo-1,2-dihydroquinolin-3-yl)methyl]amino}-2-(2-oxo-1,3-oxazolidin-3-yl)pyridine-3-carbonitrile |
| I-64 | m/z: 422.24 (M + H)+ Rt (min): 1.8533 | 1H NMR (300 MHz, DMSO-d6): δ 11.93 (br, 1H), 7.74 (s, 1H), 7.37-7.43 (m, 3H), 7.24 (m, 1H), 7.06 (m, 1H), 5.72 (d, J=, 1H) 4.16-4.44 (m, 2H), 3.70-3.78 (m., 1H), 3.10-3.25 (m, 1H), 1.82-1.92 (m, 1H), 1.66-1.78 (m, 2H), 1.54-1.64 (m, 2H), 1.14-1.16 (m, 1H), 0.25-0.50 (m, 6H) | 6-{[(6-chloro-2-oxo-1,2-dihydroquinolin-3-yl)methyl]amino}-2-[2-(propan-2-yl)pyrrolidin-1-yl]pyridine-3-carbonitrile |
| I-65 | m/z: 396.22 (M + H)+ Rt (min): 1.735 | 1H NMR (300 MHz, DMSO-d6): δ 11.93 (br, 1H), 7.74 (s, 1H), 7.37-7.43 (m, 3H), 7.24 (d, J = 8.93 Hz, 1H), 7.06 (m, 1H), 5.82 (d, J = 8.98 Hz, 1H) 4.29 (d, J = 4.97 Hz, 2H), 3.70-3.78 (m., 1H), 3.05-3.20 (m, 2H), 32.79*s, 3H), 1.64 (m, 1H)0.05 (s, 6H) | 6-{[(6-chloro-2-oxo-1,2-dihydroquinolin-3-yl)methyl]amino}-2-[methyl(2-methylpropyl)amino]pyridine-3-carbonitrile |
| I-66 | m/z: 340.92 (M + H)+ Rt (min): 1.43 | 1H NMR (300 MHz, DMSO-d6): δ 11.95 (br, 1H), 7.79 (s, 1H), 7.75 (d, J = 8.36 Hz, 1H), 7.62 (s, 1H), 7.56 (m, 1H), 7.42 (m, 1H) 7.26 (d, J = 8.68 Hz, 1H), 6.03 (d, J = 8.44 Hz, 1H), 4.21 (d, J = 5.5 Hz, 2H), 3.63 (s, 3H) | 6-{[(6-chloro-2-oxo-1,2-dihydroquinolin-3-yl)methyl]amino}-2-methoxypyridine-3-carbonitrile |

Example 48—Library Synthesis Protocol: 6-(((6-chloro-2-oxo-1,2-dihydroquinolin-3-yl)methyl)amino)nicotinonitrile (I-67)

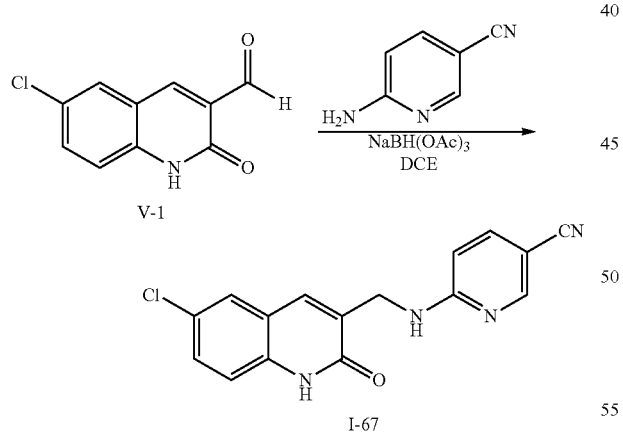

6-Chloro-2-oxo-1,2-dihydroquinoline-3-carbaldehyde V-1 (4.15 mg, 20 umol) was added as a solid to a 0.2 M solution of 6-aminonicotinonitrile in DMA (165 μL, 33 umol). An additional volume of 1,2-dichloroethane (150 mL) was added, and the mixture was agitated at room temperature for 5 minutes. The resultant mixture was charged with a 0.2M suspension of sodium triacetoxyborohydride in DCE (200 uL, 40 umol) and was agitated overnight at room temperature. After LC-MS analysis confirmed the presence of reductive amination product, the mixture was partitioned between ethyl acetate (500 μL) and saturated aqueous sodium bicarbonate solution (500 μL). The organic layer was transferred, and the aqueous layer was extracted once more with fresh ethyl acetate (500 μL). The organic layers were combined and concentrated under reduced pressure with heat (50° C.). The crude residue was dissolved in DMSO (500 μL) and purified by mass-triggered preparatory HPLC to yield the title compound (0.8 mg, 13% yield). LCMS (Method 4): Rt 1.20 min, m/z 311.00 [M+H]+.

Example 49—6-(((6-chloro-2-oxo-7-(pyridin-2-ylmethoxy)-1,2-dihydroquinolin-3-yl) methyl)amino)-2-methylnicotinonitrile (I-84)

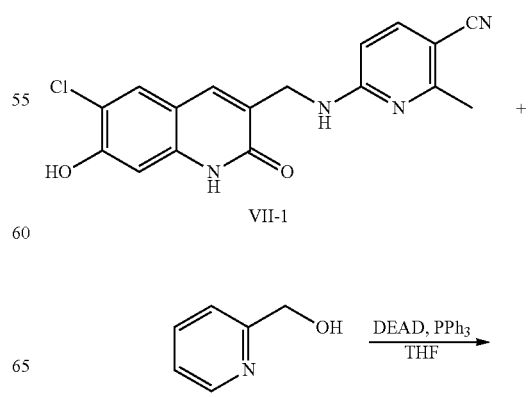

-continued

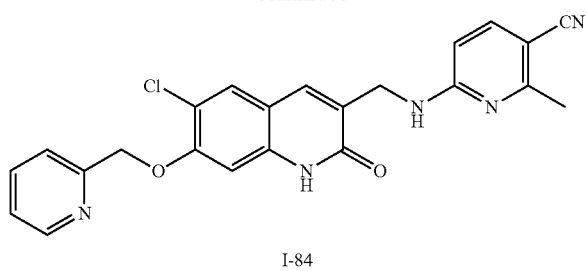

I-84

In a 1.5 mL vial was added 6-(((6-chloro-7-hydroxy-2-oxo-1,2-dihydroquinolin-3-yl)methyl)amino)-2-methylnicotinonitrile (150 μL, 0.030 mmol) and triphenylphosphine (180 μL, 0.036 mmol) in fresh dioxane to give a tan solution. Pyridin-2-ylmethanol (165 L, 0.033 mmol) was added. The vial was flushed with $N_2$. (E)-diisopropyl diazene-1,2-dicarboxylate (180 μL, 0.036 mmol) in fresh anhydrous THF was added. The vial was quickly capped and heated for 2 hours at 50° C. LCMS shows that the triphenylphosphine has been consumed but there is still some 4-(((6-chloro-7-hydroxy-2-oxo-1,2-dihydroquinolin-3-yl)methyl)amino)-2-methoxy benzonitrile present. More triphenylphosphine (180 μL, 0.036 mmol) and (E)-diisopropyl diazene-1,2-dicarboxylate (180 μL, 0.036 mmol) in fresh THF were added. The reaction was heated for two hours at 50° C. LCMS shows that the starting material has been consumed. The reaction was dried down under $N_2$. The residue was partitioned between 1 mL of 1N NaOH and 1 mL of EtOAc (×2). The combined organic extracts were dried under $N_2$ flow. The residue was submitted for mass-triggered prep HPLC purification (2.5 mg, 19% yield). LCMS (Method 4): Rt 1.76 min, m/z 432.30 $[M+H]^+$

TABLE 14

The compounds listed in Table 14 were prepared using methods similar to the one described for the preparation of Compound I-67 and I-84.

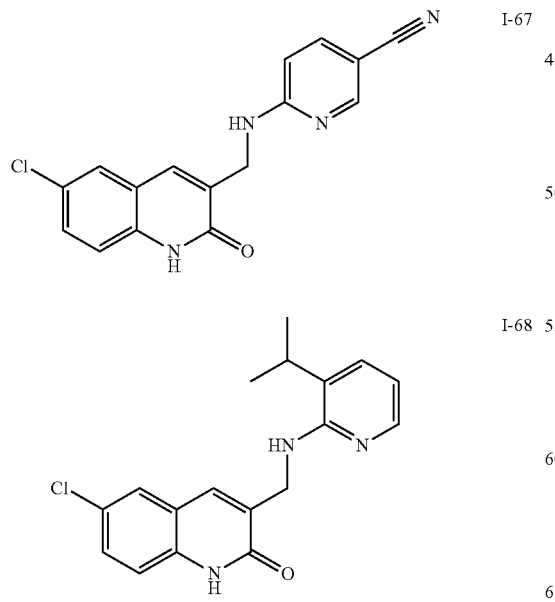

TABLE 14-continued

The compounds listed in Table 14 were prepared using methods similar to the one described for the preparation of Compound I-67 and I-84.

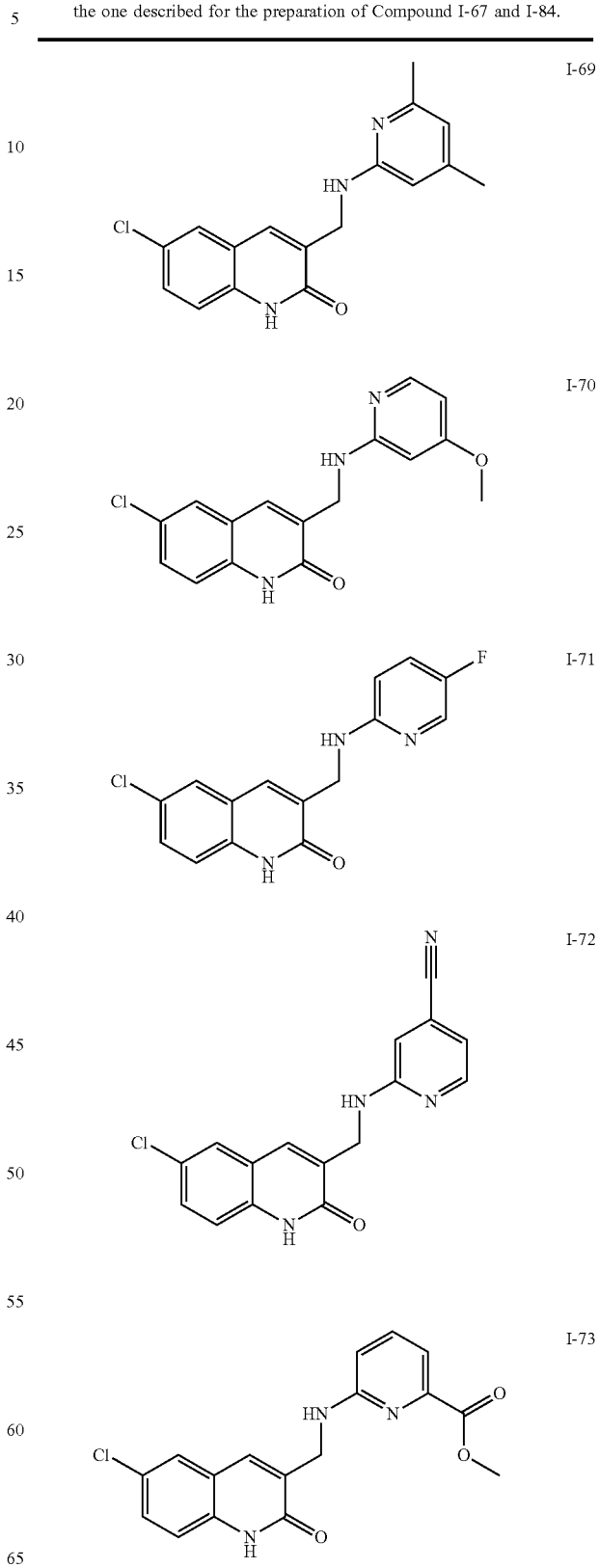

TABLE 14-continued
The compounds listed in Table 14 were prepared using methods similar to the one described for the preparation of Compound I-67 and I-84.
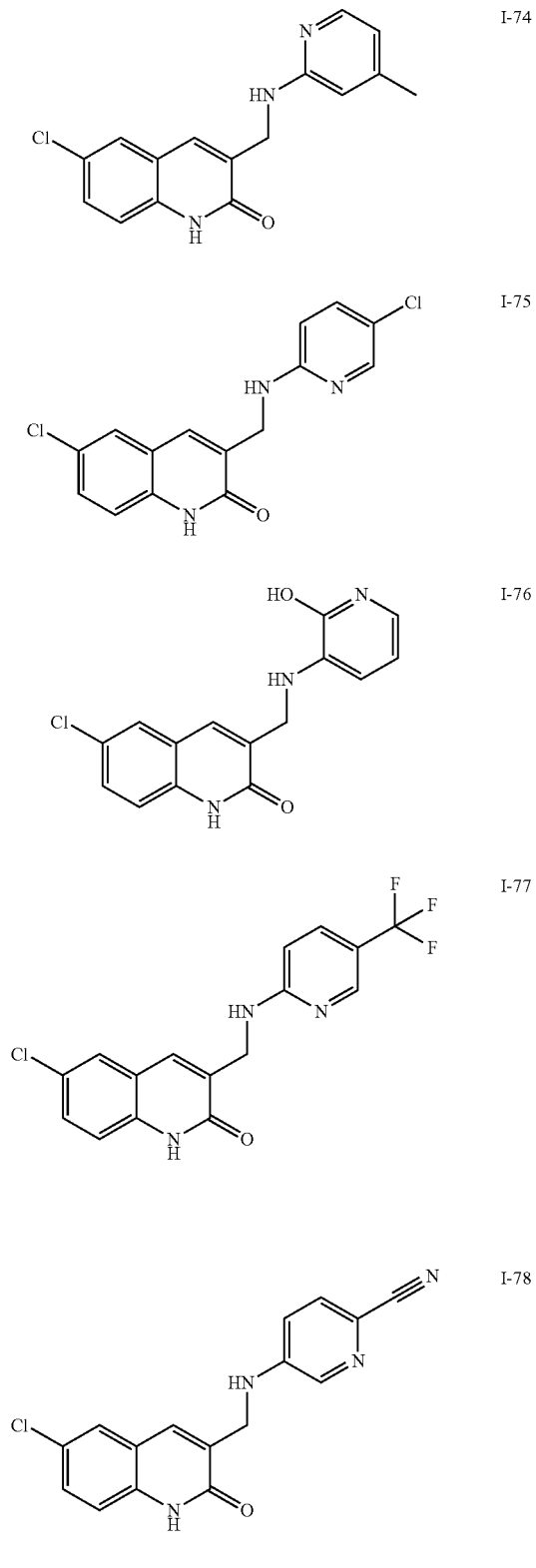
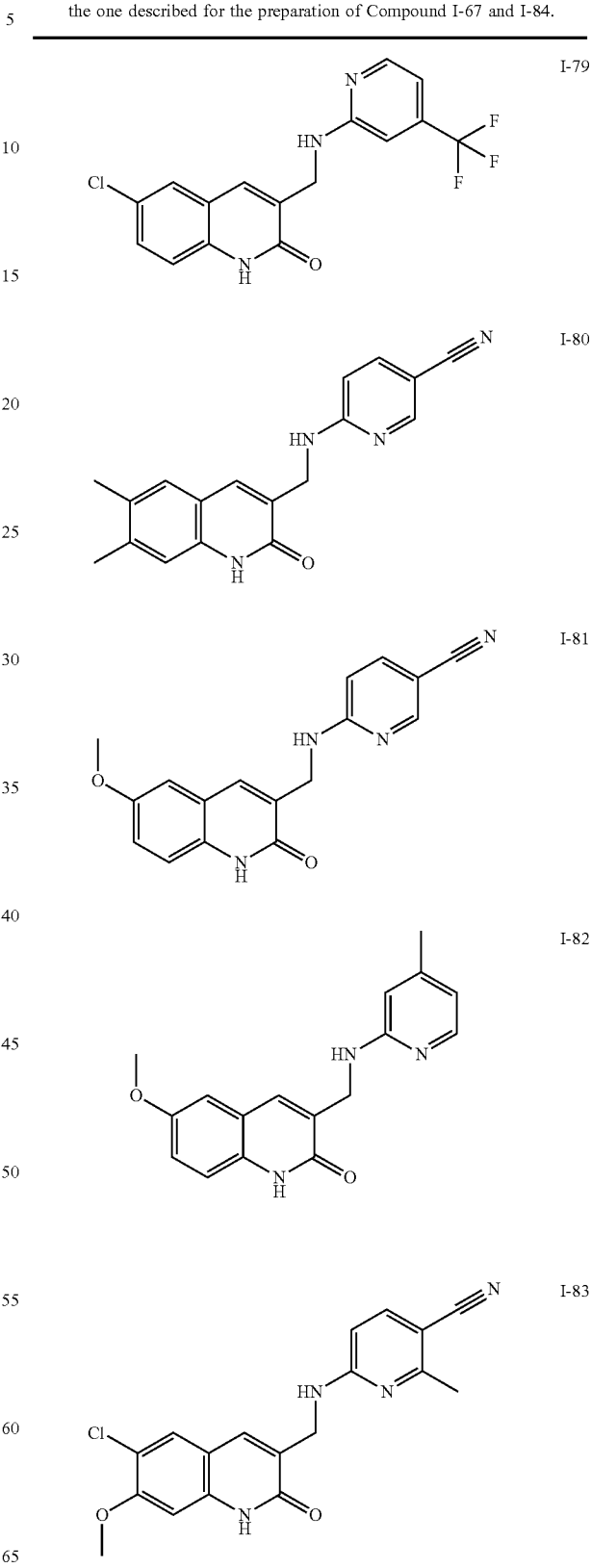

TABLE 14-continued

The compounds listed in Table 14 were prepared using methods similar to the one described for the preparation of Compound I-67 and I-84.

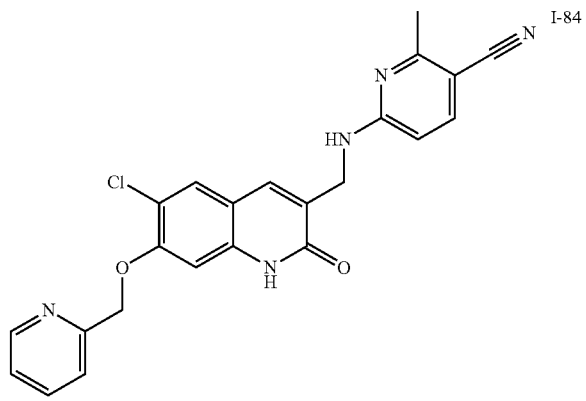

I-84

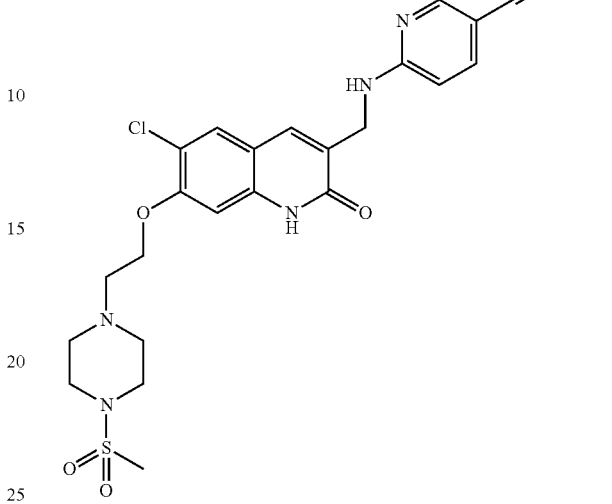

I-85

TABLE 15

LCMS signal and chemical names of each compound listed in Table 14.

| Compound | LCMS | Chemical Name |
|---|---|---|
| I-67 | m/z: 311.00 (M + H)+<br>Rt (min): 1.2 | 6-{[(6-chloro-2-oxo-1,2-dihydroquinolin-3-yl)methyl]amino}pyridine-3-carbonitrile |
| I-68 | m/z: 328.08 (M + H)+<br>Rt (min): 1.0 | 6-chloro-3-({[3-(propan-2-yl)pyridin-2-yl]amino}methyl)-1,2-dihydroquinolin-2-one |
| I-69 | m/z: 313.96 (M + H)+<br>Rt (min): 0.9 | 6-chloro-3-{[(4,6-dimethylpyridin-2-yl)amino]methyl}-1,2-dihydroquinolin-2-one |
| I-70 | m/z: 315.94 (M + H)+<br>Rt (min): 0.83 | 6-chloro-3-{[(4-methoxypyridin-2-yl)amino]methyl}-1,2-dihydroquinolin-2-one |
| I-71 | m/z: 303.93 (M + H)+<br>Rt (min): 1.18 | 6-chloro-3-{[(5-fluoropyridin-2-yl)amino]methyl}-1,2-dihydroquinolin-2-one |
| I-72 | m/z: 310.96 (M + H)+<br>Rt (min): 1.24 | 2-{[(6-chloro-2-oxo-1,2-dihydroquinolin-3-yl)methyl]amino}pyridine-4-carbonitrile |
| I-73 | m/z: 343.93 (M + H)+<br>Rt (min): 1.18 | methyl 6-{[(6-chloro-2-oxo-1,2-dihydroquinolin-3-yl)methyl]amino}pyridine-2-carboxylate |
| I-74 | m/z: 300.11 (M + H)+<br>Rt (min): 0.85 | 6-chloro-3-{[(4-methylpyridin-2-yl)amino]methyl}-1,2-dihydroquinolin-2-one |
| I-75 | m/z: 319.92 (M + H)+<br>Rt (min): 1.36 | 6-chloro-3-{[(5-chloropyridin-2-yl)amino]methyl}-1,2-dihydroquinolin-2-one |
| I-76 | m/z: 302.04 (M + H)+<br>Rt (min): 0.94 | 6-chloro-3-{[(2-hydroxypyridin-3-yl)amino]methyl}-1,2-dihydroquinolin-2-one |
| I-77 | m/z: 354.12 (M + H)+<br>Rt (min): 1.47 | 6-chloro-3-({[5-(trifluoromethyl)pyridin-2-yl]amino}methyl)-1,2-dihydroquinolin-2-one |
| I-78 | m/z: 310.96 (M + H)+<br>Rt (min): 1.14 | 5-{[(6-chloro-2-oxo-1,2-dihydroquinolin-3-yl)methyl]amino}pyridine-2-carbonitrile |
| I-79 | m/z: 353.94 (M + H)+<br>Rt (min): 1.45 | 6-chloro-3-({[4-(trifluoromethyl)pyridin-2-yl]amino}methyl)-1,2-dihydroquinolin-2-one |
| I-80 | m/z: 305.19 (M + H)+<br>Rt (min): 1.21 | 6-{[(6,7-dimethyl-2-oxo-1,2-dihydroquinolin-3-yl)methyl]amino}pyridine-3-carbonitrile |
| I-81 | m/z: 307.13 (M + H)+<br>Rt (min): 1.03 | 6-{[(6-methoxy-2-oxo-1,2-dihydroquinolin-3-yl)methyl]amino}pyridine-3-carbonitrile |
| I-82 | m/z: 296.17 (M + H)+<br>Rt (min): 0.74 | 6-methoxy-3-{[(4-methylpyridin-2-yl)amino]methyl}-1,2-dihydroquinolin-2-one |
| I-83 | m/z: 354.98 (M + H)+<br>Rt (min): 1.29 | 6-{[(6-chloro-7-methoxy-2-oxo-1,2-dihydroquinolin-3-yl)methyl]amino}-2-methylpyridine-3-carbonitrile |
| I-84 | m/z: 432.30 (M + H)+<br>Rt (min): 1.76 | 6-({[6-chloro-2-oxo-7-(pyridin-2-ylmethoxy)-1,2-dihydroquinolin-3-yl]methyl}amino)-2-methylpyridine-3-carbonitrile |

TABLE 15-continued

LCMS signal and chemical names of each compound listed in Table 14.

| Compound | LCMS | Chemical Name |
|---|---|---|
| I-85 | m/z: 531.03 (M + H)+<br>Rt (min): 1.0 | 6-[({6-chloro-7-[2-(4-methanesulfonylpiperazin-1-yl)ethoxy]-2-oxo-1,2-dihydroquinolin-3-yl}methyl)amino]-2-methylpyridine-3-carbonitrile |

Example 50—IDH1-R132H and IDH1-R132C Enzymatic Assay

Assays were performed in a 384-well black plate. An aliquot of 250 nL of compound was incubated with 10 μL of 30 nM IDH1-R132H or 10 nM IDH1-R132C recombinant protein in assay buffer (50 mM Tris pH=7.5, 150 mM NaCl, 5 mM $MgCl_2$, 0.1% (w/v) Bovine Serum Albumin, and 0.01% Triton X-100) in each well at 25° C. for 15 minutes. After the plate was centrifuged briefly, an aliquot of 10 μL of 2 mM α-ketoglutarate and 20 μM NADPH solution prepared in assay buffer was then added to each well and the reaction was maintained at 25° C. for 45 minutes. An aliquot of 10 μL of diaphorase solution (0.15 U/mL diaphorase and 30 μM Resazurin in assay buffer) was added to each well. The plate was maintained at 25° C. for 15 minutes and then read on a plate reader with excitation and emission wavelengths at 535 nm and 590 nm, respectively. The $IC_{50}$ of a given compound was calculated by fitting the dose response curve of inhibition of NADPH consumption at a given concentration with the four parameter logistic equation.

Example 51—Cellular 2-HG Assay Using HCT116 Mutant IDH1 Cells

HCT116 isogenic IDH1-R132H and IDH1-R132C mutant cells were cultured in growth media (McCoy's 5 A, 10% fetal bovine serum, 1× antibiotic-antimycotic solution and 0.3 mg/mL G418) in 5% $CO_2$ in an incubator at 37° C. To prepare the assay, cells were trypsinized and resuspended in assay media (McCoy's 5 A with no L-glutamine, 10% fetal bovine serum, 1× antibiotic-antimycotic solution and 0.3 mg/mL G418). An aliquot of 10,000 cells/100 μL was transferred to each well of a clear 96-well tissue culture plate. The cells were incubated in 5% $CO_2$ at 37° C. in an incubator overnight to allow for proper cell attachment. An aliquot of 50 μL of compound containing assay media were then added to each well and the assay plate was kept in 5% $CO_2$ at 37° C. in an incubator for 24 hours. The media was then removed from each well and 150 μL of a methanol/water mixture (80/20 v/v) was added to each well. The plates were kept at −80° C. freezer overnight to allow for complete cell lysis. An aliquot of 125 μL of extracted supernatant was analyzed by RapidFire high-throughout-mass spectrometry (Agilent) to determine the cellular 2-HG level. The $IC_{50}$ of a given compound was calculated by fitting the dose response curve of cellular 2-HG inhibition at a given concentration with the four parameter logistic equation Table 16 below provides activity of each compound according to the legend that "++++" indicates an inhibition at a concentration <0.1 μM; "+++" indicates inhibition at a concentration between 0.1 μM and 1 μM of the disclosed compound; "++" indicates inhibition at a concentration from 1 μM to 10 μM of the disclosed compound; and "+" indicates inhibition at a concentration >10 μM for enzyme IDH1 R132H and enzyme IDH1 R132C.

For HCT116 IDH1 R132H and HCT116 IDH1 R132C, "++++" indicates an inhibition at a concentration <0.01 μM; "+++" indicates inhibition at a concentration between 0.01 μM and 0.1 μM of the disclosed compound; "++" indicates inhibition at a concentration from 0.1 μM to 1 μM of the disclosed compound; and "+" indicates inhibition at a concentration >1 μM.

TABLE 16

Results of the illustrative compounds of Formula I in IDH1-R132H, IDH1-R132C, IDH1-MS-HTC116-R132H, and IDH1-MS-HTC116-R132C assays.

| Compounds | Enzyme IDH1 R132H Range IC50 (uM) | Enzyme IDH1 R132C Range IC50 (uM) | HCT IDH1 R132H Range IC50 (uM) | HCT IDH1 R132C Range IC50 (uM) |
|---|---|---|---|---|
| I-1 | ++++ | +++ | +++ | ++ |
| I-2 | ++ | ++ | | |
| I-3 | ++ | ++ | | |
| I-4 | ++++ | +++ | ++ | ++ |
| I-5 | ++++ | +++ | ++ | ++ |
| I-6 | ++++ | +++ | ++ | +++ |
| I-7 | ++++ | ++ | ++ | ++ |
| I-8 | + | | | |
| I-9 | +++ | +++ | ++ | + |
| I-10 | ++++ | ++ | | |
| I-11 | ++++ | +++ | +++ | ++ |
| I-12 | +++ | | | |
| I-13 | +++ | ++ | | |
| I-14 | ++++ | +++ | ++ | ++ |
| I-15 | +++ | | | |
| I-16 | ++ | | | |
| I-17 | + | | | |
| I-18 | +++ | ++ | | |
| I-19 | +++ | ++ | | |
| I-20 | + | | | |
| I-21 | ++++ | +++ | ++ | ++ |
| I-22 | ++++ | +++ | ++++ | ++ |
| I-23 | ++++ | ++++ | +++ | +++ |
| I-24 | ++++ | +++ | +++ | ++ |
| I-25 | ++++ | ++++ | +++ | ++ |
| I-26 | ++++ | ++++ | ++++ | +++ |
| I-27 | ++++ | ++++ | +++ | ++ |
| I-28 | ++++ | ++++ | +++ | ++++ |
| I-29 | ++++ | | +++ | +++ |
| I-30 | ++++ | +++ | +++ | +++ |
| I-31 | +++ | | | |
| I-32 | +++ | | | |
| I-33 | ++ | | | |
| I-34 | ++++ | +++ | | |
| I-35 | ++ | | | |
| I-36 | ++ | + | | |
| I-37 | ++ | | | |
| I-38 | ++ | | | |
| I-39 | ++ | +++ | | |
| I-40 | +++ | +++ | ++ | ++ |
| I-41 | ++ | ++ | | |
| I-42 | ++ | | | |
| I-43 | ++ | ++ | | |
| I-44 | ++ | ++ | | |
| I-45 | ++ | | | |
| I-46 | ++ | | | |
| I-47 | ++ | ++ | | |

TABLE 16-continued

Results of the illustrative compounds of Formula I in IDH1-R132H, IDH1-R132C, IDH1-MS-HTC116-R132H, and IDH1-MS-HTC116-R132C assays.

| Compounds | Enzyme IDH1 R132H Range IC50 (uM) | Enzyme IDH1 R132C Range IC50 (uM) | HCT IDH1 R132H Range IC50 (uM) | HCT IDH1 R132C Range IC50 (uM) |
|---|---|---|---|---|
| I-48 | ++ | ++ | | |
| I-49 | ++ | ++ | | |
| I-50 | ++ | + | | |
| I-51 | ++ | | | |
| I-52 | ++ | + | | |
| I-53 | ++ | + | | |
| I-54 | + | | | |
| I-55 | + | | | |
| I-56 | + | + | | |
| I-57 | + | | | |
| I-58 | ++++ | +++ | ++ | + |
| I-59 | +++ | ++ | | |
| I-60 | ++ | | | |
| I-61 | ++++ | | | |
| I-62 | + | | | |
| I-63 | + | | | |
| I-64 | + | | | |
| I-65 | + | | | |
| I-66 | + | | | |
| I-67 | +++ | + | | |
| I-68 | +++ | | | |
| I-69 | ++ | | | |
| I-70 | ++ | | | |
| I-71 | ++ | | | |
| I-72 | ++ | | | |
| I-73 | ++ | | | |
| I-74 | ++ | | | |
| I-75 | ++ | | | |
| I-76 | ++ | | | |
| I-77 | + | | | |
| I-78 | + | | | |
| I-79 | + | | | |
| I-80 | +++ | | | |
| I-81 | ++ | | | |
| I-82 | + | | | |
| I-83 | ++++ | + | + | + |
| I-84 | +++ | | | |
| I-85 | ++++ | +++ | | |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of formula I:

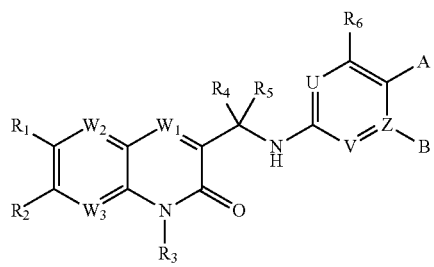

(I)

or a pharmaceutically acceptable salt thereof, wherein:
$W_1$ and $W_2$ are CH;
$W_3$ is $CR_2$;
U and V are independently N or CH, provided that U and V are not both N;
Z is C;
A is CN;
B is H or $C_1$-$C_6$ alkoxy;
$R_1$ is halogen;
$R_2$ is H;
$R_3$ is H or D;
$R_4$ and $R_5$ are independently H or $C_1$-$C_3$ alkyl; and
$R_6$ is H or $C_1$-$C_6$ alkoxy.

2. The compound of claim 1, wherein B is methoxy.

3. The compound of claim 2, wherein $R_4$ is H and $R_5$ is methyl.

4. The compound of claim 3, wherein $R_4$ is H and $R_5$ is (S)-methyl.

5. The compound of claim 4, wherein $R_1$ is chloro.

6. The compound of claim 1 having the Formula Ia:

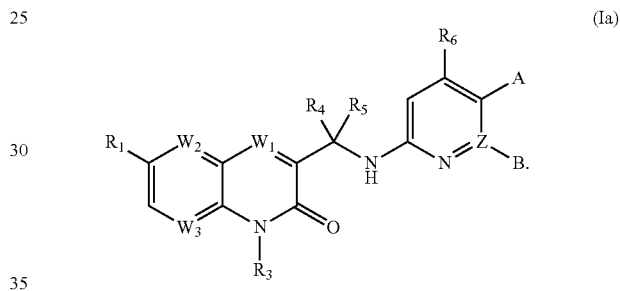

(Ia)

7. The compound of claim 1 having the Formula Ia-1:

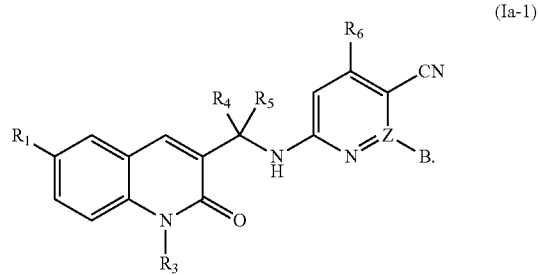

(Ia-1)

8. The compound of claim 1 having the Formula Ib:

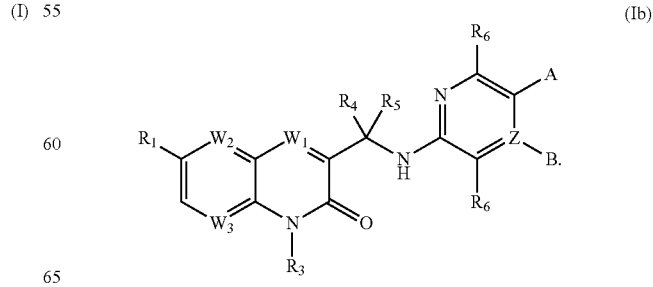

(Ib)

9. The compound of claim 8 having the Formula Ib-1:

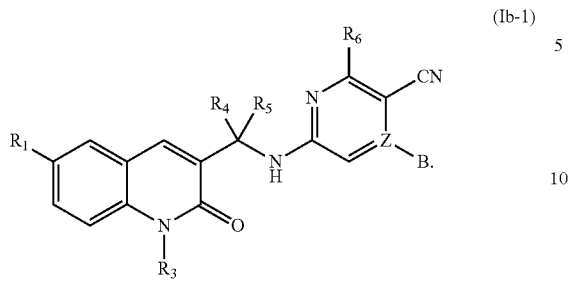
(Ib-1)

10. A pharmaceutical composition comprising 6-{[(1S)-1-(6-chloro-2-oxo-1,2-dihydroquinolin-3-yl)ethyl]amino}-4-methoxypyridine-3-carbonitrile, or a pharmaceutically acceptable salt thereof and pharmaceutically acceptable carrier.

11. A mixture comprising (S)-3-(1-aminoethyl)-6-chloro-quinolin-2(1H)-one hydrochloride and 6-chloro-4-methoxynicotinonitrile.

12. The mixture of claim 11, further comprising 6-{[(1S)-1-(6-chloro-2-oxo-1,2-dihydroquinolin-3-yl)ethyl]amino}-4-methoxypyridine-3-carbonitrile, or a pharmaceutically acceptable salt thereof.

* * * * *